US010420832B2

(12) United States Patent
Wang

(10) Patent No.: US 10,420,832 B2
(45) Date of Patent: Sep. 24, 2019

(54) SYNTHETIC PEPTIDE-BASED EMERGENCY VACCINE AGAINST FOOT AND MOUTH DISEASE (FMD)

(71) Applicant: United Biomedical, Inc., Hauppauge, NY (US)

(72) Inventor: Chang Yi Wang, Cold Spring Harbor, NY (US)

(73) Assignee: UNITED BIOMEDICAL, INC., Hauppauge, NY (US)

( * ) Notice: Subject to any disclaimer, the term of this patent is extended or adjusted under 35 U.S.C. 154(b) by 0 days.

(21) Appl. No.: 14/443,363

(22) PCT Filed: Nov. 16, 2012

(86) PCT No.: PCT/US2012/065386
§ 371 (c)(1),
(2) Date: May 15, 2015

(87) PCT Pub. No.: WO2014/077825
PCT Pub. Date: May 22, 2014

(65) Prior Publication Data
US 2015/0306203 A1 Oct. 29, 2015

(51) Int. Cl.
A61K 39/135 (2006.01)
A61K 47/64 (2017.01)
A61K 38/00 (2006.01)
A61K 39/12 (2006.01)
C12N 7/00 (2006.01)
A61K 39/00 (2006.01)

(52) U.S. Cl.
CPC ............ *A61K 39/135* (2013.01); *A61K 38/00* (2013.01); *A61K 39/12* (2013.01); *A61K 47/646* (2017.08); *C12N 7/00* (2013.01); *A61K 2039/525* (2013.01); *A61K 2039/552* (2013.01); *A61K 2039/55516* (2013.01); *A61K 2039/55566* (2013.01); *A61K 2039/6031* (2013.01); *A61K 2039/70* (2013.01); *C12N 2770/32134* (2013.01)

(58) Field of Classification Search
CPC ........ C07K 14/005; C12N 2770/32122; Y10S 530/826
See application file for complete search history.

(56) References Cited

U.S. PATENT DOCUMENTS

| 4,732,971 | A | 3/1988 | DiMarchi et al. |
| 5,106,726 | A | 4/1992 | Wang |
| 5,476,765 | A | 12/1995 | Wang |
| 5,580,859 | A | 12/1996 | Felgner |
| 5,589,466 | A | 12/1996 | Felgner |
| 5,703,055 | A | 12/1997 | Felgner |
| 5,759,551 | A | 6/1998 | Ladd et al. |
| 5,864,008 | A | 1/1999 | James et al. |
| 6,107,021 | A | * 8/2000 | Wang .................. C07K 14/005 435/5 |
| 6,713,301 | B1 | * 3/2004 | Wang ...................... C07K 7/23 435/328 |
| 2004/0009897 | A1 | 1/2004 | Sokoll |
| 2004/0259822 | A1 | 12/2004 | Avrameas et al. |
| 2010/0092500 | A1 | 4/2010 | Jackson et al. |

FOREIGN PATENT DOCUMENTS

| CN | 1354674 | 6/2002 |
| CN | 102168088 | * 8/2011 |
| TW | 200307557 | 12/2003 |
| TW | I232108 | 5/2005 |
| WO | 1983/003547 | 10/1983 |
| WO | 1991/003255 | 3/1991 |
| WO | 1994/025060 | 11/1994 |
| WO | 1995/011998 | 5/1995 |
| WO | 1997/002840 | 1/1997 |

(Continued)

OTHER PUBLICATIONS

Acharya, R., et al., "The three-dimensional structure of foot-and-mouth disease virus at 2.9 angstrom resolution", Nature, 337:709-716 (1989).
Askari, F.K., et al., "Antisense-Oligonucleotide Therapy", N Engl J Med., 334:316-318 (1996).
Babbitt, B.P., et al., "Binding of immunogenic peptides to Ia histocompatibility molecules", Nature, 317(6035):359-61 (1985).
Bachrach, et al., "Immune and Antibody Responses to an Isolated Capsid Protein of Foot-and-Mouth Disease Virus", J. Immunol., 115:1636-1641 (1975).
Barteling, S.J., et al., "Developments in foot-and-mouth disease vaccines", Vaccine, 9:75-88 (1991).
Blanco, E., et al., "Interspecies major histocompatibility complex-restricted Th cell epitope on foot-and-mouth disease virus capsid protein VP4." J. Virol., 74:4902-4907. (2000).

(Continued)

Primary Examiner — Bao Q Li
(74) Attorney, Agent, or Firm — Locke Lord, LLP; Brandon T. Schurter

(57) ABSTRACT

Synthetic FMD peptide immunogens and compositions containing the same are disclosed. Methods for detecting, treating, and preventing an FMD infection in an animal using the synthetic FMD peptide immunogens are also disclosed. In a specific embodiment, a peptide-based emergency vaccine and formulations thereof against Foot and Mouth Disease is described. Various vaccine formulations contain a mixture of peptides derived from FMDV VP1 protein; each peptide containing a B cell FMDV neutralizing/receptor binding epitope sequence linked to an artificial Th epitope to enhance the immunogenicity of each peptide. Disclosed vaccine formulations containing viral immunogens can optionally be supplemented with a mixture of peptides representing the FMDV endogenous Th epitopes derived from FMDV proteins, homologues and functional analogues thereof. Such viral peptide compositions are prepared in an acceptable delivery system as vaccine formulations and can provide protection pigs and cattle from infection upon FMDV challenge with only single administration.

21 Claims, 4 Drawing Sheets
Specification includes a Sequence Listing.

(56) References Cited

FOREIGN PATENT DOCUMENTS

| | | |
|---|---|---|
| WO | 1999/066954 | 12/1999 |
| WO | 1999/066957 | 12/1999 |
| WO | 2003/068169 | 8/2003 |

OTHER PUBLICATIONS

Brett, S.J., et al., "The invasion protein of Yersinia spp. provides co-stimulatory activity to human T cells through Interaction with beta1 integrins", Eur. J. Immunol., 23:1608-1614 (1993).
Brown, F., et al., "The Effect of Various Inactivating Agents on the Viral and Ribonucleic Acid Infectivities of Foot-and-Mouth Disease Virus and on its Attachment to Susceptible Cells." J Gen Microbiol., 31:179-186. (1963).
Brown, F., "New approaches to vaccination against foot and mouth disease." Vaccine, 10:1022-6. (1992).
Burman, A., et al.; "Specificity of the VP1 GH Loop of Foot-and-Mouth Disease Virus for αv Integrins", J. Virol. 80(19):9798-9810 (2006).
Carrillo, C., et al., "Comparative genomics of foot-and-mouth disease virus." J. Virol., 79:6487-6504. (2005).
Cease, K.B., et al., "Helper T-cell antigenic site identification in the acquired immunodeficiency syndrome virus gp120 envelope protein and induction of immunity in mice to the native protein using a 16-residue synthetic peptide", Proc. Natl. Acad. Sci USA, 84:4249-4253 (1987).
Collen, T., et al., "Heterotypic recognition of foot-and-mouth disease virus by cattle lymphocytes", J. of Gen. Virology, 71:309-315 (1990).
Collen, T., et al., "A T cell epitope in VP1 of foot-and-mouth disease virus is immunodominant for vaccinated cattle." J. Immunol., 146:749-755. (1991).
Collen, T., et al., "Heterotypic recognition of recombinant FMDV proteins by bovine T-cells: the polymerase (P3Dpol) as an immunodominant T-cell immunogen." Virus Res., 56:125-133. (1998).
Cox, S.J., et al., "Longevity of antibody and cytokine responses following vaccination with high potency emergency FMD vaccines." Vaccine. 21(13-14), 1336-1347 (2003).
Cox, S.J., "Experimental evaluation of foot-and-mouth disease vaccines for emergency use in ruminants and pigs: a review", Veterinary Research, 40(13):1-30 (2009).
Eldridge, et al., "Biodegradable microspheres as a vaccine delivery system", Molec Immunol, 28:287-294 (1991).
Ferrari, C., et al., "Identification of immunodominant T cell epitopes of the hepatitis B virus nucleocapsid antigen", J. Clin. Invest, 88:214-222 (1991).
Fields, et al., Chapter 3 in Synthetic Peptides: A User's Guide, ed. Grant, W. H. Freeman & Co., New York, NY, p. 77-183 (1992).
Filgueira, M.P., et al., "Detection and characterization of functional T cell epitopes on the structural proteins VP2, VP3 and VP4 of Foot and Mouth Disease Virus O1 Campos." Virology, 271: 234-2. (2000).
Francis, M.J., et al., "Neutralizing antibodies to all seven serotypes of foot-and-mouth disease virus elicited by synthetic peptides", Immunol., 69:171-176 (1990).
Francis, M.J., et al., "Non-responsiveness to a foot-and-mouth disease virus peptide overcome by addition of foreign helper T-cell determinants". Nature. 330(6144):168-170 (1987).
Garcia-Briones, M., et al., "Association of bovine DRB3 alleles with immune response to FMDV peptides and protection against viral challenge." Vaccine, 19:1167-1171. (2001).
Garcia-Briones, M., et al., "Immunogenicity and T cell recognition in swine of foot-and-mouth disease virus polymerase 3D." Virology, 322:264-27. (2004).
Gerner, W., et al., "Identification of novel foot-and -mouth disease virus specific T-cell epitopes in c/c and d/d haplotype miniature swine." Virus Res., 121:223-228. (2006).

Gerner, W., et al., "Identification of a novel foot-and-mouth disease virus specific T-cell epitope with immunodominant characteristics in cattle with MHC serotype A31." Vet. Res., 38:565-572. (2007).
Gerner, W., et al., "Identification of Major histocompatibility Complex Restriction and Anchor Residues of Foot-and-Mouth Disease Virus-Derived Bovine T-cell epitopes." J. Virol., 83:4039-4050. (2009).
Grant, W.H. (editor), Synthetic Peptides: A User's Guide, Freeman & Co., New York, NY, pp. 281 (1992).
Gras-Masse, H., et al., "Synthetic Vaccines and HIV-1 hypervariability: a 'mixotope' approach", Peptide Research, 5(4):211-216 (1992).
Guzman, E., et al., "An MHC-restricted CD8+ T-cell response is induced in cattle by foot-and-mouth disease virus (FMDV) infection and also following vaccination with inactivated FMDV" J. Gen. Virol., 89:667-675. (2008).
Haghparast, A., et al., "Selection of T-cell epitopes from foot-and-mouth disease virus reflects the binding affinity to different cattle MHC class II molecules." Immunogenetics, 51:733-742. (2000).

Hohlich, B.J., et al., "Induction of an antigen-specific immune response and partial protection of cattle against challenge infection with foot-and-mouth disease virus (FMDV) after lipopeptide vaccination with FMDV-specific B cell epitopes." J. of Gen. Virology, 84:3315-3324. (2003).

Kleid, D.G., et al., "Cloned viral protein vaccine for foot-and-mouth disease: responses in cattle and swine", Science, 214:1125-1129 (1981).

Laporte, J., et al., "Neutralization of the infective power of the foot-and-mouth disease virus in cell culture by using serums from pigs immunized with a purified viral protein" C.R. Acad. Sci. Paris, 276, Serie D, pp. 3399-3401 (1973).

Lubroth, J., et al., "Absence of protein 2C from clarified foot-and-mouth disease virus vaccines provides the basis for distinguishing convalescent from vaccinated animals", Vaccine, 14:419-427 (1996).

Mason, P.W., et al., "Comparisons of the complete genomes of Asian, African and European isolates of a recent foot-and-mouth disease virus type O pandemic strain (PanAsia)." J. Gen. Virol., 84:1583-1593. (2003).

Meister, G.E., et al., "Two novel T cell epitope prediction algorithms based on MHC-binding motifs; comparison of predicted and published epitopes from Mycobacterium tuberculosis and HIV protein sequences", Vaccine, 13(6):581-591 (1995).

Meloen, R.H., et al., "The use of peptides to reconstruct conformational determinants; a brief review", Ann. Biol. Clin., 49:231-242 (1991).

Moore, V., Chapter 2. In: Synthetic Peptides: A Users Guide. Grant GA, ed. New York: WH Freeman and Company: 63 7. (1992).

Morgan, D.O. and Moore, D.M., "Protection of cattle and swine against foot-and-mouth disease, using biosynthetic peptide vaccines." Am J Vet Res. 51(1):40-5. (1990).

O'Hagan, et al., "Controlled release microparticles for vaccine development", Vaccine, 9(10): 768-771 (1991).

Partidos, C.D., et al., "Immune responses in mice following immunization with chimeric synthetic peptides representing B and T cell epitopes of measles virus proteins", J. of Gen. Virology, 72:1293-1299 (1991).

Pfaff, E., et al., "Antibodies against a preselected peptide recognize and neutralize foot and mouth disease virus", The EMBO Journal, 1(7):869-874 (1982).

Rieder, E., et al., "Vaccines Prepared from Chimeras of Foot-and-Mouth Disease Virus (FMDV) Induce Neutralizing Antibodies and Protective Immunity to Multiple Serotypes of FMDV", J. Virol., 68(11):7092-7098 (1994).

Rodriguez, A., et al., "Antigenic specificity of porcine T cell response against foot and mouth disease virus structural proteins: identification of T helper epitopes in VP1." Virol., 205:24 33. (1994).

Rodriguez, L.L., et al., "A synthetic peptide containing the consensus sequence of the G-H Loop region of FMDV Type O VP1 Combined with a promiscuous T-helper epitope induces peptide specific AB but fails to protect cattle against viral challenge." Vaccine, 21:3751-3756. (2003).

(56) References Cited

OTHER PUBLICATIONS

Shen, F., et al., "Differentiation of convalescent animals from those vaccinated against foot-and-mouth disease by a peptide ELISA", Vaccine, 17:3039-3049 (1999).
Stagg, A.J., et al., "Primary human T-cell responses to the major outer membrane protein of Chlamydia trachomatis", Immunol., 79:1-9 (1993).
Strohmaier, K., et al., "Location and characterization of the antigenic portion of the FMDV immunizing protein", J. Gen. Virol., 59:295-306 (1982).
Taboga, O., et al., "A large-scale evaluation of peptide vaccines against foot-and-mouth disease: lack of solid protection in cattle and isolation of escape mutants", Journal of Virology. 71(04):2606-2614 (1997).
Takamatsu, H.H., "A sub-population of circulating porcine gammadelta T cells can act as professional antigen presenting cells." Vet Immunol Immunopathol., 87(3-4):223-4 (2002).
Tesar, et al., "Serological probes for some foot-and-mouth disease virus nonstructural proteins", Virus Genes; 3:29-44 (1989).
Valero, M.L., et al., "Cyclic peptides as conformationally restricted models of viral antigens: Application to foot-and-mouth disease virus", Biomedical Peptides, Proteins & Nucleic Acids, 1:133-140 (1995).
Van Lierop, M.J., et al., "T cell-stimulatory fragments of foot-and-mouth disease virus released by mild treatment with cathepsin D." J. Gen. Virol., 75:2937-2946. (1994).
Van Lierop, M.J., et al., "Sequences derived from the highly antigenic VP1 region 140 to 160 of foot-and-mouth disease virus do not prime for a bovine T-cell response against intact virus." J. Virol., 69:4511-4514. (1995).

Van Lierop, M.J., et al., "The influence of MHC polymorphism on the selection of T-cell determinants of FMDV in cattle." Immunology, 84:79 85. (1995).
Wang, C.Y., et al., "Long-term high-titer neutralizing activity induced by octameric synthetic HIV-1 antigen", Science, 254:285-288 (1991).
Wang, C.Y., et al., "Synthetic Peptide-based Vaccine and Diagnostic System for Effective Control of FMD." Biologicals, 29:221-228. (2001).
Wang, C.Y., et al., "Effective Synthetic peptide vaccine for foot-and-mouth disease in swine." Vaccine, 20:2603-2610. (2002).
Wang, C.Y., et al., "Site-specific peptide vaccines for immunotherapy and immunization against chronic diseases, and for veterinary applications", Vaccine, 23:2049-2056 (2005).
Zamorano, P., et al., "A 10-amino-acid linear sequence of vp1 of foot and mouth disease virus containing B- and T-cell epitopes induces protection in mice", Virology, 212:614-21, (1995).
Search Report issued in corresponding Chinese Application No. 201280071993.0, dated Jan. 7, 2016.
Supplementary European Search Report issued in corresponding European Application No. 12888444.2, dated Jun. 10, 2016.
Search Report issued in corresponding Taiwan Application No. 102139710, dated Dec. 17, 2014.
Search Report issued in corresponding Taiwan Application No. 102139710, dated Jul. 7, 2017.
International Search Report issued in corresponding International Application No. PCT/US2012/065386, dated May 2, 2013.
International Preliminary Report on Patentability (IPRP) issued in corresponding International Application No. PCT/US2012/065386, dated May 19, 2015.

* cited by examiner

Figure 1
Distribution and Location of Selected B and Th epitopes on FMDV proteins ■ T epitope
▨ B epitope

L^PRO

VP4  (S221-M235) (I223-T237)

VP2  (P359-K374)

VP3  (D582-A596)

VP1 + 2A
1. (E745-V764)  3. (V786-L800)  5. (P835-G856)  7. (T895-C911)  9. (R924-L937)
2. (I758-L777)  4. (W812-P828)  6. (V853-K893)  8. (R913-P932)

2B + 2C  (P954-V968)  (F1094-N1122)  (S1142-I1154)  (V1148-R1162)

3A + 3B1 + B2, B3  (A1446-K1460) (N1516-K1529) (T1526-L1539) (E1551-N1564) (G1578-K1592) (P1584-L1597)

3C  (I2073-D2082)

3D  (M1878-F1892) (I1918-D1932) (A2063-Q2072) (V2083-F2092) (D2107-V2122) (L2248-K2262)

SEQUENCE LISTING

<160> NUMBER OF SEQ ID NOS: 108

<210> SEQ ID NO 1
<211> LENGTH: 25
<212> TYPE: PRT
<213> ORGANISM: Artificial Sequence
<220> FEATURE:
<223> OTHER INFORMATION: UBI Foot-and-mouth disease virus (FMDV) O
      Consensus sequence VP1 134-158, cyclized.

<400> SEQUENCE: 1

Cys Lys Tyr Gly Glu Asn Ala Val Thr Asn Val Arg Gly Asp Leu Gln
1               5                   10                  15

Val Leu Ala Gln Lys Ala Ala Arg Cys
            20                  25

<210> SEQ ID NO 2
<211> LENGTH: 41
<212> TYPE: PRT
<213> ORGANISM: Artificial Sequence
<220> FEATURE:
<223> OTHER INFORMATION: Foot-and-mouth disease virus (FMDV) O Consensus
      VP1 129-168, (2570A), Peptides with both 134 and 158 AA positions
      substituted by Cys and cyclized.

<400> SEQUENCE: 2

Val Tyr Asn Gly Asn Cys Lys Tyr Gly Glu Asn Ala Val Thr Asn Val
1               5                   10                  15

Arg Gly Asp Leu Gln Val Leu Ala Gln Lys Ala Ala Arg Cys Leu Pro
            20                  25                  30

Thr Ser Phe Asn Tyr Gly Ala Ile Lys
        35                  40

<210> SEQ ID NO 3
<211> LENGTH: 41
<212> TYPE: PRT
<213> ORGANISM: Foot-and-mouth disease virus
<220> FEATURE:
<221> NAME/KEY: MISC_FEATURE
<222> LOCATION: (1)..(41)
<223> OTHER INFORMATION: Foot-and-Mouth Disease Virus (FMDV) O Consensus
      VP1 129-168, (2570A), Peptides with both 134 and 158 AA positions
      substituted by Cys and cyclized.

<400> SEQUENCE: 3

Val Tyr Asn Gly Glu Cys Arg Tyr Ser Arg Asn Ala Val Pro Asn Val
1               5                   10                  15

Arg Gly Asp Leu Gln Val Leu Ala Gln Lys Val Ala Arg Cys Leu Pro
            20                  25                  30

Thr Ser Phe Asn Tyr Gly Ala Ile Lys
        35                  40

<210> SEQ ID NO 4
<211> LENGTH: 41
<212> TYPE: PRT
<213> ORGANISM: Foot-and-mouth disease virus
<220> FEATURE:
<221> NAME/KEY: MISC_FEATURE
<222> LOCATION: (1)..(41)
<223> OTHER INFORMATION: UBI FMDV Taiwan 2956a VP1. Peptides with both
      134 and 158 AA positions substituted by Cys and cyclized.

<400> SEQUENCE: 4

Val Tyr Asn Gly Ser Cys Lys Tyr Gly Asp Thr Ser Thr Asn Asn Val
1               5                   10                  15

Arg Gly Asp Leu Gln Val Leu Ala Gln Lys Ala Glu Arg Cys Leu Pro
            20                  25                  30

Thr Ser Phe Asn Phe Gly Ala Ile Lys
        35                  40

<210> SEQ ID NO 5
<211> LENGTH: 41
<212> TYPE: PRT
<213> ORGANISM: Foot-and-mouth disease virus
<220> FEATURE:
<221> NAME/KEY: MISC_FEATURE
<222> LOCATION: (1)..(41)
<223> OTHER INFORMATION: UBI FMDV O O1K/O1BFS, VP1. Peptides with both
      134 and 158 AA positions substituted by Cys and cyclized.

<400> SEQUENCE: 5

```
Val Tyr Asn Gly Glu Cys Arg Tyr Asn Arg Asn Ala Val Pro Asn Leu
1               5                   10                  15

Arg Gly Asp Leu Gln Val Leu Ala Gln Lys Val Ala Arg Thr Leu Pro
            20                  25                  30

Thr Ser Phe Asn Tyr Gly Ala Ile Lys
        35                  40

<210> SEQ ID NO 6
<211> LENGTH: 41
<212> TYPE: PRT
<213> ORGANISM: Foot-and-mouth disease virus
<220> FEATURE:
<221> NAME/KEY: MISC_FEATURE
<222> LOCATION: (1)..(41)
<223> OTHER INFORMATION: UBI FMDV China (Gd/86) VP1. Peptides with both
      134 and 158 AA positions substituted by Cys and cyclized.

<400> SEQUENCE: 6

Val Tyr Asn Gly Ser Cys Lys Tyr Ser Asp Ala Arg Val Ser Asn Val
1               5                   10                  15

Arg Gly Asp Leu Arg Val Leu Ala Gln Lys Ala Glu Arg Ala Leu Pro
            20                  25                  30

Thr Ser Ser Asn Tyr Gly Ala Ile Lys
        35                  40

<210> SEQ ID NO 7
<211> LENGTH: 41
<212> TYPE: PRT
<213> ORGANISM: Foot-and-mouth disease virus
<220> FEATURE:
<221> NAME/KEY: MISC_FEATURE
<222> LOCATION: (1)..(41)
<223> OTHER INFORMATION: UBI FMDV O Swine/Cattle/O/MYA/7/02 VP1.
      Peptides with both 134 and 158 AA positions substituted by Cys and
      cyclized.

<400> SEQUENCE: 7

Val Tyr Asn Gly Asn Cys Lys Tyr Ala Gly Gly Ser Leu Thr Asn Val
1               5                   10                  15

Arg Gly Asp Leu Gln Val Leu Ala Gln Lys Ala Ala Arg Cys Leu Pro
            20                  25                  30

Thr Ser Phe Asn Tyr Gly Ala Ile Lys
        35                  40

<210> SEQ ID NO 8
<211> LENGTH: 41
<212> TYPE: PRT
<213> ORGANISM: Foot-and-mouth disease virus
<220> FEATURE:
<221> NAME/KEY: MISC_FEATURE
<222> LOCATION: (1)..(41)
<223> OTHER INFORMATION: UBI FMDV O/Ozk/93, VP1. Peptides with both 134
      and 158 AA positions substituted by Cys and cyclized.

<400> SEQUENCE: 8

Val Tyr Asn Gly Asn Cys Lys Tyr Ser Asp Arg Ala Val Ser Asn Val
1               5                   10                  15

Arg Gly Asp Leu Gln Val Leu Ala Gln Lys Ala Ala Arg Cys Leu Pro
            20                  25                  30

Thr Ser Phe Asn Tyr Gly Ala Ile Lys
        35                  40

<210> SEQ ID NO 9
<211> LENGTH: 41
```

```
<212> TYPE: PRT
<213> ORGANISM: Foot-and-mouth disease virus
<220> FEATURE:
<221> NAME/KEY: UBI Foot-and-Mouth Disease Virus (FMDV) O/A/58, VP1.
      Peptides with both 134 and 158 AA positions substituted by Cys and
      cyclized.
<222> LOCATION: (1)..(41)
<223> OTHER INFORMATION: UBI FMDV O/A/58, VP1. Peptides with both 134
      and 158 AA positions substituted by Cys and cyclized.

<400> SEQUENCE: 9

Val Tyr Asn Gly Asn Cys Lys Tyr Gly Val Gly Pro Val Thr Lys Val
1               5                   10                  15

Arg Gly Asp Leu Gln Val Leu Ala Gln Lys Ala Ala Arg Cys Leu Pro
            20                  25                  30

Thr Ser Phe Asn Tyr Gly Ala Ile Lys
        35                  40

<210> SEQ ID NO 10
<211> LENGTH: 41
<212> TYPE: PRT
<213> ORGANISM: Foot-and-mouth disease virus
<220> FEATURE:
<221> NAME/KEY: MISC_FEATURE
<222> LOCATION: (1)..(41)
<223> OTHER INFORMATION: UBI FMDV O/OZK/93, VP1. Peptides with both 134
      and 158 AA positions substituted by Cys and cyclized.

<400> SEQUENCE: 10

Val Tyr Asn Gly Asn Cys Lys Tyr Ser Asp Arg Pro Val Thr Lys Val
1               5                   10                  15

Arg Gly Asp Leu Gln Val Leu Ala Gln Lys Ala Ala Arg Cys Leu Pro
            20                  25                  30

Thr Ser Phe Asn Tyr Gly Ala Ile Lys
        35                  40

<210> SEQ ID NO 11
<211> LENGTH: 41
<212> TYPE: PRT
<213> ORGANISM: Foot-and-mouth disease virus
<220> FEATURE:
<221> NAME/KEY: MISC_FEATURE
<222> LOCATION: (1)..(41)
<223> OTHER INFORMATION: UBI FMDV O Lanzhou, VP1. Peptides with both 134
      and 158 AA positions substituted by Cys and cyclized.

<400> SEQUENCE: 11

Val Tyr Asn Gly Ser Cys Lys Tyr Ser Asp Ala Arg Val Ser Asn Val
1               5                   10                  15

Arg Gly Asp Leu Gln Val Leu Ala Gln Lys Ala Glu Arg Cys Leu Pro
            20                  25                  30

Ser Ser Phe Asn Tyr Gly Ala Ile Lys
        35                  40

<210> SEQ ID NO 12
<211> LENGTH: 39
<212> TYPE: PRT
<213> ORGANISM: Artificial Sequence
<220> FEATURE:
<223> OTHER INFORMATION: UBI Foot-and-Mouth Disease Virus (FMDV) Asia 1
      Consensus, VP1. Peptides with both 134 and 158 AA positions
      substituted by Cys and cyclized.

<400> SEQUENCE: 12

Val Tyr Asn Gly Lys Cys Thr Tyr Gly Glu Gln Pro Ser Arg Arg Gly
1               5                   10                  15
```

Asp Met Ala Ala Leu Ala Gln Arg Leu Ser Arg Cys Leu Pro Thr Ser
            20                  25                  30

Phe Asn Tyr Gly Ala Val Lys
        35

<210> SEQ ID NO 13
<211> LENGTH: 39
<212> TYPE: PRT
<213> ORGANISM: Foot-and-mouth disease virus
<220> FEATURE:
<221> NAME/KEY: MISC_FEATURE
<222> LOCATION: (1)..(39)
<223> OTHER INFORMATION: UBI FMDV Asia 1 Yunnan PRC, VP1. Peptides with
      both 134 and 158 AA positions substituted by Cys and cyclized.

<400> SEQUENCE: 13

Val Tyr Asn Gly Lys Cys Thr Tyr Gly Glu Glu Ser Thr Arg Arg Gly
1               5                  10                  15

Asp Phe Ala Ala Leu Ala Gln Arg Leu Ser Arg Cys Leu Pro Thr Ser
            20                  25                  30

Phe Asn Tyr Gly Ala Val Lys
        35

<210> SEQ ID NO 14
<211> LENGTH: 39
<212> TYPE: PRT
<213> ORGANISM: Foot-and-mouth disease virus
<220> FEATURE:
<221> NAME/KEY: MISC_FEATURE
<222> LOCATION: (1)..(39)
<223> OTHER INFORMATION: UBI FMDV Asia 1 KZC-2/10 PRC, VP1. Peptides
      with both 134 and 158 AA positions substituted by Cys and
      cyclized.

<400> SEQUENCE: 14

Val Tyr Asn Gly Lys Cys Thr Tyr Gly Glu Thr Thr Ala Arg Arg Gly
1               5                  10                  15

Asp Thr Ala Ala Leu Ala Gln Arg Leu Ser Gly Cys Leu Pro Thr Ser
            20                  25                  30

Phe Asn Tyr Gly Ala Val Lys
        35

<210> SEQ ID NO 15
<211> LENGTH: 39
<212> TYPE: PRT
<213> ORGANISM: Foot-and-mouth disease virus
<220> FEATURE:
<221> NAME/KEY: MISC_FEATURE
<222> LOCATION: (1)..(39)
<223> OTHER INFORMATION: UBI FMDV Asia 1 JiangSu/China/2005, VP1.
      Peptides with both 134 and 158 AA positions substituted by Cys and
      cyclized.

<400> SEQUENCE: 15

Val Tyr Asn Gly Lys Cys Thr Tyr Gly Glu Glu Ser Ser Arg Arg Gly
1               5                  10                  15

Asp Leu Ala Ala Leu Ala Arg Arg Val Asn Asn Cys Leu Pro Thr Ser
            20                  25                  30

Phe Asn Tyr Gly Ala Val Lys
        35

<210> SEQ ID NO 16
<211> LENGTH: 40
<212> TYPE: PRT

```
<213> ORGANISM: Artificial Sequence
<220> FEATURE:
<223> OTHER INFORMATION: UBI Foot-and-Mouth Disease Virus (FMDV) A
      consensus, VP1. Peptides with both 134 and 158 AA positions
      substituted by Cys and cyclized.
<220> FEATURE:
<221> NAME/KEY: MISC_FEATURE
<222> LOCATION: (1)..(40)
<223> OTHER INFORMATION: UBI FMDV A consensus, VP1. Peptides with both
      134 and 158 AA positions substituted by Cys and cyclized.

<400> SEQUENCE: 16

Val Tyr Asn Gly Thr Cys Lys Tyr Thr Val Gly Gly Ser Gly Arg Arg
1               5                   10                  15

Gly Asp Leu Gly Ser Leu Ala Ala Arg Val Ala Lys Cys Leu Pro Ala
            20                  25                  30

Ser Phe Asn Tyr Gly Ala Ile Lys
        35                  40

<210> SEQ ID NO 17
<211> LENGTH: 40
<212> TYPE: PRT
<213> ORGANISM: Foot-and-mouth disease virus
<220> FEATURE:
<221> NAME/KEY: MISC_FEATURE
<222> LOCATION: (1)..(40)
<223> OTHER INFORMATION: UBI FMDV A24 Cruzeiro California, VP1. Peptides
      with both 134 and 158 AA positions substituted by Cys and
      cyclized.

<400> SEQUENCE: 17

Val Tyr Asn Gly Thr Ser Lys Tyr Ala Val Gly Gly Ser Gly Arg Arg
1               5                   10                  15

Gly Asp Met Gly Ser Leu Ala Ala Arg Val Val Lys Gln Leu Pro Ala
            20                  25                  30

Ser Phe Asn Tyr Gly Ala Ile Lys
        35                  40

<210> SEQ ID NO 18
<211> LENGTH: 40
<212> TYPE: PRT
<213> ORGANISM: Foot-and-mouth disease virus
<220> FEATURE:
<221> NAME/KEY: MISC_FEATURE
<222> LOCATION: (1)..(40)
<223> OTHER INFORMATION: UBI FMDV A Gansu/China/60Y, VP1. Peptide with
      both 134 and 158 AA positions substituted by Cys and cyclized.

<400> SEQUENCE: 18

Val Tyr Asn Gly Thr Cys Gln Tyr Ser Thr Gly Asn Ala Gly Arg Arg
1               5                   10                  15

Gly Asp Leu Gly Ser Leu Ala Arg Val Ala Ala Gln Cys Leu Pro Ala
            20                  25                  30

Ser Phe Asn Phe Gly Ala Ile Arg
        35                  40

<210> SEQ ID NO 19
<211> LENGTH: 40
<212> TYPE: PRT
<213> ORGANISM: Foot-and-mouth disease virus
<220> FEATURE:
<221> NAME/KEY: MISC_FEATURE
<222> LOCATION: (1)..(40)
<223> OTHER INFORMATION: UBI FMDV A XinJiang/China/58Y, VP1. Peptides
      with both 134 and 158 AA positions substituted by Cys and
      cyclized.
```

```
<400> SEQUENCE: 19

Val Tyr Asn Gly Thr Cys Thr Tyr Ser Thr Gly Ser Ala Gly Arg Arg
1               5                   10                  15

Gly Asp Leu Gly Ser Leu Ala Ala Arg Val Ala Asn Cys Leu Pro Ala
            20                  25                  30

Ser Phe Asn Phe Gly Ala Ile Arg
            35                  40

<210> SEQ ID NO 20
<211> LENGTH: 40
<212> TYPE: PRT
<213> ORGANISM: Foot-and-mouth disease virus
<220> FEATURE:
<221> NAME/KEY: MISC_FEATURE
<222> LOCATION: (1)..(40)
<223> OTHER INFORMATION: UBI FMDV A22 A Mahmatli/Tur/65Y, VP1. Peptides
      with both 134 and 158 AA positions substituted by Cys and
      cyclized.

<400> SEQUENCE: 20

Val Tyr Asn Gly Thr Cys Lys Tyr Ser Ala Gly Gly Thr Gly Arg Arg
1               5                   10                  15

Gly Asp Leu Gly Pro Leu Ala Ala Arg Val Ala Ala Cys Leu Pro Ala
            20                  25                  30

Ser Phe Asn Phe Gly Ala Ile Gln
            35                  40

<210> SEQ ID NO 21
<211> LENGTH: 40
<212> TYPE: PRT
<213> ORGANISM: Foot-and-mouth disease virus
<220> FEATURE:
<221> NAME/KEY: MISC_FEATURE
<222> LOCATION: (1)..(40)
<223> OTHER INFORMATION: UBI FMDV A Argentina 2001Y, VP1. Peptides with
      both 134 and 158 AA positions substituted by Cys and cyclized.

<400> SEQUENCE: 21

Val Tyr Asn Gly Thr Cys Lys Tyr Thr Val Ser Gly Ser Ser Arg Arg
1               5                   10                  15

Gly Asp Leu Gly Ser Leu Ala Ala Arg Val Val Lys Cys Leu Pro Ala
            20                  25                  30

Ser Phe Asn Tyr Gly Ala Ile Lys
            35                  40

<210> SEQ ID NO 22
<211> LENGTH: 38
<212> TYPE: PRT
<213> ORGANISM: Foot-and-mouth disease virus
<220> FEATURE:
<221> NAME/KEY: MISC_FEATURE
<222> LOCATION: (1)..(38)
<223> OTHER INFORMATION: UBI FMDV C3 Indaial/Brazil/84Y, VP1. Peptides
      with both 134 and 158 AA positions substituted by Cys and
      cyclized.

<400> SEQUENCE: 22

Thr Tyr Thr Gly Thr Cys Ala Tyr Thr Ala Ser Ala Arg Arg Gly Asp
1               5                   10                  15

Leu Ala His Leu Ala Ala Ala His Ala Arg Cys Leu Pro Thr Ser Phe
            20                  25                  30

Asn Phe Gly Ala Val Lys
            35
```

```
<210> SEQ ID NO 23
<211> LENGTH: 38
<212> TYPE: PRT
<213> ORGANISM: Foot-and-mouth disease virus
<220> FEATURE:
<221> NAME/KEY: MISC_FEATURE
<222> LOCATION: (1)..(38)
<223> OTHER INFORMATION: UBI FMDV C3 Argentina/83c, VP1. Peptides with
      both 134 and 158 AA positions substituted by Cys and cyclized.

<400> SEQUENCE: 23

Thr Tyr Thr Gly Thr Cys Thr Tyr Thr Thr Ser Ala Arg Arg Gly Asp
1               5                   10                  15

Leu Ala His Leu Ala Thr Ala His Ala Arg Cys Leu Pro Thr Ser Phe
            20                  25                  30

Asn Phe Gly Ala Val Lys
        35

<210> SEQ ID NO 24
<211> LENGTH: 19
<212> TYPE: PRT
<213> ORGANISM: Artificial Sequence
<220> FEATURE:
<223> OTHER INFORMATION: Combinatorial modified T helper peptide from
      Measles virus
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R

<400> SEQUENCE: 24

Ile Ser Ile Xaa Glu Ile Xaa Xaa Val Ile Val Xaa Xaa Ile Glu Thr
1               5                   10                  15

Ile Leu Phe

<210> SEQ ID NO 25
<211> LENGTH: 61
<212> TYPE: PRT
<213> ORGANISM: Artificial Sequence
<220> FEATURE:
<223> OTHER INFORMATION: Peptide containing artificial T helper epitope
      from measles virus and B cell epitope from foot-and-mouth disease
      virus (FMDV)
<220> FEATURE:
<221> NAME/KEY: MISC_FEATURE
<222> LOCATION: (1)..(19)
<223> OTHER INFORMATION: Artificial combinatorial modified T helper
      peptide sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
```

```
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: linked spacer, K (20) is epsilon K.
<220> FEATURE:
<221> NAME/KEY: MISC_FEATURE
<222> LOCATION: (21)..(61)
<223> OTHER INFORMATION: UBI FMDV VP1 2570a, with both 134 and 158 AA
      positions substituted by Cys and cyclized.

<400> SEQUENCE: 25

Ile Ser Ile Ser Glu Ile Lys Gly Val Ile Val His Lys Ile Glu Thr
1               5                   10                  15

Ile Leu Phe Lys Val Tyr Asn Gly Asn Cys Lys Tyr Gly Glu Asn Ala
            20                  25                  30

Val Thr Asn Val Arg Gly Asp Leu Gln Val Leu Ala Gln Lys Ala Ala
        35                  40                  45

Arg Cys Leu Pro Thr Ser Phe Asn Tyr Gly Ala Ile Lys
    50                  55                  60

<210> SEQ ID NO 26
<211> LENGTH: 61
<212> TYPE: PRT
<213> ORGANISM: Artificial Sequence
<220> FEATURE:
<223> OTHER INFORMATION: Peptide containing artificial T helper epitope
      from measles virus and B cell epitope from foot-and-mouth disease
      virus (FMDV)
<220> FEATURE:
<221> NAME/KEY: MISC_FEATURE
<222> LOCATION: (1)..(19)
<223> OTHER INFORMATION: Combinatorial modified T helper peptide
      sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: Linked spacer, K (20) is epsilon K.
<220> FEATURE:
<221> NAME/KEY: MISC_FEATURE
<222> LOCATION: (21)..(61)
<223> OTHER INFORMATION: UBI FMDV VP1 O Campos/Brazil/58Y, with both 134
``` and 158 AA positions substituted by Cys and cyclized.

<400> SEQUENCE: 26

Ile Ser Ile Xaa Glu Ile Xaa Xaa Val Ile Val Xaa Xaa Ile Glu Thr
1               5                   10                  15

Ile Leu Phe Lys Val Tyr Asn Gly Glu Cys Arg Tyr Ser Arg Asn Ala
            20                  25                  30

Val Pro Asn Val Arg Gly Asp Leu Gln Val Leu Ala Gln Lys Val Ala
        35                  40                  45

Arg Cys Leu Pro Thr Ser Phe Asn Tyr Gly Ala Ile Lys
    50                  55                  60

<210> SEQ ID NO 27
<211> LENGTH: 61
<212> TYPE: PRT
<213> ORGANISM: Artificial Sequence
<220> FEATURE:
<223> OTHER INFORMATION: Peptide containing artificial T helper epitope
      from measles virus and B cell epitope from foot-and-mouth disease
      virus (FMDV)
<220> FEATURE:
<221> NAME/KEY: MISC_FEATURE
<222> LOCATION: (1)..(19)
<223> OTHER INFORMATION: Artificial combinatorial modified T helper
      peptide sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: Linked spacer, K (20) is epsilon K.
<220> FEATURE:
<221> NAME/KEY: MISC_FEATURE
<222> LOCATION: (21)..(61)
<223> OTHER INFORMATION: UBI FMDV VP1 O swine/Cattle/O/MYA/7/02, with
      both 134 and 158 AA positions substituted by Cys and cyclized.

<400> SEQUENCE: 27

Ile Ser Ile Xaa Glu Ile Xaa Xaa Val Ile Val Xaa Xaa Ile Glu Thr
1               5                   10                  15

Ile Leu Phe Lys Val Tyr Asn Gly Asn Cys Lys Tyr Ala Gly Gly Ser
            20                  25                  30

Leu Thr Asn Val Arg Gly Asp Leu Gln Val Leu Ala Gln Lys Ala Ala
        35                  40                  45

Arg Cys Leu Pro Thr Ser Phe Asn Tyr Gly Ala Ile Lys
    50                  55                  60

<210> SEQ ID NO 28
<211> LENGTH: 61
<212> TYPE: PRT
<213> ORGANISM: Artificial Sequence

```
<220> FEATURE:
<223> OTHER INFORMATION: Peptide containing artificial T helper epitope
      from measles virus and B cell epitope from foot-and-mouth disease
      virus (FMDV)
<220> FEATURE:
<221> NAME/KEY: MISC_FEATURE
<222> LOCATION: (1)..(19)
<223> OTHER INFORMATION: Artificial combinatorial modified T helper
      peptide sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: Linked spacer K(20) is epsilon K.
<220> FEATURE:
<221> NAME/KEY: MISC_FEATURE
<222> LOCATION: (21)..(61)
<223> OTHER INFORMATION: UBI FMDV VP1 O/Ozk/93, with both 134 and 158 AA
      positions substituted by Cys and cyclized.

<400> SEQUENCE: 28

Ile Ser Ile Xaa Glu Ile Xaa Xaa Val Ile Val Xaa Xaa Ile Glu Thr
1               5                   10                  15

Ile Leu Phe Lys Val Tyr Asn Gly Asn Cys Lys Tyr Ser Asp Arg Ala
            20                  25                  30

Val Ser Asn Val Arg Gly Asp Leu Gln Val Leu Ala Gln Lys Ala Ala
        35                  40                  45

Arg Cys Leu Pro Thr Ser Phe Asn Tyr Gly Ala Ile Lys
    50                  55                  60

<210> SEQ ID NO 29
<211> LENGTH: 59
<212> TYPE: PRT
<213> ORGANISM: Artificial Sequence
<220> FEATURE:
<223> OTHER INFORMATION: Peptide containing artificial T helper epitope
      from measles virus and B cell epitope from foot-and-mouth disease
      virus (FMDV)
<220> FEATURE:
<221> NAME/KEY: MISC_FEATURE
<222> LOCATION: (1)..(19)
<223> OTHER INFORMATION: Artificial combinatorial modified T helper
      peptide sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
```

```
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: Linked spacer, K (20) is epsilon K.
<220> FEATURE:
<221> NAME/KEY: MISC_FEATURE
<222> LOCATION: (21)..(59)
<223> OTHER INFORMATION: UBI FMDV VP1 Asia 1 JiangSu/China/2005, with
      both 134 and 158 AA positions substituted by Cys and cyclized.

<400> SEQUENCE: 29

Ile Ser Ile Xaa Glu Ile Xaa Xaa Val Ile Val Xaa Xaa Ile Glu Thr
1               5                   10                  15

Ile Leu Phe Lys Val Tyr Asn Gly Lys Cys Thr Tyr Gly Glu Glu Ser
            20                  25                  30

Ser Arg Arg Gly Asp Leu Ala Ala Leu Ala Arg Arg Val Asn Asn Cys
        35                  40                  45

Leu Pro Thr Ser Phe Asn Tyr Gly Ala Val Lys
    50                  55

<210> SEQ ID NO 30
<211> LENGTH: 60
<212> TYPE: PRT
<213> ORGANISM: Artificial Sequence
<220> FEATURE:
<223> OTHER INFORMATION: Peptide containing artificial T helper epitope
      from measles virus and B cell epitope from foot-and-mouth disease
      virus (FMDV)
<220> FEATURE:
<221> NAME/KEY: MISC_FEATURE
<222> LOCATION: (1)..(19)
<223> OTHER INFORMATION: Artificial combinatorial modified T helper
      peptide sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: Linked spacer, K (20) is epsilon k.
<220> FEATURE:
<221> NAME/KEY: MISC_FEATURE
<222> LOCATION: (21)..(60)
<223> OTHER INFORMATION: UBI FMDV VP1 A24 Cruzeiro California, with both
      134 and 158 AA positions substituted by Cys and cyclized.

<400> SEQUENCE: 30

Ile Ser Ile Xaa Glu Ile Xaa Xaa Val Ile Val Xaa Xaa Ile Glu Thr
```

-continued

```
                1               5                  10                    15
Ile Leu Phe Lys Val Tyr Asn Gly Thr Ser Lys Tyr Ala Val Gly Gly
                20                       25                    30

Ser Gly Arg Arg Gly Asp Met Gly Ser Leu Ala Ala Arg Val Val Lys
                35                       40                    45

Gln Leu Pro Ala Ser Phe Asn Tyr Gly Ala Ile Lys
                50                       55                    60
```

<210> SEQ ID NO 31
<211> LENGTH: 60
<212> TYPE: PRT
<213> ORGANISM: Artificial Sequence
<220> FEATURE:
<223> OTHER INFORMATION: Peptide containing artificial T helper epitope
      from measles virus and B cell epitope from foot-and-mouth disease
      virus (FMDV)
<220> FEATURE:
<221> NAME/KEY: MISC_FEATURE
<222> LOCATION: (1)..(19)
<223> OTHER INFORMATION: Artificial combinatorial modified T helper
      peptide sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: Linked spacer, K (20) is epsilon K.
<220> FEATURE:
<221> NAME/KEY: MISC_FEATURE
<222> LOCATION: (21)..(60)
<223> OTHER INFORMATION: UBI FMDV VP1 A Gansu/China/60Y, with both 134
      and 158 AA positions substituted by Cys and cyclized.

<400> SEQUENCE: 31

```
Ile Ser Ile Xaa Glu Ile Xaa Xaa Val Ile Val Xaa Xaa Ile Glu Thr
1               5                  10                    15

Ile Leu Phe Lys Val Tyr Asn Gly Thr Cys Gln Tyr Ser Thr Gly Asn
                20                       25                    30

Ala Gly Arg Arg Gly Asp Leu Gly Ser Leu Ala Arg Val Ala Ala Gln
                35                       40                    45

Cys Leu Pro Ala Ser Phe Asn Phe Gly Ala Ile Arg
                50                       55                    60
```

<210> SEQ ID NO 32
<211> LENGTH: 58
<212> TYPE: PRT
<213> ORGANISM: Artificial Sequence
<220> FEATURE:
<223> OTHER INFORMATION: Peptide containing artificial T helper epitope
      from measles virus and B cell epitope from foot-and-mouth disease
      virus (FMDV)
<220> FEATURE:

```
<221> NAME/KEY: MISC_FEATURE
<222> LOCATION: (1)..(19)
<223> OTHER INFORMATION: Artificial combinatorial modified T helper
      peptide sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: Linked spacer, K (20) is epsilon K.
<220> FEATURE:
<221> NAME/KEY: MISC_FEATURE
<222> LOCATION: (21)..(58)
<223> OTHER INFORMATION: UBI FMDV VP1 C3 Indaial/Brazil/84Y, with VP1
      both 134 and 158 AA positions substituted by Cys and cyclized.

<400> SEQUENCE: 32

Ile Ser Ile Xaa Glu Ile Xaa Xaa Val Ile Val Xaa Xaa Ile Glu Thr
1               5                   10                  15

Ile Leu Phe Lys Thr Tyr Thr Gly Thr Cys Ala Tyr Thr Ala Ser Ala
            20                  25                  30

Arg Arg Gly Asp Leu Ala His Leu Ala Ala His Ala Arg Cys Leu
        35                  40                  45

Pro Thr Ser Phe Asn Phe Gly Ala Val Lys
    50                  55

<210> SEQ ID NO 33
<211> LENGTH: 60
<212> TYPE: PRT
<213> ORGANISM: Artificial Sequence
<220> FEATURE:
<223> OTHER INFORMATION: Peptide containing artificial T helper epitope
      from measles virus and B cell epitope from foot-and-mouth disease
      virus (FMDV)
<220> FEATURE:
<221> NAME/KEY: MISC_FEATURE
<222> LOCATION: (1)..(19)
<223> OTHER INFORMATION: Artificial combinatorial modified T helper
      peptide sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
```

```
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: Linked spacer, K (20) is epsilon K.
<220> FEATURE:
<221> NAME/KEY: MISC_FEATURE
<222> LOCATION: (21)..(60)
<223> OTHER INFORMATION: UBI FMDV VP1 A Argentina 2001, with VP1 both
      134 and 158 AA positions substituted by Cys and cyclized.

<400> SEQUENCE: 33

Ile Ser Ile Xaa Glu Ile Xaa Xaa Val Ile Val Xaa Xaa Ile Glu Thr
1               5                   10                  15

Ile Leu Phe Lys Val Tyr Asn Gly Thr Ser Lys Tyr Thr Val Ser Gly
            20                  25                  30

Ser Ser Arg Arg Gly Asp Leu Gly Ser Leu Ala Ala Arg Val Val Lys
        35                  40                  45

Ala Leu Pro Ala Ser Phe Asn Tyr Gly Ala Ile Lys
    50                  55                  60

<210> SEQ ID NO 34
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (S221-M235)
      [FMDV VP4 20-35].

<400> SEQUENCE: 34

Ser Ile Ile Asn Asn Tyr Tyr Met Gln Gln Tyr Gln Asn Ser Met
1               5                   10                  15

<210> SEQ ID NO 35
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (I223-T237)
      [FMDV VP4 22-36].

<400> SEQUENCE: 35

Ile Asn Asn Tyr Tyr Met Gln Gln Tyr Gln Asn Ser Met Asp Thr
1               5                   10                  15

<210> SEQ ID NO 36
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (P369-K374)
      [FMDV VP2 74-88].

<400> SEQUENCE: 36

Pro Phe Gly Arg Cys Tyr Leu Leu Glu Leu Pro Thr Asp His Lys
1               5                   10                  15

<210> SEQ ID NO 37
<211> LENGTH: 15
<212> TYPE: PRT
```

```
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (D582-A596)
      [FMDV VP3 78-92].

<400> SEQUENCE: 37

Asp Leu Ser Leu Ala Ala Lys His Met Ser Asn Thr Phe Leu Ala
1               5                   10                  15

<210> SEQ ID NO 38
<211> LENGTH: 20
<212> TYPE: PRT
<213> ORGANISM: Foot-and-mouth disease virus
<220> FEATURE:
<221> NAME/KEY: MISC_FEATURE
<222> LOCATION: (1)..(20)
<223> OTHER INFORMATION: AJ539137 FMDV O, strain TAW/2/99 (E745-V7964)
      [FMDV VP1 21-40].

<400> SEQUENCE: 38

Glu Thr Gln Val Gln Arg Arg Gln His Thr Asp Val Ser Phe Ile Leu
1               5                   10                  15

Asp Arg Phe Val
            20

<210> SEQ ID NO 39
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (I759-N773)
      [VP1 35-49].

<400> SEQUENCE: 39

Ile Leu Asp Arg Phe Val Lys Val Thr Pro Lys Asp Gln Ile Asn
1               5                   10                  15

<210> SEQ ID NO 40
<211> LENGTH: 19
<212> TYPE: PRT
<213> ORGANISM: Foot-and-mouth disease virus
<220> FEATURE:
<221> NAME/KEY: MISC_FEATURE
<222> LOCATION: (1)..(19)
<223> OTHER INFORMATION: AJ539137 FMDV O, strain TAW/2/99 (I759-L777)
      [FMDV VP1 35-53].

<400> SEQUENCE: 40

Ile Leu Asp Arg Phe Val Lys Val Thr Pro Lys Asp Gln Ile Asn Val
1               5                   10                  15

Leu Asp Leu

<210> SEQ ID NO 41
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (V786-L800)
      [FMDV VP1 62-76].

<400> SEQUENCE: 41

Val Gly Ala Leu Leu Arg Thr Ala Thr Tyr Tyr Phe Ala Asp Leu
```

<210> SEQ ID NO 42
<211> LENGTH: 21
<212> TYPE: PRT
<213> ORGANISM: Foot-and-mouth disease virus
<220> FEATURE:
<221> NAME/KEY: MISC_FEATURE
<222> LOCATION: (1)..(21)
<223> OTHER INFORMATION: AJ539137 FMDV O, strain TAW/2/99 (G808-P828)
      [FMDV VP1 84-104].

<400> SEQUENCE: 42

Gly Asn Leu Thr Trp Val Pro Asn Gly Ala Pro Glu Thr Ala Leu Asp
1               5                   10                  15

Asn Thr Thr Asn Pro
            20

<210> SEQ ID NO 43
<211> LENGTH: 22
<212> TYPE: PRT
<213> ORGANISM: Foot-and-mouth disease virus
<220> FEATURE:
<221> NAME/KEY: MISC_FEATURE
<222> LOCATION: (1)..(22)
<223> OTHER INFORMATION: AJ539137 FMDV O, strain TAW/2/99 (P835-G856)
      [FMDV VP1 111-132].

<400> SEQUENCE: 43

Pro Leu Thr Arg Leu Ala Leu Pro Tyr Thr Ala Pro His Arg Val Leu
1               5                   10                  15

Ala Thr Val Tyr Asn Gly
            20

<210> SEQ ID NO 44
<211> LENGTH: 17
<212> TYPE: PRT
<213> ORGANISM: Foot-and-mouth disease virus
<220> FEATURE:
<221> NAME/KEY: MISC_FEATURE
<222> LOCATION: (1)..(17)
<223> OTHER INFORMATION: AJ539137 FMDV O, strain TAW/2/99 (T895-C911)
      [FMDV VP1 167-183].

<400> SEQUENCE: 44

Thr Arg Val Thr Glu Leu Leu Tyr Arg Met Lys Arg Ala Glu Thr Tyr
1               5                   10                  15

Cys

<210> SEQ ID NO 45
<211> LENGTH: 22
<212> TYPE: PRT
<213> ORGANISM: Foot-and-mouth disease virus
<220> FEATURE:
<221> NAME/KEY: MISC_FEATURE
<222> LOCATION: (1)..(22)
<223> OTHER INFORMATION: AJ539137 FMDV O, strain TAW/2/99 (P912-V933)
      [FMDV VP1 188-209].

<400> SEQUENCE: 45

Pro Arg Pro Leu Leu Ala Ile His Pro Ser Lys Ala Arg His Lys Gln
1               5                   10                  15

Lys Ile Val Ala Pro Val
            20

<210> SEQ ID NO 46

```
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (R924-L937)
      [FMDV VP1 200-213].

<400> SEQUENCE: 46

Arg His Lys Gln Lys Ile Val Ala Pro Val Lys Gln Leu Leu
1               5                   10

<210> SEQ ID NO 47
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (P954-V968)
      [FMDV 2B 1-15].

<400> SEQUENCE: 47

Pro Phe Phe Phe Ser Asp Val Arg Ser Asn Phe Ser Lys Leu Val
1               5                   10                  15

<210> SEQ ID NO 48
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (F1093-K1106)
      [FMDV 2B 140-153].

<400> SEQUENCE: 48

Phe Phe Arg Ser Thr Pro Glu Asp Leu Glu Arg Ala Glu Lys
1               5                   10

<210> SEQ ID NO 49
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (L1108-N1122)
      [FMDV 2C 1-15].

<400> SEQUENCE: 49

Leu Lys Ala Arg Asp Ile Asn Asp Ile Phe Ala Ile Leu Lys Asn
1               5                   10                  15

<210> SEQ ID NO 50
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (S1143-I1157)
      [FMDV 2C 36-50].

<400> SEQUENCE: 50

Ser Glu Glu Lys Phe Val Thr Met Thr Asp Leu Val Pro Gly Ile
1               5                   10                  15
```

```
<210> SEQ ID NO 51
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (V1148-R1162)
      [FMDV 2C 41-55].

<400> SEQUENCE: 51

Val Thr Met Thr Asp Leu Val Pro Gly Ile Leu Glu Lys Gln Arg
1               5                   10                  15

<210> SEQ ID NO 52
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (A1446-K1450)
      [FMDV 3A 21-35].

<400> SEQUENCE: 52

Ala Ala Ile Glu Phe Phe Glu Gly Met Val His Asp Ser Ile Lys
1               5                   10                  15

<210> SEQ ID NO 53
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (N1516-K1529)
      [FMDV 3A 91-104].

<400> SEQUENCE: 53

Asn Glu Tyr Ile Glu Lys Ala Ser Ile Thr Thr Asp Asp Lys
1               5                   10

<210> SEQ ID NO 54
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (T1551-L1564)
      [FMDV 3A 101-114].

<400> SEQUENCE: 54

Thr Asp Asp Lys Thr Leu Asp Glu Ala Glu Lys Asn Pro Leu
1               5                   10

<210> SEQ ID NO 55
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (E1551-N1564)
      [FMDV 3A 126-139].

<400> SEQUENCE: 55

Glu Lys Thr Leu Pro Gly His Lys Ala Ser Asp Asp Val Asn
1               5                   10
```

<210> SEQ ID NO 56
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (G1579-K1592)
      [FMDV 3B1 1-14].

<400> SEQUENCE: 56

Gly Pro Tyr Ala Gly Pro Met Glu Arg Gln Lys Pro Leu Lys
1               5                   10

<210> SEQ ID NO 57
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (P1584-L1597)
      [FMDV 3B1 6-19].

<400> SEQUENCE: 57

Pro Leu Glu Arg Gln Lys Pro Leu Lys Val Arg Ala Lys Leu
1               5                   10

<210> SEQ ID NO 58
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (P1607-A1620)
      [FMDV 3B2 6-19].

<400> SEQUENCE: 58

Pro Met Glu Arg Gln Lys Pro Leu Lys Val Lys Val Lys Ala
1               5                   10

<210> SEQ ID NO 59
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (P1631-N1644)
      [FMDV 3B3 6-19].

<400> SEQUENCE: 59

Pro Val Lys Lys Pro Val Ala Leu Lys Val Lys Ala Lys Asn
1               5                   10

<210> SEQ ID NO 60
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (M1878-F1892)
      [FMDV 3D 16-30].

<400> SEQUENCE: 60

Met Arg Lys Thr Lys Leu Ala Pro Thr Val Ala His Gly Val Phe
1               5                   10                  15

<210> SEQ ID NO 61
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (I1918-D1932)
      [FMDV 3D 56-70].

<400> SEQUENCE: 61

Ile Phe Ser Lys His Lys Gly Asn Thr Lys Met Ser Glu Glu Asp
1               5                   10                  15

<210> SEQ ID NO 62
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (A2108-V2122)
      [FMDV 3D 246-260].

<400> SEQUENCE: 62

Ala Asn His Cys Ser Asp Ala Met Asn Ile Met Phe Glu Glu Val
1               5                   10                  15

<210> SEQ ID NO 63
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (L2248-K2262)
      [FMDV 3D 386-400].

<400> SEQUENCE: 63

Leu Lys Arg His Phe His Met Asp Tyr Gly Thr Gly Phe Tyr Lys
1               5                   10                  15

<210> SEQ ID NO 64
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (I1918-D1932)
      as homologue of [FMDV 3D 56-70].

<400> SEQUENCE: 64

Leu Phe Ser Arg His Arg Gly Asn Thr Lys Met Ser Glu Glu Asp
1               5                   10                  15

<210> SEQ ID NO 65
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (A2108-V2122)
      as homologue of [FMDV 3D 246-260].

<400> SEQUENCE: 65

Ala Asn His Cys Ser Asp Ala Met Asn Leu Met Phe Glu Glu Val

<210> SEQ ID NO 66
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (L2248-K2262)
      as homologue of [FMDV 3D386-400].

<400> SEQUENCE: 66

Ile Arg Lys His Phe His Met Asp Tyr Gly Thr Gly Phe Tyr Arg
1               5                   10                  15

<210> SEQ ID NO 67
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (F1093-K1106)
      as homologue of [FMDV 2B 140-153].

<400> SEQUENCE: 67

Phe Phe Lys Ser Thr Pro Glu Asp Val Glu Lys Ala Glu Arg
1               5                   10

<210> SEQ ID NO 68
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (F1093-K1106)
      as homologue of [FMDV 2B 140-153].

<400> SEQUENCE: 68

Phe Phe Arg Ser Thr Pro Glu Glu Ile Glu Arg Ala Glu Lys
1               5                   10

<210> SEQ ID NO 69
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (N1516-K1529)
      as homologue of [FMDV 3A 91-104].

<400> SEQUENCE: 69

Asn Asp Tyr Leu Glu Arg Ala Asn Leu Thr Thr Asp Pro Arg
1               5                   10

<210> SEQ ID NO 70
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (N1516-K1529)
      as homologue of [FMDV 3A 91-104].

<400> SEQUENCE: 70

Asn Glu Tyr Ile Glu Lys Val Ser Ile Thr Thr Asp Asp Lys
1               5                   10

<210> SEQ ID NO 71
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (M1878-F1892)
      as homologue of [FMDV 3D 16-30].

<400> SEQUENCE: 71

Met Lys Arg Thr Arg Ile Ala Pro Thr Leu Ala His Gly Ile Phe
1               5                   10                  15

<210> SEQ ID NO 72
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (M1878-F1892)
      as homologue of [FMDV 3D 16-30].

<400> SEQUENCE: 72

Met Arg Lys Thr Lys Val Ala Pro Thr Ile Ala His Gly Leu Phe
1               5                   10                  15

<210> SEQ ID NO 73
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (S221-M235) as
      homologue of [FMDV VP4 20-34].

<400> SEQUENCE: 73

Ser Leu Leu Asn Asn Tyr Tyr Met Gln Gln Tyr Gln Asn Ser Met
1               5                   10                  15

<210> SEQ ID NO 74
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (S221-M235) as
      homologue of [FMDV VP4 20-34].

<400> SEQUENCE: 74

Ser Val Val Asn Asn Tyr Tyr Met Gln Gln Tyr Gln Asn Ser Met
1               5                   10                  15

<210> SEQ ID NO 75
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (P360-K374) as
      homologue of [FMDV VP2 74-88].

<400> SEQUENCE: 75

Pro Phe Gly Lys Cys Tyr Ile Ile Glu Ile Pro Thr Asp His Arg
1               5                   10                  15

<210> SEQ ID NO 76
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (P360-K374) as
      homologue of [FMDV VP2 74-88].

<400> SEQUENCE: 76

Pro Phe Gly Arg Cys Tyr Val Val Glu Val Pro Thr Asp His Lys
1               5                   10                  15

<210> SEQ ID NO 77
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (D582-A596) as
      homologue of [FMDV VP3 78-92].

<400> SEQUENCE: 77

Asp Val Ser Ile Ala Ala Gly His Met Ser Asn Thr Tyr Leu Ser
1               5                   10                  15

<210> SEQ ID NO 78
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (D582-A596) as
      homologue of [FMDV VP3 78-92].

<400> SEQUENCE: 78

Asp Val Ser Val Ala Ala Lys His Met Ser Asn Thr Phe Leu Val
1               5                   10                  15

<210> SEQ ID NO 79
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (I1918-D1932)
      [FMDV 3D 56-70].
<220> FEATURE:
<221> NAME/KEY: MISC_FEATURE
<222> LOCATION: (1)..(1)
<223> OTHER INFORMATION: I or L
<220> FEATURE:
<221> NAME/KEY: MISC_FEATURE
<222> LOCATION: (4)..(4)
<223> OTHER INFORMATION: K or R
<220> FEATURE:
<221> NAME/KEY: MISC_FEATURE
<222> LOCATION: (6)..(6)
<223> OTHER INFORMATION: K or R
<220> FEATURE:
<221> NAME/KEY: MISC_FEATURE
<222> LOCATION: (10)..(10)
<223> OTHER INFORMATION: K or R

```
<400> SEQUENCE: 79

Xaa Phe Ser Xaa His Xaa Gly Asn Thr Xaa Met Ser Glu Glu Asp
1               5                   10                  15

<210> SEQ ID NO 80
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O strain TAW/2/99 (A2108-V2122)
      [FMDV 3D 246-260].
<220> FEATURE:
<221> NAME/KEY: MISC_FEATURE
<222> LOCATION: (10)..(10)
<223> OTHER INFORMATION: I or L

<400> SEQUENCE: 80

Ala Asn His Cys Ser Asp Ala Met Asn Xaa Met Phe Glu Glu Val
1               5                   10                  15

<210> SEQ ID NO 81
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (L2248-K2262)
      [FMDV 3D386-400].
<220> FEATURE:
<221> NAME/KEY: MISC_FEATURE
<222> LOCATION: (1)..(1)
<223> OTHER INFORMATION: L or I
<220> FEATURE:
<221> NAME/KEY: MISC_FEATURE
<222> LOCATION: (2)..(2)
<223> OTHER INFORMATION: K or R
<220> FEATURE:
<221> NAME/KEY: MISC_FEATURE
<222> LOCATION: (3)..(3)
<223> OTHER INFORMATION: R or K
<220> FEATURE:
<221> NAME/KEY: MISC_FEATURE
<222> LOCATION: (15)..(15)
<223> OTHER INFORMATION: K or R

<400> SEQUENCE: 81

Xaa Xaa Xaa His Phe His Met Asp Tyr Gly Thr Gly Phe Tyr Xaa
1               5                   10                  15

<210> SEQ ID NO 82
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (F1093-K1106)
      [FMDV 2B 140-153].
<220> FEATURE:
<221> NAME/KEY: MISC_FEATURE
<222> LOCATION: (3)..(3)
<223> OTHER INFORMATION: R or K
<220> FEATURE:
<221> NAME/KEY: MISC_FEATURE
<222> LOCATION: (8)..(8)
<223> OTHER INFORMATION: D or E
<220> FEATURE:
<221> NAME/KEY: MISC_FEATURE
<222> LOCATION: (9)..(9)
<223> OTHER INFORMATION: L or I or V
```

```
<220> FEATURE:
<221> NAME/KEY: MISC_FEATURE
<222> LOCATION: (11)..(11)
<223> OTHER INFORMATION: R or K
<220> FEATURE:
<221> NAME/KEY: MISC_FEATURE
<222> LOCATION: (14)..(14)
<223> OTHER INFORMATION: K or R

<400> SEQUENCE: 82

Phe Phe Xaa Ser Thr Pro Glu Xaa Xaa Glu Xaa Ala Glu Xaa
1               5                   10

<210> SEQ ID NO 83
<211> LENGTH: 14
<212> TYPE: PRT
<213> ORGANISM: Foot-and-mouth disease virus
<220> FEATURE:
<221> NAME/KEY: MISC_FEATURE
<222> LOCATION: (1)..(14)
<223> OTHER INFORMATION: AJ539137 FMDV O, strain TAW/2/99 (N1516-K1529)
      (FMDV 3A 91-104)
<220> FEATURE:
<221> NAME/KEY: MISC_FEATURE
<222> LOCATION: (2)..(2)
<223> OTHER INFORMATION: E or D
<220> FEATURE:
<221> NAME/KEY: MISC_FEATURE
<222> LOCATION: (4)..(4)
<223> OTHER INFORMATION: I or L
<220> FEATURE:
<221> NAME/KEY: MISC_FEATURE
<222> LOCATION: (6)..(6)
<223> OTHER INFORMATION: K or R
<220> FEATURE:
<221> NAME/KEY: MISC_FEATURE
<222> LOCATION: (8)..(8)
<223> OTHER INFORMATION: N or S
<220> FEATURE:
<221> NAME/KEY: MISC_FEATURE
<222> LOCATION: (9)..(9)
<223> OTHER INFORMATION: I or L
<220> FEATURE:
<221> NAME/KEY: MISC_FEATURE
<222> LOCATION: (13)..(13)
<223> OTHER INFORMATION: D or P
<220> FEATURE:
<221> NAME/KEY: MISC_FEATURE
<222> LOCATION: (14)..(14)
<223> OTHER INFORMATION: K or R

<400> SEQUENCE: 83

Asn Xaa Tyr Xaa Glu Xaa Ala Xaa Xaa Thr Thr Asp Xaa Xaa
1               5                   10

<210> SEQ ID NO 84
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (M1878-F1892)
      [FMDV 3D 16-30].
<220> FEATURE:
<221> NAME/KEY: MISC_FEATURE
<222> LOCATION: (2)..(2)
<223> OTHER INFORMATION: R or K
<220> FEATURE:
<221> NAME/KEY: MISC_FEATURE
<222> LOCATION: (3)..(3)
<223> OTHER INFORMATION: K or R
<220> FEATURE:
<221> NAME/KEY: MISC_FEATURE
<222> LOCATION: (5)..(5)
```

```
<223> OTHER INFORMATION: K or R
<220> FEATURE:
<221> NAME/KEY: MISC_FEATURE
<222> LOCATION: (6)..(6)
<223> OTHER INFORMATION: L or I or V
<220> FEATURE:
<221> NAME/KEY: MISC_FEATURE
<222> LOCATION: (10)..(10)
<223> OTHER INFORMATION: V or L or I
<220> FEATURE:
<221> NAME/KEY: MISC_FEATURE
<222> LOCATION: (14)..(14)
<223> OTHER INFORMATION: V or I or L

<400> SEQUENCE: 84

Met Xaa Xaa Thr Xaa Xaa Ala Pro Thr Val Ala His Gly Val Phe
1               5                   10                  15

<210> SEQ ID NO 85
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (S221-M235)
      [FMDV VP4 20-34].
<220> FEATURE:
<221> NAME/KEY: MISC_FEATURE
<222> LOCATION: (2)..(2)
<223> OTHER INFORMATION: I or L or V
<220> FEATURE:
<221> NAME/KEY: MISC_FEATURE
<222> LOCATION: (3)..(3)
<223> OTHER INFORMATION: I or L or V

<400> SEQUENCE: 85

Ser Xaa Xaa Asn Asn Tyr Tyr Met Gln Gln Tyr Gln Asn Ser Met
1               5                   10                  15

<210> SEQ ID NO 86
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (P360-K374)
      [FMDV VP2 74-88].
<220> FEATURE:
<221> NAME/KEY: MISC_FEATURE
<222> LOCATION: (4)..(4)
<223> OTHER INFORMATION: R or K
<220> FEATURE:
<221> NAME/KEY: MISC_FEATURE
<222> LOCATION: (7)..(7)
<223> OTHER INFORMATION: L or I or V
<220> FEATURE:
<221> NAME/KEY: MISC_FEATURE
<222> LOCATION: (8)..(8)
<223> OTHER INFORMATION: L or I or V
<220> FEATURE:
<221> NAME/KEY: MISC_FEATURE
<222> LOCATION: (10)..(10)
<223> OTHER INFORMATION: L or I or V
<220> FEATURE:
<221> NAME/KEY: MISC_FEATURE
<222> LOCATION: (15)..(15)
<223> OTHER INFORMATION: K or R

<400> SEQUENCE: 86

Pro Phe Gly Xaa Cys Tyr Xaa Xaa Glu Xaa Pro Thr Asp His Xaa
1               5                   10                  15
```

<210> SEQ ID NO 87
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (D582-A596)
      [FMDV VP3 78-92].
<220> FEATURE:
<221> NAME/KEY: MISC_FEATURE
<222> LOCATION: (2)..(2)
<223> OTHER INFORMATION: L or I or V
<220> FEATURE:
<221> NAME/KEY: MISC_FEATURE
<222> LOCATION: (4)..(4)
<223> OTHER INFORMATION: L or I or V
<220> FEATURE:
<221> NAME/KEY: MISC_FEATURE
<222> LOCATION: (7)..(7)
<223> OTHER INFORMATION: K or G
<220> FEATURE:
<221> NAME/KEY: MISC_FEATURE
<222> LOCATION: (13)..(13)
<223> OTHER INFORMATION: F or Y
<220> FEATURE:
<221> NAME/KEY: MISC_FEATURE
<222> LOCATION: (15)..(15)
<223> OTHER INFORMATION: A or S or V

<400> SEQUENCE: 87

Asp Xaa Ser Leu Ala Ala Xaa His Met Ser Asn Thr Xaa Leu Xaa
1               5                   10                  15

<210> SEQ ID NO 88
<211> LENGTH: 65
<212> TYPE: PRT
<213> ORGANISM: Artificial Sequence
<220> FEATURE:
<223> OTHER INFORMATION: Peptide containing artificial T helper epitope
      from measles virus and B cell epitopes from foot-and-mouth disease
      virus (FMDV)
<220> FEATURE:
<221> NAME/KEY: MISC_FEATURE
<222> LOCATION: (1)..(19)
<223> OTHER INFORMATION: Combinatorial modified T helper sequence.
<220> FEATURE:
<221> NAME/KEY: MISC_FEATURE
<222> LOCATION: (1)..(65)
<223> OTHER INFORMATION: UBITh(R) 3-K- [FMDV 2B 140-153]-K- [FMDV 3A
      91-104]-K-[FMDV 3D 16-30] from AJ539137 FMDV O, strain TAW/2/99.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: K is linked spacer.
<220> FEATURE:

```
<221> NAME/KEY: MISC_FEATURE
<222> LOCATION: (35)..(35)
<223> OTHER INFORMATION: K is linked spacer.
<220> FEATURE:
<221> NAME/KEY: MISC_FEATURE
<222> LOCATION: (50)..(50)
<223> OTHER INFORMATION: K is linked spacer.

<400> SEQUENCE: 88

Ile Ser Ile Xaa Glu Ile Xaa Xaa Val Ile Val Xaa Xaa Ile Glu Thr
1               5                   10                  15

Ile Leu Phe Lys Phe Phe Arg Ser Thr Pro Glu Asp Leu Glu Arg Ala
            20                  25                  30

Glu Lys Lys Asn Glu Tyr Ile Glu Lys Ala Ser Ile Thr Thr Asp Asp
        35                  40                  45

Lys Lys Met Arg Lys Thr Lys Leu Ala Pro Thr Val Ala His Gly Val
    50                  55                  60

Phe
65

<210> SEQ ID NO 89
<211> LENGTH: 67
<212> TYPE: PRT
<213> ORGANISM: Artificial Sequence
<220> FEATURE:
<223> OTHER INFORMATION: Peptide containing artificial T helper epitope
      from measles virus and B cell epitopes from foot-and-mouth disease
      virus (FMDV)
<220> FEATURE:
<221> NAME/KEY: MISC_FEATURE
<222> LOCATION: (1)..(9)
<223> OTHER INFORMATION: Combinatorial modified T helper sequence.
<220> FEATURE:
<221> NAME/KEY: MISC_FEATURE
<222> LOCATION: (1)..(67)
<223> OTHER INFORMATION: UBITh(R) 3-K- [FMDV VP4 20-34]-K-[FMDV VP2
      74-88]-K-[FMDV VP378-92] from AJ539137 FMDV O, strain TAW/2/99.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: k is linked spacer.
<220> FEATURE:
<221> NAME/KEY: MISC_FEATURE
<222> LOCATION: (36)..(36)
<223> OTHER INFORMATION: k is linked spacer.
<220> FEATURE:
<221> NAME/KEY: MISC_FEATURE
<222> LOCATION: (52)..(52)
<223> OTHER INFORMATION: K is linked spacer.

<400> SEQUENCE: 89

Ile Ser Ile Xaa Glu Ile Xaa Xaa Val Ile Val Xaa Xaa Ile Glu Thr
```

```
              1               5                  10                 15
            Ile Leu Phe Lys Ser Ile Ile Asn Asn Tyr Tyr Met Gln Gln Tyr Gln
                             20                 25                 30
            Asn Ser Met Lys Pro Phe Gly Arg Cys Tyr Leu Leu Glu Leu Pro Thr
                        35                 40                 45
            Asp His Lys Lys Asp Leu Ser Leu Ala Ala Lys His Met Ser Asn Thr
                   50                 55                 60
            Phe Leu Ala
            65

<210> SEQ ID NO 90
<211> LENGTH: 67
<212> TYPE: PRT
<213> ORGANISM: Artificial Sequence
<220> FEATURE:
<223> OTHER INFORMATION: Peptide containing artificial T helper epitope
      from measles virus and B cell epitopes from foot-and-mouth disease
      virus (FMDV)
<220> FEATURE:
<221> NAME/KEY: MISC_FEATURE
<222> LOCATION: (1)..(19)
<223> OTHER INFORMATION: Combinatorial modified T helper sequence.
<220> FEATURE:
<221> NAME/KEY: MISC_FEATURE
<222> LOCATION: (1)..(67)
<223> OTHER INFORMATION: UBITh(R) 3-K-[FMDV 3D 56-70]-K-[FMDV 3D 248-
      260]-K-[FMDV 3D 386-400] AJ539137 FMDV O, strain TAW/2/99.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: K is linked spacer sequence.
<220> FEATURE:
<221> NAME/KEY: MISC_FEATURE
<222> LOCATION: (21)..(21)
<223> OTHER INFORMATION: I or L
<220> FEATURE:
<221> NAME/KEY: MISC_FEATURE
<222> LOCATION: (24)..(24)
<223> OTHER INFORMATION: K or R
<220> FEATURE:
<221> NAME/KEY: MISC_FEATURE
<222> LOCATION: (26)..(26)
<223> OTHER INFORMATION: K or R
<220> FEATURE:
<221> NAME/KEY: MISC_FEATURE
<222> LOCATION: (30)..(30)
<223> OTHER INFORMATION: K or R
<220> FEATURE:
<221> NAME/KEY: MISC_FEATURE
<222> LOCATION: (36)..(36)
<223> OTHER INFORMATION: K is linked spacer.
<220> FEATURE:
<221> NAME/KEY: MISC_FEATURE
<222> LOCATION: (46)..(46)
```

```
<223> OTHER INFORMATION: I or L
<220> FEATURE:
<221> NAME/KEY: MISC_FEATURE
<222> LOCATION: (52)..(52)
<223> OTHER INFORMATION: K is linked spacer.
<220> FEATURE:
<221> NAME/KEY: MISC_FEATURE
<222> LOCATION: (53)..(53)
<223> OTHER INFORMATION: L or I
<220> FEATURE:
<221> NAME/KEY: MISC_FEATURE
<222> LOCATION: (54)..(54)
<223> OTHER INFORMATION: K or R
<220> FEATURE:
<221> NAME/KEY: MISC_FEATURE
<222> LOCATION: (55)..(55)
<223> OTHER INFORMATION: R or K
<220> FEATURE:
<221> NAME/KEY: MISC_FEATURE
<222> LOCATION: (67)..(67)
<223> OTHER INFORMATION: K or R

<400> SEQUENCE: 90

Ile Ser Ile Xaa Glu Ile Xaa Xaa Val Ile Val Xaa Xaa Ile Glu Thr
1               5                   10                  15

Ile Leu Phe Lys Xaa Phe Ser Xaa His Xaa Gly Asn Thr Xaa Met Ser
            20                  25                  30

Glu Glu Asp Lys Ala Asn His Cys Ser Asp Ala Met Asn Xaa Met Phe
        35                  40                  45

Glu Glu Val Lys Xaa Xaa Xaa His Phe His Met Asp Tyr Gly Thr Gly
    50                  55                  60

Phe Tyr Xaa
65

<210> SEQ ID NO 91
<211> LENGTH: 65
<212> TYPE: PRT
<213> ORGANISM: Artificial Sequence
<220> FEATURE:
<223> OTHER INFORMATION: Peptide containing artificial T helper epitope
      from measles virus and B cell epitopes from foot-and-mouth disease
      virus (FMDV)
<220> FEATURE:
<221> NAME/KEY: MISC_FEATURE
<222> LOCATION: (1)..(19)
<223> OTHER INFORMATION: Combinatorial modified T helper sequence.
<220> FEATURE:
<221> NAME/KEY: MISC_FEATURE
<222> LOCATION: (1)..(65)
<223> OTHER INFORMATION: UBITh(R) 3-K- [FMDV 2B 140-153]-K-[FMDV 3A
      91-104]-K-[FMDV 3D 16-30] from  AJ539137 FMDV O, strain TAW/2/99.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
```

```
-continued

<222> LOCATION: (20)..(20)
<223> OTHER INFORMATION: K is linked spacer.
<220> FEATURE:
<221> NAME/KEY: MISC_FEATURE
<222> LOCATION: (23)..(23)
<223> OTHER INFORMATION: R or K
<220> FEATURE:
<221> NAME/KEY: MISC_FEATURE
<222> LOCATION: (28)..(28)
<223> OTHER INFORMATION: D or E
<220> FEATURE:
<221> NAME/KEY: MISC_FEATURE
<222> LOCATION: (29)..(29)
<223> OTHER INFORMATION: L or I or V
<220> FEATURE:
<221> NAME/KEY: MISC_FEATURE
<222> LOCATION: (31)..(31)
<223> OTHER INFORMATION: R or K
<220> FEATURE:
<221> NAME/KEY: MISC_FEATURE
<222> LOCATION: (34)..(34)
<223> OTHER INFORMATION: K or R
<220> FEATURE:
<221> NAME/KEY: MISC_FEATURE
<222> LOCATION: (35)..(35)
<223> OTHER INFORMATION: K is linked spacer.
<220> FEATURE:
<221> NAME/KEY: MISC_FEATURE
<222> LOCATION: (37)..(37)
<223> OTHER INFORMATION: E or D
<220> FEATURE:
<221> NAME/KEY: MISC_FEATURE
<222> LOCATION: (39)..(39)
<223> OTHER INFORMATION: I or L
<220> FEATURE:
<221> NAME/KEY: MISC_FEATURE
<222> LOCATION: (41)..(41)
<223> OTHER INFORMATION: K or R
<220> FEATURE:
<221> NAME/KEY: MISC_FEATURE
<222> LOCATION: (43)..(43)
<223> OTHER INFORMATION: N or S
<220> FEATURE:
<221> NAME/KEY: MISC_FEATURE
<222> LOCATION: (44)..(44)
<223> OTHER INFORMATION: I or L
<220> FEATURE:
<221> NAME/KEY: MISC_FEATURE
<222> LOCATION: (48)..(48)
<223> OTHER INFORMATION: D or P
<220> FEATURE:
<221> NAME/KEY: MISC_FEATURE
<222> LOCATION: (49)..(49)
<223> OTHER INFORMATION: K or R
<220> FEATURE:
<221> NAME/KEY: MISC_FEATURE
<222> LOCATION: (50)..(50)
<223> OTHER INFORMATION: K is linked spacer.
<220> FEATURE:
<221> NAME/KEY: MISC_FEATURE
<222> LOCATION: (52)..(52)
<223> OTHER INFORMATION: R or K
<220> FEATURE:
<221> NAME/KEY: MISC_FEATURE
<222> LOCATION: (53)..(53)
<223> OTHER INFORMATION: K or R
<220> FEATURE:
<221> NAME/KEY: MISC_FEATURE
<222> LOCATION: (55)..(55)
<223> OTHER INFORMATION: K or R
<220> FEATURE:
<221> NAME/KEY: MISC_FEATURE
<222> LOCATION: (56)..(56)
<223> OTHER INFORMATION: L or I or V
<220> FEATURE:
<221> NAME/KEY: MISC_FEATURE
<222> LOCATION: (60)..(60)
<223> OTHER INFORMATION: V or L or I
<220> FEATURE:
```

```
<221> NAME/KEY: MISC_FEATURE
<222> LOCATION: (64)..(64)
<223> OTHER INFORMATION: V or I or L

<400> SEQUENCE: 91

Ile Ser Ile Xaa Glu Ile Xaa Xaa Val Ile Val Xaa Xaa Ile Glu Thr
1               5                   10                  15

Ile Leu Phe Lys Phe Phe Xaa Ser Thr Pro Glu Xaa Xaa Glu Xaa Ala
            20                  25                  30

Glu Xaa Lys Asn Xaa Tyr Xaa Glu Xaa Ala Xaa Xaa Thr Thr Asp Asp
        35                  40                  45

Xaa Lys Met Xaa Lys Thr Xaa Xaa Ala Pro Thr Val Ala His Gly Val
    50                  55                  60

Phe
65

<210> SEQ ID NO 92
<211> LENGTH: 67
<212> TYPE: PRT
<213> ORGANISM: Artificial Sequence
<220> FEATURE:
<223> OTHER INFORMATION: Peptide containing artificial T helper epitope
      from measles virus and B cell epitopes from foot-and-mouth disease
      virus (FMDV)
<220> FEATURE:
<221> NAME/KEY: MISC_FEATURE
<222> LOCATION: (1)..(67)
<223> OTHER INFORMATION: UBITh(R) 3-K- [FMDV VP420-34]-K-[FMDV VP2
      74-88]-K- [FMDV VP3 78-92] from AJ539137 FMDV O, strain TAW/2/99.
<220> FEATURE:
<221> NAME/KEY: MISC_FEATURE
<222> LOCATION: (1)..(19)
<223> OTHER INFORMATION: Combinatorial T helper sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: K is linked spacer.
<220> FEATURE:
<221> NAME/KEY: MISC_FEATURE
<222> LOCATION: (22)..(22)
<223> OTHER INFORMATION: I or L or V
<220> FEATURE:
<221> NAME/KEY: MISC_FEATURE
<222> LOCATION: (23)..(23)
<223> OTHER INFORMATION: I or L or V
<220> FEATURE:
<221> NAME/KEY: MISC_FEATURE
<222> LOCATION: (36)..(36)
<223> OTHER INFORMATION: K is linked spacer.
<220> FEATURE:
<221> NAME/KEY: MISC_FEATURE
<222> LOCATION: (37)..(37)
<223> OTHER INFORMATION: P or A
```

-continued

```
<220> FEATURE:
<221> NAME/KEY: MISC_FEATURE
<222> LOCATION: (40)..(40)
<223> OTHER INFORMATION: H or R or K
<220> FEATURE:
<221> NAME/KEY: MISC_FEATURE
<222> LOCATION: (41)..(41)
<223> OTHER INFORMATION: L or C or S
<220> FEATURE:
<221> NAME/KEY: MISC_FEATURE
<222> LOCATION: (42)..(42)
<223> OTHER INFORMATION: E or H or Y
<220> FEATURE:
<221> NAME/KEY: MISC_FEATURE
<222> LOCATION: (43)..(43)
<223> OTHER INFORMATION: L or I or V
<220> FEATURE:
<221> NAME/KEY: MISC_FEATURE
<222> LOCATION: (44)..(44)
<223> OTHER INFORMATION: L or I or V
<220> FEATURE:
<221> NAME/KEY: MISC_FEATURE
<222> LOCATION: (46)..(46)
<223> OTHER INFORMATION: L or I or V
<220> FEATURE:
<221> NAME/KEY: MISC_FEATURE
<222> LOCATION: (48)..(48)
<223> OTHER INFORMATION: T or A or S
<220> FEATURE:
<221> NAME/KEY: MISC_FEATURE
<222> LOCATION: (49)..(49)
<223> OTHER INFORMATION: D or E
<220> FEATURE:
<221> NAME/KEY: MISC_FEATURE
<222> LOCATION: (51)..(51)
<223> OTHER INFORMATION: H or K or R
<220> FEATURE:
<221> NAME/KEY: MISC_FEATURE
<222> LOCATION: (52)..(52)
<223> OTHER INFORMATION: K is linked spacer.
<220> FEATURE:
<221> NAME/KEY: MISC_FEATURE
<222> LOCATION: (54)..(54)
<223> OTHER INFORMATION: L or V
<220> FEATURE:
<221> NAME/KEY: MISC_FEATURE
<222> LOCATION: (56)..(56)
<223> OTHER INFORMATION: L or I or V
<220> FEATURE:
<221> NAME/KEY: MISC_FEATURE
<222> LOCATION: (59)..(59)
<223> OTHER INFORMATION: K or G
<220> FEATURE:
<221> NAME/KEY: MISC_FEATURE
<222> LOCATION: (65)..(65)
<223> OTHER INFORMATION: F or Y
<220> FEATURE:
<221> NAME/KEY: MISC_FEATURE
<222> LOCATION: (67)..(67)
<223> OTHER INFORMATION: A or S or V

<400> SEQUENCE: 92

Ile Ser Ile Xaa Glu Ile Xaa Xaa Val Ile Val Xaa Xaa Ile Glu Thr
1               5                   10                  15

Ile Leu Phe Lys Ser Xaa Xaa Asn Asn Tyr Tyr Met Gln Gln Tyr Gln
            20                  25                  30

Asn Ser Met Lys Xaa Phe Gly Xaa Xaa Xaa Xaa Glu Xaa Pro Xaa
        35                  40                  45

Xaa His Xaa Lys Asp Xaa Ser Ile Ala Ala Xaa His Met Ser Asn Thr
    50                  55                  60

Xaa Leu Xaa
65
```

```
<210> SEQ ID NO 93
<211> LENGTH: 67
<212> TYPE: PRT
<213> ORGANISM: Artificial Sequence
<220> FEATURE:
<223> OTHER INFORMATION: Peptide containing artificial T helper epitope
      from measles virus and B cell epitopes from foot-and-mouth disease
      virus (FMDV)
<220> FEATURE:
<221> NAME/KEY: MISC_FEATURE
<222> LOCATION: (1)..(19)
<223> OTHER INFORMATION: Combinatorial T helper sequence.
<220> FEATURE:
<221> NAME/KEY: MISC_FEATURE
<222> LOCATION: (1)..(67)
<223> OTHER INFORMATION: UBITh(R) 3-K- FMDV Th library from polyprotein
      type O, A, C and Asia-1 and type O-1 (ABR19839) sequence based
      construct [S221-M235]-K-[P360-K374]-K-[D582-A596].
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: K is linked spacer.
<220> FEATURE:
<221> NAME/KEY: MISC_FEATURE
<222> LOCATION: (22)..(22)
<223> OTHER INFORMATION: I or L or V
<220> FEATURE:
<221> NAME/KEY: MISC_FEATURE
<222> LOCATION: (23)..(23)
<223> OTHER INFORMATION: I or L or V
<220> FEATURE:
<221> NAME/KEY: MISC_FEATURE
<222> LOCATION: (36)..(36)
<223> OTHER INFORMATION: K is linked spacer.
<220> FEATURE:
<221> NAME/KEY: MISC_FEATURE
<222> LOCATION: (37)..(37)
<223> OTHER INFORMATION: P or N or S or A
<220> FEATURE:
<221> NAME/KEY: MISC_FEATURE
<222> LOCATION: (40)..(40)
<223> OTHER INFORMATION: R or H or K
<220> FEATURE:
<221> NAME/KEY: MISC_FEATURE
<222> LOCATION: (41)..(41)
<223> OTHER INFORMATION: C or M or I or S
<220> FEATURE:
<221> NAME/KEY: MISC_FEATURE
<222> LOCATION: (42)..(42)
<223> OTHER INFORMATION: Y or H or E
<220> FEATURE:
<221> NAME/KEY: MISC_FEATURE
<222> LOCATION: (43)..(43)
<223> OTHER INFORMATION: L or I or V
<220> FEATURE:
<221> NAME/KEY: MISC_FEATURE
<222> LOCATION: (44)..(44)
<223> OTHER INFORMATION: L or I or V
<220> FEATURE:
```

```
<221> NAME/KEY: MISC_FEATURE
<222> LOCATION: (46)..(46)
<223> OTHER INFORMATION: L or I or V
<220> FEATURE:
<221> NAME/KEY: MISC_FEATURE
<222> LOCATION: (48)..(48)
<223> OTHER INFORMATION: T or S or H
<220> FEATURE:
<221> NAME/KEY: MISC_FEATURE
<222> LOCATION: (49)..(49)
<223> OTHER INFORMATION: D or E
<220> FEATURE:
<221> NAME/KEY: MISC_FEATURE
<222> LOCATION: (50)..(50)
<223> OTHER INFORMATION: H or P
<220> FEATURE:
<221> NAME/KEY: MISC_FEATURE
<222> LOCATION: (51)..(51)
<223> OTHER INFORMATION: K or R
<220> FEATURE:
<221> NAME/KEY: MISC_FEATURE
<222> LOCATION: (52)..(52)
<223> OTHER INFORMATION: K is linked spacer.
<220> FEATURE:
<221> NAME/KEY: MISC_FEATURE
<222> LOCATION: (54)..(54)
<223> OTHER INFORMATION: L or V
<220> FEATURE:
<221> NAME/KEY: MISC_FEATURE
<222> LOCATION: (56)..(56)
<223> OTHER INFORMATION: L or I or V
<220> FEATURE:
<221> NAME/KEY: MISC_FEATURE
<222> LOCATION: (57)..(57)
<223> OTHER INFORMATION: A or S
<220> FEATURE:
<221> NAME/KEY: MISC_FEATURE
<222> LOCATION: (59)..(59)
<223> OTHER INFORMATION: K or R or G
<220> FEATURE:
<221> NAME/KEY: MISC_FEATURE
<222> LOCATION: (62)..(62)
<223> OTHER INFORMATION: S or A
<220> FEATURE:
<221> NAME/KEY: MISC_FEATURE
<222> LOCATION: (65)..(65)
<223> OTHER INFORMATION: F or Y
<220> FEATURE:
<221> NAME/KEY: MISC_FEATURE
<222> LOCATION: (67)..(67)
<223> OTHER INFORMATION: A or S

<400> SEQUENCE: 93

Ile Ser Ile Xaa Glu Ile Xaa Xaa Val Ile Val Xaa Xaa Ile Glu Thr
1               5                   10                  15

Ile Leu Phe Lys Ser Xaa Xaa Asn Asn Tyr Tyr Met Gln Gln Tyr Gln
            20                  25                  30

Asn Ser Met Lys Xaa Phe Gly Xaa Xaa Xaa Xaa Glu Xaa Pro Xaa
        35                  40                  45

Xaa Xaa Xaa Lys Asp Xaa Ser Xaa Ala Ala Xaa His Met Xaa Asn Thr
    50                  55                  60

Xaa Leu Xaa
65

<210> SEQ ID NO 94
<211> LENGTH: 84
<212> TYPE: PRT
<213> ORGANISM: Artificial Sequence
<220> FEATURE:
<223> OTHER INFORMATION: Peptide containing artificial T helper epitope
      from measles virus and B cell epitopes from foot-and-mouth disease
      virus (FMDV)
<220> FEATURE:
```

```
<221> NAME/KEY: MISC_FEATURE
<222> LOCATION: (1)..(19)
<223> OTHER INFORMATION: Combinatorial T helper sequence.
<220> FEATURE:
<221> NAME/KEY: MISC_FEATURE
<222> LOCATION: (1)..(84)
<223> OTHER INFORMATION: UBITh(R) 3-K- FMDV Th library from polyprotein
      type O, A, C

```
<222> LOCATION: (35)..(35)
<223> OTHER INFORMATION: N or H or Q
<220> FEATURE:
<221> NAME/KEY: MISC_FEATURE
<222> LOCATION: (36)..(36)
<223> OTHER INFORMATION: V or T or I
<220> FEATURE:
<221> NAME/KEY: MISC_FEATURE
<222> LOCATION: (37)..(37)
<223> OTHER INFORMATION: L or I
<220> FEATURE:
<221> NAME/KEY: MISC_FEATURE
<222> LOCATION: (38)..(38)
<223> OTHER INFORMATION: D or M
<220> FEATURE:
<221> NAME/KEY: MISC_FEATURE
<222> LOCATION: (39)..(39)
<223> OTHER INFORMATION: L or V or M
<220> FEATURE:
<221> NAME/KEY: MISC_FEATURE
<222> LOCATION: (40)..(40)
<223> OTHER INFORMATION: K is linked spacer.
<220> FEATURE:
<221> NAME/KEY: MISC_FEATURE
<222> LOCATION: (42)..(42)
<223> OTHER INFORMATION: N or K or P
<220> FEATURE:
<221> NAME/KEY: MISC_FEATURE
<222> LOCATION: (43)..(43)
<223> OTHER INFORMATION: L or V or A
<220> FEATURE:
<221> NAME/KEY: MISC_FEATURE
<222> LOCATION: (50)..(50)
<223> OTHER INFORMATION: A or S
<220> FEATURE:
<221> NAME/KEY: MISC_FEATURE
<222> LOCATION: (51)..(51)
<223> OTHER INFORMATION: P or K
<220> FEATURE:
<221> NAME/KEY: MISC_FEATURE
<222> LOCATION: (52)..(52)
<223> OTHER INFORMATION: E or V or D
<220> FEATURE:
<221> NAME/KEY: MISC_FEATURE
<222> LOCATION: (53)..(53)
<223> OTHER INFORMATION: T or A
<220> FEATURE:
<221> NAME/KEY: MISC_FEATURE
<222> LOCATION: (56)..(56)
<223> OTHER INFORMATION: D or E or N
<220> FEATURE:
<221> NAME/KEY: MISC_FEATURE
<222> LOCATION: (58)..(58)
<223> OTHER INFORMATION: T or Q or H
<220> FEATURE:
<221> NAME/KEY: MISC_FEATURE
<222> LOCATION: (59)..(59)
<223> OTHER INFORMATION: T or S
<220> FEATURE:
<221> NAME/KEY: MISC_FEATURE
<222> LOCATION: (62)..(62)
<223> OTHER INFORMATION: K is linked spacer.
<220> FEATURE:
<221> NAME/KEY: MISC_FEATURE
<222> LOCATION: (66)..(66)
<223> OTHER INFORMATION: L or I
<220> FEATURE:
<221> NAME/KEY: MISC_FEATURE
<222> LOCATION: (68)..(68)
<223> OTHER INFORMATION: A or P
<220> FEATURE:
<221> NAME/KEY: MISC_FEATURE
<222> LOCATION: (69)..(69)
<223> OTHER INFORMATION: I or L or V
<220> FEATURE:
<221> NAME/KEY: MISC_FEATURE
<222> LOCATION: (70)..(70)
<223> OTHER INFORMATION: H or D or Q
<220> FEATURE:
```

```
<221> NAME/KEY: MISC_FEATURE
<222> LOCATION: (71)..(71)
<223> OTHER INFORMATION: P or T or V
<220> FEATURE:
<221> NAME/KEY: MISC_FEATURE
<222> LOCATION: (72)..(72)
<223> OTHER INFORMATION: S or T or N
<220> FEATURE:
<221> NAME/KEY: MISC_FEATURE
<222> LOCATION: (73)..(73)
<223> OTHER INFORMATION: K or Q or G
<220> FEATURE:
<221> NAME/KEY: MISC_FEATURE
<222> LOCATION: (74)..(74)
<223> OTHER INFORMATION: A or D
<220> FEATURE:
<221> NAME/KEY: MISC_FEATURE
<222> LOCATION: (76)..(76)
<223> OTHER INFORMATION: H or R
<220> FEATURE:
<221> NAME/KEY: MISC_FEATURE
<222> LOCATION: (79)..(79)
<223> OTHER INFORMATION: K or E or P
<220> FEATURE:
<221> NAME/KEY: MISC_FEATURE
<222> LOCATION: (80)..(80)
<223> OTHER INFORMATION: I or L
<220> FEATURE:
<221> NAME/KEY: MISC_FEATURE
<222> LOCATION: (81)..(81)
<223> OTHER INFORMATION: V or I
<220> FEATURE:
<221> NAME/KEY: MISC_FEATURE
<222> LOCATION: (84)..(84)
<223> OTHER INFORMATION: V or E or A

<400> SEQUENCE: 94

Ile Ser Ile Xaa Glu Ile Xaa Xaa Val Ile Val Xaa Xaa Ile Glu Thr
1               5                   10                  15

Ile Leu Phe Lys Xaa Xaa Asp Arg Phe Xaa Xaa Xaa Xaa Xaa Xaa
            20                  25                  30

Xaa Xaa Xaa Xaa Xaa Xaa Xaa Lys Gly Xaa Xaa Thr Trp Val Pro Asn
        35                  40                  45

Gly Xaa Pro Xaa Xaa Ala Leu Xaa Asn Xaa Xaa Asn Pro Lys Pro Arg
    50                  55                  60

Pro Xaa Leu Xaa Xaa Xaa Xaa Xaa Xaa Arg Xaa Lys Gln Xaa Xaa
65                  70                  75                  80

Xaa Ala Pro Xaa

<210> SEQ ID NO 95
<211> LENGTH: 74
<212> TYPE: PRT
<213> ORGANISM: Artificial Sequence
<220> FEATURE:
<223> OTHER INFORMATION: Peptide containing artificial T helper epitope
      from measles virus and B cell epitopes from foot-and-mouth disease
      virus (FMDV)
<220> FEATURE:
<221> NAME/KEY: MISC_FEATURE
<222> LOCATION: (1)..(19)
<223> OTHER INFORMATION: Combinatorial T helper sequence.
<220> FEATURE:
<221> NAME/KEY: MISC_FEATURE
<222> LOCATION: (1)..(74)
<223> OTHER INFORMATION: UBITh(R) 3-K- FMDV Th library from polyprotein
      type O, A, C and Asia-1 and type O-1 (ABR19839) sequence based
      construct [V786-L800]-K-[P835-G856]-K-[A1446-K1460].
<220> FEATURE:
<221> NAME/KEY: MISC_FEATURE
<222> LOCATION: (4)..(4)
<223> OTHER INFORMATION: S or T
<220> FEATURE:
```

```
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: K is linked spacer.
<220> FEATURE:
<221> NAME/KEY: MISC_FEATURE
<222> LOCATION: (24)..(24)
<223> OTHER INFORMATION: L or M
<220> FEATURE:
<221> NAME/KEY: MISC_FEATURE
<222> LOCATION: (27)..(27)
<223> OTHER INFORMATION: T or A or S
<220> FEATURE:
<221> NAME/KEY: MISC_FEATURE
<222> LOCATION: (28)..(28)
<223> OTHER INFORMATION: A or S
<220> FEATURE:
<221> NAME/KEY: MISC_FEATURE
<222> LOCATION: (33)..(33)
<223> OTHER INFORMATION: A or S
<220> FEATURE:
<221> NAME/KEY: MISC_FEATURE
<222> LOCATION: (36)..(36)
<223> OTHER INFORMATION: K is linked spacer.
<220> FEATURE:
<221> NAME/KEY: MISC_FEATURE
<222> LOCATION: (38)..(38)
<223> OTHER INFORMATION: L or V or F
<220> FEATURE:
<221> NAME/KEY: MISC_FEATURE
<222> LOCATION: (55)..(55)
<223> OTHER INFORMATION: V or A
<220> FEATURE:
<221> NAME/KEY: MISC_FEATURE
<222> LOCATION: (57)..(57)
<223> OTHER INFORMATION: N or T
<220> FEATURE:
<221> NAME/KEY: MISC_FEATURE
<222> LOCATION: (59)..(59)
<223> OTHER INFORMATION: K is lined spacer.
<220> FEATURE:
<221> NAME/KEY: MISC_FEATURE
<222> LOCATION: (66)..(66)
<223> OTHER INFORMATION: E or D
<220> FEATURE:
<221> NAME/KEY: MISC_FEATURE
<222> LOCATION: (73)..(73)
<223> OTHER INFORMATION: I or V

<400> SEQUENCE: 95

Ile Ser Ile Xaa Glu Ile Xaa Xaa Val Ile Val Xaa Xaa Ile Glu Thr
1               5                   10                  15

Ile Leu Phe Lys Val Gly Ala Xaa Leu Arg Xaa Xaa Thr Tyr Tyr Phe
            20                  25                  30

Xaa Asp Leu Lys Pro Xaa Thr Arg Leu Ala Leu Pro Tyr Thr Ala Pro
        35                  40                  45

His Arg Val Leu Ala Thr Xaa Tyr Xaa Gly Lys Ala Ala Ile Glu Phe
    50                  55                  60

Phe Xaa Gly Met Val His Asp Ser Xaa Lys
```

<210> SEQ ID NO 96
<211> LENGTH: 24
<212> TYPE: PRT
<213> ORGANISM: Foot-and-mouth disease virus
<220> FEATURE:
<221> NAME/KEY: MISC_FEATURE
<222> LOCATION: (1)..(24)
<223> OTHER INFORMATION: A12 (134-159) from FMDV VP1.

<400> SEQUENCE: 96

Asn Lys Tyr Ser Ala Ser Gly Ser Gly Val Arg Gly Asp Phe Gly Ser
1               5                   10                  15

Leu Ala Pro Arg Val Ala Arg Gln
            20

<210> SEQ ID NO 97
<211> LENGTH: 35
<212> TYPE: PRT
<213> ORGANISM: Foot-and-mouth disease virus
<220> FEATURE:
<221> NAME/KEY: MISC_FEATURE
<222> LOCATION: (1)..(35)
<223> OTHER INFORMATION: A12 (134-169) from FMDV VP1.

<400> SEQUENCE: 97

Asn Lys Tyr Ser Ala Ser Gly Ser Gly Val Arg Gly Asp Phe Gly Ser
1               5                   10                  15

Leu Ala Pro Arg Val Ala Arg Gln Leu Pro Ala Ser Phe Asn Tyr Gly
            20                  25                  30

Ala Ile Lys
        35

<210> SEQ ID NO 98
<211> LENGTH: 35
<212> TYPE: PRT
<213> ORGANISM: Foot-and-mouth disease virus
<220> FEATURE:
<221> NAME/KEY: MISC_FEATURE
<222> LOCATION: (1)..(35)
<223> OTHER INFORMATION: A12 [134(N-C)-158(Q-C)-169] from FMDV VP1,
      cyclized.

<400> SEQUENCE: 98

Cys Lys Tyr Ser Ala Ser Gly Ser Gly Val Arg Gly Asp Phe Gly Ser
1               5                   10                  15

Leu Ala Pro Arg Val Ala Arg Cys Leu Pro Ala Ser Phe Asn Tyr Gly
            20                  25                  30

Ala Ile Lys
        35

<210> SEQ ID NO 99
<211> LENGTH: 40
<212> TYPE: PRT
<213> ORGANISM: Foot-and-mouth disease virus
<220> FEATURE:
<221> NAME/KEY: MISC_FEATURE
<222> LOCATION: (1)..(40)
<223> OTHER INFORMATION: A12 [129-134(N-C)-158(Q-C)-169] from FMDV VP1,
      cyclized.

<400> SEQUENCE: 99

Val Tyr Asn Gly Thr Cys Lys Tyr Ser Ala Ser Gly Ser Gly Val Arg
1               5                   10                  15

```
Gly Asp Phe Gly Ser Leu Ala Pro Arg Val Ala Arg Cys Leu Pro Ala
            20                  25                  30

Ser Phe Asn Tyr Gly Ala Ile Lys
        35                  40

<210> SEQ ID NO 100
<211> LENGTH: 60
<212> TYPE: PRT
<213> ORGANISM: Foot-and-mouth disease virus
<220> FEATURE:
<221> NAME/KEY: MISC_FEATURE
<222> LOCATION: (1)..(19)
<223> OTHER INFORMATION: Combinatorial T helper sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: S or T
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: K is epsilon K as a linked spacer.
<220> FEATURE:
<221> NAME/KEY: MISC_FEATURE
<222> LOCATION: (21)..(60)
<223> OTHER INFORMATION: A12 [129-134(N-C)-158(Q-C)-169] from FMDV VP1,
      cyclized.

<400> SEQUENCE: 100

Ile Ser Ile Xaa Glu Ile Xaa Xaa Val Ile Val Xaa Xaa Ile Glu Thr
1               5                   10                  15

Ile Leu Phe Lys Val Tyr Asn Gly Thr Cys Lys Tyr Ser Ala Ser Gly
            20                  25                  30

Ser Gly Val Arg Gly Asp Phe Gly Ser Leu Ala Pro Arg Val Ala Arg
        35                  40                  45

Cys Leu Pro Ala Ser Phe Asn Tyr Gly Ala Ile Lys
    50                  55                  60

<210> SEQ ID NO 101
<211> LENGTH: 56
<212> TYPE: PRT
<213> ORGANISM: Foot-and-mouth disease virus
<220> FEATURE:
<221> NAME/KEY: MISC_FEATURE
<222> LOCATION: (1)..(56)
<223> OTHER INFORMATION: UBITh-K - O library [134-158 (T-C)-169],
      cyclized
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
```

```
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: K is epsilon K as a linked spacer.
<220> FEATURE:
<221> NAME/KEY: MISC_FEATURE
<222> LOCATION: (24)..(24)
<223> OTHER INFORMATION: G or S
<220> FEATURE:
<221> NAME/KEY: MISC_FEATURE
<222> LOCATION: (25)..(25)
<223> OTHER INFORMATION: E or D
<220> FEATURE:
<221> NAME/KEY: MISC_FEATURE
<222> LOCATION: (36)..(36)
<223> OTHER INFORMATION: Q or R
<220> FEATURE:
<221> NAME/KEY: MISC_FEATURE
<222> LOCATION: (43)..(43)
<223> OTHER INFORMATION: A or E

<400> SEQUENCE: 101

Ile Ser Ile Xaa Glu Ile Xaa Xaa Val Ile Val Xaa Xaa Ile Glu Thr
1               5                   10                  15

Ile Leu Phe Lys Cys Lys Tyr Xaa Xaa Asn Ala Val Thr Asn Val Arg
            20                  25                  30

Gly Asp Leu Xaa Val Leu Ala Gln Lys Ala Xaa Arg Cys Leu Pro Thr
        35                  40                  45

Ser Phe Asn Tyr Gly Ala Ile Lys
    50                  55

<210> SEQ ID NO 102
<211> LENGTH: 59
<212> TYPE: PRT
<213> ORGANISM: Foot-and-mouth disease virus
<220> FEATURE:
<221> NAME/KEY: MISC_FEATURE
<222> LOCATION: (1)..(19)
<223> OTHER INFORMATION: Combinatorial T helper sequence.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MISC_FEATURE
<222> LOCATION: (20)..(20)
<223> OTHER INFORMATION: K is epsilon K as a linked spacer.
<220> FEATURE:
```

```
<221> NAME/KEY: MISC_FEATURE
<222> LOCATION: (21)..(59)
<223> OTHER INFORMATION: Asia library [129-134(T-C)-158(R-C)-169] from
      FMDV VP1, cyclized
<220> FEATURE:
<221> NAME/KEY: MISC_FEATURE
<222> LOCATION: (34)..(34)
<223> OTHER INFORMATION: R or T
<220> FEATURE:
<221> NAME/KEY: MISC_FEATURE
<222> LOCATION: (35)..(35)
<223> OTHER INFORMATION: R or E
<220> FEATURE:
<221> NAME/KEY: MISC_FEATURE
<222> LOCATION: (43)..(43)
<223> OTHER INFORMATION: Q or L
<220> FEATURE:
<221> NAME/KEY: MISC_FEATURE
<222> LOCATION: (51)..(51)
<223> OTHER INFORMATION: T or V
<220> FEATURE:
<221> NAME/KEY: MISC_FEATURE
<222> LOCATION: (53)..(53)
<223> OTHER INFORMATION: F or N

<400> SEQUENCE: 102

Ile Ser Ile Xaa Glu Ile Xaa Xaa Val Ile Val Xaa Xaa Ile Glu Thr
1               5                   10                  15

Ile Leu Phe Lys Val Tyr Asn Gly Lys Cys Thr Tyr Gly Glu Gln Pro
            20                  25                  30

Ser Xaa Xaa Gly Asp Met Ala Ala Leu Ala Xaa Arg Leu Ser Arg Cys
        35                  40                  45

Leu Pro Xaa Ser Xaa Asn Tyr Gly Ala Val Lys
        50                  55

<210> SEQ ID NO 103
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (P360-K374) as
      homologue of [FMDV VP2 74-88].

<400> SEQUENCE: 103

Pro Phe Gly Lys Ser Tyr Ile Ile Glu Ile Pro Thr Asp His Arg
1               5                   10                  15

<210> SEQ ID NO 104
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
<223> OTHER INFORMATION: AJ539137 FMDV O, strain TAW/2/99 (P360-K374) as
      homologue of [FMDV VP2 74-88].

<400> SEQUENCE: 104

Pro Phe Gly Arg Ser Tyr Val Val Glu Val Pro Thr Asp His Lys
1               5                   10                  15

<210> SEQ ID NO 105
<211> LENGTH: 15
<212> TYPE: PRT
<213> ORGANISM: Foot-and-mouth disease virus
<220> FEATURE:
<221> NAME/KEY: MISC_FEATURE
<222> LOCATION: (1)..(15)
```

<223> OTHER INFORMATION: AJ539137 FMDV O, strain TAW/2/99 (P360-K374)
    [FMDV VP2 74-88].
<220> FEATURE:
<221> NAME/KEY: MISC_FEATURE
<222> LOCATION: (4)..(4)
<223> OTHER INFORMATION: R or K
<220> FEATURE:
<221> NAME/KEY: MISC_FEATURE
<222> LOCATION: (5)..(5)
<223> OTHER INFORMATION: S or C
<220> FEATURE:
<221> NAME/KEY: MISC_FEATURE
<222> LOCATION: (7)..(7)
<223> OTHER INFORMATION: L or I or V
<220> FEATURE:
<221> NAME/KEY: MISC_FEATURE
<222> LOCATION: (8)..(8)
<223> OTHER INFORMATION: L or I or V
<220> FEATURE:
<221> NAME/KEY: MISC_FEATURE
<222> LOCATION: (10)..(10)
<223> OTHER INFORMATION: L or I or V
<220> FEATURE:
<221> NAME/KEY: MISC_FEATURE
<222> LOCATION: (15)..(15)
<223> OTHER INFORMATION: K or R

<400> SEQUENCE: 105

Pro Phe Gly Xaa Xaa Tyr Xaa Xaa Glu Xaa Pro Thr Asp His Xaa
1               5                   10                  15

<210> SEQ ID NO 106
<211> LENGTH: 211
<212> TYPE: PRT
<213> ORGANISM: Foot-and-mouth disease virus
<220> FEATURE:
<221> NAME/KEY: MISC_FEATURE
<222> LOCATION: (1)..(211)
<223> OTHER INFORMATION: NCBI Reference Sequence: NP_740460.1

<400> SEQUENCE: 106

Thr Thr Ser Ala Gly Glu Ser Ala Asp Pro Val Thr Ala Thr Val Glu
1               5                   10                  15

Asn Tyr Gly Gly Glu Thr Gln Val Gln Arg Arg Gln His Thr Asp Ile
                20                  25                  30

Ala Phe Ile Leu Asp Arg Phe Val Lys Val Lys Pro Lys Glu Gln Val
            35                  40                  45

Asn Val Leu Asp Leu Met Gln Ile Pro Ala His Thr Leu Val Gly Ala
        50                  55                  60

Leu Leu Arg Thr Ala Thr Tyr Tyr Phe Ser Asp Leu Glu Leu Ala Val
65                  70                  75                  80

Lys His Glu Gly Asp Leu Thr Trp Val Pro Asn Gly Ala Pro Glu Thr
                85                  90                  95

Ala Leu Asp Asn Thr Thr Asn Pro Thr Ala Tyr His Lys Glu Pro Leu
            100                 105                 110

Thr Arg Leu Ala Leu Pro Tyr Thr Ala Pro His Arg Val Leu Ala Thr
        115                 120                 125

Val Tyr Asn Gly Ser Ser Lys Tyr Gly Asp Thr Ser Thr Asn Asn Val
    130                 135                 140

Arg Gly Asp Leu Gln Val Leu Ala Gln Lys Ala Glu Arg Thr Leu Pro
145                 150                 155                 160

Thr Ser Phe Asn Phe Gly Ala Ile Lys Ala Thr Arg Val Thr Glu Leu
                165                 170                 175

Leu Tyr Arg Met Lys Arg Ala Glu Thr Tyr Cys Pro Arg Pro Leu Leu
            180                 185                 190

-continued

```
Ala Ile Gln Pro Ser Asp Ala Arg His Lys Gln Arg Ile Val Ala Pro
            195                 200                 205
Ala Lys Gln
    210

<210> SEQ ID NO 107
<211> LENGTH: 2332
<212> TYPE: PRT
<213> ORGANISM: Foot-and-mouth disease virus
<220> FEATURE:
<221> NAME/KEY: MISC_FEATURE
<222> LOCATION: (1)..(2332)
<223> OTHER INFORMATION: GenBank: AJ539137.1

<400> SEQUENCE: 107

Met Ser Thr Thr Asp Cys Phe Ile Ala Leu Leu Tyr Ala Phe Arg Glu
1               5                   10                  15
Ile Lys Thr Leu Phe Leu Ser Arg Ala Gln Gly Lys Met Glu Phe Thr
            20                  25                  30
Leu His Asn Gly Glu Arg Lys Thr Phe Tyr Ser Arg Pro Asn Asn His
        35                  40                  45
Asp Asn Cys Trp Leu Asn Thr Ile Leu Gln Leu Phe Arg Tyr Val Asp
    50                  55                  60
Glu Pro Phe Phe Asp Trp Val Tyr Tyr Ser Pro Glu Asn Leu Thr Leu
65                  70                  75                  80
Asp Ala Ile Lys Gln Leu Glu Glu Ile Thr Gly Leu Glu Leu His Glu
                85                  90                  95
Gly Gly Pro Pro Ala Leu Val Ile Trp Asn Ile Lys His Leu Leu Asn
            100                 105                 110
Thr Gly Ile Gly Thr Ala Ser Arg Pro Ser Glu Val Cys Met Val Asp
        115                 120                 125
Gly Thr Asp Met Cys Leu Ala Asp Phe His Ala Gly Ile Phe Leu Lys
    130                 135                 140
Gly Gln Glu His Ala Val Phe Ala Cys Val Thr Ser Asn Gly Trp Tyr
145                 150                 155                 160
Ala Ile Asp Asp Glu Asp Phe Tyr Pro Trp Thr Pro Asp Pro Ser Asp
                165                 170                 175
Val Leu Val Phe Val Pro Tyr Asp Gln Glu Pro Leu Asn Gly Glu Trp
            180                 185                 190
Lys Ala Lys Val Gln Lys Arg Leu Arg Gly Ala Gly Gln Ser Ser Pro
        195                 200                 205
Ala Thr Gly Ser Gln Asn Gln Ser Gly Asn Thr Gly Ser Ile Ile Asn
    210                 215                 220
Asn Tyr Tyr Met Gln Gln Tyr Gln Asn Ser Met Asp Thr Gln Leu Gly
225                 230                 235                 240
Asp Asn Ala Ile Ser Gly Gly Ser Asn Glu Gly Ser Thr Asp Thr Thr
                245                 250                 255
Ser Thr His Thr Thr Asn Thr Gln Asn Asn Asp Trp Phe Ser Lys Leu
            260                 265                 270
Ala Ser Ser Ala Phe Ser Gly Leu Phe Gly Ala Leu Leu Ala Asp Lys
        275                 280                 285
Lys Thr Glu Glu Thr Thr Leu Leu Glu Asp Arg Ile Leu Thr Thr Arg
    290                 295                 300
Asn Gly His Thr Thr Ser Thr Thr Gln Ser Ser Val Gly Val Thr Tyr
305                 310                 315                 320
```

```
Gly Tyr Ala Thr Ala Glu Asp Phe Val Ser Gly Pro Asn Thr Ser Gly
                    325                 330                 335

Leu Glu Thr Arg Val Val Gln Ala Glu Arg Phe Phe Lys Thr His Leu
            340                 345                 350

Phe Asp Trp Val Thr Ser Asp Pro Phe Gly Arg Cys Tyr Leu Leu Glu
        355                 360                 365

Leu Pro Thr Asp His Lys Gly Val Tyr Gly Ser Leu Thr Asp Ser Tyr
    370                 375                 380

Ala Tyr Met Arg Asn Gly Trp Asp Val Glu Val Thr Ala Val Gly Asn
385                 390                 395                 400

Gln Phe Asn Gly Gly Cys Leu Leu Val Ala Met Val Pro Glu Leu Cys
                405                 410                 415

Ser Ile Asp Lys Arg Glu Leu Tyr Gln Leu Thr Leu Phe Pro His Gln
            420                 425                 430

Phe Ile Asn Pro Arg Thr Asn Met Thr Ala His Ile Thr Val Pro Phe
        435                 440                 445

Val Gly Val Asn Arg Tyr Asp Gln Tyr Lys Val His Lys Pro Trp Thr
    450                 455                 460

Leu Val Val Met Val Val Ala Pro Leu Thr Val Asn Thr Glu Gly Ala
465                 470                 475                 480

Pro Gln Ile Lys Val Tyr Ala Asn Ile Ala Pro Thr Asn Val His Val
                485                 490                 495

Ala Gly Glu Phe Pro Ser Lys Glu Gly Ile Phe Pro Val Ala Cys Ser
            500                 505                 510

Asp Gly Tyr Gly Gly Leu Val Thr Thr Asp Pro Lys Thr Ala Asp Pro
        515                 520                 525

Ala Tyr Gly Lys Val Phe Asn Pro Pro Arg Asn Met Leu Pro Gly Arg
    530                 535                 540

Phe Thr Asn Phe Leu Asp Val Ala Glu Ala Cys Pro Thr Phe Leu His
545                 550                 555                 560

Phe Glu Gly Asp Val Pro Tyr Val Thr Thr Lys Thr Asp Ser Asp Arg
                565                 570                 575

Val Leu Ala Gln Phe Asp Leu Ser Leu Ala Ala Lys His Met Ser Asn
            580                 585                 590

Thr Phe Leu Ala Gly Leu Ala Gln Tyr Tyr Thr Gln Tyr Ser Gly Thr
        595                 600                 605

Ile Asn Leu His Phe Met Phe Thr Gly Pro Thr Asp Ala Lys Ala Arg
    610                 615                 620

Tyr Met Ile Ala Tyr Ala Pro Pro Gly Met Glu Pro Pro Lys Thr Pro
625                 630                 635                 640

Glu Ala Ala Ala His Cys Ile His Ala Glu Trp Asp Thr Gly Leu Asn
                645                 650                 655

Ser Lys Phe Thr Phe Ser Ile Pro Tyr Leu Ser Ala Ala Asp Tyr Ala
            660                 665                 670

Tyr Thr Ala Ser Asp Val Ala Glu Thr Thr Asn Val Gln Gly Trp Val
        675                 680                 685

Cys Leu Phe Gln Ile Thr His Gly Lys Ala Asp Gly Asp Ala Leu Val
    690                 695                 700

Val Leu Ala Ser Ala Gly Lys Asp Phe Glu Leu Arg Leu Pro Val Asp
705                 710                 715                 720

Ala Arg Thr Gln Thr Thr Ser Thr Gly Glu Ser Ala Asp Pro Val Thr
                725                 730                 735

Ala Thr Val Glu Asn Tyr Gly Gly Glu Thr Gln Val Gln Arg Arg Gln
```

-continued

```
                740                 745                 750
His Thr Asp Val Ser Phe Ile Leu Asp Arg Phe Val Lys Val Thr Pro
            755                 760                 765
Lys Asp Gln Ile Asn Val Leu Asp Leu Val Gln Thr Pro Ala His Thr
            770                 775                 780
Leu Val Gly Ala Leu Leu Arg Thr Ala Thr Tyr Tyr Phe Ala Asp Leu
785                 790                 795                 800
Glu Val Ala Val Lys His Glu Gly Asn Leu Thr Trp Val Pro Asn Gly
                805                 810                 815
Ala Pro Glu Thr Ala Leu Asp Asn Thr Thr Asn Pro Thr Ala Tyr His
            820                 825                 830
Lys Ala Pro Leu Thr Arg Leu Ala Leu Pro Tyr Thr Ala Pro His Arg
            835                 840                 845
Val Leu Ala Thr Val Tyr Asn Gly Asn Cys Lys Tyr Gly Glu Ser Pro
850                 855                 860
Val Thr Asn Val Arg Gly Asp Leu Gln Val Leu Ala Gln Lys Ala Ala
865                 870                 875                 880
Arg Thr Leu Pro Thr Ser Phe Asn Tyr Gly Ala Ile Lys Ala Thr Arg
            885                 890                 895
Val Thr Glu Leu Leu Tyr Arg Met Lys Arg Ala Glu Thr Tyr Cys Pro
            900                 905                 910
Arg Pro Leu Leu Ala Ile His Pro Ser Lys Ala Arg His Lys Gln Lys
            915                 920                 925
Ile Val Ala Pro Val Lys Gln Leu Leu Asn Phe Asn Leu Leu Lys Leu
            930                 935                 940
Ala Gly Asp Val Glu Ser Asn Pro Gly Pro Phe Phe Ser Asp Val
945                 950                 955                 960
Arg Ser Asn Phe Ser Lys Leu Val Glu Thr Ile Asn Gln Met Gln Glu
            965                 970                 975
Asp Met Ser Thr Lys His Gly Pro Asp Phe Asn Arg Leu Val Ser Ala
            980                 985                 990
Phe Glu Glu Leu Ala Thr Gly Val Lys Ala Ile Arg Thr Gly Leu Asp
            995                 1000                1005
Glu Ala Lys Pro Trp Tyr Lys Leu Ile Lys Leu Leu Ser Arg Leu
            1010                1015                1020
Ser Cys Met Ala Ala Val Ala Ala Arg Ser Lys Asp Pro Val Leu
            1025                1030                1035
Val Ala Ile Met Leu Ala Asp Thr Gly Leu Glu Ile Leu Asp Ser
            1040                1045                1050
Thr Phe Val Val Lys Lys Ile Ser Asp Ser Leu Ser Ser Leu Phe
            1055                1060                1065
His Val Pro Ala Pro Val Phe Ser Phe Gly Ala Pro Ile Leu Leu
            1070                1075                1080
Ala Gly Leu Val Lys Val Ala Ser Ser Phe Phe Arg Ser Thr Pro
            1085                1090                1095
Glu Asp Leu Glu Arg Ala Glu Lys Gln Leu Lys Ala Arg Asp Ile
            1100                1105                1110
Asn Asp Ile Phe Ala Ile Leu Lys Asn Gly Glu Trp Leu Val Lys
            1115                1120                1125
Leu Ile Leu Ala Ile Arg Asp Trp Ile Lys Ala Trp Ile Ala Ser
            1130                1135                1140
Glu Glu Lys Phe Val Thr Met Thr Asp Leu Val Pro Gly Ile Leu
            1145                1150                1155
```

```
Glu Lys Gln Arg Asp Leu Asn Asp Pro Ser Lys Tyr Lys Glu Ala
    1160            1165            1170

Lys Glu Trp Leu Asp Asn Ala Arg Gln Ala Cys Leu Lys Ser Gly
    1175            1180            1185

Asn Ile His Ile Ala Asn Leu Cys Lys Val Val Ala Pro Ala Pro
    1190            1195            1200

Ser Arg Ser Arg Pro Glu Pro Val Val Val Cys Leu Arg Gly Lys
    1205            1210            1215

Ser Gly Gln Gly Lys Ser Phe Leu Ala Asn Val Leu Ala Gln Ala
    1220            1225            1230

Ile Ser Thr His Phe Thr Gly Arg Thr Asp Ser Val Trp Tyr Cys
    1235            1240            1245

Pro Pro Asp Pro Asp His Phe Asp Gly Tyr Asn Gln Gln Thr Val
    1250            1255            1260

Val Val Met Asp Asp Leu Gly Gln Asn Pro Asp Gly Lys Asp Phe
    1265            1270            1275

Lys Tyr Phe Ala Gln Met Val Ser Thr Thr Gly Phe Ile Pro Pro
    1280            1285            1290

Met Ala Ser Leu Glu Asp Lys Gly Lys Pro Phe Asn Ser Lys Val
    1295            1300            1305

Ile Ile Ala Thr Thr Asn Leu Tyr Ser Gly Phe Thr Pro Arg Thr
    1310            1315            1320

Met Val Cys Pro Asp Ala Leu Asn Arg Arg Phe His Phe Asp Ile
    1325            1330            1335

Asp Val Ser Ala Lys Asp Gly Tyr Lys Ile Asn Asn Lys Leu Asp
    1340            1345            1350

Ile Asn Lys Ala Leu Glu Asp Thr His Thr Asn Pro Val Ala Met
    1355            1360            1365

Phe Gln Tyr Asp Cys Ala Leu Leu Asn Gly Met Ala Val Glu Met
    1370            1375            1380

Lys Arg Met Gln Gln Asp Met Phe Lys Pro Gln Pro Pro Leu Gln
    1385            1390            1395

Asn Val Tyr Gln Leu Val Gln Glu Val Ile Asp Arg Val Glu Leu
    1400            1405            1410

His Glu Lys Val Ser Ser His Pro Ile Phe Lys Gln Ile Ser Ile
    1415            1420            1425

Pro Ser Gln Lys Ala Val Leu Tyr Phe Leu Ile Glu Lys Gly Gln
    1430            1435            1440

His Glu Ala Ala Ile Glu Phe Phe Glu Gly Met Val His Asp Ser
    1445            1450            1455

Ile Lys Glu Glu Leu Arg Pro Leu Ile Gln Gln Thr Ser Phe Val
    1460            1465            1470

Lys Arg Ala Phe Lys Arg Leu Lys Glu Asn Phe Glu Ile Val Ala
    1475            1480            1485

Leu Cys Leu Thr Leu Leu Ala Asn Ile Val Ile Met Ile Arg Glu
    1490            1495            1500

Thr Arg Lys Arg Gln Gln Met Val Asp Asp Ala Val Asn Glu Tyr
    1505            1510            1515

Ile Glu Lys Ala Ser Ile Thr Thr Asp Asp Lys Thr Leu Asp Glu
    1520            1525            1530

Ala Glu Lys Asn Pro Leu Glu Thr Ser Gly Ala Thr Thr Val Gly
    1535            1540            1545
```

-continued

```
Phe Arg Glu Lys Thr Leu Pro Gly His Lys Ala Ser Asp Asp Val
    1550                1555                1560

Asn Ser Glu Pro Ala Lys Pro Val Glu Glu Pro Gln Ala Glu
    1565                1570                1575

Gly Pro Tyr Thr Gly Pro Leu Glu Arg Gln Lys Pro Leu Lys Val
    1580                1585                1590

Arg Ala Lys Leu Pro Gln Gln Glu Gly Pro Tyr Ala Gly Pro Met
    1595                1600                1605

Glu Arg Gln Lys Pro Leu Lys Val Lys Val Lys Ala Pro Val Val
    1610                1615                1620

Lys Glu Gly Pro Tyr Glu Gly Pro Val Lys Lys Pro Val Ala Leu
    1625                1630                1635

Lys Val Lys Ala Lys Asn Leu Ile Val Thr Glu Ser Gly Ala Pro
    1640                1645                1650

Pro Thr Asp Leu Gln Lys Met Val Met Gly Asn Thr Lys Pro Val
    1655                1660                1665

Glu Leu Ile Leu Asp Gly Lys Thr Val Ala Ile Cys Cys Ala Thr
    1670                1675                1680

Gly Val Phe Gly Thr Ala Tyr Leu Val Pro Arg His Leu Phe Ala
    1685                1690                1695

Glu Lys Tyr Asp Lys Ile Met Leu Asp Gly Arg Ala Met Thr Asp
    1700                1705                1710

Ser Asp Tyr Arg Val Phe Glu Phe Glu Ile Lys Val Lys Gly Gln
    1715                1720                1725

Asp Met Leu Ser Asp Ala Ala Leu Met Val Leu His Arg Gly Asn
    1730                1735                1740

Arg Val Arg Asp Ile Thr Lys His Phe Arg Asp Val Ala Arg Met
    1745                1750                1755

Lys Lys Gly Thr Pro Val Val Gly Val Ile Asn Asn Ala Asp Val
    1760                1765                1770

Gly Arg Leu Ile Phe Ser Gly Glu Ala Leu Thr Tyr Lys Asp Ile
    1775                1780                1785

Val Val Cys Met Asp Gly Asp Thr Met Pro Gly Leu Phe Ala Tyr
    1790                1795                1800

Lys Ala Ala Thr Lys Ala Gly Tyr Cys Gly Gly Ala Val Leu Ala
    1805                1810                1815

Lys Asp Gly Ala Glu Thr Phe Ile Val Gly Thr His Ser Ala Gly
    1820                1825                1830

Gly Asn Gly Val Gly Tyr Cys Ser Cys Val Ser Arg Ser Met Leu
    1835                1840                1845

Leu Lys Met Lys Ala His Ile Asp Pro Glu Pro His His Glu Gly
    1850                1855                1860

Leu Ile Val Asp Thr Arg Asp Val Glu Glu Arg Val His Val Met
    1865                1870                1875

Arg Lys Thr Lys Leu Ala Pro Thr Val Ala His Gly Val Phe Asn
    1880                1885                1890

Pro Glu Phe Gly Pro Ala Ala Leu Ser Asn Lys Asp Pro Arg Leu
    1895                1900                1905

Asn Glu Gly Val Val Leu Asp Glu Ala Ile Phe Ser Lys His Lys
    1910                1915                1920

Gly Asn Thr Lys Met Ser Glu Glu Asp Lys Ala Leu Phe Arg Arg
    1925                1930                1935

Cys Ala Ala Asp Tyr Ala Ser Arg Leu His Ser Val Leu Gly Thr
```

-continued

```
            1940                1945                1950
Ala Asn Ala Pro Leu Ser Thr Tyr Glu Ala Ile Lys Gly Val Asp
    1955                1960                1965
Gly Leu Asp Ala Met Glu Pro Asp Thr Ala Pro Gly Leu Pro Trp
    1970                1975                1980
Ala Leu Gln Gly Lys Arg Arg Gly Ala Leu Ile Asp Phe Glu Asn
    1985                1990                1995
Gly Thr Val Gly Pro Glu Val Glu Ala Ala Leu Lys Leu Met Glu
    2000                2005                2010
Lys Arg Glu Tyr Lys Phe Val Cys Gln Thr Phe Leu Lys Asp Glu
    2015                2020                2025
Ile Arg Pro Met Glu Lys Val Arg Ala Gly Lys Thr Arg Ile Val
    2030                2035                2040
Asp Val Leu Pro Val Glu His Ile Leu Tyr Thr Arg Met Met Ile
    2045                2050                2055
Gly Arg Phe Cys Ala Gln Met His Leu Asn Asn Gly Pro Gln Ile
    2060                2065                2070
Gly Ser Ala Val Gly Cys Asn Pro Asp Val Asp Trp Gln Arg Phe
    2075                2080                2085
Gly Thr His Phe Ala Gln Tyr Arg Asn Val Trp Asp Val Asp Tyr
    2090                2095                2100
Ser Ala Phe Asp Ala Asn His Cys Ser Asp Ala Met Asn Ile Met
    2105                2110                2115
Phe Glu Glu Val Phe Asn Thr Asp Phe Gly Phe His Pro Asn Ala
    2120                2125                2130
Glu Trp Ile Leu Lys Thr Leu Val Asn Thr Glu His Ala Tyr Glu
    2135                2140                2145
Asn Lys Arg Ile Thr Val Glu Gly Gly Met Pro Ser Gly Cys Ser
    2150                2155                2160
Ala Thr Ser Ile Ile Asn Thr Ile Leu Asn Asn Ile Tyr Val Leu
    2165                2170                2175
Tyr Ala Leu Arg Arg His Tyr Glu Gly Val Glu Leu Asp Ser Tyr
    2180                2185                2190
Thr Met Ile Ser Tyr Gly Asp Asp Ile Val Val Ala Ser Asp Tyr
    2195                2200                2205
Asp Leu Asp Phe Glu Ala Leu Arg Pro His Phe Lys Ser Leu Gly
    2210                2215                2220
Gln Thr Ile Thr Pro Ala Asp Lys Ser Asp Lys Gly Phe Val Leu
    2225                2230                2235
Gly His Ser Ile Thr Asp Val Thr Phe Leu Lys Arg His Phe His
    2240                2245                2250
Met Asp Tyr Gly Thr Gly Phe Tyr Lys Pro Val Met Ala Ser Lys
    2255                2260                2265
Thr Leu Glu Ala Ile Leu Ser Phe Ala Arg Arg Gly Thr Ile Gln
    2270                2275                2280
Glu Lys Leu Ile Ser Val Ala Gly Leu Ala Ile His Ser Gly Pro
    2285                2290                2295
Asp Glu Tyr Arg Arg Leu Phe Glu Pro Phe Gln Gly Leu Phe Glu
    2300                2305                2310
Ile Pro Ser Tyr Arg Ser Leu Tyr Leu Arg Trp Val Asn Ala Val
    2315                2320                2325
Cys Gly Asp Ala
    2330
```

```
<210> SEQ ID NO 108
<211> LENGTH: 2332
<212> TYPE: PRT
<213> ORGANISM: Foot-and-mouth disease virus
<220> FEATURE:
<221> NAME/KEY: MISC_FEATURE
<222> LOCATION: (1)..(2332)
<223> OTHER INFORMATION: GenBank: ABR19839.1
<220> FEATURE:
<221> NAME/KEY: MISC_FEATURE
<222> LOCATION: (268)..(268)
<223> OTHER INFORMATION: Xaa may be any amino acid
<220> FEATURE:
<221> NAME/KEY: MISC_FEATURE
<222> LOCATION: (360)..(360)
<223> OTHER INFORMATION: Xaa may be any amino acid

<400> SEQUENCE: 108

Met Asn Thr Thr Asp Cys Phe Thr Ala Leu Ile His Ile Phe Arg Glu
1               5                   10                  15

Ile Arg Thr Leu Phe Leu Ser Arg Thr Gln Gly Lys Met Glu Phe Thr
            20                  25                  30

Leu Tyr Asn Gly Glu Lys Lys Thr Phe Tyr Ser Arg Pro Asn Asn His
        35                  40                  45

Asp Asn Cys Trp Leu Asn Ala Ile Leu Gln Leu Phe Arg Tyr Val Asp
    50                  55                  60

Glu Pro Phe Phe Asp Trp Val Tyr Asp Ser Pro Glu Asn Leu Thr Val
65                  70                  75                  80

Glu Ala Ile Arg Gln Leu Glu Gly Leu Thr Gly Leu Glu Leu His Glu
                85                  90                  95

Gly Gly Pro Pro Ala Leu Val Ile Trp Asn Ile Lys His Leu Leu His
            100                 105                 110

Thr Gly Ile Gly Thr Ala Ser Arg Pro Ser Glu Val Cys Met Val Asp
        115                 120                 125

Gly Thr Asp Met Cys Leu Ala Asp Phe His Ala Gly Ile Phe Leu Lys
    130                 135                 140

Gly Gln Glu His Ala Val Phe Ala Cys Val Thr Ser Asp Gly Trp Phe
145                 150                 155                 160

Ala Ile Asp Asp Glu Asp Phe Tyr Pro Trp Thr Pro Asp Pro Ser Asp
                165                 170                 175

Val Leu Val Phe Val Pro Tyr Asp Gln Glu Pro Leu Asn Gly Asp Trp
            180                 185                 190

Lys Ala Lys Val Gln Arg Arg Leu Lys Gly Ala Gly Gln Ser Ser Pro
        195                 200                 205

Ala Thr Trp Ser Gln Asn Gln Ser Gly Asn Thr Gly Ser Ile Ile Asn
    210                 215                 220

Asn Tyr Tyr Met Gln Gln Tyr Gln Asn Ser Met Asp Thr Gln Leu Gly
225                 230                 235                 240

Asp Asn Ala Thr Ser Gly Gly Ser Asn Glu Gly Ser Thr Asp Thr Thr
                245                 250                 255

Ser Thr His Thr Thr Asn Thr Gln Asn Asn Asp Xaa Phe Ser Lys Leu
            260                 265                 270

Ala Ser Ser Ala Phe Ser Gly Leu Phe Gly Ala Leu Leu Ala Asp Lys
        275                 280                 285

Lys Thr Glu Glu Thr Thr Leu Leu Glu Asp Arg Ile Leu Thr Thr Arg
    290                 295                 300

Asn Gly His Thr Thr Ser Thr Thr Gln Ser Ser Val Gly Val Thr Tyr
```

```
            305                 310                 315                 320
    Gly Tyr Ala Thr Ala Glu Asp Phe Val Ser Gly Pro Asn Thr Ser Gly
                    325                 330                 335

Leu Glu Thr Arg Val Ala Gln Ala Glu Arg Phe Phe Lys Thr His Leu
                    340                 345                 350

Phe Asp Trp Val Thr Ser Asp Xaa Phe Gly Arg Cys His Leu Leu Glu
                    355                 360                 365

Leu Pro Thr Asp His Lys Gly Ile Tyr Gly Leu Ile Asp Ser Tyr
                370                 375                 380

Ala Tyr Met Arg Asn Gly Trp Asp Val Glu Val Thr Ala Val Gly Asn
    385                 390                 395                 400

Gln Phe Asn Gly Gly Cys Leu Leu Val Ala Met Val Pro Glu Leu Cys
                    405                 410                 415

Ser Ile Gln Lys Arg Glu Leu Tyr Gln Leu Thr Leu Phe Pro His Gln
                    420                 425                 430

Phe Ile Asn Pro Arg Thr Asn Met Thr Ala His Ile Thr Val Pro Phe
                    435                 440                 445

Val Gly Val Asn Arg Tyr Asp Gln Tyr Lys Val His Lys Pro Trp Thr
                450                 455                 460

Leu Val Val Met Val Val Ala Pro Leu Thr Val Asn Thr Glu Gly Ala
    465                 470                 475                 480

Pro Gln Ile Lys Val Tyr Ala Asn Ile Ala Pro Thr Asn Val His Val
                    485                 490                 495

Ala Gly Glu Phe Pro Ser Lys Glu Gly Ile Phe Pro Val Ala Cys Ser
                    500                 505                 510

Asp Gly Tyr Gly Gly Leu Val Thr Thr Asp Pro Lys Thr Ala Asp Pro
                515                 520                 525

Ala Tyr Gly Lys Val Phe Asn Pro Pro Arg Asn Met Leu Pro Gly Arg
                530                 535                 540

Phe Thr Asn Leu Leu Asp Val Ala Glu Ala Cys Pro Thr Phe Leu His
    545                 550                 555                 560

Phe Glu Gly Asp Val Pro Tyr Val Thr Thr Lys Thr Asp Ser Asp Arg
                    565                 570                 575

Val Leu Thr Gln Phe Asp Leu Ser Leu Ala Ala Lys His Met Ser Asn
                    580                 585                 590

Thr Phe Leu Ala Gly Leu Ala Gln Tyr Tyr Thr Gln Tyr Ser Gly Thr
                    595                 600                 605

Ile Asn Leu His Phe Met Phe Thr Gly Pro Thr Asp Ala Lys Ala Arg
                610                 615                 620

Tyr Met Ile Ala Tyr Ala Pro Pro Gly Met Glu Pro Pro Lys Thr Pro
    625                 630                 635                 640

Glu Thr Ala Ala His Cys Ile His Ala Glu Trp Asp Thr Gly Leu Asn
                    645                 650                 655

Ser Lys Phe Thr Phe Ser Ile Pro Tyr Leu Ser Ala Ala Asp Tyr Ala
                    660                 665                 670

Tyr Thr Ala Ser Ser Thr Ala Glu Thr Thr Asn Val Gln Gly Trp Val
                675                 680                 685

Cys Leu Phe Gln Ile Thr His Gly Lys Ala Asp Gly Asp Ala Leu Val
                690                 695                 700

Val Leu Ala Ser Ala Gly Lys Asp Phe Asp Leu Arg Leu Pro Val Asp
    705                 710                 715                 720

Ala Arg Thr Gln Thr Thr Ser Pro Gly Glu Ser Ala Asp Pro Val Thr
                    725                 730                 735
```

```
Ala Thr Val Glu Asn Tyr Gly Gly Val Thr Gln Ala Gln Arg Arg Gln
                 740                 745                 750

His Thr Asp Val Ser Phe Ile Leu Asp Arg Phe Val Lys Val Thr Pro
                 755                 760                 765

Gln Asp Gln Ile Asn Val Leu Asp Leu Met Gln Ile Pro Ala His Thr
        770                 775                 780

Leu Val Gly Ala Leu Leu Arg Thr Ser Thr Tyr Tyr Phe Ala Asp Leu
785                 790                 795                 800

Glu Leu Ala Val Lys His Gly Asn Leu Thr Trp Val Pro Asn Gly
                805                 810                 815

Ala Pro Glu Ala Ala Leu Asp Asn Thr Thr Asn Pro Val Tyr His
            820                 825                 830

Lys Ala Pro Leu Thr Arg Leu Ala Leu Pro Tyr Thr Ala Pro His Arg
                835                 840                 845

Val Leu Ala Thr Val Tyr Asn Gly Asn Cys Lys Tyr Ser Gly Ser Ser
850                 855                 860

Ala Thr Asn Val Arg Gly Asp Leu Gln Val Leu Ala Gln Arg Ala Ala
865                 870                 875                 880

Arg Thr Leu Pro Thr Ser Phe Asn Tyr Gly Ala Ile Lys Ala Thr Arg
                885                 890                 895

Val Thr Glu Leu Leu Tyr Arg Met Lys Arg Ala Glu Thr Tyr Cys Pro
            900                 905                 910

Arg Pro Leu Leu Ala Ile His Pro Ser Glu Ala Arg His Lys Gln Lys
                915                 920                 925

Ile Val Ala Pro Val Lys Gln Leu Leu Asn Phe Asp Leu Leu Lys Leu
        930                 935                 940

Ala Gly Asp Val Glu Ser Asn Pro Gly Pro Phe Phe Phe Ser Asp Val
945                 950                 955                 960

Arg Ser Asn Phe Ser Lys Leu Val Glu Thr Ile Asn Gln Met Gln Glu
                965                 970                 975

Asp Met Ser Thr Lys His Gly Pro Asp Phe Asn Arg Leu Val Ser Ala
            980                 985                 990

Phe Glu Glu Leu Ala Thr Gly Val Lys Ala Ile Arg Thr Gly Leu Asp
                995                1000                1005

Glu Ala Lys Pro Trp Tyr Lys Leu Ile Lys Leu Leu Ser Arg Leu
           1010                1015                1020

Ser Cys Met Ala Ala Val Ala Arg Ser Lys Asp Pro Val Leu
       1025                1030                1035

Val Ala Ile Met Leu Ala Asp Thr Gly Leu Glu Ile Leu Asp Ser
       1040                1045                1050

Thr Phe Val Val Lys Lys Ile Ser Asp Ser Leu Ser Ser Leu Phe
       1055                1060                1065

His Val Pro Ala Pro Ala Phe Ser Phe Gly Ala Pro Leu Leu Leu
       1070                1075                1080

Ala Gly Leu Val Lys Val Ala Ser Ser Phe Phe Arg Ser Thr Pro
       1085                1090                1095

Glu Glu Leu Glu Arg Ala Glu Lys Gln Leu Lys Ala Arg Asp Ile
       1100                1105                1110

Asn Asp Ile Phe Ala Ile Leu Lys Asn Gly Glu Trp Leu Val Lys
       1115                1120                1125

Leu Ile Leu Ala Ile Arg Asp Trp Ile Lys Ala Trp Ile Ala Ser
       1130                1135                1140
```

-continued

| | | | | | | | | | | | |
|---|---|---|---|---|---|---|---|---|---|---|---|
| Glu | Glu | Lys | Phe | Val | Thr | Met | Thr | Asp | Leu | Val | Pro | Gly | Ile | Leu |
| | 1145 | | | | | 1150 | | | | | 1155 | | | |
| Glu | Lys | Gln | Arg | Asp | Leu | Asn | Asp | Pro | Ser | Lys | Tyr | Lys | Glu | Ala |
| | 1160 | | | | | 1165 | | | | | 1170 | | | |
| Lys | Glu | Trp | Leu | Asp | Asn | Ala | Arg | Gln | Ala | Cys | Leu | Lys | Ser | Gly |
| | 1175 | | | | | 1180 | | | | | 1185 | | | |
| Asn | Val | His | Ile | Ala | Asn | Leu | Cys | Lys | Val | Val | Ala | Pro | Ala | Pro |
| | 1190 | | | | | 1195 | | | | | 1200 | | | |
| Ser | Arg | Ser | Arg | Pro | Glu | Pro | Val | Val | Val | Cys | Leu | Arg | Gly | Lys |
| | 1205 | | | | | 1210 | | | | | 1215 | | | |
| Ser | Gly | Gln | Gly | Lys | Ser | Phe | Leu | Ala | Asn | Val | Leu | Ala | Gln | Ala |
| | 1220 | | | | | 1225 | | | | | 1230 | | | |
| Ile | Ser | Thr | His | Phe | Thr | Gly | Arg | Thr | Asp | Ser | Val | Trp | Tyr | Cys |
| | 1235 | | | | | 1240 | | | | | 1245 | | | |
| Pro | Pro | Asp | Pro | Asp | His | Phe | Asp | Gly | Tyr | Asn | Gln | Gln | Thr | Val |
| | 1250 | | | | | 1255 | | | | | 1260 | | | |
| Val | Val | Met | Asp | Asp | Leu | Gly | Gln | Asn | Pro | Asp | Gly | Lys | Asp | Phe |
| | 1265 | | | | | 1270 | | | | | 1275 | | | |
| Lys | Tyr | Phe | Ala | Gln | Met | Val | Ser | Thr | Thr | Gly | Phe | Ile | Pro | Pro |
| | 1280 | | | | | 1285 | | | | | 1290 | | | |
| Met | Ala | Ser | Leu | Glu | Asp | Lys | Gly | Lys | Pro | Phe | Asn | Ser | Lys | Val |
| | 1295 | | | | | 1300 | | | | | 1305 | | | |
| Ile | Ile | Ala | Thr | Thr | Asn | Leu | Tyr | Ser | Gly | Phe | Thr | Pro | Arg | Thr |
| | 1310 | | | | | 1315 | | | | | 1320 | | | |
| Met | Val | Cys | Pro | Asp | Ala | Leu | Asn | Arg | Arg | Phe | His | Phe | Asp | Ile |
| | 1325 | | | | | 1330 | | | | | 1335 | | | |
| Asp | Val | Ser | Ala | Lys | Asp | Gly | Tyr | Lys | Ile | Asn | Asn | Lys | Leu | Asp |
| | 1340 | | | | | 1345 | | | | | 1350 | | | |
| Ile | Ile | Lys | Ala | Leu | Glu | Asp | Thr | His | Thr | Asn | Pro | Val | Ala | Met |
| | 1355 | | | | | 1360 | | | | | 1365 | | | |
| Phe | Gln | Tyr | Asp | Cys | Ala | Leu | Leu | Asn | Gly | Met | Ala | Val | Glu | Met |
| | 1370 | | | | | 1375 | | | | | 1380 | | | |
| Lys | Arg | Met | Gln | Gln | Asp | Met | Phe | Lys | Pro | Gln | Pro | Pro | Leu | Gln |
| | 1385 | | | | | 1390 | | | | | 1395 | | | |
| Asn | Val | Tyr | Gln | Leu | Val | Gln | Glu | Val | Ile | Glu | Arg | Val | Glu | Leu |
| | 1400 | | | | | 1405 | | | | | 1410 | | | |
| His | Glu | Lys | Val | Ser | Asn | His | Pro | Ile | Phe | Lys | Gln | Ile | Ser | Ile |
| | 1415 | | | | | 1420 | | | | | 1425 | | | |
| Pro | Ser | Gln | Lys | Ser | Val | Leu | Tyr | Phe | Leu | Ile | Glu | Lys | Gly | Gln |
| | 1430 | | | | | 1435 | | | | | 1440 | | | |
| His | Glu | Ala | Ala | Ile | Glu | Phe | Phe | Glu | Gly | Met | Val | His | Asp | Ser |
| | 1445 | | | | | 1450 | | | | | 1455 | | | |
| Ile | Lys | Glu | Glu | Leu | Arg | Pro | Leu | Val | Gln | Gln | Thr | Ser | Phe | Val |
| | 1460 | | | | | 1465 | | | | | 1470 | | | |
| Lys | Arg | Ala | Phe | Lys | Arg | Leu | Lys | Glu | Asn | Phe | Glu | Ile | Val | Ala |
| | 1475 | | | | | 1480 | | | | | 1485 | | | |
| Leu | Cys | Leu | Thr | Leu | Leu | Ala | Asn | Ile | Val | Ile | Met | Ile | Arg | Glu |
| | 1490 | | | | | 1495 | | | | | 1500 | | | |
| Thr | Arg | Lys | Arg | Gln | Gln | Met | Val | Asp | Asp | Ala | Val | Asn | Glu | Tyr |
| | 1505 | | | | | 1510 | | | | | 1515 | | | |
| Ile | Glu | Lys | Ala | Asn | Ile | Thr | Thr | Asp | Asp | Lys | Thr | Leu | Asp | Glu |
| | 1520 | | | | | 1525 | | | | | 1530 | | | |
| Ala | Glu | Lys | Asn | Pro | Leu | Glu | Thr | Ser | Gly | Ala | Ser | Thr | Val | Gly |

-continued

```
            1535                1540                1545
Phe Arg Glu Arg Thr Leu Pro Gly Gln Lys Ala Ser Asp Asp Val
    1550                1555                1560

Asn Ser Glu Pro Ala Lys Pro Val Asp Glu Gln Pro Gln Ala Glu
    1565                1570                1575

Gly Pro Tyr Ala Gly Pro Leu Glu Arg Gln Lys Pro Leu Lys Val
    1580                1585                1590

Arg Ala Lys Leu Pro Gln Gln Glu Gly Pro Tyr Ala Gly Pro Met
    1595                1600                1605

Glu Arg Gln Lys Pro Leu Lys Val Lys Ala Lys Ala Pro Val Val
    1610                1615                1620

Lys Glu Gly Pro Tyr Glu Gly Pro Val Lys Lys Pro Val Ala Leu
    1625                1630                1635

Lys Val Lys Ala Lys Asn Leu Ile Val Thr Glu Ser Gly Ala Pro
    1640                1645                1650

Pro Thr Asp Leu Gln Lys Met Val Met Gly Asn Thr Lys Pro Val
    1655                1660                1665

Glu Leu Ile Leu Asp Gly Lys Thr Val Ala Ile Cys Cys Ala Thr
    1670                1675                1680

Gly Val Phe Gly Thr Ala Tyr Leu Val Pro Arg His Leu Phe Ala
    1685                1690                1695

Glu Lys Tyr Asp Lys Ile Met Leu Asp Gly Arg Ala Met Thr Asp
    1700                1705                1710

Ser Asp Tyr Arg Val Phe Glu Phe Glu Ile Lys Val Lys Gly Gln
    1715                1720                1725

Asp Met Leu Ser Asp Ala Ala Leu Met Val Leu His Arg Gly Asn
    1730                1735                1740

Arg Val Arg Asp Ile Thr Lys His Phe Arg Asp Thr Ala Arg Met
    1745                1750                1755

Lys Lys Gly Thr Pro Val Val Gly Val Ile Asn Asn Ala Asp Val
    1760                1765                1770

Gly Arg Leu Ile Phe Ser Gly Glu Ala Leu Thr Tyr Lys Asp Ile
    1775                1780                1785

Val Val Cys Met Asp Gly Asp Thr Met Pro Gly Leu Phe Ala Tyr
    1790                1795                1800

Arg Ala Ala Thr Lys Ala Gly Tyr Cys Gly Gly Ala Val Leu Ala
    1805                1810                1815

Lys Asp Gly Ala Asp Thr Phe Ile Val Gly Thr His Ser Ala Gly
    1820                1825                1830

Gly Asn Gly Val Gly Tyr Cys Ser Cys Val Ser Arg Ser Met Leu
    1835                1840                1845

Leu Lys Met Lys Ala His Ile Asp Pro Glu Pro His His Glu Gly
    1850                1855                1860

Leu Ile Ile Asp Thr Arg Asp Val Glu Glu Arg Val His Val Met
    1865                1870                1875

Arg Lys Thr Lys Leu Ala Pro Thr Val Ala His Gly Val Phe Asn
    1880                1885                1890

Pro Glu Phe Gly Pro Ala Ala Leu Ser Asn Lys Asp Pro Arg Leu
    1895                1900                1905

Asn Glu Gly Val Val Leu Asp Glu Val Ile Phe Ser Lys His Lys
    1910                1915                1920

Gly Asp Thr Lys Met Ser Glu Glu Asp Lys Ala Leu Phe Arg Arg
    1925                1930                1935
```

```
Cys Ala Ala Asp Tyr Ala Ser Arg Leu His Ser Glu Leu Gly Thr
1940                1945                1950

Ala Asn Ala Pro Leu Ser Ile Tyr Glu Ala Ile Lys Gly Val Asp
1955                1960                1965

Gly Leu Asp Ala Met Glu Pro Asp Thr Ala Pro Gly Leu Pro Trp
1970                1975                1980

Ala Leu Gln Gly Lys Arg Arg Gly Ala Leu Ile Asp Phe Glu Asn
1985                1990                1995

Gly Thr Val Gly Pro Glu Val Thr Ala Ala Leu Glu Leu Met Glu
2000                2005                2010

Lys Arg Glu Tyr Lys Phe Ala Cys Gln Thr Phe Leu Lys Asp Glu
2015                2020                2025

Ile Arg Pro Met Glu Lys Val Arg Ala Gly Lys Thr Arg Ile Val
2030                2035                2040

Asp Val Leu Pro Val Glu His Ile Leu Tyr Thr Arg Met Met Ile
2045                2050                2055

Gly Arg Phe Cys Ala Gln Met His Ala Asn Asn Gly Pro Arg Ile
2060                2065                2070

Gly Ser Ala Val Gly Cys Asn Pro Asp Val Asp Trp Gln Arg Phe
2075                2080                2085

Gly Thr His Phe Ala Gln Tyr Arg Asn Val Trp Asp Val Asp Tyr
2090                2095                2100

Ser Ala Phe Asp Ala Asn His Cys Ser Asp Ala Met Asn Ile Met
2105                2110                2115

Phe Glu Glu Val Phe Arg Thr Glu Phe Gly Phe His Pro Asn Ala
2120                2125                2130

Glu Trp Ile Leu Lys Thr Leu Val Asn Thr Glu His Ala Tyr Glu
2135                2140                2145

Asn Lys Arg Ile Thr Val Glu Gly Gly Met Pro Ser Gly Cys Ser
2150                2155                2160

Ala Thr Ser Ile Ile Asn Thr Ile Leu Asn Asn Ile Tyr Val Leu
2165                2170                2175

Tyr Ala Leu Arg Arg His Tyr Glu Gly Val Glu Leu Asp Thr Tyr
2180                2185                2190

Thr Met Ile Ser Tyr Gly Asp Asp Ile Val Val Ala Ser Asp Tyr
2195                2200                2205

Asp Leu Asp Phe Glu Ala Leu Lys Pro His Phe Lys Ser Leu Gly
2210                2215                2220

Gln Thr Ile Thr Pro Ala Asp Lys Ser Asp Lys Gly Phe Val Leu
2225                2230                2235

Gly His Ser Ile Thr Asp Val Thr Phe Leu Lys Arg His Phe His
2240                2245                2250

Met Asp Tyr Gly Thr Gly Phe Tyr Lys Pro Val Met Ala Ser Lys
2255                2260                2265

Thr Leu Glu Ala Ile Leu Ser Phe Ala Arg Arg Gly Thr Ile Gln
2270                2275                2280

Glu Lys Leu Ile Ser Val Ala Gly Leu Ala Val His Ser Gly Pro
2285                2290                2295

Asp Glu Tyr Arg Arg Leu Phe Glu Pro Phe Gln Gly Leu Phe Glu
2300                2305                2310
```

-continued

```
Ile Pro Ser Tyr Arg Ser Leu Tyr Leu Arg Trp Val Asn Ala Val
    2315                2320                2325
Cys Gly Asp Ala
    2330
```

SYNTHETIC PEPTIDE-BASED EMERGENCY VACCINE AGAINST FOOT AND MOUTH DISEASE (FMD)

This application is a national phase entry under 35 U.S.C. § 371 of International Application Number PCT/US2012/065386, filed on Nov. 16, 2012, entitled "SYNTHETIC PEPTIDE-BASED EMERGENCY VACCINE AGAINST FOOT AND MOUTH DISEASE (FMD)", which is hereby incorporated by reference in its entirety.

FIELD OF THE INVENTION

This disclosure relates to a peptide-based emergency vaccine and formulations thereof against Foot and Mouth Disease Virus (FMDV) for the control of Foot and Mouth Disease (FMD).

BACKGROUND OF THE INVENTION

Foot-and-Mouth Disease (FMD) is the most contagious animal disease. The causative agent, Foot-and-Mouth Disease Virus (FMDV), is an aphthovirus of the Picornaviridae family that has a positive sense RNA genome encoding four capsid proteins (VP1-VP4) and non-structural polypeptides (2A-2C and 3A-3D) (review by Carrillo, C. et al, 2005).

FMDV rapidly replicates and can spread through the air (aerosol transmittable) among infected and in-contact susceptible animals, including cloven-hoofed animals such as cattle, pigs, sheep and goats. FMD is on the A list of animal infectious disease of the Office International des Epizooties (OIE) and has been recognized as the most important constraint to international trade in animals and animal products. Currently, FMD is controlled by quarantine and destruction of infected and exposed animals; and, in most countries, by vaccination with chemically inactivated virus compositions. Because of the detrimental economic consequences resulting from its presence, countries that are free of the disease have introduced a number of measures to retain this status without vaccination.

Seven distinct serotypes of FMDV have been described and each serotype is further divided into multiple subtypes. These serotypes include: A, O, C, Asia, and the South African types SAT-1, 2, and 3, with A, O, and Asia being the most common. Adding to the genetic complexity and variability of the virus, FMDV can mutate at a high rate on a random basis.

A significant difficulty in formulating vaccines for FMDV is the remarkable antigenic diversity of the virus and the lack of cross-protection between serotypes. That is, animals vaccinated against, or recovered from, a virus of one serotype are susceptible to infection with viruses from the remaining six serotypes. Moreover, the degree of antigenic variation within a serotype is such that a vaccine effective against one subtype may not be protective against another subtype within that same serotype.

Current FMD vaccines contain a mixture of inactivated viruses including a reference strain of each relevant serotype or subtype, which is determined by monitoring the virus strains present in local circulation. To prevent outbreaks from emerging FMD variants, field isolates must be periodically monitored and compared to the current vaccine in production. Thus, to ensure that the vaccine is current and effective, the production of inactivated FMD virus vaccines require: (1) growing and inactivating several virus strains to be included in the vaccine, (2) monitoring the potency and efficacy of each inactivated strain, and (3) reformulating the vaccine product periodically to include current strains to prevent loss of protective efficacy by emerging new variants.

Producing and maintaining an efficient inactivated virus vaccine is onerous and complicated in view of the significant antigenic variation between and among the FMDV serotypes. Several known issues and disadvantages associated with inactivated FMDV vaccines include: biohazard and biosecurity risks, product instability and variability, and unintended, detrimental side effects in treated animals.

For example, manufacturing inactivated virus vaccines create biohazard/biosecurity risks because the virus must be produced in a high-containment facility to prevent contamination of the immediate environment. Additionally, the innocuousness of the inactivated virus product cannot be completely assured. In fact, several recent cases of FMDV in Europe have been traced to incompletely inactivated virus. These potential biohazard/biosecurity risks limit the number of qualified vaccine suppliers to just a few. Such limitations can hamper the ability of a region to effectively and immediately respond to an outbreak.

Current FMD vaccines also suffer from product instability as well as lot-to-lot variability. As discussed above, vaccines must be monitored and reformulated periodically to include both current and emerging strains of FMDV. Moreover, each region of the world will require protection from a different current/emerging strain of FMDV at any given time. Thus, complex and undefined compositions of inactivated virus vaccines being produced throughout the world. These complex mixtures of inactivated virus vaccines must be continuously inspected at regular intervals to ensure immunopotency.

In addition to the above issues, current FMDV vaccines have been shown to cause unintended, detrimental side effects in treated animals. For example, reports of allergic reactions, anaphylactic shock, and spontaneous death have been reported in animals treated with current vaccines.

The disadvantages of the existing inactivated viral lysate based commercial vaccines have encouraged research to create safer and better-defined subunit products (Brown, F. 1992). However, to be an acceptable replacement to the inactivated virus, such subunit products must have an equivalent immunogenicity to that of the inactivated virus vaccines and provide a wide spectrum of protection against antigenic variants. Most importantly, the subunit products need to meet the OIE guidelines for challenge studies after only single administration of the vaccine in order to be qualified as an FMD emergency vaccine.

To overcome some of the problems associated with existing commercial viral lysate based FMD vaccines, the inventor and her research team have made significant strides over the past 15 years in developing synthetic peptide based FMDV vaccines to protect swine from FMDV challenge. In particular, the inventor successfully developed an effective FMDV vaccine that is capable of eliciting a broad range of neutralizing antibodies against FMDV using a formulation containing an optimized VP1 looped B cell epitope peptide. Immunogenicity of this VP1 looped B cell epitope peptide can be further enhanced by covalently linking the peptide to an artificial T helper epitope (Wang, C Y and Shen, M, 2000; Wang, C Y et al, 2001; Wang, C Y, et al, 2002). This vaccine has been shown to effectively protect swine from FMDV challenge after multiple administrations of a formulation (Wang, C Y, et al. 2002). The VP1 looped B cell epitope peptide formulation has proven to be an important vaccine in protecting animals from classical FMDV virus strains.

To qualify as an "emergency" FMD vaccine under OIE protocol, a formulation must induce a rapid protective immunity with wide antigenic coverage in the FMD serotypes after only a single administration. Although multiple administrations of the VP1 looped B cell epitope peptide formulation provide effective protection against classical FMDV virus strains, single administrations of the formulation have not been able to protect swine against FMDV challenge on an emergency basis. Additionally, the VP1 looped B cell epitope peptide formulation has not been shown to protect cattle from FMDV challenge after one or two administrations (Rodriguez, LL. et al. 2003).

There is an urgent need to explore the extensive literature in the public domain, identify and validate correlates of the protective immune responses required in an FMD emergency vaccine so as to allow development of a safe and efficacious peptide based FMD vaccine and formulations thereof for emergency and general protective use against FMDV.

In view of the disadvantages and limitations of vaccines currently available for FMD, there remains an urgent need for an emergency vaccine formulation that is capable of protecting swine and cattle from FMDV after only a single administration.

REFERENCES

Blanco, E., et al., "Interspecies major histocompatibility complex-restricted Th cell epitope on foot-and-mouth disease virus capsid protein VP4." *J. Virol.*, 74:4902-4907. (2000)

Brown, F., et al. "The Effect of Various Inactivating Agents on the Viral and Ribonucleic Acid Infectivities of Foot-and-Mouth Disease Virus and on its Attachment to Susceptible Cells." *J Gen Microbiol.*, 31:179-186. (1963)

Brown F., "New approaches to vaccination against foot-and-mouth disease." *Vaccine*, 10:1022-6. (1992)

Carrillo, C., et al., "Comparative genomics of foot-and-mouth disease virus." *J. Virol.*, 79:6487-6504. (2005)

Collen, T., et al., "A T cell epitope in VP1 of foot-and-mouth disease virus is immunodominant for vaccinated cattle." *J. Immunol.*, 146:749-755. (1991)

Collen, T., et al., "Heterotypic recognition of recombinant FMDV proteins by bovine T-cells: the polymerase (P3Dpol) as an immunodominant T-cell immunogen." *Virus Res.*, 56:125-133. (1998)

Cox S J, et al., "Longevity of antibody and cytokine responses following vaccination with high potency emergency FMD vaccines." *Vaccine.* 21 (13-14), 1336-1347 (2003)

Filgueira, M P, et al., "Detection and characterization of functional T cell epitopes on the structural proteins VP2, VP3 and VP4 of Foot and Mouth Disease Virus O1 Campos." *Virology*, 271: 234-2. (2000)

Garcia-Briones, M. et al., "Association of bovine DRB3 alleles with immune response to FMDV peptides and protection against viral challenge." *Vaccine*, 19:1167-1171. (2001)

Garcia-Briones, M, et al., "Immunogenicity and T cell recognition in swine of foot-and-mouth disease virus polymerase 3D." *Virology*, 322:264-27. (2004)

Gerner, W., et al., "Identification of novel foot-and-mouth disease virus specific T-cell epitopes in c/c and d/d haplotype miniature swine." *Virus Res.*, 121:223-228. (2006)

Gerner, W., et al., "Identification of a novel foot-and-mouth disease virus specific T-cell epitope with immunodominant characteristics in cattle with MHC serotype A31." *Vet. Res.*, 38:565-572. (2007)

Gerner W., et al., "Identification of Major histocompatibility Complex Restriction and Anchor Residues of Foot-and-Mouth Disease Virus-Derived Bovine T-cell epitopes." *J. Virol.*, 83:4039-4050. (2009)

Guzman, E., et al., "An MHC-restricted CD8$^+$ T-cell response is induced in cattle by foot-and-mouth disease virus (FMDV) infection and also following vaccination with inactivated FMDV." *J. Gen. Virol.*, 89:667-675. (2008)

Haghparast, A., et al., "Selection of T-cell epitopes from foot-and-mouth disease virus reflects the binding affinity to different cattle MHC class II molecules." *Immunogenetics*, 51:733-742. (2000)

Hohlich, B J, et al., "Induction of an antigen-specific immune response and partial protection of cattle against challenge infection with foot-and-mouth disease virus (FMDV) after lipopeptide vaccination with FMDV-specific B cell epitopes." *J. of Gen. Virology*, 84:3315-3324. (2003)

Mason, P W, et al., "Comparisons of the complete genomes of Asian, African and European isolates of a recent foot-and-mouth disease virus type O pandemic strain (PanAsia)." *J. Gen. Virol.*, 84:1583-1593. (2003)

Moore V, Chapter 2. In: *Synthetic Peptides: A Users Guide*. Grant G A, ed. New York: WH Freeman and Company: 63-7. (1992)

Morgan D O and Moore D M. "Protection of cattle and swine against foot-and-mouth disease, using biosynthetic peptide vaccines." *Am J Vet Res.* 51(1):40-5. (1990)

Rodriguez A, et al., "Antigenic specificity of porcine T cell response against foot-and-mouth disease virus structural proteins: identification of T helper epitopes in VP1." *Virol.*, 205:24-33. (1994)

Rodriguez, L L, et al., "Synthetic peptide containing the consensus sequence of the G-H Loop region of FMDV Type O VP1 Combined with a promiscuous T-helper epitope induces peptide specific AB but fails to protect cattle against viral challenge." *Vaccine*, 21:3751-3756. (2003)

Takamatsu H H, "A sub-population of circulating porcine gammadelta T cells can act as professional antigen presenting cells." *Vet Immunol Immunopathol.*, 87 (3-4): 223-4 (2002)

Van Lierop, M J, et al., "T cell-stimulatory fragments of foot-and-mouth disease virus released by mild treatment with cathepsin D." *J. Gen. Virol.*, 75:2937-2946. (1994)

Van Lierop, M J, et al., "Sequences derived from the highly antigenic VP1 region 140 to 160 of foot-and-mouth disease virus do not prime for a bovine T-cell response against intact virus." *J. Virol.*, 69:4511-4514. (1995a)

Van Lierop M J, et al., "The influence of MHC polymorphism on the selection of T-cell determinants of FMDV in cattle." *Immunology*, 84:79-85. (1995b)

Wang C Y, Shen M., "Synthetic peptide vaccines for foot-and-mouth disease." U.S. Pat. No. 6,107,021. (2000)

Wang, C Y, et al., "Synthetic Peptide-based Vaccine and Diagnostic System for Effective Control of FMD." *Biologicals*, 29:221-228. (2001)

Wang, C Y, et al., "Effective Synthetic peptide vaccine for foot-and-mouth disease in swine." *Vaccine*, 20:2603-2610. (2002)

SUMMARY OF THE INVENTION

The present disclosure is directed to synthetic peptides that are useful for the detection, treatment, and/or prevention of foot-and-mouth disease (FMD) in an animal. The synthetic peptides of the disclosure include peptide antigens that can be used to sensitively and specifically detect FMD infection in an animal. The synthetic peptides also include peptide immunogens having both B cell (B) and T helper cell (Th) epitopes that act together to stimulate the generation of protective immune responses to FMD infection. In certain embodiments, the synthetic peptides are both peptide antigens as well as peptide immunogens. In some embodiments, the synthetic peptides are used to detect the presence of antibodies to FMD virus (FMDV) in an animal. In other embodiments, the synthetic peptides are used to treat animals in that test positive for the presence of FMDV and/or in animals that have been exposed to animals that tested positive to FMDV. In yet other embodiments, the synthetic peptides are used to prevent FMD infection in an animal.

The present disclosure is also directed to compositions containing synthetic peptides. Such compositions can be used for the detection, treatment, and/or prevention of FMD in an animal. In certain embodiments, compositions containing the synthetic peptides are used for detecting the presence of antibodies to FMDV in a sample. In other embodiments, compositions containing the synthetic peptides are pharmaceutical compositions for treating and/or preventing FMD infection in an animal. In a particular embodiment, the pharmaceutical composition is used to elicit an immune response to FMDV in an animal. In a specific embodiment, the pharmaceutical composition is a vaccine composition that can prevent FMD infection in an animal exposed to the virus.

The present disclosure also includes methods for detecting, treating, and/or preventing FMD infection in an animal. The disclosed methods utilize the synthetic peptides and compositions containing the synthetic peptides also disclosed herein.

In certain embodiments, the present disclosure is directed to a peptide-based pharmaceutical composition that qualifies as an emergency vaccine according to OIE guidelines because the composition provides animals with sufficient and adequate protection against FMD infection after a single administration. In these embodiments, the pharmaceutical composition that can be used as an emergency vaccine contains peptide immunogens that mimic antigenic sites on native FMD proteins as well as pathogen proteins derived from endogenous T cell epitopes. The described formulations efficiently elicit functional antibodies against target FMD proteins to provide animals with protection from FMD challenge.

In various embodiments, synthetic peptide immunogens can contain VP1 looped peptides having a B cell antigenic site capable of eliciting neutralizing antibodies against FMDV (SEQ ID NOs: 1 and 2), homologues thereof (e.g. SEQ ID NOs: 3-23, 96-99), and combinations thereof.

The disclosed VP1 looped peptides can also contain a T helper epitope (SEQ ID NO: 24) that is covalently linked to the amino- or carboxyl-terminus of the peptide antigen to enhance the immunogenicity of the B cell antigenic peptide (e.g. SEQ ID NOs: 25-33, 100-102). In certain variations, the peptide immunogens are supplemented with a mixture of peptides representing T helper epitopes to provide host cell-mediated immunity. Such peptides include T helper epitopes derived from the FMDV VP1, VP2, VP3, VP4, 2A, 2B, 2C, 3A, 3B and 3D proteins (e.g. SEQ ID NOs: 34-63), homologues and functional analogues thereof, as well as combinatorial sequences derived library peptides (e.g. SEQ ID NOs: 64-87) and FMDV Th epitope peptides designed in an UBITh® enhanced cassette form (e.g. SEQ ID NOs: 88-95).

The present disclosure also provides methods for eliciting both antibody and cell mediated immune responses against FMDV in an animal. Such methods provide FMD cross protection to animals that are FMDV antibody-free upon viral challenge with FMDV. In specific embodiments, the disclosed methods include a step of administering a pharmaceutical composition containing a combined FMDV B and T helper epitope cluster of peptides to an animal.

The present disclosure also provides a method for the low cost manufacture and quality control of FMD immunogenic peptides, an emergency vaccine formulation containing the same, as well as a delivery system capable of protecting animals from FMDV challenge on an emergency basis with only a single administration of the vaccine formulation.

BRIEF DESCRIPTION OF THE DRAWINGS

FIG. 1 is a schematic that illustrates the distribution and location of B and Th epitopes on FMDV proteins according to a particular embodiment disclosed herein. The amino acid positions identified in the drawing for the proteins are based on the sequence of FMDV $O_{Taiwan\ 99}$ genomic sequence. The name of each of the gene product (VP4, VP2, VP3, VP1+2A, 2B+2C, 3A+3B1+B2, B3, 3C and 3D) is identified followed by open bars of different lengths based on the sizes of the respective encoded proteins. B and T cell epitopes are also identified based on their respective sizes (number of amino acids) and location (amino acid number within the protein where the epitope is derived) of the epitopes with each epitope being marked by its first and last amino acids and their numbering within that protein (e.g., for VP4: S221-M235 signifies that the T cell epitope is 15 amino acids in length beginning with Serine at amino acid position 221 and ending at Methionine at amino acid position 235 within the VP4 protein).

DETAILED DESCRIPTION OF THE INVENTION

Figure 2:
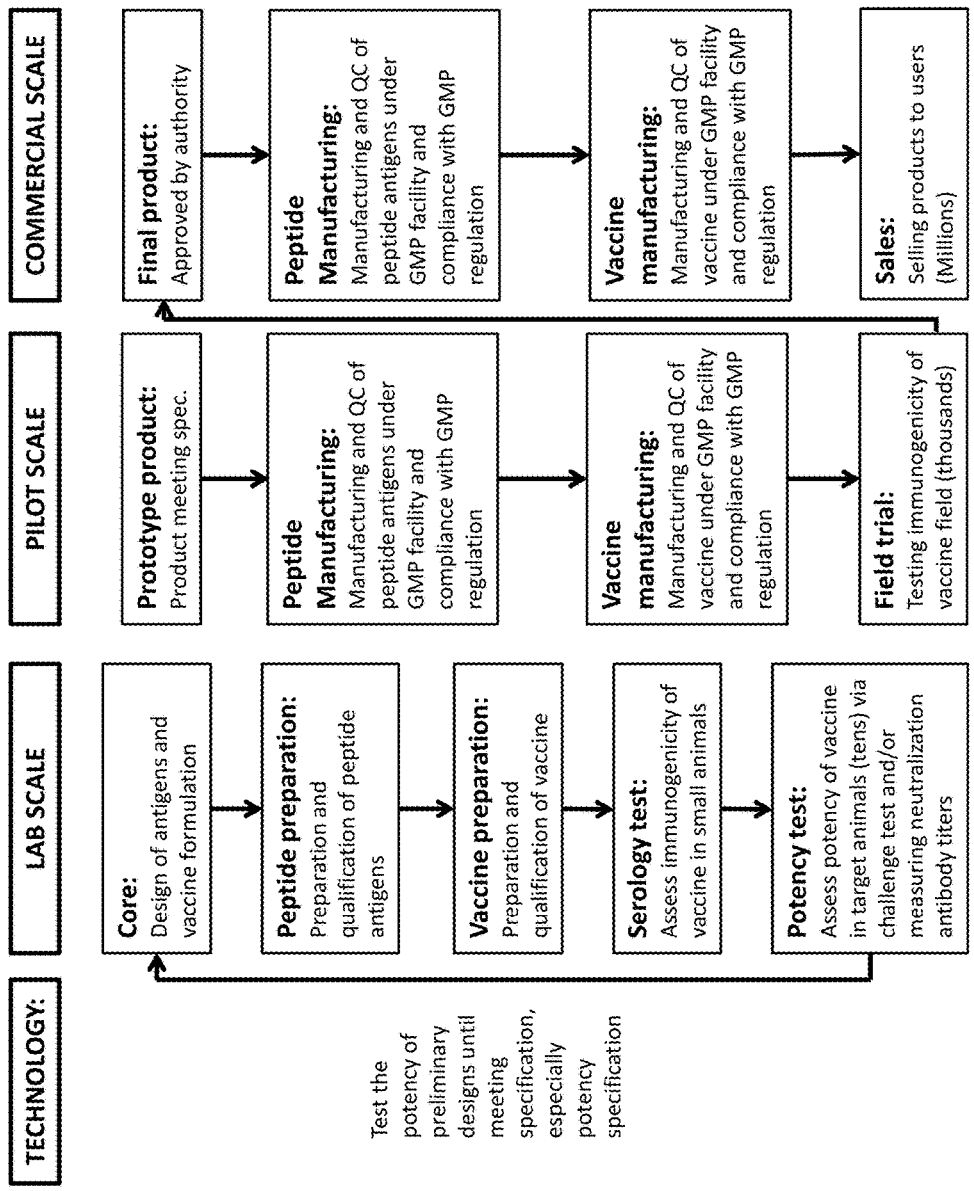
FIG. 2 is a flowchart identifying the development process, from discovery to commercialization, of a vaccine formulation according to a particular embodiment disclosed herein.

The present disclosure is directed to synthetic peptides that are useful for the detection, treatment, and/or prevention of foot-and-mouth disease (FMD) in an animal. The synthetic peptides of the disclosure include peptide antigens that can be used to sensitively and specifically detect antibodies to FMD virus in an animal. The synthetic peptides also include peptide immunogens having both B cell (B) and T helper cell (Th) epitopes that act together to stimulate the generation of protective immune responses to FMD infection. In certain embodiments, the synthetic peptides are both peptide antigens as well as peptide immunogens. In some embodiments, the synthetic peptides are used to detect the presence of antibodies to FMD virus (FMDV) in an animal. In other embodiments, the synthetic peptides are used to treat animals in that test positive for the presence of FMDV and/or in animals that have been exposed to animals that tested positive to FMDV. In yet other embodiments, the synthetic peptides are used to prevent FMD infection in an animal.

The present disclosure is also directed to compositions containing synthetic peptides. Such compositions can be used for the detection, treatment, and/or prevention of FMD in an animal. In certain embodiments, compositions containing the synthetic peptides are used for detecting the presence of FMDV in a sample. In other embodiments, compositions containing the synthetic peptides are pharmaceutical compositions for treating and/or preventing FMD infection in an animal. In a particular embodiment, the pharmaceutical composition is used to elicit an immune response to FMDV in an animal. In a specific embodiment, the pharmaceutical composition is a vaccine composition that can prevent FMD infection in an animal exposed to the virus.

The present disclosure also includes methods for detecting, treating, and/or preventing FMD infection in an animal. The disclosed methods utilize synthetic peptides and compositions containing synthetic peptides disclosed herein.

a. B Cell Epitopes—FMDV Synthetic Peptide Immunogens

Amino acid sequences for synthetic peptide immunogens were obtained by aligning and evaluating B cell antigenic sites in VP1 structure proteins from multiple, homologous FMDV serotype O strains. Based on the alignment shown in Table 2, an antigenic consensus sequence of 25 amino acids, corresponding to amino acid residues 134 to 158 of full-length FMDV VP1 structure protein was obtained (SEQ ID NO: 1). (An example of amino acid numbering for a full-length VP1 sequence can be found in Genbank Accession No. NP_740460). Amino acids corresponding to positions 134 and 158 were substituted with cysteine residues to allow the peptide to form an intra-disulfide loop structure. A longer FMDV antigenic consensus peptide containing 41 amino acids (SEQ ID NO: 2) was also obtained from this alignment. The second consensus sequence encompasses SEQ ID NO: 1 and includes additional flanking sequences at both the N- and C-termini. The second consensus sequence corresponds to amino acid residues 129 to 168 of a full-length FMDV VP1 structural protein with amino acids corresponding to positions 134 and 158 substituted with cysteine residues. The two consensus sequences are identified as shown in Table 1.

Consensus sequences for VP1 B cell epitopes from serotypes O, Asia 1, and A were also obtained through similar homologue alignments and are shown as SEQ ID NOs: 2, 12, and 16 in Table 2. Amino acids for the variable positions within each consensus sequence were assigned based on the amino acid that appeared most frequently within the respective serotype strain at those positions.

Effective and acceptable variations of the synthetic peptide immunogens SEQ ID NO: 1 and 2 include immunologically functional homologues that have corresponding sequences and conformational elements from mutant and variant strains of FMDV. Homologous FMDV antigenic peptides have amino acid residues that closely correlate with VP1 structural protein positions 129 to 168 of the originating variant FMDV $O_{Taiwan}$ strain and the consensus sequence derived from multiple strains of FMDV serotype O (Mason, P W et al, 2003). Such homologues can be readily identified through sequence alignment programs such as ClustalW (produced by Julie D. Thompson, Toby Gibson of European Molecular Biology Laboratory, Germany and Desmond Higgins of European Bioinformatics Institute, Cambridge, UK. Algorithmic). Table 2 shows the FMDV $O_{Consensus}$ sequence (2570a, SEQ ID NO: 2) as well as a ClustalW alignment of twenty-two antigenic sequences in FMDV VP1 structure protein taken from multiple serotypes and diverse strains including: $O_{Campos}$, $O_{Taiwan}$, $O_{Myanmar}$, $O_{Ozk}$, $O_{Lanzou}$, Asia $1_{Yunnan}$, Asia $1_{Jiansu}$, $A_{24}$, $A_{Gansu}$, $A_{Xinjiang}$, $C_{Indaial}$, $C3_{Belgium}$, $C3_{Argentina}$, etc. (SEQ ID NOs: 3 to 23).

Additional homologous of VP1 that are included in the present invention include peptides and proteins that contain the characteristic "RGD" (Arg-Gly-Asp) cell receptor binding sequence invariably found in the looped structure of VP1 sequences from all FMDV strains. This RGD sequence corresponding to amino acid positions 145 to 147 of the VP1 protein.

As shown in Table 2, the number of amino acids found down stream (toward the C-terminus) of the "RGD" sequence is the same between the various VP1 sequences. However, the number of amino acids upstream (toward the N-terminus) from the RGD sequence varies depending on the particular serotype (e.g., O, Asia 1, A, or C). Within each serotype, the N-terminal sequences have at least 75% identity to the consensus sequence for that particular serotype (e.g. SEQ ID NOs: 13 to 15 when compared to SEQ ID NO: 12 for serotype Asia 1; and SEQ ID NOs: 17 to 19 when compared to SEQ ID NO: 16 for serotype A). In one embodiment, the variant $O_{Myanmar/7/02}$ strain homologue (SEQ ID NO: 7) has over 85% identity to SEQ ID NO: 2 (with the residues different from those in the consensus sequence being shown as shaded). In another embodiment, the variant strain $O_{Ozk/93}$ homologue (SEQ ID NO: 8) has approximately 90% identity to SEQ ID NO: 2 (with the residues different from those in the consensus sequence being shown as shaded).

Homologous VP1 peptides, shown in Table 2 and otherwise described, can be combined in a composition at an appropriate ratio and administered to an animal to effectively elicit neutralizing antibodies that target specific FMDV strains. Accordingly, pharmaceutical compositions containing homologous VP1 peptides are effective vaccines for preventing FMD infection. For example, formulations containing homologous VP1 peptide(s) prepared as a water-in-oil (w/o) emulsion (e.g., with ISA50V2) or as a water-in-oil-in-water (w/o/w) emulsion (e.g., with Emulsigen), are effective in preventing FMD infection.

Various embodiments and examples are provided below that discuss the use of effects of compositions containing multiple VP1 sequence peptides. For example, Examples 6, 7, 9 and 10 describe a multivalent FMDV swine and/or cattle vaccine composition containing a combination of three FMDV serotype O VP1 peptides corresponding to sequences of $O_{consensus}$, $O_{swine/cattle/O/Mya/7/02}$ (abbreviated as $O_{Myanmar}$) and $O_{Ozk/93}$ (abbreviated as $O_{Ozk}$). The composition containing this mixture of peptides can produce a potent trivalent swine vaccine to counter the infection imposed by multiple divergent O strains. Similarly, a multi-serotype vaccine using a combination of VP1 peptides with $O_{Consensus}$ (2570a), Asia $1_{JiangSu/China/2005}$ (abbreviated as Asia $1_{JiangSu}$) and $A_{Gansu/China/60Y}$ (abbreviated as $A_{Gansu}$) can be mixed to form a trivalent serotype cattle vaccine to counter the infection imposed by strains from multiple FMDV serotypes in China. Furthermore, an effective multi-serotype cattle vaccine adapted for South America contains a combination of VP1 sequence peptides from $O_{Campos/Brazil/58Y}$ (abbreviated as $O_{Campos}$), $A_{24\ Cruzeiro\ California}$ (abbreviated as $A_{24}$), and $C_{Indaial/Brazil/84Y}$ (abbreviated as $C_{Indaial}$) is effective at countering FMD infections imposed by strains from multiple serotypes most prevalent in South America.

The location of the B cell epitope on the FMDV VP1 protein that was selected to be included in the synthetic peptides of the present invention, relative to other regions and proteins of FMDV, is shown in FIG. 1. The protein sequences are based on the sequence of FMDV $O_{Taiwan\ 99}$ genome/encoded amino acid sequence) (GenBank Accession No. AJ539137).

Immunologically functional analogues of the synthetic peptide immunogens are also effective in eliciting an immune response in an animal and are included as part of the present invention. Immunologically functional analogues includes variants of the consensus sequences of SEQ ID NOs: 1, 2, 12, and 16 and/or homologues of SEQ ID NOs: 3-11, 13-15, and 17-23 that retain substantially the same antigenicity and immunogenicity as the original peptide. For example, variants that are functional analogues can have a conservative substitution in an amino acid position; a change in overall charge; a covalent attachment to another moiety; or amino acid additions, insertions, or deletions; and/or any combination thereof.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In one embodiment, the immunologically functional analogue of a particular peptide contains the same amino acid sequence as the original peptide and further includes three lysines (Lys-Lys-Lys) added to the amino terminus of the peptide. In this embodiment, the inclusion of three lysines to the original peptide sequence changes the overall charge of the original peptide, but does not alter the function of the original peptide.

In a particular embodiment, the functional analogue has at least 50% identity to the original amino acid sequence. In another embodiment, the functional analogue has at least 80% identity to the original amino acid sequence. In yet another embodiment, the functional analogue has at least 85% identity to the original amino acid sequence. In still another embodiment, the functional analogue has at least 90% identity to the original amino acid sequence.

b. FMDV Endogenous T Helper (Th) Epitopes

Compositions containing synthetic immunogen peptides can include FMDV endogenous Th epitope peptides. The presence of Th epitopes in pharmaceutical/vaccine formulations prime the immune response in treated animals by initiating antigen specific T cell activation, a critical correlate for FMDV protection. Additionally, formulations that include carefully selected immunodominant Th epitopes present on FMDV proteins can produce broad cell mediated immunity, which makes the formulations effective in treating and protecting animals having diverse genetic makeups, such as cattle.

Animals immunized with a single administration of formulations containing immunogen peptides with B cell epitopes in combination with T helper epitope peptides from FMDV proteins are able to trigger lymphocyte proliferative responses upon subsequent exposure to FMDV from either a natural infection or an FMDV challenge test. The proliferative responses lead to cytokine production, including IFN-γ production, which enhances cell-mediated immune responses to a variety of cytopathic viral infections in animals.

The Th epitope peptides of SEQ ID NOs: 34-63 were identified using in vitro T cell proliferation assays and by evaluating in vivo and in vitro cytokine IFN-γ production in host animals immunized with FMD formulations/vaccines containing the Th epitopes. Additionally, formulations containing (a) FMDV B epitope cluster VP1 peptides and (b) large pool combinations of the FMDV endogenous Th peptides were analyzed to determine the appropriate pharmaceutical composition capable of effectively and consistently producing the necessary cellular immunity in a variety of host animals having a diverse genetic background, such as cattle. In addition to monitoring the in vitro IFN-γ production in immunized/vaccinated hosts, neutralizing antibody titers were also evaluated to determine if these hosts were capable of mounting neutralizing antibodies against FMDV with only a single administration of the formulation.

In various embodiments, FMDV endogenous Th epitope peptides are derived from antigenic segments of FMDV proteins VP1, VP2, VP3, VP4, 2A, 2B, 3A, 3B and 3D. Table 4 identifies specific FMDV endogenous Th peptides (SEQ ID NOs: 34-63) that were found to be particularly useful when used in formulations of the present invention. Specifically, the FMDV endogenous Th epitopes listed in Table 4 are recognized by swine and cattle T cells obtained from hosts immunized with (a) FMDV viral lysate formulations/vaccines and (b) peptide formulations containing FMDV candidate Th peptides. The distribution and location of the Th epitopes on the FMDV VP1, VP2, VP3, VP4, 2A, 2B, 2C, 3A, 3B, and 3D proteins (listed in Table 4), relative to other regions and proteins of FMDV, are shown in FIG. 1. The protein sequences are based on the sequence of FMDV $O_{Taiwan\ 99}$ genome/encoded amino acid sequence) (GenBank Accession No. AJ539137).

Homologues of the Th epitopes identified in Table 4 are also effective and included in the present invention. For example, SEQ ID NOs: 64-78 are homologous Th epitope sequences from FMDV $O_{TAW/2/99}$ (Genbank Accession No. AJ539137). Table 5 provides sequence alignments of comparing the Th epitopes from FMDV O$_{Taiwan/99}$ with homologous Th epitopes from FMDV O$_{TAW/2/99}$. Specifically, Table 5 aligns homologous Th epitopes from FMDV 3D protein (SEQ ID NOs: 61 vs 64; 62 vs 65; 63 vs 66; 60 vs 71 and 72); FMDV 2B protein (SEQ ID NOs: 48 vs 67 and 68), FMDV 3A protein (SEQ ID NOs: 53 vs 69 and 70), FMDV VP4 protein (SEQ ID NOs: 34 vs 73 and 74), FMDV VP2 protein (SEQ ID NOs: 36 vs 75 and 76), and FMDV VP3 protein (SEQ ID NOs: 37 vs 77 and 78).

Immunologically functional analogues of the FMDV endogenous Th epitope peptides are also effective and included as part of the present invention. Immunologically functional analogues includes variants of SEQ ID NOs: 34-63 and/or homologues of SEQ ID NOs: 64-78 that retain substantially the same immunogenicity as the original peptide. For example, variants that are functional analogues can have a conservative substitution in an amino acid position; a change in overall charge; a covalent attachment to another moiety; or amino acid additions, insertions, or deletions; and/or any combination thereof.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In a particular embodiment, the functional analogue has at least 50% identity to the original amino acid sequence. In another embodiment, the functional analogue has at least 80% identity to the original amino acid sequence. In yet another embodiment, the functional analogue has at least 85% identity to the original amino acid sequence. In still another embodiment, the functional analogue has at least 90% identity to the original amino acid sequence.

In one embodiment, the immunologically functional analogue of a particular peptide contains the same amino acid sequence as the original peptide and further includes three lysines (Lys-Lys-Lys) added to the amino terminus of the peptide. In this embodiment, the inclusion of three lysines to the original peptide sequence changes the overall charge of the original peptide, but does not alter the function of the original peptide.

Table 6 identifies another variation of a functional analogue for Th epitope peptide. In particular, SEQ ID NOs: 39 and 40 are functional analogues of each other because they differ only by the deletion (SEQ ID NO: 39) or the inclusion (SEQ ID NO: 40) of four amino acids at the C-terminus. The differences between these two analogous sequences would not affect the function of the Th epitopes contained within these sequences.

In other variations, FMDV endogenous Th epitope peptides can be presented as a combinatorial sequence, which contains a mixture of amino acid residues represented at specific positions within the peptide framework based on the variable residues of homologues for that particular peptide. An assembly of combinatorial peptides can be synthesized in one process by adding a mixture of the designated protected amino acids, instead of one particular amino acid, at a specified position during the synthesis process. Such combinatorial FMDV endogenous Th peptide assemblies can allow broad Th epitope coverage for animals having a diverse genetic background. Representative combinatorial sequences of FMDV endogenous Th peptides include SEQ ID NOs: 79-87, which are shown in Table 7. These combinatorial sequences are derived from SEQ ID NOs: 34-63 (shown in Table 4) for the representative FMDV endogenous Th epitopes.

In various embodiments, T cell immunogenicity can be enhanced by linking multiple FMDV endogenous Th epitope sequences together in a single peptide. The Th epitope sequences that are linked together can be the same Th epitope sequence (to create a peptide having a repeating Th epitope sequence); different Th epitope sequences (to create a peptide having a variety of Th epitope sequences); or combinations thereof. Additionally, Th epitope sequences can be linked together with a spacer or without a spacer. In certain embodiments a spacer is used to facilitate the intracellular cleavage of a peptide containing multiple FMDV Th epitopes as single sequence at the appropriate location. In some embodiments the spacer contains an amino acid. In a preferred embodiment, the spacer is lysine.

Th epitope peptides of the present invention provide broad reactivity and immunogenicity to animals from genetically diverse populations of target animal species. Peptides found to be particularly useful in formulations of the present invention include peptides containing a cluster of multiple FMDV Th epitopes, such as SEQ ID NOs: 34-78, and peptides containing a combinatorial sequence of Th epitope sequences, such as SEQ ID NOs: 79-87. In certain embodiments, FMDV endogenous Th epitope cluster peptides can further enhance the T cell immunogenicity by linking the Th epitopes to an artificial Th (UBITh®) (SEQ ID NO: 24) as shown in Table 7 (SEQ ID NOs: 88-95).

c. Spacer

Synthetic FMDV peptide immunogens, including homologues and analogues thereof, can be covalently linked, with or without a spacer, to a peptide containing a sequence known to contain a Th epitope. The linked peptides can offer enhanced immunogenicity over the equivalent immunogens that are not covalently linked to Th epitope peptides.

In some embodiments, a peptide containing an artificial Th epitope is covalently linked to the N-terminus of a synthetic FMDV peptide immunogen. In some variations, a spacer is present between the two sequences. Preferably, the spacer is the single amino acid εNLys. In a specific embodiment, the artificial Th epitope peptide of SEQ ID NO: 24 is covalently linked to the N-terminus of the synthetic FMDV peptide immunogen of SEQ ID NO: 2 through an εNLys spacer (also shown in Table 3 as SEQ ID NO: 25). Additional exemplary peptides containing a Th epitope sequence covalently linked to the amino terminus of a synthetic FMD peptide immunogen are shown in Table 3. In particular, Th epitope peptide SEQ ID NO: 24 is linked to the amino terminus of various synthetic FMDV peptide immunogens through a –εNLys spacer (SEQ ID NOs: 25 to 33).

d. Compositions

The present disclosure is also directed to compositions containing synthetic peptides. The compositions can be used for the detection, treatment, and/or prevention of FMD in an animal. In certain embodiments, compositions containing synthetic peptides having FMDV B cell epitopes are used for detecting the presence of antibodies to FMDV in a sample. In other embodiments, compositions containing synthetic peptides having FMDV B cell epitopes are pharmaceutical compositions for treating and/or preventing FMD infection in an animal. In certain embodiments, a pharmaceutical composition containing synthetic peptides having FMDV B cell epitopes is used to elicit an immune response to FMDV in an animal. Pharmaceutical composition containing synthetic peptides having FMDV B cell epitopes can be used as a vaccine for FMDV.

Pharmaceutical compositions containing synthetic FMDV peptide immunogens efficiently elicit functional antibodies against target FMD proteins to provide animals with protection from FMD challenge. In fact, animals that receive only a single administration of these pharmaceutical compositions are sufficiently and adequately protected against FMD infection. Thus, multiple administrations or booster doses are not required to provide animals with full protection from FMD infection. Accordingly, pharmaceutical compositions containing synthetic FMDV peptide immunogens qualify as emergency vaccines according to OIE guidelines.

Compositions of the present disclosure can contain one or more synthetic FMDV peptide immunogens. For example, the compositions can contain synthetic FMDV peptide immunogens having the consensus sequence (SEQ ID NOs: 1 or 2) shown in Table 1, and/or homologues or analogues thereof as shown in Table 2, and/or combinations thereof. Additionally, the FMDV peptide immunogens used in the compositions can be linked to an artificial combinatorial T helper epitope to enhance the B cell immunogenicity of the compositions. In a preferred embodiment, synthetic FMDV peptide immunogens are linked to an artificial combinatorial T helper epitope of SEQ ID NO: 24. Representative FMDV VP1 peptide immunogens from various serotypes are identified in Table 3.

Compositions containing FMDV peptide immunogens can also contain one or more FMDV endogenous Th epitope peptides. For example, the compositions can include Th epitope peptides derived from FMDV VP1, VP2, VP3, VP4, 2A, 2B, 2C, 3A, 3B, and 3D proteins. Th epitope peptides found to be particularly useful in compositions include the peptides shown in Tables 4, 5, 6, and 7 (SEQ ID NOs: 34-95) and in Tables 18, 19, 25, and 26 described in Examples 9 and 10). Pharmaceutical compositions, including vaccine formulations, can elicit FMDV-specific antibody responses and trigger the onset of peptide antigen specific T cell reaction that protect swine and cattle against FMDV infection with just a single administration.

Additionally, compositions can contain carriers and/or other additives in a pharmaceutically acceptable delivery system. Accordingly, a composition containing the synthetic FMDV peptide immunogens can be formulated as a pharmaceutical vaccine formulation using adjuvants, pharmaceutically-acceptable carriers or other ingredients routinely provided in vaccine formulations. Among the ingredients that can be used in this invention are adjuvants or emulsifiers including alum, incomplete Freund's adjuvant, liposyn, saponin, squalene, L121, Emulsigen, monophosphoryl lipid A (MPL), QS21, ISA 35, ISA 206, ISA50V2, and ISA 720 as well as the other efficacious adjuvants and emulsifiers. In a particular embodiment, the delivery vehicle and adjuvant is Montanide™ ISA 50V2 (an oil vaccine adjuvant composition comprised of vegetable oil and mannide oleate for production of water-in-oil emulsions), Tween® 80 (also known as: Polysorbate 80 or Polyoxyethylene (20) sorbitan monooleate), a CpG oligonucleotide, and/or any combination thereof. In another embodiment, the pharmaceutical composition is a water-in-oil-in-water (i.e. w/o/w) emulsion with Emulsigen or Emulsigen D as the adjuvant (as described in Example 9, Table 19 for Groups 27, 28, 31, and 32). Also provided are other ingredients routinely incorporated with vaccine formulations, and instructions for dosage (Examples 9 and 10) such that a balanced B and T cell immune response can be mounted upon single administration and offer protection upon viral challenges.

Pharmaceutical compositions can be formulated as immediate release or for sustained release formulations. Additionally the pharmaceutical compositions can be formulated for induction of systemic, or localized mucosal, immunity through immunogen entrapment and coadministration with microparticles. Such delivery systems are readily determined by one of ordinary skill in the art.

Various vaccine formulations containing peptides of the present disclosure are effective for protecting hoofed animals against FMDV. For example, a pharmaceutical composition that is useful as an FMDV vaccine formulation, contains a synthetic FMDV peptide immunogen and a veterinarily acceptable delivery vehicle or adjuvant, wherein the synthetic FMDV peptide immunogen has an amino acid sequence selected from the group consisting of:
  a) SEQ ID NOs: 1-2;
  b) a homologue of (a);
  c) an antigenically and immunologically functional analogue of (a) or (b),
  d) (a), (b), or (c) having at least one conservative amino acid substitution, amino acid addition, and/or amino acid deletion; and
  e) any combination of (a)-(d).

In a specific formulation, the synthetic FMD peptide immunogen is selected from the group consisting of SEQ ID NOs: 2, 7, and 8.

In another formulation, the composition contains a synthetic FMDV peptide immunogen linked to an artificial combinatorial Th peptide through a spacer, and has the sequence of SEQ ID NO: 25.

Other formulations further contain an equal ratio by weight of thirty FMDV Th epitope peptides of SEQ ID NOs: 34 to 63 present in an amount between about 0.1 µg to about 1 mg per dose. In a specific formulation, the amount of the equal ratio by weight of SEQ ID NOs: 34 to 63 is between about 1 µg to about 100 µg per dose.

In yet another formulation, the composition comprises a mixture of synthetic FMDV peptide antigens of SEQ ID NOs: 25, 27, and 28 and a pool with equal ratio by weight of FMDV endogenous Th epitope peptides of SEQ ID NOs: 34 to 63, in a veterinarily acceptable delivery vehicle or adjuvant, wherein the amount of peptide antigen is between about 10 µg to about 1 mg per dose.

e. Administration

Pharmaceutical compositions and vaccine formulations can be administered by any convenient route including subcutaneous, oral, intramuscular, or other parenteral or enteral routes. Similarly the vaccines can be administered as a single dose or multiple doses. Immunization schedules are readily determined by the ordinarily skilled artisan.

The pharmaceutical compositions are formulated to contain an effective amount of synthetic peptide immunogens and a pharmaceutically acceptable carrier. The pharmaceutical compositions are also formulated in a suitable dosage unit form generally containing from about 0.5 µg to about 1 mg of the immunogen per kg body weight. When delivered in multiple doses, the pharmaceutical compositions may be conveniently divided into an appropriate amount per dosage unit form. The administered dosage will depend on the age, weight and general health of the subject as is well known in the vaccine and therapeutic arts.

Pharmaceutical compositions containing synthetic FMDV peptide immunogens, such as vaccine formulations, can produce an effective response even when provided in a single administration. A single administration of these pharmaceutical compositions is sufficient to prime animals having a diverse population of T helper cells including swine, cattle, sheep, goats and other susceptible wild species. In particular, pharmaceutical compositions containing the synthetic FMDV peptide immunogens in combination with Th epitope peptides, can elicit balanced B (neutralizing antibodies) and T cell (cytokine release, etc.) immune responses to protect animals from subsequent viral challenges.

Single administration immunizations using formulations containing synthetic FMDV peptide immunogens in combination with Th epitope peptides were extensively evaluated according to OIE, Taiwan and PRC guidelines (discussed further in Examples 9 and 10). The results that were obtained from these tests repeatedly and reproducibly demonstrated the efficacy of these formulations in protecting immunized hosts against FMD infection. Accordingly, these tests validated the design of the FMDV formulation as well as the ability to use the FMDV formulation as an emergency FMDV vaccine in animals.

f. Methods for Manufacturing

The present disclosure is also directed to methods for manufacturing the synthetic FMDV peptide immunogens, Th epitope peptides, compositions and pharmaceutical formulations/vaccines for eliciting immune responses and protecting animals against FMDV infection.

Using the synthetic FMDV peptide immunogens provides a number of significant advantages over traditional inactivated virus vaccines. For example, traditional inactivated virus vaccines can require expensive biological containment equipment pose serious biohazardous risks to individuals working directly in the laboratory as well as the public in the event that containment equipment/protocols fail. In contrast, no biohazardous materials are used in the manufacture of peptide antigens, which drastically reduces health and safety risks and eliminates the need for expensive biological containment equipment. Also, site-specific immunogens present high molar concentrations of selected epitopes, which helps to ensure the safety and immunopotency of the vaccine employing FMDV antigenic peptide.

Additionally, the use of defined synthetic peptides having known B cell and Th epitopes as immunogens eliminates undesired non-FMDV-specific immune responses caused by the presence of antigenic materials originating from FMDV-infected or recombinant virus-infected host cells or from recombinant protein expression systems that may be co-purified with FMDV and/or recombinant proteins, when these reagents are used as the immunogenic ingredients of a vaccine. For example, sera from pigs may have antibodies to host cells, or to recombinant *Escherichia coli*, yeast or baculovirus, which can be cross-reactive with the antigenic materials used in diagnostic tests based on the biologically derived antigens. Such immune responses generated by vaccines having these extraneous immunogens as ingredients will be non-protective. In contrast, pigs or cattle receiving the presently described synthetic FMDV peptide vaccine of will generate focused immune responses devoid of untoward antibodies or other immune responses to proteins originating from host cells or expression vectors.

Furthermore, an inconsistency or error that may be introduced during the production of inactivated viruses can prevent an appropriate and/or desired immune response in a treated animal. However, inconsistencies and/or errors might be introduced during the synthesis of long synthetic FMDV peptide immunogens most often do not hinder or prevent a desired immune response in a treated animal. In fact, inconsistencies/errors that might be introduced during the peptide synthesis generate multiple peptide analogues along with the targeted peptide syntheses. These analogues can include amino acid insertion, deletion, substitution, and premature termination. As described above, such peptide analogues are suitable in peptide preparations as contributors to antigenicity and immunogenicity when used in immunological application either as solid phase antigen for purpose of immunodiagnosis or as immunogens for purpose of vaccination.

During 25 years of experience in immunological applications of synthetic peptides, the applicant has found that the range in structural variability that allows for retention of an intended immunological activity is far more accommodating than the range in structural variability allowed for retention of a specific drug activity by a small molecule drug or the desired activities and undesired toxicities found in large molecules that are co-produced with biologically-derived drugs. Thus, peptide analogues, either intentionally designed or inevitably produced by errors of the synthetic process as a mixture of deletion sequence byproducts that have chromatographic and immunologic properties similar to the intended peptide, are frequently as effective as a purified preparation of the desired peptide. Designed analogues and unintended analogue mixtures are effective as long as a discerning QC procedure is developed to monitor both the manufacturing process and the product evaluation process so as to guarantee the reproducibility and efficacy of the final products employing these peptides.

In view of the advantages described above, peptides described in the present disclosure can be readily synthesized using standard techniques, such as the solid phase method of synthesis and the myriad of available improvements on that process (Moore, V, 1992). The peptides can also be made using recombinant DNA technology including nucleic acid molecules, vectors, and/or host cells. As such, nucleic acid molecules encoding the FMDV B cell and T cell epitope cluster antigenic peptide and immunologically functional analogues of the FMDV B cell epitope cluster antigenic peptide and compliments thereof are also encompassed by the present disclosure as part of the present invention. Similarly, vectors, including expression vectors, comprising nucleic acid molecules as well as host cells containing the vectors are also encompassed by the present disclosure as part of the present invention.

Various exemplary embodiments also encompass methods of producing the FMDV antigenic peptides and immunologically functional analogues of the FMDV antigenic peptides. For example, methods can include a step of incubating a host cell containing an expression vector containing a nucleic acid molecule encoding an FMDV antigenic peptide and/or immunologically functional analogue thereof under such conditions where the peptide and/or analogue is expressed.

Additionally, peptides can be produced by solid-phase synthesis. The quality of peptides produced by this chemical process can be controlled and defined and, as a result, reproducibility of antigenicity, immunogenicity and yield can be assured.

g. Specific Embodiments

Specific embodiments of the present invention include, but are not limited to, the following:

(1) A foot and mouth disease (FMD) vaccine composition, comprising
 a) a synthetic FMDV VP1 peptide antigen;
 b) a synthetic FMDV T helper epitope peptide; and
 c) a veterinarily acceptable delivery vehicle or adjuvant, wherein the FMDV VP1 peptide antigen in (a) comprises an amino acid sequence selected from the group consisting of:
  i) SEQ ID NOs: 1 or 2;
  ii) a homologue of (a); and
  iii) any combination of (a) or (b),
and wherein the synthetic FMDV T helper epitope peptide in (b) is not covalently linked to the peptide antigen in (a).

(2) The FMD vaccine according to 1, wherein the peptide antigen in (a) comprises the amino acid sequence of SEQ ID NO: 1.

(3) The FMD vaccine according to 1, wherein the peptide antigen in (a) comprises the amino acid sequence of SEQ ID NO: 2.

(4) The FMD vaccine according to 1, wherein the homologue in (b) is a homologue of SEQ ID NO: 2 comprising the amino acid sequence selected from the group consisting of SEQ ID NOs: 3 to 23.

(5) The FMD vaccine according to 1, wherein the peptide antigen in (a) is covalently linked on the amino- or carboxyl-terminus to a peptide comprising a Th epitope sequence.

(6) The FMD vaccine according to 5, wherein the Th epitope sequence is SEQ ID NO: 24.

(7) The FMD vaccine according to 5, wherein the T helper epitope is covalently linked to the peptide antigen through a spacer comprising an epsilon lysine residue.

(8) The FMD vaccine according to 1, wherein the FMDV T helper epitope peptide in (b) is selected from the group consisting of SEQ ID NOs: 34 to 95 and combinations thereof.

(9) The FMD vaccine according to 1, wherein the total amount of peptide antigen in (a) is between about 10 µg to about 1 mg per dose.

(10) The FMD vaccine according to 1, wherein the delivery vehicle or adjuvant is selected from the group consisting of Montanide ISA 50V, Polyoxyethylene (20) sorbitan monooleate, Emulsigen, Emulsigen D, and a CpG oligonucleotide.

(11) A foot and mouth disease (FMD) vaccine composition, comprising
  a) a synthetic FMDV VP1 peptide antigen selected from the group consisting of SEQ ID NOs: 25-33 and combinations thereof;
  b) a synthetic FMDV T helper epitope peptide selected from the group consisting of SEQ ID NOs: 34-95; and
  c) a veterinarily acceptable delivery vehicle or adjuvant.

(12) The FMD vaccine of 11, wherein the peptide antigen in (a) is SEQ ID NOs: 25, 27, 28, 29 and/or combinations thereof.

(13) The FMD vaccine of 11, wherein the FMDV T helper epitope peptide in (b) is SEQ ID NOs: 34-63, 90, and combinations thereof.

(14) The FMD vaccine of 11, wherein the peptide antigen in (a) is SEQ ID NOs: 25, 27, 28, 29 and/or combinations thereof, and wherein the FMDV T helper epitope peptide in (b) is SEQ ID NOs: 34-63, 90, and combinations thereof.

(15) A method for eliciting an immune response in an animal comprising providing a single administration of a pharmaceutically effective amount of the vaccine in 14 to the animal.

(16) The method of 15, wherein the animal is a pig.

(17) A method for protecting an animal from FMD infection comprising providing a single administration of a pharmaceutically effective amount of the vaccine in 14 to the animal.

(18) The method of 17, wherein the animal is a pig.

(19) The FMD vaccine of 11, wherein the peptide antigen in (a) is SEQ ID NOs: 25, 27, 28, 29, 31, and/or combinations thereof

(20) A method for eliciting an immune response in an animal comprising providing a single administration of a pharmaceutically effective amount of the vaccine in 19 to the animal.

(21) The method of 20, wherein the animal is a cow.

(22) A method for protecting an animal from FMD infection comprising providing a single administration of a pharmaceutically effective amount of the vaccine in 19 to the animal.

(23) The method of 22, wherein the animal is a cow.

(24) The FMD vaccine of 11, wherein the peptide antigen in (a) is SEQ ID NOs: 26, 30, 32, 33, and/or combinations thereof

(25) The FMD vaccine of 11, wherein the FMDV T helper epitope peptide in (b) is SEQ ID NOs: 91-95, and combinations thereof.

(26) The FMD vaccine of 11, wherein the peptide antigen in (a) is SEQ ID NOs: 26, 30, 32, 33, and/or combinations thereof, and wherein the FMDV T helper epitope peptide in (b) is SEQ ID NOs: 91-95, and combinations thereof.

(27) A method for eliciting an immune response in an animal comprising providing a single administration of a pharmaceutically effective amount of the vaccine in 26 to the animal.

(28) The method of 27, wherein the animal is a cow.

(29) A method for protecting an animal from FMD infection comprising providing a single administration of a pharmaceutically effective amount of the vaccine in 26 to the animal.

(30) The method of 29, wherein the animal is a cow.

The following examples serve to illustrate the present invention and are not to be used to limit the scope of the invention.

EXAMPLE 1

Synthesis of FMDV Peptides

Methods for synthesizing FMDV peptides that were included in pharmaceutical compositions are described. The peptides can be synthesized in small-scale amounts, which are useful for laboratory pilot and field studies, as well as large-scale (kilogram) amounts, which are useful for industrial/commercial production of vaccine and assay formulations.

A large repertoire of FMDV antigenic peptides representing both FMDV B and T cell epitope cluster sites from the FMDV VP1, VP2, VP3, VP4, 2A, 2B, 2C, 3A, 3B, and 3D proteins having sequences with lengths from approximately 10 to 70 amino acids were designed. For some peptides, an amino acid substitution was made at a suitable site to allow formation of a cyclic peptide to exert constraint for local structure preservation so as to maximize the cross-reaction with the corresponding native protein (e.g., substitution to a cysteine residue). Representative FMDV antigenic peptides are identified in Table 2 (SEQ ID NOs: 1-23).

Also synthesized were antigenic peptides linked to an artificial combinatorial Th peptide to enhance the respective immunogenicities of each peptide. Representative FMDV antigenic peptides linked to the combinatorial Th peptide of SEQ ID NO: 24 (UBITh®) are identified in Table 3 (SEQ ID NOs: 24-33) and Tables 7 and 8 (SEQ ID NOs: 89-102).

All peptides used for immunogenicity testing were synthesized using Applied BioSystems Peptide Synthesizer Models 430A, 431 and 433, using Fmoc chemistry. Each peptide was produced by an independent synthesis on a solid-phase support, with Fmoc protection at the N-terminus and side chain protecting groups of trifunctional amino acids. Completed peptides were cleaved from the solid support and side chain protecting groups were removed by 90% trifluoroacetic acid. Synthetic peptide preparations were evaluated by Matrix-Assisted Laser Desorption Time-Of-Flight (MALDTOF) Mass Spectrometry to ensure correct amino acid content. Synthetic peptides were also evaluated by Reverse Phase HPLC to confirm the synthesis profile and concentration of the preparation.

Despite rigorous control of the synthesis process (including monitoring the coupling efficiency), peptide analogues were also produced due to unintended events during elongation cycles, including amino acid insertion, deletion, substitution, and premature termination. Thus, synthesized preparations typically included multiple peptide analogues along with the targeted peptide. Despite the inclusion of such unintended peptide analogues, the resulting synthesized peptide preparations were nevertheless suitable for use in immunological applications including immunodiagnosis (as antibody capture antigens) and vaccination (as peptide immunogens). Typically, such peptide analogues, either intentionally designed or generated through synthetic process as a mixture of byproducts, are frequently as effective as a purified preparation of the desired peptide, as long as a discerning QC procedure is developed to monitor both the manufacturing process and the product evaluation process to guarantee the reproducibility and efficacy of the final product employing these peptides.

All peptides were subjected to labor intensive and time sensitive serological or in vitro IFN-γ production screening processes (including iterative cycles of peptide synthesis, vaccine formulation, animal immunization) and serological and in vitro IFN-γ production testing to yield candidate peptides for further testing in target animals for respective diagnostic and vaccine applications. Specific formulations used in various examples are described below.

EXAMPLE 2

Assays and Reagents

Assays and reagents for evaluating synthetic peptides and formulations of the present invention were developed and described below.

a. FMDV VP1 (aa134-168) or VP1 (aa129-168) Peptide-Based ELISAs

ELISA assays for evaluating various samples described in the following Examples were developed and described below.

The wells of 96-well plates were coated individually for 1 hour at 37° C. with 100 μL of individual target peptides, at 2 μg/mL (unless noted otherwise), in 10 mM NaHCO$_3$ buffer, pH 9.5 (unless noted otherwise).

The peptide-coated wells were incubated with 250 μL of 3% by weight of gelatin in PBS in 37° C. for 1 hour to block non-specific protein binding sites, followed by three washes with PBS containing 0.05% by volume of TWEEN® 20 and dried. Sera to be analyzed were diluted 1:20 (unless noted otherwise) with PBS containing 20% by volume normal goat serum, 1% by weight gelatin and 0.05% by volume TWEEN® 20. One hundred microliters (100 μL) of the diluted specimens were added to each of the wells and allowed to react for 60 minutes at 37° C.

The wells were then washed six times with 0.05% by volume TWEEN® 20 in PBS in order to remove unbound antibodies. Horseradish peroxidase-conjugated goat anti-swine IgG was used as a labeled tracer to bind with the antibody/peptide antigen complex formed in positive wells. One hundred microliters of the peroxidase-labeled goat anti-swine IgG at a pre-titered optimal dilution and in 1% by volume normal goat serum with 0.05% by volume TWEEN® 20 in PBS, was added to each well and incubated at 37° C. for another 30 minutes. The wells were washed six times with 0.05% by volume TWEEN® 20 in PBS to remove unbound antibody and reacted with 100 μL of the substrate mixture containing 0.04% by weight 3', 3', 5',5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 μL of 1.0M H$_2$SO$_4$ and absorbance at 450 nm (A$_{450}$) determined.

Serum dilutions were done in accordance with the purpose for detecting FMDV antibodies in the animal sera: (a) For identification of potential natural infection, a dilution of 1:20 was used, the A$_{450}$ reading was recorded, and a built-in intrinsic negative control for cutoff calculation was used; or (b) For the determination of antibody titers of pigs that received peptide-based FMDV vaccine formulations, 10-fold serial dilutions of sera from 1:10 to 1:10,000 were tested, and the titer of a tested serum, expressed as Log$_{10}$, was calculated by linear regression analysis of the A$_{450}$ with the cutoff A$_{450}$ set at 0.5. Detection of isotype-specific anti-FMDV antibodies (e.g. IgG1, IgG2 and IgA) in sera were measured, when necessary, using monoclonal antibodies specific for these isotypes supplied by Serotec. Antibody titers were similarly determined as described above.

FMDV VP1 B cell epitope cluster peptides (SEQ ID NOs: 1-23), at 2 μg/mL using 100 μL per well in 10 mL NaHCO$_3$ buffer, pH 9.5, were used as the coating antigens in the respective VP1 ELISAs.

b. Non-Structural Protein 3B Peptide-Based ELISAs

ELISAs for serum antibody reactivity with FMDV non-structural (NS) protein 3B were performed as previously reported (Wang, C Y et al 2001) at a dilution of 1:21. Sera from peptide-immunized and negative bovine controls were included in each test. Results obtained are reported in OD units after subtraction of the cutoff OD value (generally 0.220 OD).

This FMDV NS 3B peptide-based ELISA assay is capable of differentiating vaccinated animals from infected animals. Specifically, vaccinated and infected animals can be distinguished based on whether sera obtained from the animal reacts to non-structural FMDV proteins. In particular, sera obtained from animals immunized with vaccine formulations of the present disclosure do not react with the non-structural FMDV proteins because the vaccine formulations only contain epitopes from the structural protein VP1. Thus, only sera samples obtained from infected animals react with non-structural FMDV proteins.

c. Differentiation of Infected from Vaccinated Animals (DIVA) Diagnostic System

Use of FMDV NS 3B peptide-based ELISAs combined with serotype specific FMDV VP1 peptide-based ELISAs provides a valuable and convenient tool for (1) distinguishing infected from vaccinated animals and (2) identifying the particular serotype of FMDV that the animal is infected with or vaccinated against. Accordingly, this combination of ELISA assays provides a convenient and valuable assessment of FMDV vaccine efficacy upon viral challenges through serological means.

d. Immunogenicity Evaluation

Animals were immunized according to methods described in Examples below. Following the administration of the vaccine formulations, blood samples were obtained and the immunogenicity was evaluated.

Specifically, samples from immunized animals were obtained at 0, 3, and 5 weeks post initial immunization (wpi) for cattle and at 0, 4, and 6 wpi for pigs. The samples were heated at 56° C. for 30 minutes to inactivate serum complement factors. Immunogenicity of the formulations containing the synthetic peptides was evaluated by peptide-based ELISAs using corresponding FMDV VP1 antigenic peptides as the solid phase antigen as described above. Serially diluted experimental animal sera were tested and positive titers were expressed as $Log_{10}$ of the reciprocal dilution.

Seropositive samples were pooled by group and the neutralization activity was determined for various isolates of FMDV as described below.

e. FMDV Viruses

Animals were subjected to challenge studies (discussed in Examples below) using various strains of FMDV, including FMDV $A_{12}$ and $A_{24}$ of serotype A; $O_1$, $O_2$, $O_{Taiwan}$, $O_{Ozk}$, $O_{Myanmar}$, of serotype O; Asia $1_{XJ}$ strain; etc. The FMDV strains used in these experiments were grown in monolayers of baby hamster kidney (BHK) cells, and purified under containment at the Plum Island Animal Disease Center, USDA (Greenport, N.Y.) and/or National Institute of Animal Health, Taiwan (NIAHT). Virus was also obtained for industry use from PRC's Ministry of Agriculture reference laboratory, Lanzhou Veterinary Research Institute of the Chinese Academy of Agriculture Sciences, essentially as described previously (Brown 1963), with a treatment of the pellet by either 1% SDS or 1% Nonidet P-40 before centrifugation through a 15-45% sucrose gradient.

Purified virus peaks were identified and isolated by pumping the contents of each centrifuge tube through the flow cell of a spectrophotometer set at 260 nm.

f. Serological Evaluation of FMDV Neutralization Activity as Neutralization Index Serum samples were processed from blood obtained from animals and kept at −20° C. until tested. Enumeration of the viruses neutralized by a 1:100 dilution of serum samples was accomplished by neutralization determinations on a series of increasing input viral loads, using aliquots (10,000 $MPD_{50}$) of the various serotypes prepared as described above.

Sera samples were evaluated using methods described previously (Morgan 1990). Samples that displayed a 2.5 $Log_{10}$ reduction of FMDV microplaques at 1:100 dilution were considered to be highly predictive of protective immunity against FMDV infection.

g. FMDV-Specific Neutralizing Antibody Assay: A Standard Beta Neutralization Test A standard beta neutralization test was performed in 96-well plates by incubating serial two-fold dilutions of each serum with 100 or 200 $TCID_{50}$ (50% Tissue Culture Infectious Dose) of FMDV for 30 min at 37° C. Remaining viral activity was determined in 96-well plates containing fresh monolayers of BHK-21 cells. Serum neutralization titers were determined as the $log_{10}$ serum dilution neutralizing 50% of the virus inoculum.

For example, the quantitative assay for antibodies that neutralize FMDV $O_{1\ Taiwan}$ was performed against BHK-21 cells in flat-bottomed microtiter plates using equal volumes of 200 µl. Fifty microliters (50 µl) of pre- and post-immunization diluted serum was collected from the individual experimental animals. These sera were separately mixed with a 50 µl aliquot containing 200 $TCID_{50}$ of FMDV $O_{1\ Taiwan}$ and incubated for one hour at 37° C. One hundred microliters (100 µl) of culture medium (MEM (Gibco) supplemented with 10.0% fetal bovine serum) containing $2.5 \times 10^5$ BHK-21 cells was then added to each assay. Cultures were examined microscopically after 48 hours for cytopathic effect (CE). Titers were expressed as the reciprocal of the final dilution of serum giving 50% inhibition of the 200 $TCID_{50}$ virus-induced CE.

h. Animals Used in the Immunogenicity Studies

Guinea Pigs: Immunogenicity studies were conducted in mature, naïve, adult male and female Duncan-Hartley Guinea Pigs (300-350 g/BW). The experiments utilized 3 guinea pigs per group.

Pigs of approximately 4 to 12 weeks of age from a specific pathogen-free (SPF) farm were ear marked for immunogenicity studies and divided into groups containing 3 to 5 piglets/group according to study protocol.

Cattle: Immunogenicity studies were conducted in healthy steers between 2 to 6 months of age that were obtained from local providers and divided into groups containing 3 to 5 cows/group according to study protocol. Animals used in a viral challenge study were housed in a biosafety level-3-agriculture containment facility and were allowed to acclimatize for 1 week prior to initiation of the study.

Goats: Immunogenicity studies were conducted in healthy goats obtained from local providers.

Prior to immunization, serum samples from individual animals were tested for the presence of FMDV-specific neutralizing antibodies to confirm that the animals had not been previously vaccinated or infected with FMDV. Sera from these animals were also evaluated using the ELISA assays for NS 3B and FMDV VP1 described above to further ensure that the animals were free of antibodies to these proteins as well.

Each animal was immunized with 25 to 300 µg per dose of the vaccine, depending on species and protocol.

i. Compositions

Pharmaceutical compositions and vaccine formulations used in each experiment are described in greater detail in the Examples described below. Briefly, the formulations specified in each of the study groups generally contained: (1) a single VP1 B cell epitope cluster peptide immunogen selected from SEQ ID NOs: 1-23, 25-32; (2) a mixture of VP1 B cell epitope cluster peptide immunogens including homologues selected from SEQ ID NOs: 1-23, and 25-32; or (3) a mixture of VP1 B cell epitope cluster peptide immunogens selected from SEQ ID NOs: 1-23 and 25-32 supplemented with a mixture of FMDV endogenous Th epitope cluster peptides selected from SEQ ID NOs: 33-92. The peptides were emulsified in a specific adjuvant formulation. Vaccines were usually prepared by dissolving the synthetic FMDV peptide immunogens in water at about 25 to 300 µg/mL and formulated with Seppic Montanide ISA 50V2 into water-in-oil (w/o) emulsions (1:1 in volume). The vaccine formulations were kept at room temperature for about 30 min and vortexed for about 10 to 15 seconds prior to immunization.

Some animals were immunized with 2 doses of a specific vaccine formulation, which were administered at time 0 (prime) and 3 wpi (booster) intramuscularly (IMO). These immunized animals were then tested to evaluate the immunogenicity of the synthetic FMDV epitope immunogens present in the vaccine formulation. The remaining animals were immunized with a single dose of a specific vaccine formulation to assess whether the peptides used in the formulation were capable of efficiently mounting a respectable neutralizing antibody response to qualify as an emergency vaccine for FMDV.

EXAMPLE 3

T Cell Functional Assays for Screening and Identification of FMDV Endogenous TH Epitope Cluster Peptides The procedures for T cell functional experiments are described in detail as follows.

a. Isolation, Freezing, and Defrosting of Peripheral Blood Mononuclear Cells (PBMCs)

Heparinized blood was collected, and PBMC were isolated by density gradient centrifugation using Ficoll-Hypaque. After two washes in phosphate-buffered saline (PBS), PBMC were resuspended in cell culture medium consisting of RPMI 1640 supplemented with 10% FCS. For some experiments, isolated PBMC were frozen, stored in liquid $N_2$, and defrosted for subsequent in vitro cultivation.

b. Serum IFN-γ Quantitation

A sandwich ELISA was used to quantitate IFN-γ in serum samples collected from pigs or cattle. The IFN-γ was quantitated before vaccination and on day 21 or 28 before the animals were challenged with FMDV. The assay was carried out by first coating individual wells of the Maxisorb ELISA plates (Nunc) with the capture antibody (purchased from PBL Biomedical Laboratories, USA) at 0.5 µg per well. Sites not occupied by the immobilized antibodies were blocked by adding 200 µl of ELISA blocking buffer into each assay well. After washing the plates 4 times each time with 200 µl of PBS containing 0.025% Tween 20 (PBS-T20), serum samples individually diluted in ELISA dilution buffer (at 1 in 10, 25 and 75) were added to the assay wells. The plates were incubated for 1 hr. at 37° C. to allow binding of the cytokine to the solid phase anti-IFN-γ capture antibody. The plates were then washed 4 times with PBS, and the detection of anti-IFN-γ antibody was added to the assay wells at 0.25 µg per well. Following incubation for 1 hr. at 37° C., the plates were washed, and 100 µl of protein A conjugate was added to each test well. Excess conjugate was washed off (6 times with PBS) after the 1 hr. incubation period, and 100 µl of the recommended substrate solution was then added for reaction detection. Color development in the individual assay well was stopped 30 min later by adding 50 µl of 1N $H_2SO_4$ to it, and color intensity was recorded by measuring absorbance at 450 nm. Results were calculated first by comparing the measured $A_{450}$ values obtained from an individual serum against a calibration graph that was constructed by assaying dilutions of a standard recombinant IFN-γ (PBL Biomedical Laboratories, USA) under the same test conditions. The IFN-γ response in the serum of each animal at 28 days post vaccination was represented by subtracting the value measured for the animal before immunization. Final results were expressed as pg/ml of serum.

c. Assay of IFN-γ Produced by PBMC

PBMCs from vaccinated animals were cultured at 2.5× $10^6$ cells/mL in individual wells of a 24 well culture plate (Nunc) in the presence of 10.0 µg of the selected vaccine immunogen composition. Negative control cultures containing PBMC alone without stimulating antigen were also included. All cultures were kept at 37° C. for 3 days in a 5.0% $CO_2$ incubator. Supernatants were collected 3 days after culture initiation, and IFN-γ contents were measured using the quantitative assay described above.

EXAMPLE 4

FMDV Challenge Procedures in Swine and Cattle Animals

The challenge procedure was, in general, based on the protocol described in the foot-and-mouth disease chapter of the OIE Manual of Standards. The FMDV strains used in the challenge procedures included: $O-1_{Taiwan(99)}$, $O-1_{Myanmar(02)}$, $O-1_{Ozk(China, 93)}$, $O-1_{Campos}$, and Asia $1_{(XJ\ or\ Jiansu,\ China,\ 05)}$. The procedure for swine challenge studies conducted in China was modified by administering the FMDV virus through intramuscular route according to Ministry of Agriculture guidelines.

a. Swine

The standardized protection infectious dose ($PD_{50}$) (i.e., the dosage when 50% of the tested animals were protected) was measured in animals. The $PD_{50}$ in swine was determined by using 15 pigs weighing around 40 kg (randomly divided into three groups each containing 5 pigs) in potency tests. The three groups were administered 1 dose, ⅓ dose and ⅑ dose of the test vaccine formulations, respectively. Modifications to the dosing were also used for assessment of a particular formulation's potency, such as dosages containing 2×, 1×, 0.5× and 0.25× dose. Additionally, rapid screening of formulations using a 1× dose was also frequently used.

For assessment of vaccine formulation efficacy, pigs were divided into groups containing 3 (instead of 5) pigs per group depending on experimental design and availability of the animals at the time for the particular study. Each pig in these three groups was inoculated behind the ears with vaccine via intramuscular (IM) route. 28 days after a single vaccination, 15 vaccinated pigs, along with 2 control pigs, were each challenged by inoculating the animals with 1,000 $ID_{50}$ of virulent virus from swine FMD O-type strain as indicated.

In an ideal experiment, vesicular lesions should have been found in at least one hoof of control pigs after 10 days of monitoring. Additionally, no FMD symptoms or signs should be observed in vaccinated pigs, otherwise the protection of vaccine fails. $PD_{50}$ of the vaccine product was calculated using the Reed-Muench Method on the basis of the results of challenge tests. Target doses of the vaccine should minimally contain 3 $PD_{50}$ in order to pass the quality release test.

In Taiwan, viral challenge was conducted through inoculation with 1×10$^5$ $TCID_{50}$, previously titered in tissue culture, of FMDV $O_{1\ Taiwan}$ virus (about at least 10 times higher than the amount of viruses administered according to the PRC guidelines) into the heel bulbs of the pigs fore legs inside the P3 facility at the National Institute for Animal Health, Tamsui, Taiwan, in accordance with Council of Agriculture guidelines. Experimental animals were monitored for clinical signs of FMD over a 14-day observation period. These observations included (1) daily recording of body temperature, (2) monitoring of any development of lameness in the legs of the animals, and (2) monitoring any acquired vesicular lesions on the coronary bands of the legs and snouts of the animals. $PD_{50}$ of the vaccine product was calculated using Reed-Muench Method on the basis of the results of challenge tests. Target doses of the vaccine should minimally contain 3 $PD_{50}$ to allow vaccine release.

b. Cattle

In bovine, the viral challenge was introduced by intradermolingual (IDL) inoculation of 1 mL (100 μL in each of 10 sites on the tongue) of macerate, titered and adjusted to contain a total $1 \times 10^4$ $TCID_{50}$ of FMDV (Bovine Infectious Unit or BIU). Animals were examined daily monitoring rectal temperatures, and a protection score based on the time of appearance and the number and severity of lesions was determined.

Total protection was defined as complete absence of lesions (score 0) and score values below 8 were considered as partial protection. Clinical score was calculated as follows
 i) an elevated body temperature of 40° C. (score of 1), >40.5 (score of 2), or >41 (score 3);
 ii) reduced appetite (1 point) or no food intake and food left over from the day before (2 points);
 iii) lameness (1 point) or reluctance to stand (2 points);
 iv) presence of heat and pain after palpation of the coronary bands (1 point) or not standing on the affected foot (2 points);
 v) vesicles on the feet, dependent on the number of feet affected, with a maximum of 4 points; and
 vi) visible mouth lesions on the tongue (1 points), gums or lips (1 point) or snout (1 point), with a maximum of 3 points.

All experiments with live animals were performed under the guidelines of the OIE Manual of Standards, Ministry of Agriculture, PRC or Council of Agriculture, Taiwan. Modifications to the dosing were also used for assessment of a particular formulation's potency, such as dosages containing 2×, 1×, 0.5× and 0.25× dose. Also, rapid screening of formulations using a 1× dose was also frequently used.

EXAMPLE 5

Comparative Analysis of the Complete Genome Sequences of FMDV Isolates Using FMDV $O_{Taiwan\ 99}$ Isolate Sequence as the Amino Acid Framework Structure and Location of the FMDV B and Endogenous Th Epitopes for Peptide Immunogen Design After thorough review of the FMDV genome organization, FMDV serotype $O_{Taiwan\ 99}$ polyprotein amino acid sequence was employed as the base for the identification and design of FMDV antigenic peptides. Such peptides, once with the framework established, can be adjusted to represent sequences for multiple serotypes for regional applications. Alignment of the FMDV $O_{Taiwan\ 99}$ sequence with the complete genome sequences of 103 FMDV isolates representing all seven serotypes, accessed through the corresponding GenBank accession numbers as described previously (Carrillo 2005), identified highly conserved FMDV protein regions indicating functional constraints for variability as well as novel viral motifs with potential biological relevance. Specifically, the sequences around the FMDV VP1 protein "RGD" receptor binding site and their serotype related consensus sequences (i.e. the most frequently appeared amino acid for each position based on comparison of sequences of FMDV isolates of a specific serotype being designed) were the blueprint for the design of B cell epitope cluster peptide immunogens, whereas the highly conserved FMDV protein regions were the target sites for design of the FMDV endogenous Th epitope cluster peptide immunogens. After screening by both serological and cellular assays with procedures described in detail Example 3, a series of referenced B and T helper cell epitope cluster peptides (SEQ ID NOs.: 1 to 102) were identified for application in FMDV vaccine formulations representing different strains and serotypes as shown in FIG. 1 and Tables 1 to 8.

EXAMPLE 6

Analysis of FMDV B Cell Epitope Cluster Peptide Immunogens as Key Components for FMDV Peptide Based Vaccines a. Design History Each vaccine or immunotherapeutic product requires its own design focus and approach based on the specific disease mechanism and the target protein(s) required for intervention. The targets that designs are modeled after can include cellular proteins involved in a disease pathway or an infectious agent in which several proteins may be involved.

Prior knowledge on the B and T cell epitope identification and distribution is also beneficial to the molecular design process. An extensive process of serological validation is required once the target molecule(s) are selected. Subsequently, consecutive pilot immunogenicity studies in small animals are conducted to evaluate the functional properties of the antibodies elicited by the vaccine formulations of the designer peptides. Such serological application is then carried out in animals of the target species for further validation of the vaccine immunogenicity and functional properties of the elicited antibodies. All studies are conducted in multiple parallel groups with sera collected from the immunized hosts for evaluation. Early challenge studies in the target species are also carried out to further validate the direction of the design. Target peptides are then prepared in varying mixtures to evaluate subtle difference in functional property related to the respective interactions among peptide constructs when used in combinations to prepare for respective formulation designs. After additional evaluations, the final peptide constructs, peptide compositions and formulations thereof, along with the respective physical parameters of the formulations are established leading to the final product development process.

Extensive design experience allows for the development of the next generation vaccine products from discovery to commercialization as shown in FIG. 2 at an accelerated pace.

During the development of the specific FMDV peptides and compositions, the following development objectives were considered 1) identifying a VP1 loop domain target site sufficient for eliciting broadly neutralizing antibodies, 2) designing the peptide target site for optimum presentation to the immune system, 3) selecting UBITh® sites for immunopotency in the porcine and ruminant target species, 4) incorporating these essential components into a peptide immunogen design that could be produced cost effectively, and 5) developing vaccine formulations, dose size, and immunization protocol for protective immunity. The overall goal of analyzing and evaluating FMDV peptide immunogens required intensive empirical investigation of the FMDV sequence database and molecular models followed by the synthesis of a large number of candidate immunogens for vaccine formulations to immunize animals. A total of 831 pigs and 860 cattle were in immunogenicity and neutralizing antibody titer studies to find compositions and formulations capable of effectively protecting swine and cattle animals upon viral challenge after only single administration. In total, 25 studies in swine, and 32 studies in cattle, in addition to early studies in guinea pigs and goats that were involved in developing this invention.

b. Identification of Most Potent VP1 Loop Domain Targets

The critical element for an effective peptide vaccine for FMDV is the selection of a precise sequence from the G-H loop domain of VP1 that is optimal for presentation of B cell epitopes that elicit the production of neutralizing antibodies. The frame for the optimal presentation of a domain by a peptide immunogen can be affected by a shift as small as a single amino acid position. Available molecular model for the conformational structure of the VP1 capsid protein were examined and sequence comparisons within this hypervariable region were evaluated in determining that synthetic immunogens with good cross-reactivities for VP1 should include an extended segment of the loop domain.

Peptide immunogens having VP1 target sites were produced covering aa134-159 or aa134-169 based on the sequence of FMDV $A_{12}$ of serotype A as shown in Table 8. The immunogenicity of the peptides were determined in compositions containing the peptides alone, or in compositions that also included FMDV endogenous Th epitopes or extrinsic Th epitopes for supplemental T cell help. Immunogenicity assays were also conducted on peptides that did and did not have cyclic constraints to stabilize the loop structure. Cyclization of peptides was facilitated by substituting amino acid residues in specific positions with cysteine residues to create a disulfide bond (e.g., VP1 positions 134 (N->C) and 158 (Q->C)).

Compositions containing various peptides were evaluated for immunopotency in guinea pigs. Table 9 provides the experimental results obtained from an evaluation of various peptides. Table 9 shows:

i. Longer peptide constructs provided better neutralizing responses. For example, SEQ ID NO: 97 provided better neutralizing responses compared to SEQ ID NO: 96. Additionally, further extensions of the target sites to residue 129 (SEQ ID NO: 99) also proved to be valuable for certain applications.

ii. Cyclized peptides provided higher neutralization activities compared to peptides that did not contain this structure. For example, cyclic peptide SEQ ID NO: 98 provided higher neutralization activities compared to SEQ ID NO: 97.

iii. Extrinsic Th provided by a Th site from an artificial Th epitope UBITh® (SEQ ID NO: 24) linked to the FMDV VP1 domain raised neutralization efficacy over those constructs that did not contain this epitope. For example, SEQ ID NO: 100 provided better neutralization activity compared to SEQ ID NOs: 99, 98, 97 and 96.

iv. Immunogenicity was further enhanced by the addition of extrinsic Th epitopes in the compositions.

In view of these results, a cyclic peptide containing the extended VP1 target site from amino acids 129 to 169 was determined to be the most immunopotent (e.g., SEQ ID NO: 99).

c. Design of Serotype-specific VP1 Target Sites

The FMDV sequence database for global FMDV, provided by the world reference lab in Pirbright, UK, was searched to obtain the variable VP1 loop domains (amino acids 129-169) for subtypes from serotypes O, A, Asia, C, and others. Consensus amino acids for each position were then designed as shown in Table 2. Combinatorial library target sequences as shown in Table 8 (SEQ ID NOs: 101 and 102) having multiple amino acids in a single position, were also made to encompass even more broadly the antigenic variability of the VP1 loop domain.

A comparison of the immunogenicity trial using a single consensus sequence (Table 11, SEQ ID NO: 25) with the immunogenicity trial using the combinatorial library targets (Table 10, SEQ ID NO: 98 and 99) shows that the consensus sequence provided equivalent efficacy over the breadth of serotype coverage as judged by VP1 based ELISA titers for immunogenicity and by neutralizing indexes for FMDV stains of the respective serotypes for these two approaches (Tables 10 and 11). Accordingly, for ease of manufacture and QC, the single consensus sequence cyclized target VP1 sites and some specific VP1 sequences chosen from specific serotypes based on regional needs were selected as shown in SEQ ID NOs: 2-23 and 25-33.

d. Selection of Potent Th epitope to enhance VP1 immunogenicity

Previous investigators identified Th sites within FMDV antigens, such as the VP1 21-40 epitope, and incorporated them into their design of synthetic VP1 immunogens. However, immunogenicity studies in pigs and cattle have shown that these FMDV endogenous Th sites are not completely effective to enhance the VP1 immunogenicity in the target species due to their limited promiscuity and genetic restriction. Accordingly, the partially effective FMDV Th epitope was not used, but replaced with the more potent UBITh® artificial Th epitope to enhance the FMDV VP1 looped peptide immunogen. The artificial UBITh® sites incorporate Th motifs, including combinatorial library Th positions, that were designed to accommodate the variable T cell responsiveness of genetically diverse populations. This change in Th epitopes resulted in a loss of a potential homologous anti-FMDV memory response (in case of exposure), but provided broader and more potent immune responsiveness. The artificial UBITh® sequence (SEQ ID NO: 24) has proven immunopotency in multiple species, including swine.

Constructs used in the experiment summarized by Table 10 included the artificial UBITh® site (SEQ ID NO: 24), epsilon Lysine as the spacer, and cyclic VP1 target sites from amino acid positions 134 to 169 for either serotype O or serotype Asia designed as combinatorial libraries (SEQ ID NOs: 101 and 102). Both constructs were immunogenic as shown by antibody and neutralization responses (expressed as neutralization index) of immunized guinea pigs.

Table 11 shows the responsiveness of guinea pigs to a similar serotype O immunogen having the UBITh® site (SEQ ID NO: 24) linked through an epsilon Lysine spacer to a cyclic VP1 target site from amino acid positions 129 to 169 with a consensus O sequence (SEQ ID NO: 25). This VP1 construct containing O consensus sequence also showed strong immunogenicity as evidenced by the potent broad neutralizing antibody response as early as 3 weeks post initial immunization (Table 11).

e. Unexpected Breadth of Neutralizing Response

The guinea pig immune sera analyzed for neutralizing activities in Tables 10 and 11 showed unexpectedly broad neutralizations. Specifically, the serotype O immunogens of SEQ ID NOs: 101 and 25 elicited neutralizing antibodies against two O subtypes, and also provided for neutralization of subtypes from serotypes A and Asia. These results suggest a potential of the UBITh® FMDV immunogens for broad efficacy against multiple serotypes by individual immunogens.

Such breadth in serotype neutralizations can also be provided by combining several immunogens as shown in Table 12 (UBI FMDV O vaccine which contained a mixture of three peptides SEQ ID NOs: 25, 27, and 28) into a single vaccine when sera from immunized and challenged pigs demonstrated breadth in neutralizing indexes against $O_{Taiwan}$, $O_{Manisa}$, $O_{Campos}$ and $O_{Myanmar}$.

f. Immunization/Challenge Trials in Swine

In three separate immunization/challenge trials in swine, the target species, the first Untied Biomedical, Inc. (UBI) synthetic peptide vaccine for FMDV, the UBITh® FMDV-O Vaccine, was proven to be protective against infectious challenge with FMDV $O1_{Taiwan}$ strain. The trials were done in 3 separate institutions including the National Institute of Animal Health Taiwan (NIAHT) and the USDA Plum Island Animal Disease Center (PIADC).

Results from these experiments are summarized in Table 13. Groups 1-4 were given 2 doses of UBITh® FMDV-$O_{Consensus}$ (SEQ ID NO: 25, peptide 2570) Vaccine. Doses ranged from 25, 50, 100 to 300 µg (Groups 1 to 4). Groups 5-7 were placebo controls.

All pigs were challenged by injection into a heelbulb with $10^{4.5}$ $TCID_{50}$ of FMDV $O1_{Taiwan}$ (virus was grown either in baby hamster kidney cells or in pigs). Pigs were challenged at intervals of 2 to 10 weeks following their last immunizations. All immunized pigs were protected including the 15 UBITh®-immunized pigs. Protective immunity persisted in the UBITh®-immunized pigs, through week 10. Evidence of protective immunity up to 20 weeks following the last immunization, as shown by neutralizing antibody titer in experimentally immunized but unchallenged pigs, was also obtained.

The vaccinated animals all had significant serum levels of neutralizing antibodies and were protected from challenge. The infectivities of the virus challenge stocks used in the 3 separate trials were established by the 100% infection rate of the placebo-immunized pigs. Accordingly, the results from all 3 trials were validated. In view of the results obtained, the UBITh® FMDV-$O_{Consensus}$ (SEQ ID NO: 25, peptide 2570) vaccine provided full protective immunity with as little as 2 immunizations of dose size 25 µg (Group 1).

2. Breadth of Protective Immunity in Challenged Swine

Another challenge study was conducted with UBITh® FMDV O vaccine containing an equal amount of three VP1 O constructs (containing sequences from strains 2570a consensus, $O_{Ozk/93}$, $O_{Myanmar}$ represented by SEQ ID NOs: 25, 27 and 28 respectively) at a dose of 25 µg per dose and immunized at weeks 0 and 3 on a two-dose regimen. All six pigs were challenged similarly by FMDV $O1$ $T_{Taiwan}$ and all were protected. Sera was collected from the six pigs immunized for the challenge trial and neutralizing antibodies were determined for highly prevalent FMDV O subtypes, $O1_{Taiwan}$, $O_{Manisa}$, $O_{Myanmar}$ and $O_{Campos}$ (Table 12). All pigs produced levels of $O1_{Taiwan}$ neutralizing antibodies compatible with solid immunity, which also contained stronger neutralizing responses against $O_{Manisa}$, $O_{Myanmar}$ and $O_{Campos}$, indicative of more dependable protective immunity across serotype O subtypes.

h. Immunogenicity in Ruminants

The immunogenicity of the UBITh® FMDV-O $O_{Consensus}$ (SEQ ID NO: 25, peptide 2570) Vaccine was shown in a ruminant species in an immunogenicity trial of 12 goats. Goats were immunized with either two doses on weeks 0 and 8 or three doses on weeks 0, 4, and 8. The doses were 30 µg, 100 µg, or 300 µg. Efficacy was evaluated by determining serum levels of neutralizing antibodies against FMDV $O1_{Taiwan}$. Neutralizing antibody levels predictive of protection were obtained out to 12 weeks following the last immunization on week 8 (i.e., throughout the 20 week duration of the study). Both the two dose and three dose schedules were equally effective, and the 30 µg dose was as effective as the 300 µg dose. Thus immunogenicity has been shown for the UBITh® FMDV-O Vaccine in a target ruminant species, at a dose size and vaccine formulation equivalent to that used for protective immunity in swine when administered at 2 or 3 doses.

i. Conclusions and Interpretations of the Findings

Results from the experiments described above can be summarized as follows:

UBITh® FMDV VP1 based O Vaccine (SEQ ID NO: 25) effectively protected all (15/15) vaccinated pigs from FMDV $O_{Taiwan}$ challenge in studies conducted in four experimental groups at three international institutes, after two immunizations at doses of 25, 50, 100 and 300 µg per dose. All (10/10) control animals were infected by day 2 of viral challenge.

UBITh® FMDV O Vaccine containing a mixture of VP1 O constructs (SEQ ID NOs: 25, 27 and 28 at equal ratio, 25 µg per dose for two doses given at 0 and 3 weeks post initial immunization) elicited broadly protective neutralizing antibodies against multiple FMDV O isolates including $O_{Taiwan}$, $O_{Campos}$, $O_{Myanmar}$ and $O_{Manisa}$ in swine.

UBITh® FMDV O Vaccine displayed equivalent immunogenicity in a ruminant species, goat, to that seen in pigs. This result is predictive that the present UBI formulation will be effective in cattle in a dose range comparable to the immunogenic dose range for pigs.

Individual UBITh® synthetic FMDV immunogens elicited neutralizing antibodies simultaneously against serotypes A, O and Asia 1 in guinea pigs, showing potential for unexpectedly broad efficacy across multiple serotypes.

UBITh® FMDV O peptide employing serotype $O_{Consensus}$ sequence can elicit neutralizing antibodies, measured by neutralizing index, against multiple serotypes including subtypes from serotypes A, Asia 1 and O.

UBITh® FMDV vaccine immunogens are "functional site"-directed and synthetic in nature. The formulated vaccines are safe, potent, broadly neutralizing, reproducible and stable, thus bypassing the production and quality control-related difficulties and disadvantages associated with conventional killed virus vaccines.

The availability of a completely safe chemically-defined vaccine can expedite the eradication of FMDV by encouraging vaccination even in regions approaching FMD-free status.

EXAMPLE 7

Peptide Homologues of Synthetic FMDV Peptide Immunogens as Key Components for FMDV Peptide Based Multivalent Vaccines Tailored for Regional Needs Foot-and-mouth disease vaccines traditionally represent the largest share of the veterinary vaccine market worldwide in terms of sales, with 26.4% of the entire livestock biological business. Owing to the high variability of FMDV serotypes and subtypes, the antigen composition of the classical viral lysate based FMD vaccines is tailored for specific world regions and, in many cases, to specific countries or regions within them. The current use of the vaccine in FMD-endemic regions requires an in-depth investigation of the epidemiology of disease and vaccine harmonization studies to (1) determine whether the vaccine will be effective against the strain(s) circulating in the target area and (2) ensure the actual profile of the vaccine is suitable for control and eradication.

With the advent of the molecular virology, a large part of the capsid protein VP1 sequence of foot-and-mouth disease virus could easily be amplified by reverse transcription-dependent polymerase chain reaction (RT-PCR) from virus isolates obtained from tissue samples from FMD cases submitted according to the national surveillance practice, as well as multiple tissue and probang samples collected from FMDV outbreaks. The identified VP1 sequences could be aligned. The alignment comprises sequences of the serotypes with the genetic relation to other isolates indicated. The VP1 sequences of the strain(s) circulating in the target area can easily be obtained based on the amino acid framework (VP1 129-168) established in this invention disclosure and peptide homologues for this framework (Table 2, SEQ ID NOs: 2-23) representing the identified VP1 sequence for the regionally identified FMDV outbreaks and for such designed VP1 peptide homologues (Table 3, SEQ ID NOs: 25-33) to be included in the vaccine formulations to ensure their suitability for control and eradication, tailored for the specific regional needs.

Specific formulations containing peptide homologues derived from synthetic FMDV peptide immunogens (having VP1 aa129 to aa168) as a key ingredient when administered in two or more doses include the examples shown in Table 14:
  (a) Monovalent swine FMDV serotype O vaccine with peptide homologue (SEQ ID NO: 25);
  (b) Bivalent swine FMDV serotype O vaccine with a mixture of two peptide homologues (SEQ ID NOs: 25 and 28) in equal ratio by weight;
  (c) Trivalent swine FMDV serotype O vaccine with a mixture of three peptide homologues (SEQ ID NOs: 25, 27 and 28) in equal ratio by weight;
  (d) Bivalent cattle/ruminant FMDV serotypes O and Asia 1 vaccine with a mixture of two peptide homologues (SEQ ID NOs: 25 and 29) in equal ratio for use in Asia;
  (e) Trivalent cattle/ruminant FMDV serotype O, Asia $1_{Jiansu}$ and $A_{Gansu}$ vaccine (SEQ ID NOs: 25, 29 and 31) in equal ratio for use in China;
  (f) Trivalent cattle/ruminant FMDV serotype $O_{Campos}$, A24, $C_{Indaial}$ vaccine (SEQ ID NOs: 26, 30 and 32) in equal ratio for use in Brazil;
  (g) Trivalent cattle/ruminant FMDV serotype $O_{Campos}$, $A_{24/Argentina\ 2001}$, and $C_{Indaial}$ vaccine (SEQ ID NOs: 26, 30, 33 and 32) in equal ratio for use in Argentina.

The suitability of the designed peptide homologues for use in the final vaccine formulation could be assessed through detection of relative immunogenicity and cross-reactivity to the FMDV VP1 antigens from different isolates by specific FMDV VP1 sequence based peptide ELISAs as described in Example 1.

As shown in Tables 15 to 17, the VP1 homologue-based vaccine formulations (a) to (g) (containing homologues of SEQ ID NOs: 25-33) satisfy specific regional needs (e.g. China, South east Asia, Brazil and Argentina). Specifically, these formulations provide the desired immunogenicity for the VP1 sequences of the targeted serotypes (e.g. $O_{Taiwan}$, $O_{Campos}$, $O_{Ozk}$, $O_{Myanmar}$, Asia 1, $A_{Gansu}$, $A_{24}$, $A_{Argentina\ 2001}$, $C_{Indaial}$). In addition, functional immunogenicity has also been observed for these FMDV vaccine formulations as demonstrated by their ability to elicit neutralizing antibodies towards the targeted serotypes including, but not limited to, serotype $O_{Taiwan99}$ (as described in Example 6, Table 12). The total FMDV neutralizing antibody-inducing VP1 based B cell components employed in the vaccine formulations can be as low as 25 µg per dose when administered at 2 doses within an immunization schedule.

EXAMPLE 8

FMDV Vaccine Formulations Containing Only VP1 Protein Derived B Cell Epitope Cluster Peptides Failed as an Emergency Vaccine Against FMDV Viral Challenges Upon Single Administration Specific formulations incorporating synthetic FMD peptide homologues were prepared as described in Example 7. These formulations were capable of eliciting FMDV neutralizing immune responses in both swine and cattle/ruminant FMDV vaccines after administration of two or more doses. However, these formulations were unable to consistently protect swine and cattle from FMDV viral challenge with a single administration of the formulation, as required by the OIE viral challenge procedure. The inability of these formulations to offer animals with full protection from FMDV challenge using a single administration poses a serious hurdle for the commercialization of the VP1 peptide homologue based FMDV vaccine formulations.

Figure 3B:
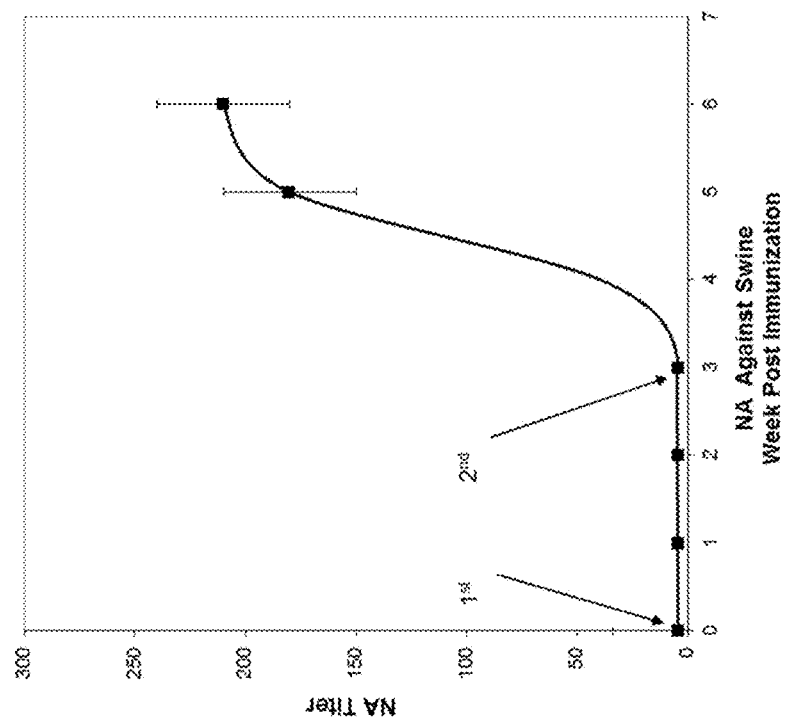
FIG. 3B is a graph showing neutralizing antibody (NA) titers from swine that received two administrations of UBITh® VP1 vaccine (SEQ ID NO: 25). Fifteen FMDV-free swine, aged 3 to 5 weeks, were immunized at 0 and 3 weeks. Sera were collected weekly between 0 and 6 weeks and assayed for NA titers after each immunization.
Figure 3A:
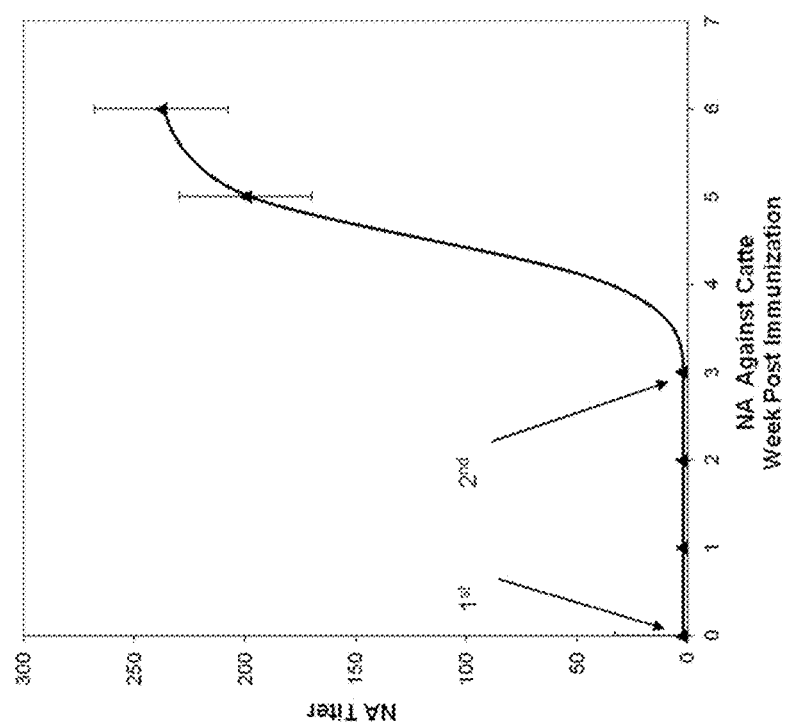
FIG. 3A is a graph showing neutralizing antibody (NA) titers from cattle that received two administrations of UBITh® VP1 vaccine (SEQ ID NO: 25). Fifteen FMDV-free cattle, aged 6-12 months, were immunized at 0 and 3 weeks. Sera were collected weekly between 0 and 6 weeks and assayed for NA titers after each immunization.

A close review of the kinetics for neutralizing antibody development for all VP1 homologue based vaccine formulations revealed that the neutralizing antibody titers remained low or close to the background titers ($<=3$) up to four weeks after the single administration (FIGS. 3A and 3B). The neutralizing antibody titers in both pigs and cattle rose to significantly high levels at week 6 only after the second administration at 4 weeks post initial administration (FIGS. 3A and 3B; and Tables 15-17). Such delay in the generation of high titer neutralizing antibodies suggests a lack of (or reduced level of) certain immune response elements in the VP1 based peptide vaccine. These missing/reduced elements appear to be present in the FMDV viral lysate based vaccine, which is capable of mounting protection as an emergency vaccine.

A prime and rapid recall response which causes significant reduction of viral replication upon viral exposure could be the element missing from the VP1 homologue based vaccine formulation required in a fully protective immune response upon single administration. Potent T helper responses are generated after two or more doses when the foreign UBITh® epitope is linked to the VP1 peptide homologues, as evidenced by the significant rise in neutralizing antibody titers shown in FIGS. 3A and 3B; and Tables 15 to 17. However, an emergency vaccine must quickly and sufficiently prime the immune system of an animal with a single administration of the vaccine formulation to be effective in providing a fast recall response upon viral infection.

The following Examples describe experiments that evaluate the fast-acting T cell response by employing vaccine formulations containing multi-component FMDV derived B and T epitopes.

EXAMPLE 9

Rationales, Screening, Identification and Optimization of Multi-Component B and T Epitope Based FMDV Vaccine Formulations for a Single Administration Emergency Vaccine As described in Example 8, repeated attempts in the development of an emergency FMD vaccine formulation using a combination of FMDV VP1 derived B cell epitope cluster peptides alone was unable to consistently generate high titer neutralizing antibodies at 3 to 4 weeks post initial immunization with a single administration. Thus, these formulations were unable to protect animals upon FMDV challenge. Extensive efforts were expended to identify the required immunological elements for the development of a successful high potency Emergency FMD vaccine.

The commercial FMD viral lysate based emergency vaccine induces naïve pig γδ T cell proliferation and these naïve pig γδ T cells express various cytokine/chemokine mRNA after exposure to FMD vaccine viral antigens. One of the marked changes observed in animals receiving high potency emergency FMD vaccine is the high level of systemic production of cytokines including IFN-γ (Cox 2003). When PBL from FMD immune pigs (vaccinated and virus challenged animals) were stimulated in vitro with FMDV antigens immediately after FMD virus challenge and recovery, γδ T cells were the major proliferating subpopulation found indicating such γδ T cell proliferation may be a characteristic of certain viral infections. Direct cell to cell interaction between γδ T cells and MHC class II+ CD4+ T cells were observed as clusters of cells showing clear synapse formation and such interactions exhibited as T cell proliferation can be blocked by monoclonal antibodies against MHC class II and CD4 indicating antigen presentation capability by γδ T cells via MHC class II (Takamatsu 2002). The involvement of γδ T cells in induction of inflammation and differential cytokine production revealed an important role for γδ T cells in immunoregulation, controlling both innate and adaptive immune responses. These cells may possess features associated with professional Antigen Presenting Cells (APC). The importance of γδ T cells involvement in generating fast immune responses against FMDV antigens in the viral lysate based high potency emergency FMD vaccine prompted us to extensively evaluate the design, screening, and selection for inclusion of one or more of FMDV endogenous T epitope cluster peptides in our synthetic peptide based high potency emergency FMD vaccines through in vitro measurement of IFN-γ production as indicators for the onset of T cell activation mediated by FMDV endogenous Th epitope cluster peptides.

Specific T cell functional assays as described in details in Example 3 were used to screen and identify FMDV endogenous Th epitope cluster peptides derived from antigenic segments of FMDV proteins VP1, VP2, VP3, VP4, 2A, 2B, 3A, 3B and 3D that are recognized by swine and cattle T cells derived from hosts immunized with (a) FMDV viral lysate vaccines and (b) peptide formulations containing FMDV candidate Th peptides.

a. Identification of FMDV Endogenous Th Cluster Peptides in Swine and Cattle Animals by In Vitro Measurement of IFN-γ Production as an Indicator for the Onset of Immune T Cell Activation Upon in vitro stimulation, primed T cells from animals immunized with the formulations incorporating FMDV endogenous Th epitope peptides released IFN-γ, and consistently enhanced the production of FMDV neutralizing antibodies. Such an assay is far easier to reproduce and thus has been used as a robust screening assay for evaluation of the potency and for identification of the FMDV endogenous Th epitope cluster for inclusion in the ultimate FMDV vaccine formulations.

The design for T cell epitope cluster peptide immunogen was carried out by first testing peptides having sequences showing clusters of MHC class II binding motifs for their ability to induce IFN-γ response in culture of peripheral blood mononuclear cells (PBMCs) obtained from FMDV $O_{Taiwan99}$ viral lysate vaccine-immunized, later challenged and recovered pigs and cows. From this screening, peptides that were able to trigger low, medium and high IFN-γ production were grouped for further screening and design for incorporation in the vaccine formulations. FIG. 1 shows the distribution/localization of selected B and endogenous T cell epitopes on the FMDV VP4, VP2, VP3, VP1, 2B, 2C, 3A, 3B, 3C and 3D proteins that were identified by methods described in Examples 1 and 3 and used in subsequent vaccine formulation applications.

The sequences for each of the T cell epitope cluster peptides derived from FDMV $O_{Taiwan99}$ strain are identified in Table 4 (SEQ ID NOs: 34-63). The FMDV Th peptides were aligned with homologous FMDV T helper epitope sequences from other FMDV strains as shown in Table 5 (SEQ ID NOs: 64-78). To improve the solubility of these rather hydrophobic peptide antigens, three lysine residues (KKK) were added to the N-terminus of the individual T helper peptide immunogens. A pool of these T cell cluster peptides containing some or all the identified Th peptide immunogens in equal ratio by weight (SEQ ID NOs: 34-87) were used as a supplement to the mixture of VP1 peptide homologues in vaccine formulations to further enhance the immunogenicity of the FMDV B cell cluster peptide immunogens in both swine and cattle. These vaccine formulations were used in extensive experiments where neutralizing antibody titers at weeks 0 and 3 were measured/evaluated in vitro as indications for in vivo protective efficacy upon single administration (Tables 18, 19). These pooled FMDV Th peptides can also act as FMDV T cell peptide immunogens for cell mediated immunity.

To further broaden the T cell epitope coverage for animals having a diverse genetic background, combinatorial peptides, based on the respective nine T epitope-specific homologous sequences (Table 19, Group 7, SEQ ID NOs: 79-87), were designed as well. Similarly, three lysine residues (KKK) were added to the N-terminus of the respective combinatorial T epitope cluster peptide immunogens to improve their water solubility for further formulation use. A pool of these T epitope cluster combinatorial peptide immunogens was also used as a supplement in vaccine formulations to further enhance the immunogenicity of the FMDV VP1 B cell epitope cluster peptide immunogens and on their own as FMDV T cell peptide immunogens for cell mediated immunity (Table 19).

Through extensive testing, a list of preferred FMDV endogenous Th cluster peptides for swine are SEQ ID NOs: 61 to 63; and for cattle are SEQ ID NOs: 34 to 60. These short peptides can be made soluble by the addition of Lysine residues (e.g. KKK) at the N-terminus of the Th epitope cluster peptides. The immunogenicity of these peptides can be enhanced by making a combinatorial peptide sequence using each Th epitope based on the serotype(s) employed for the combinatorial library sequence design (e.g. O, Asia1, A, C, etc.) and further linking the selected individual FMDV Th cluster peptides (as a single sequence or as a combinatorial sequence) in a cassette form to the UBITh® epitope (SEQ ID NO: 24) as combo FMDV Th constructs. Exemplary sequences containing these features are as shown in Table 7 as SEQ ID NOs: 88 to 95.

Due to the particularly diverse genetic background of cattle, various combinations of preselected FMDV endogenous Th peptides derived from a large pool of peptides able to trigger the onset of antigen specific T cell reaction in animals receiving vaccine formulations already containing the optimized FMDV B epitope cluster VP1 peptides were tested for universal immunogenicity in the animals (Table 19). The ability to trigger the onset of antigen specific T cell reaction by animals receiving only single administration of such vaccine formulations is exemplified by the significant titers of neutralizing antibodies the vaccines were able to mount in both pigs and cattle (Tables 18 and 19). In the absence of these FMDV endogenous Th epitope cluster peptides, the vaccines were only able to mount negligible (i.e. <=3) titer of neutralizing antibodies after receiving single administration of the vaccines (FIGS. 3A and 3B) for weeks 0 and 3 post initial immunization for each of the formulations containing only VP1 peptide immunogen homologues.

Figure 4B:
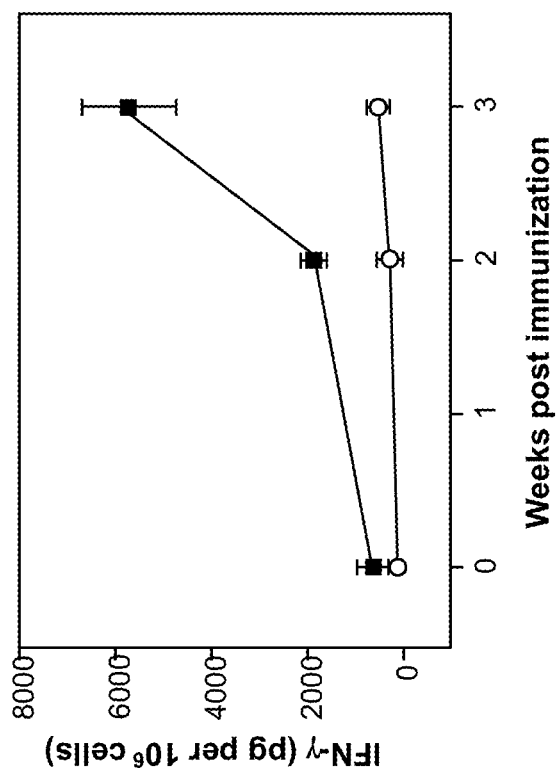
FIG. 4B is a graph illustrating the cellular immune response (IFN-γ production) induced by PBMCs in pigs receiving a single administration of a UBITh® FMD vaccine formulation containing a VP1 derived B cell epitope ($O_{Consensus}$ SEQ ID NO: 25) and UBITh® enhanced endogenous FMDV Th cassette cluster peptide (SEQ ID NO: 90) at a 10:1 ratio by weight in ISA50V2 water in oil (w/o 50/50) emulsion at 27.5 µg/mL per dose (closed square ■) compared to unvaccinated negative control animals (open circles ○). Animals were bled on day 28 before challenge and the final values were corrected for by subtraction of day 0 baseline values.
Figure 4A:
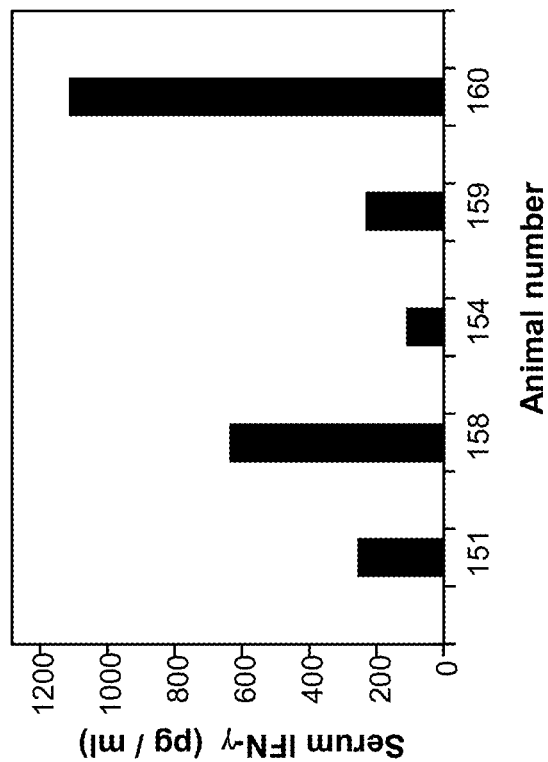
FIG. 4A is a graph illustrating the cellular immune response (IFN-γ production) induced by PBMCs in pigs receiving a single administration of a UBITh® FMD vaccine formulation containing a VP1 derived B cell epitope ($O_{Consensus}$ SEQ ID NO: 25) and UBITh® enhanced endogenous FMDV Th cassette cluster peptide (SEQ ID NO: 90) at a 10:1 ratio by weight in ISA50V2 water in oil (w/o 50/50) emulsion at 27.5 µg/mL per dose. Animals were bled weekly and the capability of their PBMCs to respond in vitro to recall vaccine peptide antigens with IFN-γ response was determined as described in Example 3.

A simple FMDV vaccine formulation was prepared containing (1) the FMDV VP1 B immunogen from serotype O (SEQ ID NO: 25); (2) 10% (by weight) of a designed FMDV Th epitope peptide construct (SEQ ID NO: 90); and (3) three swine FMDV Th epitopes in a cassette form linked by UBITh® (SEQ ID NO: 24). This formulation was given to pigs in a single administration and the level of IFN-γ was measured both in vitro from PBMCs and in vivo by quantitative ELISA assay of serum (as described in Example 3) over a four-week period. An increasing production level of IFNγ with time after immunization was observed in this study, as shown in FIGS. 4A and 4B.

This finding further confirmed that the selected FMDV endogenous Th epitope cluster peptides could prime the T cells of the immunized host immediately after immunization. Upon exposure to FMDV by either natural infection or through a challenge study, the exposed viral antigens initiate the onset of antigen specific T cell reactions through the formerly FMDV vaccine T helper peptide antigen primed memory T cells. These carefully selected immunodominant Th epitopes present on FMDV VP1, VP2, VP3, VP4, 2A, 2B, 2C, 3A, 3B and 3D proteins provide prior priming of the FMDV related Th cells and allow triggering of significant lymphocyte proliferative responses in immunized hosts upon exposure to FMDV leading to the production of cytokines, including IFN-γ, even after only single administration of the respective vaccine formulations. The cytokines were known to play a key role in cell-mediated immune responses against a variety of cytopathic viral infections in animals.

b. Identification of the Most Optimal Vaccine Formulations for Use as an Emergency Vaccine in Both Swine and Cattle as Determined by Neutralization Assays The lymphoproliferative response to FMDV in vaccinated and challenged animals was generally found to be significantly higher for formulations incorporating FMDV endogenous Th epitope cluster peptides than those without. Inclusion of the specific T-cell epitope in the peptide formulation allows priming of T cells that can more efficiently recognize the viral epitopes presented in the context of a subsequent virus encounter.

IFN-γ is a major activator of macrophages, enhancing their antimicrobial activity and their capacity for processing and presenting antigens to T lymphocytes. It has been reported that IFN-γ stimulates MHC expression in antigen-presenting cells and efficiently inhibits FMDV replication. Thus, the activation of these early mechanisms are relevant for the induction of protective immune responses against FMDV required of an emergency vaccine upon single administration. In the presence of FMDV endogenous Th epitope cluster peptides, the FMDV VP1 reactive B cells would be activated, leading to a rapid B cell proliferation and production of antibodies. These FMDV endogenous Th epitope cluster peptides would also activate T helper cells, leading to cytokine secretion resulting in a suitable environment for generation of B cell memory. These findings suggest that the better clinical protection conferred by the combined FMDV VP1 B and endogenous Th peptides compared to VP1 B peptides alone, is mostly due to the induction of a more efficient lymphoproliferative response and IFNγ release which also leads to better induction, thus higher titers of neutralizing antibodies as part of the early event.

Standard neutralization assays were employed for the screening of vaccine formulations that would best trigger such early protective immune responses in vivo required by an emergency vaccine. Sera collected three weeks from the initial immunization were evaluated in the vaccinated swine (Table 18) and Cattle (Table 19). Since the neutralization antibody assay has been used as a surrogate assay to replace the expensive and cumbersome physical challenge test by certain national agencies as part of the release criteria for an emergency FMDV vaccine, systematic studies with the many FMDV vaccine formulations utilizing varying combinations and ratios of FMDV VP1 derived B and endogenous Th epitope cluster peptides were conducted and evaluated for their respective protective efficacy by this surrogate neutralization antibody assay which was briefly described in Example 2.

Specifically, three to five FMDV-free animals per group for swine and cattle at age of 8-12 weeks and 6-12 months respectively were immunized at week 0 by various combinations of multi-component B and T epitope peptide based FMDV vaccine formulations after single administration with sera collected for neutralizing antibody titer testing.

1. Swine

Data from 13 groups of animals from the swine study is shown in Table 18. Formulations used in these experiments were prepared as described below. All pigs were immunized with 1 mL of emulsion as the vaccine formulation.

Group 1—contained only the prototype FMDV VP1 O consensus peptide (SEQ ID NO: 25).

Groups 2 to 4—were prepared with the prototype FMDV VP1 O consensus peptide (SEQ ID NO: 25) in combination with a mixture of equal ratio by weight of endogenous FMDV Th peptides (e.g., SEQ ID NOs: 34-63, SEQ ID NOs: 61-63, or SEQ ID NO: 90) at a B:Th ratio of 10:1 by weight at 25+2.5 µg/mL in an water in oil emulsion using ISA50V2 as the adjuvant (Seppics, France) containing 0.1% Tween 80.

Groups 5 to 7—were immunized with FMDV VP1 $O_{Consensus}$ (SEQ ID NO: 25) and $O_{Ozk}$ (SEQ ID NO: 28) as the FMDV vaccine B cell component, at equal ratio by weight at 25 µg/mL in total, which were respectively supplemented by a mixture of equal ratio by weight of endogenous FMDV Th peptides (e.g., SEQ ID NOs: 34-63, SEQ ID NOs: 61-63, or SEQ ID NO: 90) at a B:Th ratio of 10:1 by weight at 25+2.5 µg/mL in a water in oil emulsion using ISA50V2 as the adjuvant (Seppics, France) containing 0.1% Tween 80.

Groups 8 to 10 were immunized with FMDV VP1 $O_{Consensus}$ (SEQ ID NO: 25) and $O_{Ozk}$ (SEQ ID NO: 28) and $O_{Myanmar}$ (SEQ ID NO: 27) as the FMDV vaccine B cell component, at equal ratio by weight at 25 µg/mL in total, which were respectively supplemented by a mixture of equal ratio by weight of endogenous FMDV Th peptides with SEQ ID NOs: 34-63, SEQ ID NOs: 61-63, and SEQ ID NO: 90 at a B:Th ratio of 10:1 by weight at 25+2.5 µg/mL in a water in oil emulsion using ISA50V2 as the adjuvant (Seppics, France) containing 0.1% Tween 80.

Groups 11 to 13 were immunized with FMDV VP1 $O_{Consensus}$ (SEQ ID NO: 25) and $O_{Ozk}$ (SEQ ID NO: 28) $O_{Myanmar}$ (SEQ ID NO: 27) and Asia $1_{Jiangsu}$ (SEQ ID NO: 29) as the FMDV vaccine B cell component, at equal ratio by weight at 25 µg/mL in total, which were respectively supplemented by a mixture of equal ratio by weight of endogenous FMDV Th peptides (e.g., SEQ ID NOs: 34-63, SEQ ID NOs: 61-63, and SEQ ID NO: 90) at a B:Th ratio of 10:1 by weight at 25+2.5 μg/mL in a water in oil emulsion using ISA50V2 as the adjuvant (Seppics, France) containing 0.1% Tween 80.

In summary, all pigs were free from FMDV antibodies at week 0 when the respective studies were initiated at the various time points. Single administration of the multi-component FMDV vaccine formulations containing the various FMDV VP1 derived B and endogenous Th epitope cluster peptides elicited the generation of significant antibodies directed against the (or one of the) targeted peptide $O_{Consensus}$ (SEQ ID NO: 25) by ELSIA with a $Log_{10}$ Titer between 2 to 3 (i.e. 10E2 to 10E3).

2. Cattle

Data from a total of 32 groups of animals with three animals per group from the cattle study is shown in Table 19. Formulations used in these experiments were prepared as described below. All cattle were immunized with 2 mL of emulsion as the vaccine formulation.

Groups 1 to 8 were prepared from the prototype FMDV VP1 $O_{Consensus}$ peptide (SEQ ID NO: 25) in combination with, respectively, a mixture of equal ratio by weight of endogenous FMDV Th peptides including SEQ ID NOs: 34-63 (30Ths); SEQ ID NOs: 34-39, 44, 46-51, 53-63 (24Ths); SEQ ID NO: 34-39, 44, 46-51, 53-60 (21 Ths); SEQ ID NOs: 34, 36, 37, 40-43, 45, 48, 52, 53, 60-63 (15Ths); SEQ ID NOs: 34, 36, 37, 48, 50, 53 (6 Ths); SEQ ID NOs: 62-78 (17 Th homologues); SEQ ID NOs: 79-87 (9 Ths short libraries); and SEQ ID NO: 88, 89 (2 UBITh® enhanced Th cassettes), respectively, all at equal ratio by weight and at a B:Th ratio of 10:1 by weight at 50+5 μg/mL in a water in oil emulsion using ISA50V2 as the adjuvant (Seppics, France) containing 0.1% Tween 80.

Groups 9 to 11 were immunized with FMDV VP1 $O_{Consensus}$ (SEQ ID NO: 25), $O_{Ozk}$ (SEQ ID NO: 28) and $O_{Myanmar}$ (SEQ ID NO: 27) as the FMDV vaccine B cell component, at equal ratio by weight at 50 μg/mL in total, which were respectively supplemented by a mixture of equal ratio by weight of endogenous FMDV Th peptides with SEQ ID NOs: 88, 89 (2 UBITh® enhanced Th cassettes); SEQ ID NOs: 91,92 (2 UBITh® enhanced Th cassettes); SEQ ID NOs: 91, 93-95 (4 UBITh® enhanced Th cassettes), and SEQ ID NOs: 34, 36, 37, 40-43, 45, 48, 52, 53, 60-63 (15 Ths) all at an equal ratio by weight and at a B:Th ratio of 10:1 by weight at 50+5 μg/mL in a water in oil emulsion using ISA50V2 as the adjuvant (Seppics, France) containing 0.1% Tween 80. All cattle were immunized with 2 mL of emulsion as the vaccine formulation.

Groups 12 to 16 were immunized with FMDV VP1 $O_{come}$. (SEQ ID NO: 25), $O_{Ozk}$ (SEQ ID NO: 28) and $O_{Myanmar}$ (SEQ ID NO: 27) as the FMDV vaccine B cell component, at equal ratio by weight at 50 μg/mL in total, which were respectively supplemented by a mixture of equal ratio by weight of endogenous FMDV Th peptides with SEQ ID NOs: 34, 36, 37, 40-43, 45, 48, 52, 53, 60-63 (15Ths) all at equal ratio by weight and at a B:Th ratio of 1:1, 5:1, 10:1, 50:1 and 100:1 by weight in a water in oil emulsion using ISA50V2 as the adjuvant (Seppics, France) containing 0.1% Tween 80. All cattle were immunized with 2 mL of emulsion as the vaccine formulation.

Groups 17 to 19 were immunized with FMDV VP1 $O_{Consensus}$ (SEQ ID NO: 25), $O_{Ozk}$ (SEQ ID NO: 28), $O_{Myanmar}$ (SEQ ID NO: 27) and Asia $1_{Jiangsu}$ (SEQ ID NO: 29) as the FMDV vaccine B cell component, at equal ratio by weight at 50 μg/mL in total, which were respectively supplemented by a mixture of equal ratio by weight of endogenous FMDV Th peptides with SEQ ID NOs: SEQ ID NOs: 34, 36, 37, 40-43, 45, 48, 52, 53, 60-63 (15Ths); SEQ ID NOs: 88, 89 (2 UBITh® enhanced Th cassettes); SEQ ID NOs: 91,92 (2 UBITh® enhanced Th cassettes); SEQ ID NOs: 91, 93-95 (4 UBITh® enhanced Th cassettes) all at equal ratio by weight and at a B:Th ratio of 10:1 by weight at 50+5 μg/mL in a water in oil emulsion using ISA50V2 as the adjuvant (Seppics, France) containing 0.1% Tween 80. All cattle were immunized with 2 mL of emulsion as the vaccine formulation.

Groups 25 and 26 were immunized with FMDV VP1 $O_{Campos}$ (SEQ ID NO: 26), $A_{24}$ (SEQ ID NO: 30), and $C_{Indaial}$ (SEQ ID NO: 32) as the FMDV vaccine B cell component, at equal ratio by weight at 50 μg/mL in total, which were respectively supplemented by a mixture of equal ratio by weight of endogenous FMDV Th peptides with SEQ ID NOs: 91,92 (2 UBITh® enhanced Th cassettes); SEQ ID NOs: 91, 93-95 (4 UBITh® enhanced Th cassettes) all at equal ratio by weight and at a B:Th ratio of 10:1 by weight at 50+5 μg/mL in a water in oil emulsion using ISA50V2 as the adjuvant (Seppics, France) containing 0.1% Tween 80. All cattle were immunized with 2 mL of emulsion as the vaccine formulation.

Groups 27 and 28 were immunized with FMDV VP1 $O_{Campos}$ (SEQ ID NO:26), $A_{24}$ (SEQ ID NO: 30), and $C_{Indaial}$ (SEQ ID NO: 32) as the FMDV vaccine B cell component, at equal ratio by weight at 50 μg/mL in total, which were respectively supplemented by a mixture of equal ratio by weight of endogenous FMDV Th peptides with SEQ ID NOs: 91,92 (2 UBITh® enhanced Th cassettes); SEQ ID NOs: 91, 93-95 (4 UBITh enhanced Th cassettes) all at equal ratio by weight and at a B:Th ratio of 10:1 by weight at 50+5 μg/mL in a water in oil emulsion using Emulsigen D (12%) as the adjuvant. All cattle were immunized with 2 mL of emulsion as the vaccine formulation.

Groups 29 and 30 were immunized with FMDV VP1 $O_{Campos}$ (SEQ ID NO: 26), $A_{Argentina2001}$ (SEQ ID NO: 33), and $C_{Indaial}$ (SEQ ID NO: 32) as the FMDV vaccine B cell component, at equal ratio by weight at 50 μg/mL in total, which were respectively supplemented by a mixture of equal ratio by weight of endogenous FMDV Th peptides with SEQ ID NOs: 91,92 (2 UBITh® enhanced Th cassettes); SEQ ID NOs: 91, 93-95 (4 UBITh® enhanced Th cassettes) all at equal ratio by weight and at a B:Th ratio of 10:1 by weight at 50+5 μg/mL in a water in oil emulsion using ISA50V2 as the adjuvant (Seppics, France) containing 0.1% Tween 80. All cattle were immunized with 2 mL of emulsion as the vaccine formulation.

Groups 31 and 32 were immunized with FMDV VP1 $O_{Campos}$ (SEQ ID NO: 26), $A_{Argentina2001}$ (SEQ ID NO: 33), and C (SEQ ID NO: 32) as the FMDV vaccine B cell component, at equal ratio by weight at 50 μg/mL in total, which were respectively supplemented by a mixture of equal ratio by weight of endogenous FMDV Th peptides with SEQ ID NOs: 91,92 (2 UBITh® enhanced Th cassettes); SEQ ID NOs: 91, 93-95 (4 UBITh® enhanced Th cassettes) all at equal ratio by weight and at a B:Th ratio of 10:1 by weight at 50+5 μg/mL in a water in oil emulsion using Emulsigen D (12%) as the adjuvant. All cattle were immunized with 2 mL of emulsion as the vaccine formulation.

In summary, all cattle animals were free from FMDV antibodies at week 0 when the respective studies were initiated at the various time points. Single administration of the multi-component FMDV vaccine formulations containing the various FMDV VP1 derived B and endogenous Th epitope cluster peptides allowed generation of significant antibodies directed against the (or one of the) targeted peptide $O_{Consensus}$ (SEQ ID NO: 25), even when the target peptide immunogen was at a fraction of the B components due to presence of other related VP1 B immunogen of different serotypes (mostly due to high cross-reactivity amongst these VP1 peptide immunogens) usually with a titer in the range of $Log_{10}$ Titer between 2 to 3.

Unexpectedly, formulations having a wide ranges in the ratios of B:Th peptides were effective in eliciting an immune response in the animals tested. That is, the % range for inclusion of such FMDV endogenous Th cluster peptides can vary from as low as 1% (i.e. Th to B ratio of 1:100) to as high as 50% (i.e. Th to B ratio at 1:1) (see Groups 12 to 16 in the cattle immunization study) were effective formulations for elicit in animals significant rise in neutralizing antibodies in their sera collected at 3 weeks post initial immunization.

In general, a 10% to 20% FMDV Th cluster peptides to FMDV VP1 B epitope cluster peptides (i.e. a 1:5 or 1:10 ratio) was selected and used in the final peptide based FMDV vaccine formulations to mount balanced B and T immune responses in animals receiving single administration via intramuscular injection route of the FMDV vaccine formulation.

EXAMPLE 10

Protection of Pigs and Cattle Animals from FMDV Viral Challenges after Receiving Multi-Component B and T Epitope Based FMDV Vaccine Formulations as a Single Administration Emergency Vaccine a. Challenge Studies Conducted in the Pies:

With the optimized multi-component B and T epitope based FMDV vaccine formulations designed for a single administration emergency vaccine giving rise to significant neutralizing antibody titers in sera collected at 3 weeks post initial immunization, six additional challenge studies were conducted in Tamsui, Taiwan to evaluate and validate the protective efficacy for selected representative formulations previously tested in Example 9.

In particular, FMDV challenge studies using the FMDV $O_{Taiwan}$ strain were performed on vaccinated animals. The challenge studies were performed according to similar protocols/methods. One representative/exemplary challenge study is described in detail in this Example (below). Specifically, the challenge study as shown in Table 20 (corresponds to Groups 5, 6, and 7 of Study II; Groups 12, 13, and 14 of Study IV; and Groups 15, 16, 17, 18, and 19 of Study V as shown in Table 25) is described/evaluated in detail in Tables 20 to 24. The other groups involved in such challenge studies conducted in swine and cattle were presented in a summarized form in Tables 25 and 26 respectively.

Animals: Thirty-two (32) SPF crossbred pigs aged 8 weeks old (at 0 wpi) were utilized in the challenge studies. The pigs were FMD-free and were not previously immunized with an FMD vaccine (i.e., naïve). Pigs were housed in Animal Health Research Institute (AHRI), Council of Agriculture, Executive Yuan. The study was conducted at AHRI from initial immunization until completion of the challenge study.

Special Husbandry Conditions: The different groups were housed in communal cages depending on the realistic situation. The control group was housed in an individual room. Animals showing signs of infection were removed to a separate room.

Virus: FMDV $O_{TAW/97\ K}$ strain.

Kits: FMDV Nonstructural Protein ELISA Kit and FMD peptide 2570a EIA titration kit were used as described in Example 1.

Grouping: The 32 pigs were divided into 11 groups randomly. The animal ID number, dose volume, injection route, and injection site were summarized in Table 20.

Bleed Schedule: At 0, 2, 4 week (s) post vaccination (WPV) and 14 days post challenge (DPC).

Vaccination: The vaccination was given at 0 WPV at the respective designated doses.

Challenge Schedule: At 4 weeks after immunization, the vaccinated and controlled pigs were challenged with FMDV O-Taiwan (pig-passaged virus) in the heel bulbs of right foreleg via SC route. The amount of virus was 0.5 ml ($10^5$ $TCID_{50}$).

Monitoring Assay(s): After viral challenge, the development of clinical signs and syndromes of FMD in pigs was monitored for 14 days with body temperature recorded daily.

The body temperatures of pigs after viral challenge were recorded in Table 21. The temperatures of pigs were slightly elevated but mostly below 40° C. during the 14 days post challenge (DPC) monitored.

Neutralization Titers: The pigs were bled at 0, 2, and 4 weeks post vaccination (WPV), and 14 DPC. Sera from each animal was collected from clotted samples by centrifugation and subjected to virus neutralization assay. Neutralization titers and the geometric means were calculated and shown in Table 22. Significant neutralizing antibody (NA) titers were observed for all formulations in a dose dependent fashion. Although the geometric mean of NA titers were lower than 16 at 4 WPV for certain groups, all of the animals were protected in all experimental groups (100%) at 14 DPC whereas two out of two animals in control Placebo group or negative control were both infected with clinical signs detected as early as day 2. Group 19 of Study V used FMDV viral lysate based serotype O vaccine (from Russia) as positive control where all three animals were protected upon single administration.

FMDV NS ELISA: The serum samples were assayed with FMDV Nonstructural Protein ELISA at AHRI with results shown in Table 23. Before challenge, the entire groups tested were naïve, showing no reactivity to FMDV NS protein. Only animals in the Placebo negative control group showed positive reactivity to NS protein at 14 DPC indicating their infective nature.

Anti-VP1 (peptide 2570a) ELISA Titration: The results of anti-VP1 antibody titers were tested by VP1 peptide 2570a based ELISA as described in Example 1 with results shown in Table 24. Most pigs developed significant immune responses at even two weeks after immunization.

All animals from the experimental groups, except the ones in the negative Placebo control group, were protected from FMDV challenge, regardless of their NA titers when FMDV peptide vaccine formulations included endogenous FMDV Th peptides as shown in their respective formulations.

Although some of the geometric means of the neutralizing antibody titers at 4 WPV in the experimental groups were below 16, the pigs were all protected. This gave clear indication that in addition to neutralizing antibodies, there are other factors that are involved in the protection of animals upon viral challenges. The inclusion of endogenous FMDV Th peptides in either short or the long cassette format all demonstrated their critical role in eliciting cellular immunity upon single administration of the peptide vaccine formulations. There could be as many as 30 FMDV Ths (SEQ ID NOs: 34-63) or as few as 3 previously refined and selected Ths (SEQ ID NOs: 61-63) to offer such cellular immunity in swine which afford such protection when in combination with the VP1 looped peptide(s). Combination vaccines incorporating sequences from FMDV VP1 O homologues gave equally effective, if not more, protection of the pigs from FMDV challenge by $O_{Taiwan}$ strain. There was no antibody against FMDV NS protein detected in the experimental groups receiving the respective vaccine formulations throughout the period monitored which further illustrated the thorough protection of these animals from FMDV infection even in the face of high dose FMDV viral challenge (10×OIE required viral dosage). In all formulations tested, those pigs receiving only 0.5 mL per dose was equally protected when compared to those receiving 2 mL per dose.

Thirteen (13) of the Groups (Groups 1-3, 5-7, 8-10, 12-15) used FMDV $O_{cons}$. (SEQ ID NO: 25) as the FMDV VP1 derived B epitope immunogen. Group 16 used FMDV $O_{Consensus}$, $O_{Ozk}$, $O_{Myanmar}$ (SEQ ID NOs: 25, 28, and 27), and Group 17 used FMDV $O_{Consensus}$, $O_{Ozk}$, $O_{Myanmar}$ and Asia $1_{Jiangsu}$ (SEQ ID NOs: 25, 28, 27, and 29) as the FMDV VP1 derived B epitope immunogens (at equal ratio by weight) respectively. The remaining Groups used Placebo control.

In all these formulations, except for the placebo control groups, endogenous FMDV Th epitope cluster peptides were added to the FMDV VP1 B epitope components in all groups as indicated in detail as shown in Table 25. Studies II and IV were conducted with the groups in each of the studies administered with 2 mL, 1 mL, 0.5 mL per dose to test the potency ($PD_{50}$) of the respective vaccine formulations. All experimental animals were monitored for clinical signs of FMD over a 14-day observation period. Varied ratios of FMDV VP1 $O_{Consensus}$ (SEQ ID NO: 25) and UBITh® enhanced FMDV Th cassette peptide (SEQ ID NO: 90) from 1:1, 5:1 and 10:1 were also tested for Groups 8 to 10 in Study III. A similar study of varied ratios were also conducted for Study V with FMDV VP1 combo peptide immunogens and UBITh® enhanced FMDV Th cassette peptide (SEQ ID NO: 90) for 5:1 and 10:1 for Groups 15 and 16 respectively.

In summary, all animals in all placebo control or negative (no injection) groups were infected by FMDV $O_{Taiwan}$ strain as early as day 2 upon the challenge, indicating the validity of all challenge tests. Full protection of all pigs in all experimental groups was observed, as demonstrated by negative clinical signs throughout the period monitored and negative signals by FMDV NS ELISA, despite application of 10× higher dose of FMDV viral isolate than the amount required by OIE in these challenge studies. Calculation of $PD_{50}$ through dosing study indicated at least $PD_{50}$ of >11.23 in both Groups II and IV.

Out of 30 FMDV Th epitope peptides (SEQ ID NO: 34-63), three FMDV Th peptides were selected (SEQ ID NOs: 61-63) for effective protection of pigs from FMDV viral challenge. The presentation of these three FMDV swine Th epitope peptides were enhanced by using a cassette-like design by linking these three peptides through a lysine spacer which was further linked to the UBITh® (SEQ ID NO: 24) at its N-terminus as shown in SEQ ID NO: 90. Such FMDV Th epitope peptides could be supplemented to the FMDV VP1 derived B epitope peptide immunogen at varying ratios to the B peptide immunogen to offer protection against FMDV viral challenge. In Study V of the challenge test, full protection was achieved in the presence of 10% endogenous Th epitope peptides when the B epitope peptide composition is presented either as a monovalent O serotype peptide (SEQ ID NO: 25, 2570 kb), or as a O serotype combo formulation (SEQ ID NOs: 25, 28, and 27), or as a multivalent serotypes O and Asia 1 combination formulation (SEQ ID NOs: 25, 28, 27 and 29) indicating the adaptability in immunogenicity of the VP1 B epitope peptides.

b. Challenge Studies Conducted in Cattle:

In bovine, the viral challenge was introduced by a modified intramuscular injection on the back of the neck of the animal of $1 \times 10^4$ $TCID_{50}$ of FMDV (Bovine Infectious Unit or BIU). OS/99 strain was used for serotype O challenge and Asia 1 highly virulent strain was used for serotype Asia 1 challenge. Animals were examined daily, upon viral challenge after receiving single administration of respective FMDV vaccine formulations 28 days, monitoring rectal temperatures, and a protection score based on the time of appearance and the number and severity of lesions was determined. All experiments with live animals were performed under the guidelines Ministry of Agriculture, PRC. Modifications of the dosing such as using 2λ, 1×, and 0.5× dose of the test vaccine was also used for assessment of a particular formulation's potency. For quick screening of formulations with protective efficacy, 1× was used. For assessment of vaccine formulation efficacy, animals were divided into 3 to 5 animals per group depending on experimental design and availability of the animals at the time of the study.

In Study I, animals in Groups 1 to 4 (as shown in Table 26) with peptide vaccine formulations containing the optimized FMDV VP1 derived B cell epitope cluster peptide immunogen (SEQ ID NO: 25) as the key component of the vaccine formulation in the absence of any endogenous FMDV Th epitope peptide, or in the presence of 10% exogenous Th epitope peptides derived from DT, TT, and PT toxoid proteins were unable to protect the animals from FMDV serotype $O_{OS/99}$ strain challenge. With the optimized multi-component B and T epitope based FMDV vaccine formulations for a single administration emergency vaccine, four additional challenge studies were conducted to evaluate the protective efficacy for selected representative formulations previously tested in Example 9 as shown in Table 26.

Eight (8) Groups (Groups 6-8 and 10-14 of Studies II and III) used FMDV $O_{Consensus}$ (SEQ ID NO: 25) as the FMDV VP1 derived B epitope immunogen. Study IV (Group 16) used FMDV $O_{Consensus}$, $O_{Ozk}$, $O_{Myanmar}$ (SEQ ID NOs: 25, 28, and 27) as the FMDV VP1 derived B epitope immunogen (at equal ratio by weight). Study V (Group 18) used FMDV $O_{Consensus}$, $O_{Ozk}$, $O_{Myanmar}$, Asia $1_{Jiangsu}$, and $A_{Gansu}$ (SEQ ID NOs: 25, 28, 27, 29, and 31) as the FMDV VP1 derived B epitope immunogen (at equal ratio by weight).

In all these formulations, except for the placebo control groups and those experimental groups in Study I, endogenous FMDV Th epitope cluster peptides with SEQ ID NOs: 34-63, (30 Ths) for Group 10 of Study III; peptides with SEQ ID NOs: 34-39, 44, 46-51, and 53-60 (21 Ths) for Group 11 of Study III; a mixture of UBITh® enhanced FMDV Th cassette peptides with SEQ ID NO: 88 and 89 for Groups 6 to 8 of Study II, and a mixture of another four cassette FMDV Th peptides with SEQ ID NOs: 91, 93, 94, and 95 for Group 16 of Study IV and Group 18 of Study V, were added to the FMDV VP1 B epitope components as indicated in detail as shown in Table 26.

Groups 6, 7, and 8 of Studies II were tested for vaccine formulation potency with animals in the respective groups being administered with 2 mL, 1 mL, 0.5 mL per dose of the vaccine formulations when 4 out of 5; 4 out of 5; and 3 out of 5 animals were protected in the respective groups indicating significant potency of the vaccine formulation.

In summary, all animals in all placebo control groups were infected by FMDV $O_{OS/99}$ or Asia 1 strain employed for the challenge study as early as day 2 upon the challenge, indicating the validity of all challenge tests. Significant (4 out of 5; or 3 out of 5) or full protection were achieved in all experimental groups, as demonstrated by negative clinical signs in the protected animals throughout the period monitored. We were able to select out of thirty (30) FMDV Th epitope peptides (SEQ ID NO: 34-63), the twenty-one (21) (SEQ ID NOs: 34-39, 44, 46-51, 53-60 (21 Ths) at equal ratio (by weight), the fifteen (15) Ths (SEQ ID NOs: 34, 36, 37, 40-43, 45, 48, 52, 53, 60-63) (15 Ths) at equal ratio (by weight) and finally the six (6) FMDV Th peptides (SEQ ID NOs: 34, 36, 37, 48, 50, 53) (6 Ths) at equal ratio (by weight) for effective protection over a diverse genetic background of cattle. The presentation of these fifteen and further down to six (6) FMDV cattle Th epitope peptides were enhanced by making a cassette like design by linking three Th peptides through a lysine spacer and then linked that to the UBITh® (SEQ ID NO: 24) at its N-terminus as FMDV Th cassette peptides (SEQ ID NOs: 88, 89, 91, 92, 93, 94, 95). Such FMDV Th epitope cassette peptides could be supplemented to the FMDV VP1 derived B epitope peptide immunogen at 10 or 20% to help mount the much needed FMDV T cell immunity. In Studies IV and V, protection of 4 out of 5 animals for Groups 16 and 18 by FMDV serotype $O_{OS/99}$ strain (Study IV) or highly virulent FMDV Asia 1 strain (Study V) respectively was achieved in the presence of 10% endogenous Th epitope peptides selected from 12 FMDV Th epitopes that were presented in a cassette form on four UBITh® enhanced peptides (SEQ ID NOs: 91, 93, 94, 95) while the B epitope peptide composition was presented either as a Combo O serotype formulation (SEQ ID NOs: 25, 28, and 27), or as a multivalent serotypes O, Asia 1 and $A_{Gansu}$ formulation (SEQ ID NOs: 25, 28, 27, 29, and 31) indicating the adaptability in immunogenicity of the VP1 B epitope peptides.

EXAMPLE 11

Sample Product Inserts for UBITh® FMDV Multivalent Vaccines UBITh® Foot-and-Mouth Disease (FMD) Synthetic Peptide Trivalent Vaccine (Brazil) to Prevent FMD Brazil Types O Virus/$A_{24}$/$C_{Indaial}$ Virus Infection in Cattle The following are sample product inserts to be for UBITh® FMDV multivalent vaccines UBITh® foot-and-mouth disease (FMD) synthetic peptide vaccines in Brazil and China.
  a. Brazil
  Sterile Water-in-Oil Emulsion for Injection
  CAUTION: for veterinary use only.
  DESCRIPTION: UBITh® Foot-and-Mouth Disease (FMD) Synthetic Peptide Trivalent Vaccine (Brazil) is a water-in-oil emulsion trivalent vaccine containing three UBITh® FMD VP1 synthetic peptide constructs. Each peptide construct is composed of a synthetic peptide having an immunodominant VP1 epitope from serotypes Brazil O, $A_{24}$ and $C_{Indaial}$ foot-and-mouth disease virus (FMDV) based on the needs of specific South America regions which is linked by synthesis to an UBITh® epitope, an artificial T helper (Th) cell peptide, as an antigen. Four additional Th peptides are included to further enhance the cell-mediated immunity towards these three FMDV serotypes. The three UBITh® FMD VP1 constructs are mixed at equal ratio and supplemented with a small fraction of the mixture of the four Th constructs. The FMDV B and T epitope related synthetic constructs mixture is then mixed with an oil adjuvant to form a water-in-oil emulsion.

INDICATIONS FOR USE: UBITh® Foot-and-Mouth Disease (FMD) Synthetic Peptide Trivalent Vaccine (Brazil) is used for prevention of foot-and-mouth disease virus serotypes Brazil O, $A_{24}$ and C Indaial infection of cattle.

DOSAGE AND ADMINISTRATION: UBITh® Foot-and-Mouth Disease (FMD) Synthetic Peptide Trivalent Vaccine (Brazil) The vaccine formulation is administered via intramuscular injection into the area of neck in front of the shoulder. Maintain as closely as possible a 45-degree angle between the needle and the skin surface to avoid vaccine flow out of the needle hole when the needle is withdrawn. One single dose is recommended for emergency use. For cattle without any prior FMD vaccination, two immunizations of 2 mL at 4-5 weeks apart should be administered to increase immunity and prolong immune response and thus provide better protection against FMDV infection. An additional immunization may be performed every 6 months thereafter. In an area of with FMDV infected animals, revaccination every 6 months is recommended. The dosage delivered is 2.0 mL.
Directions for Use
  Prior to use, warm vaccine product to room temperature.
  Mix the vaccine contents thoroughly before use.
  Remove contents with sterilized syringes and needles.
  Use all contents immediately once bottle is opened.
Destroy containers and all unused contents by a procedure allowed by government regulations.
  b. China
  UBITh® Foot-and-Mouth Disease (FMD) Synthetic Peptide Trivalent Vaccine (China) to Prevent FMD China Types O/Asia 1/$A_{Gansu}$ Virus Infection in Cattle
  Sterile Water-in-Oil Emulsion for Injection
  CAUTION: for veterinary use only.
  DESCRIPTION: UBITh® Foot-and-Mouth Disease (FMD) Synthetic Peptide Trivalent
  Vaccine (China) is a water-in-oil emulsion trivalent vaccine containing three UBITh® FMD VP1 synthetic peptide constructs. Each peptide construct is composed of a synthetic peptide having an immunodominant VP1 epitope from serotypes China Type O, Asia 1 and $A_{Gansu}$ foot-and-mouth disease virus (FMDV) based on the needs of China and Asia regions which is linked by synthesis to an UBITh® epitope, an artificial T helper (Th) cell peptide, as an antigen. Four additional Th peptides are included to further enhance the cell-mediated immunity towards these three FMDV serotypes. The three UBITh® FMD VP1 constructs are mixed at equal ratio and supplemented with a small fraction of the mixture of the four Th constructs. The FMDV B and T epitope related synthetic constructs mixture is then mixed with an oil adjuvant to form a water-in-oil emulsion.

INDICATIONS FOR USE: UBITh® Foot-and-Mouth Disease (FMD) Synthetic Peptide Trivalent Vaccine (China) is used for prevention of foot-and-mouth disease serotypes China Type O/Asia 1/A Gansu virus infection of cattle.

DOSAGE AND ADMINISTRATION: UBITh® Foot-and-Mouth Disease (FMD) Synthetic Peptide Trivalent Vaccine (China) is administered via intramuscular injection into the area of neck in front of the shoulder. Maintain as closely as possible a 45-degree angle between the needle and the skin surface to avoid vaccine flow out of the needle hole when the needle is withdrawn. One single dose is recommended for emergency use. For cattle without any prior FMD vaccination, two immunizations of 2 mL at 4-5 weeks apart should be administered to increase immunity and prolong immune response and thus provide better protection against FMDV infection. An additional immunization may be performed every 6 months thereafter. In an area with FMDV infected animals, revaccination every 6 months is recommended. The dosage delivered is 2.0 mL.

Directions for Use

Prior to use, warm vaccine product to room temperature. Mix the vaccine contents thoroughly before use. Remove contents with sterilized syringes and needles. Use all contents immediately once bottle is opened. Destroy containers and all unused contents by a procedure allowed by government regulations.

TABLE 1

Optimized FMDV VP1 sequences for incorporation into designer UBITh® FMD vaccines for B epitope presentation

| | | |
|---|---|---|
| UBI FMDV O$_{Consensus}$ sequence VP1 134-158, cyclized | SEQ ID No. 1 | CKYGENAVTNVRGDLQVLAQKAARC |
| FMDV O Consensus VP1 129-168, cyclized (2570a) | SEQ ID No. 2 | VYNGNCKYGENAVTNVRGDLQVLAQKAARCLPTSFNYGAIK |

TABLE 2

Alignments for Consensus and Homologous VP1 Immunogenic Sequences from various FMDV strains of diverse Serotypes (O, Asia 1, A and C)
UB1 FMDV VP1 Peptides (with both 134 and 158 AA positions substituted by Cys)

| | | |
|---|---|---|
| O Consensus (2570A) | VYNGNCKYGENAVTNVRGDLQVLAQKAARCLPTSFNYGAIK | (SEQ ID No. 2) |
| O Campos/Brazil/58Y | VYNGECRYSRNAVPNVRGDLQVLAQKVARCLPTSFNYGAIK | (SEQ ID No. 3) |
| O Taiwan 2956a | VYNGSCKYGDTSTNNVRGDLQVLAQKAERCLPTSFNFGAIK | (SEQ ID No. 4) |
| O O1K/O1BFS | VYNGECRYNRNAVPNLRGDLQVLAQKVARCLPTSFNYGAIK | (SEQ ID No. 5) |
| O China (Gd/86) | VYNGSCKYSDARVSNVRGDLRVLAQKAERCLPTSSNYGAIK | (SEQ ID No. 6) |
| O Swine/Cattle/O/MYA/7/02 | VYNGNCKYAGGSLTNVRGDLQVLAQKAARCLPTSFNYGAIK | (SEQ ID No. 7) |
| O/Ozk/93 | VYNGNCKYSDRAVSNVRGDLQVLAQKAARCLPTSFNYGAIK | (SEQ ID No. 8) |
| O/A/58 | VYNGNCKYGVGPVTKVRGDLQVLAQKAARCLPTSFNYGAIK | (SEQ ID No. 9) |
| O/OZK/93 | VYNGNCKYSDRPVTKVRGDLQVLAQKAARCLPTSFNYGAIK | (SEQ ID No. 10) |
| O Lanzhou | VYNGSCKYSDARVSNVRGDLQVLAQKAERCLPSSFNYGAIK | (SEQ ID No. 11) |
| Asia 1 Consensus | VYNGKCTY--GEQPSRRGDMAALAQRLSRCLPTSFNYGAVK | (SEQ ID No. 12) |
| Asia 1 Yunnan PRC | VYNGKCTY--GEESTRRGDFAALAQRLSRCLPTSFNYGAVK | (SEQ ID No. 13) |
| Asia 1 KZC-2/10 PRC | VYNGKCTY--GETTARRGDTAALAQRLSGCLPTSFNYGAVK | (SEQ ID No. 14) |
| Asia 1 JiangSu/China/2005 | VYNGKCTY--GEESSRRGDLAALARRVNNCLPTSFNYGAVK | (SEQ ID No. 15) |
| A Consensus | VYNGTCKYTVGGSG-RRGDLGSLAARVAKCLPASFNYGAIK | (SEQ ID No. 16) |
| A24 Cruzerio California | VYNGTCKYAVGGSG-RRGDMGSLAARVYKCLPASFNYGAIK | (SEQ ID No. 17) |
| A Gansu/China/60Y | VYNGTCQYSTGNAG-RRGDLGSLARVAAQCLPASFNFGAIR | (SEQ ID No. 18) |
| A XinJiang/China/58Y | VYNGTCTYSTGSAG-RRGDLGSLAARVANCLPASFNFGAIR | (SEQ ID No. 19) |
| A22 A Mahmatli/Tur/65Y | VYNGTCKYSAGGTGRRGDLGPLAARVAKCLPASFNFGAIQ | (SEQ ID No. 20) |
| A Argentina 2001Y | VYNGTCKYTVSGSSRRGDLGSLAARVVKCLPASFNYGAIK | (SEQ ID No. 21) |

TABLE 2-continued

Alignments for Consensus and Homologous VP1 Immunogenic Sequences from various FMDV strains of diverse Serotypes (O, Asia 1, A and C)
UB1 FMDV VP1 Peptides (with both 134 and 158 AA positions substituted by Cys)

| | | |
|---|---|---|
| C3 Indaial/Brazil/84Y | TYTGTCAYTASA---RRGDLAHLAAAHARCLPTSFNFGAVK | (SEQ ID No. 22) |
| C3 Argentina/83c | TYTGTCTYTTSA---RRGDLAHLATAHARCLPTSFNFGAVK | (SEQ ID No. 23) |

TABLE 3

Examples of FMDV peptide immunogens derived from FMDV VP1 SEQuences from diverse Serotypes (O, Asia 1, A and C) of the same amino acid sequence framework

| Description | SEQ ID No. | SEQuence |
|---|---|---|
| UBITh ® | 24 | ISISEIKGVIVHKIETILF<br>  T   RT    TR |
| UBITh ®-εK-UBI FMDV VP1 2570a, cyclized | 25 | ISISEIKGVIVHKIETILF-εK-VYNGNCKYG<br>  T   RT    TR<br>ENAVTNVRGDLQVLAQKAARCLPTSFNYGAIK |
| UBITh ®-εK-UBI FMDV VP1 O Campos/Brazil/58Y, cyclized | 26 | ISISEIKGVIVHKIETILF-εK-VYNGECRYS<br>  T   RT    TR<br>RNAVPNVRGDLQVLAQKVARCLPTSFNYGAIK |
| UBITh ®-εK-UBI FMDV VP1 O swine/Cattle/O/MYA/7/02, cyclized | 27 | ISISEIKGVIVHKIETILF-εK-VYNGNCKYA<br>  T   RT    TR<br>GGSLTNVRGDLQVLAQKAARCLPTSFNYGAIK |
| UBITh ®-εK-UBI FMDV VP1 O/Ozk/93, cyclized | 28 | ISISEIKGVIVHKIETILF-εK-VYNGNCKYS<br>  T   RT    TR<br>DRAVSNVRGDLQVLAQKAARCLPTSFNYGAIK |
| UBITh ®-εK-UBI FMDV VP1 Asia 1 JiangSu/China/2005, cyclized | 29 | ISISEIKGVIVHKIETILF-εK-VYNGKCTY-<br>  T   RT    TR<br>-GEESSRRGDLAALARRVNNCLPTSFNYGAVK |
| UBITh ®-εK-UBI FMDV VP1 A24 Cruzeiro California, cyclized | 30 | ISISEIKGVIVHKIETILF-εK-VYNGTCKYA<br>  T   RT    TR<br>VGGSG-RRGDMGSLAARVVKCLPASFNYGAIK |
| UBITh ®-εK-UBI FMDV VP1 A Gansu/China/60Y, cyclized | 31 | ISISEIKGVIVHKIETILF-εK-VYNGTCQYS<br>  T   RT    TR<br>TGNAG-RRGDLGSLARVAAQCLPASFNFGAIR |
| UBITh ®-εK-UBI FMDV VP1 C3 Indaial/Brazil/84Y, cyclized | 32 | ISISEIKGVIVHKIETILF-εK-TYTGTCAYT<br>  T   RT    TR<br>ASA---RRGDLAHLAAAHARCLPTSFNFGAVK |
| UBITh ®-εK-UBI FMDV VP1 A Argentina 2001, cyclized | 33 | ISISEIKGVIVHKIETILF-εK-VYNGTCKYT<br>  T   RT    TR<br>VSG-SSRRGDLGSLAARVVKACPASFNYGAIK |

TABLE 4

FMDV Endogenous Th Peptides Derived from FMDV O, strain TAW/2/99 (GenBank Accession No. AJ539137)

| Genomic aa position | FMDV Protein | Protein aa position | SEQ ID No | SEQuence |
|---|---|---|---|---|
| S221-M235 | Vp4 | 20-35 | 34 | SIINNYYMQQYQNSM |
| I223-T237 | Vp4 | 22-36 | 35 | INNYYMQQYQNSMDT |
| P360-K374 | Vp2 | 74-88 | 36 | PFGRCYLLELPTDHK |
| D582-A596 | Vp3 | 78-92 | 37 | DLSLAAKHMSNTFLA |
| E745-V7964 | Vp1 | 21-40 | 38 | ETQVQRRQHTDVSFILDRFV |

TABLE 4-continued

FMDV Endogenous Th Peptides Derived from FMDV O, strain TAW/2/99 (GenBank Accession No. AJ539137)

| Genomic aa position | FMDV Protein | Protein aa position | SEQ ID No | SEQuence |
|---|---|---|---|---|
| I759-N773 | Vp1 | 35-49 | 39 | ILDRFVKVTPKDQIN |
| I759-L777 | Vp1 | 35-53 | 40 | ILDRFVKVTPKDQINVLDL |
| V786-L800 | Vp1 | 62-76 | 41 | VGALLRTATYYFADL |
| G808-P828 | Vp1 | 84-104 | 42 | GNLTWVPNGAPETALDNTTNP |
| P835-G856 | Vp1 | 111-132 | 43 | PLTRLALPYTAPHRVLATVYNG |
| T895-C911 | Vp1 | 167-183 | 44 | TRVTELLYRMKRAETYC |
| P912-V933 | Vp1 | 188-209 | 45 | PRPLLAIHPSKARHKQKIVAPV |
| R924-L937 | Vp1 | 200-213 | 46 | RHKQKIVAPVKQLL |
| P954-V968 | 2B | 1-15 | 47 | PFFFSDVRSNFSKLV |
| F1093-K1106 | 2B | 140-153 | 48 | FFRSTPEDLERAEK |
| L1108-N1122 | 2C | 1-15 | 49 | LKARDINDIFAILKN |
| S1143-I1157 | 2C | 36-50 | 50 | SEEKFVTMTDLVPGI |
| V1148-B1162 | 2C | 41-55 | 51 | VTMTDLVPGILEKQR |
| A1446-K1450 | 3A | 21-35 | 52 | AAIEFFEGMVHDSIK |
| N1516-K1529 | 3A | 91-104 | 53 | NEYIEKASITTDDK |
| T1551-L1564 | 3A | 101-114 | 54 | TDDKTLDEAEKNPL |
| E1551-N1564 | 3A | 126-139 | 55 | EKTLPGHKASDDVN |
| G1579-K1592 | 3B1 | 1-14 | 56 | GPYAGPMERQKPLK |
| P1584-L1597 | 3B1 | 6-19 | 57 | PLERQKPLKVRAKL |
| P1607-A1620 | 3B2 | 6-19 | 58 | PMERQKPLKVKVKA |
| P1631-N1644 | 3B3 | 6-19 | 59 | PVKKPVALKVKAKN |
| M1878-F1892 | 3D | 16-30 | 60 | MRKTKLAPTVAHGVF |
| I1918-D1932 | 3D | 56-70 | 61 | IFSKHKGNTKMSEED |
| A2108-V2122 | 3D | 246-260 | 62 | ANHCSDAMNIMFEEV |
| L2248-K2262 | 3D | 386-400 | 63 | LKRHFHMDYGTGFYK |

TABLE 5

Example homologues of FMDV Endogenous Th peptides derived from the same amino acid sequence framework

| | | | |
|---|---|---|---|
| AJ539137 FMDV O, strain TAW/2/99 (I1918-D1932) | FMDV 3D 56-70 Homologue | IFSKHKGNTKMSEED LFSRHRGNTKMSEED | (SEQ ID No. 61) (SEQ ID No. 64) |
| AJ539137 FMDV O, strain TAW/2/99 (A2108-V2122) | FMDV 3D 246-260 Homologue | ANHCSDAMNIMFEEV ANHCSDAMNLMFEEV | (SEQ ID No. 62) (SEQ ID No. 65) |
| AJ539137 FMDV O, strain TAW/2/99 (L2248-K2262) | FMDV 3D386-400 Homologue | LKRHFHMDYGTGFYK IRKHFHMDYGTGFYR | (SEQ ID No. 63) (SEQ ID No. 66) |
| AJ539137 FMDV O, strain TAW/2/99 (F1093-K1106) | FMDV 2B 140-153 Homologue Homologue | FFRSTPEDLERAEK FFKSTPEDVEKAER FFRSTPEEIERAEK | (SEQ ID No. 48) (SEQ ID No. 67) (SEQ ID No. 68) |

TABLE 5-continued

Example homologues of FMDV Endogenous Th peptides derived from the
same amino acid sequence framework

| | | | |
|---|---|---|---|
| AJ539137 FMDV O, strain TAW/2/99 (N1516-K1529) | FMDV 3A 91-104 Homologue Homologue | NEYIEKASITTDDK NDYLERANLTTDPR NEYIEKVSITTDDK | (SEQ ID No. 53) (SEQ ID No. 69) (SEQ ID No. 70) |
| AJ539137 FMDV O, strain TAW/2/99 (M1878-F1892) | FMDV 3D 16-30 Homologue Homologue | MRKTKLAPTVAHGVF MKRTRIAPTLAHGIF MRKTKVAPTIAHGLF | (SEQ ID No. 60) (SEQ ID No. 71) (SEQ ID No. 72) |
| AJ539137 FMDV O, strain TAW/2/99 (S221-M235) | FMDV VP4 20-34 Homologue Homologue | SIINNYYMQQYQNSM SLLNNYYMQQYQNSM SVVNNYYMQQYQNSM | (SEQ ID No. 34) (SEQ ID No. 73) (SEQ ID No. 74) |
| AJ539137 FMDV O, strain TAW/2/99 (P360-K374) | FMDV VP2 74-88 Homologue Homologue | PFGRCYLLELPTDHK PFGKCYIIEIPTDHR PFGRCYVVEVPTDHK | (SEQ ID No. 36) (SEQ ID No. 75) (SEQ ID No. 76) |
| AJ539137 FMDV O, strain TAW/2/99 (D582-A596) | FMDV VP3 78-92 Homologue Homologue | DLSLAAKHMSNTFLA DVSIAAGHMSNTYLS DVSVAAKHMSNTFLV | (SEQ ID No. 37) (SEQ ID No. 77) (SEQ ID No. 78) |

TABLE 6

Examples of functional analogues of FMDV Endogenous Th peptides

| | | |
|---|---|---|
| FMDV AJ539137, Type O/TAW/2/99 (I759-N773) VP1 35-49 | SEQ ID No. 39 | ILDRFVKVTP KDQIN |
| FMDV AJ539137, Type O/TAW/2/99 (I759-L777) VP1 35-53 | SEQ ID No. 40 | ILDRFVKVTP KDQINVLDL |

TABLE 7

(1 of 3)
FMDV Endogenous Th Peptide Library

| | |
|---|---|
| AJ539137 FMDV O. strain TAW/2/99 (I1918-D1932)(FMDV 3D 56-70) SEQ ID No. 79 | IFSKHKGNTKMSEED L   R R   R |
| AJ539137 FMDV O, strain TAW/2/99 (A2108-V2122)(FMDV 3D 246-260) SEQ ID No. 80 | ANHCSDAMNIMFEEV L |
| AJ539137 FMDV O. strain TAW/2/99 (L2248-K2262)(FMDV 3D386-400) SEQ ID No. 81 | LKRHFHMDYGTGFYK IRK          R |
| AJ539137 FMDV O, strain TAW/2/99 (F1093-K1106)(FMDV 2B 140-153) SEQ ID No. 82 | FFRSTPEDLERAEK K    EI K  R V |
| AJ539137 FMDV O, strain TAW/2/99 (N1516-K1529)(FMDV 3A 91-104) SEQ ID No. 83 | NEYIEKASITTDDK D L R NL   PR |
| AJ539137 FMDV O, strain TAW/2/99 (M1878-F1892)(FMDV 3D 16-30) SEQ ID No. 84 | MRKTKLAPTVAHGVF KR RI  L  I V  I  L |
| AJ539137 FMDV O, strain TAW/2/99 (S221-M235)(FMDV VP4 20-34) SEQ ID No. 85 | SIINNYYMQQYQNSM LL VV |
| AJ539137 FMDV O, strain TAW/2/99 (P360-K374)(FMDV VP2 74-88) SEQ ID No. 86 | PFGRCYLLELPTDHK K II I   R VV V |
| AJ539137 FMDV O, strain TAW/2/99 (D582-A596)(FMDV VP3 78-92) SEQ ID No. 87 | DLSLAAKHMSNTFLA V I  G     Y S V          V |

TABLE 7-continued (2 of 3)
FMDV Endogenous Th Peptide Library

| Name | Sequence |
|---|---|
| UBITh ® 3-K-(2B 140-153)-K-(3A 91-104)-K-(3D 16-30) SEQ ID No. 88 | ISISEIKGVIVHKIETILF-K-FFRSTPEDLERAEK-K-NEYIEKASI<br>    T  RT    TR<br>TTDDK-K-MRKTKLAPTVAHGVF |
| UBITh ® 3-K-(VP4 20-34)-K-(VP2 74-88)-K-(VP3 78-92) SEQ ID No. 89 | ISISEIKGVIVHKIETILF-K-SIINNYYMQQYQNSM-K-PFGRCYLL<br>    T  RT    TR<br>ELPTDHK-K-DLSLAAKHMSNTFLA |
| UBITh ® 3-K-(3D 56-70)-K-(3D 248-260)-K-(3D 386-400) SEQ ID No. 90 | ISISEIKGVIVHKIETILF-K-IFSKHKGNTKMSEED-K-ANHCSDAM<br>    T  RT    TR        L R R     R<br>NIMFEEV-K-LKRHFHMDYGTGFYK<br>L       IRK        R |
| UBITh ® 3-K-(2B 140-153)-K-(3A 91-104)-K-(3D 16-30) SEQ ID No. 91 | ISISEIKGVIVHKIETILF-K-FFRSTPEDLERAEK-K-NEYIEKASI<br>    T  RT    TR           K   EI K  R    D L R NL<br>                                          V<br>TTDDK-K-MRKTKLAPTVAHGVF<br>  PR    KR RI  L   I<br>              V  I   L |
| UBITh ® 3-K-(VP4 20-34)-K-(VP2 74-88)-K-(VP3 78-92) SEQ ID No. 92 | ISISEIKGVIVHKIETILF-K-SIINNYYMQQYQNSM-K-PFGRCYLL<br>    T  RT    TR        LL                K II<br>                     VV                    VV<br>ELPTDHK-K-DLSLAAKHMSNTFLA<br>  I    R   V I G     Y S<br>  V         V         V |

(3 of 3)
FMDV Endogenous Th Peptide Library

| Name | Sequence |
|---|---|
| UBITh ® 3-K-FMDV Th library from polyprotein type O, A, C and Asia-1 and type O-1 (ABR19839) sequence based construct (S221-M235)-K-(P360-K374)-K-(D582-A596) SEQ ID No. 93 | UBITh3-K-SIINNYYMQQYQNSM-K-PFGRCYLLELPTDHK-K-DLS<br>         LL           K  II I   R    V<br>         VV               VV V       V<br>LAAKHMSNTFLA<br>I  G    YS<br>         V |
| UBITh ® 3-K-FMDV Th library from polyprotein type O, A, C and Asia-1 and type O-1 (ABR19839) sequence based construct (I759-L777)-K-(G808-P828)-K-(P912-V933) SEQ ID No. 94 | UBITh3-K-ILDRFVKVTPKDQINVLDL-K-GNLTWVPNGAPETALDD<br>        VM      AQLQVSSNTHTIMV    KV      S  VA    E<br>                  EIKAVKPQQI   M      PA       KD   N<br>NTTNP-K-PRPLLAIHPSKARHKQKIVAPV<br>  QS           LDTTQD R   ELI  E<br>  H         I  PVQVNG      P    A |
| UBITh ® 3-K-FMDV Th library from polyprotein type O, A, C and Asia-1 and type O-1 (ABR19839) sequence based construct (V786-L800)-K-(P835-G856)-K-(A1446-K1460) SEQ ID No. 95 | UBITh3-K-VGALLRTATYYFADL-K-PLTRLALPYTAPHRVLATVYN<br>       M     AS     S       V                  A T<br>                  S             F<br>G-K-AAIEFFEGMVHDSIK<br>          V<br>          D |

UBITh ® 3 = SEQ ID NO. 24

TABLE 8

Examples of FMDV peptide immunogens derived from FMDV VP1 SEQuences from Sero-
types A, O and Asia as a single sequence or as a combinatorial library sequence

| Name | Sequence |
|---|---|
| $A_{12}$ (134-159) SEQ ID No. 96 | NKYSASGSG-VRGDFGSLAPRVARQ |
| $A_{12}$ (134-169) SEQ ID No. 97 | NKYSASGSG-VRGDFGSLAPRVARQLPASFNYGAIK |
| $A_{12}$ [134(N→C)$^a$-158(Q→C)$^b$-169] SEQ ID No. 98 | CKYSASGSG-VRGDFGSLAPRVARCLPASFNYGAIK |
| $A_{12}$ [129-134(N→C)$^a$-158(Q→C)$^b$-169] SEQ ID No. 99 | VYNGTCKYSASGSG-VRGDFGSLAPRVARCLPASFNYGAIK |
| UBITh$^e$-εK-$A_{12}$ [129-134(N→C)$^a$-158 (Q→C)$^b$-169] SEQ ID No. 100 | UBITh ®-εK-VYNGTCKYSASGSG-VRGDFGSLAPRVARC LPASFNYGAIK |

TABLE 8-continued

Examples of FMDV peptide immunogens derived from FMDV VP1 SEQuences from Serotypes A, O and Asia as a single sequence or as a combinatorial library sequence

| | |
|---|---|
| UBITh$^e$-εK-O$_{library}$ [134-158 (T→C)$^c$-169], cyclized SEQ ID No. 101 | UBITh ®-εK------CKYGENAVTNVRGDLQVLAQKAARC<br>　　　　　　　　　　　　SD　　　　R　　　E<br>LPTSFNYGAIK |
| UBITh$^e$-εK-Asia$_{library}$ [129-134(T→C)$^c$-158 (R→C)$^d$-169], cyclized SEQ ID No. 102 | UBITh ®-εK-VYNGKCTY--GEQPSRRGDMAALAQRLSRC<br>　　　　　　　　　TS　　　　　　L　　　　VN<br>LPTSFNYGAVK |

$^a$N$_{134}$ of the native sequence is replaced by C.
$^b$Q$_{158}$ of the native VP1 sequence is replaced by C.
$^c$T$_{134}$ of the native sequence is replaced by C.
$^d$R$_{158}$ of the native sequence is replaced by C.
$^e$UBITh = SEQ ID NO. 24

TABLE 9

Optimization of FMDV Target Antigenic Peptide by SEQuence Conformation and Immunostimulatory Elements

| Peptide SEQ ID No | Description of Target Antigenic Peptide | No. of Animals Responding$^c$ (n = 3) | Log$_{10}$ Anti-FMDV-VP1 ELISA Titer$^d$ | Log$_{10}$ of FMDV-A$_{FP}$ (TCID$_{50}$) neutralized by serum$^{d,e}$ |
|---|---|---|---|---|
| 96 | A$_{12}$ (134-159) | 3 | 4.144 | 2.5 |
| 97 | A$_{12}$ (134-169) | 3 | 4.395 | 4.0 |
| 98 | A$_{12}$ [134(N→C)$^a$-158(Q→C)$^b$-169] | 3 | 5.189 | 6.0 |
| 99 | A$_{12}$ [129-134(N→C)$^a$-158(Q→C)$^b$-169] | 3 | 5.532 | 6.5 |
| 100 | UBITh-εK-A$_{12}$ [129-134(N→C)$^a$-158(Q→C)$^b$-169] | 3 | 5.812 | 7.0 |

$^a$N$_{134}$ of the native sequence is replaced by C.
$^b$Q$_{158}$ of the native VP1 sequence is replaced by C.
$^c$No. of animal responding from group of 3 at 5 weeks post initial immunization.
$^d$Test results for pooled sera from ELISA-reactive animals.
$^e$Serum for neutralization Index assay diluted 1:10.

TABLE 10

Immunogenic VP1 Peptide library for Improved Immunogenicity and Breadth of FMDV Neutralization

| SEQ ID No | Description of Target Antigenic Peptide | WPI$^d$ | No. of Animals Responding (n = 3) | Log$_{10}$ Anti-FMDV-VP1$^e$ ELISA Titer | Log$_{10}$ of FMDV (TCID$_{50}$) neutralized by serum$^{e,f}$ | | | | | | |
|---|---|---|---|---|---|---|---|---|---|---|---|
| | | | | | A$_{12\,FP}$ | O-1$_{JH}$ | A$_{FL}$ | O-1$_{P2}$ | A$_{23}$ | Asia$_1$ | A$_1$ |
| 101 | UBITh-εK- O complete library [134-158 (T→C)$^a$-169] cyclized | 5 | 3 | 5.158 | 3.0 | ≥4.5 | 2.0 | | | | 5.0 |
| | | 10 | | | | | | 2.5 | 4.5 | ≥6.0 | |
| 102 | UBITh-εK- Asia library [134(T→C)$^b$ -158(R→C)$^c$ -169] cyclized | 5 | 3 | 5.256 | 3.0 | ≥4.5 | 2.0 | | | | 4.5 |
| | | 10 | | | | | | 1.0 | 3.0 | 2.5 | |

$^a$T$_{158}$ of the native sequence is replaced by C.
$^b$T$_{134}$ of the native sequence is replaced by C.
$^c$R$_{158}$ of the native sequence is replaced by C.
$^d$Weeks post-initial immunization.
$^e$Reactivities for pooled sera from ELISA-reactive animals.
$^f$Serum for neutralization index assay diluted 1:100.

UBI's optimized synthetic FMDV immunogens elicited in guinea pigs neutralizing antibodies simultaneously against multiple serotypes such as A, O and Asia 1, showing potential for unexpected broad efficacy across serotypes.

TABLE 11

Immunogenic Consensus VP1 Peptide for Broad FMDV Neutralization

| Peptide SEQ ID No | Description of Target Antigenic Peptide | WPI[b] | $Log_{10}$ Anti-FMDV-VP1 ELISA Titer[c] | $Log_{10}$ of FMDV ($TCID_{50}$) neutralized by serum[c,d] | | | |
|---|---|---|---|---|---|---|---|
| | | | | $A_{12\ FP}$ | $O\text{-}1_{PI}$ | $O\text{-}1_{Taiwan}$ | $Asia_1$ |
| 25 | UBITh-εK-O Consensus [129-158 (T→C)[a]-169] | 3 | 4.155 | 2.5 | 4.0 | 5.0 | 2.0 |
| | | 5 | 4.864 | 2.5 | | 5.0 | 2.0 |

[a]$T_{158}$ of the native sequence is replaced by C.
[b]Weeks post initial immunization.
[c]Reactivities for pooled sera from ELISA-reactive animals.
[d]Serum for neutralization index assay diluted 1:100.
UBI's optimized synthetic FMDV O Vaccine employing consensus sequence derived from multiple serotype O sequences can elicit potent neutralizing antibodies as early as 3 weeks post initial immunization against multiple serotypes such as A, Asia 1 and O, including $O_{Taiwan}$.

TABLE 12

Protection from FMDV $O_{Taiwan}$ Challenge by UBI FMDV $O_{Consensus}$ vaccine

| Description | Group No. | Group Size (n) | Neutralizing Antibody Titer | Number Infected/n | Per Cent Protected |
|---|---|---|---|---|---|
| UBI FMDV O consensus vaccine | 1 | 6 | 62 | 0/6 | 100% |
| | 2 | 4 | 422 | 0/4 | 100% |
| | 3 | 2 | 256 | 0/2 | 100% |
| | 4 | 3 | 112 | 0/3 | 100% |
| Negative controls | 5 | 4 | <3 | 4/4 | 0% |
| | 6 | 3 | <3 | 3/3 | 0% |
| | 7 | 3 | <3 | 3/3 | 0% |

UBITh FMDV $O_{Consensus}$ Vaccine, after two immunizations at weeks 0 and 3, effectively protected all (15/15) vaccinated pigs from FMDV $O_{Taiwan}$ challenge in studies conducted in four experimental groups at three international institutes. All (10/10) negative control animals were infected by day 2 following viral challenge.

TABLE 13

Broad FMDV O Neutralization by Sera from UBI-USDA PIADC Challenge Trial in Swine

| Vaccine | $O_{Taiwan}$ | $O_{Manisa}$ | $O_{Campos}$ | $O_{Myanmar}$ |
|---|---|---|---|---|
| UBI FMDV $O_{Mixture}$ (SEQ ID Nos: 25, 27 and 28 at equal ratio) Peptide vaccine | 3.0 | 3.0 | 2.5 | 2.5 |
| | 2.5 | 2.5 | 2.5 | 2.5 |
| | 2.5 | 2.5-3.0 | 2.5 | 3.0 |
| | 3.0 | 2.5 | 2.5 | 2.5 |
| | 3.5 | 4.0 | 3.0 | 3.0 |
| | 3.5 | 3.5-4.0 | 3.5 | 3.5 |

All sera were diluted 1/100 and tested on serial dilutions of the indicated FMDV O subtype. The neutralization index values shown are the Log10 of the endpoint $TCID_{50}$, at which 50% of input virus was inactivated.
UBITh FMDV O mixture Vaccine elicited in the swine more broadly protective neutralizing antibodies against multiple FMDV O subtypes after two immunizations at weeks 0 and 3.

TABLE 14

FMDV VP1 immunogen based Vaccine formulations for Mono, Bi, and Trivalent vaccines targeting specific serotypes tailored for regional needs

| Formulation Code | Description of UBITh ® FMDV Vaccine | VP1 Immunogen Content | Region Applicable |
|---|---|---|---|
| (a) | Monovalent FMDV vaccine serotype O with consensus sequence | SEQ ID No: 25 | China and South/East Asia |
| (b) | Bivalent FMDV vaccine serotype O with consensus sequence plus O Ozk/93 | SEQ ID No: 25 SEQ ID No: 28 | China and South/East Asia |
| (c) | Trivalent FMDV vaccine serotype O with consensus sequence plus O Ozk/93 and O Myanmar | SEQ ID No: 25 SEQ ID No: 28 SEQ ID No: 27 | China and South/East Asia |
| (d) | Bivalent cattle/Ruminant FMDV vaccine for serotypes O and Asia1 Jiansu | SEQ ID No: 25 SEQ ID No: 28 SEQ ID No: 27 SEQ ID No: 29 | China and South/East Asia |
| (e) | Trivalent cattle/Ruminant FMDV vaccine for serotypes O (Consensus, Ozk/93 and Myanmar), Asia1 Jiansu and A Gansu | SEQ ID No: 25 SEQ ID No: 28 SEQ ID No: 27 SEQ ID No: 29 SEQ ID No: 31 | China and South/East Asia |
| (f) | Trivalent cattle/Ruminant FMDV vaccine for serotypes O Campos, A24 and C Indaial | SEQ ID No: 26 SEQ ID No: 30 SEQ ID No: 32 | Brazil |
| (g) | Trivalent cattle/Ruminant FMDV vaccine for serotypes O Campos, A Argentina$_{2001}$ and C Indaial | SEQ ID No: 26 SEQ ID No: 33 SEQ ID No: 32 | Argentina |

Immunogen Content = 25 ug/mL containing equal ratio by weight of individual VP1 peptide immunogens
Amount of Immunogen per Dose for Swine = 25 μg/mL/dose/IM
Amount of Immunogen per Dose for Cattle = 100 μg/2 mL/dose/IM
IM = (Intramuscular)

TABLE 15

Immunogenicity Assessment after Two Shots for FMDV VPI Immunogen Peptides in Pigs by target peptide based ELISAs and Neutralizing Antibody Titers

| | | | 0 wpi | | | | 6 wpi | | | |
|---|---|---|---|---|---|---|---|---|---|---|
| | | | FMDV VPI Peptide ELISA at 1/100 dil | | | | FMDV VPI Peptide ELISA $Log_{10}$ Titer | | | |
| Code of Formulation | Description of UBITh® FMDV O vaccine | Animal No. | SEQ ID No: 2 | SEQ ID No: 8 | SEQ ID No: 7 | NA vs O Taiwan | SEQ ID No: 2 | SEQ ID No: 8 | SEQ ID No: 7 | NA vs O Taiwan |
| (a) | Monovalent FMDV vaccine serotype O with Consensus VPI sequence (2570a) (SEQ ID No: 25) | 4668 | 0.061 | 0.064 | 0.069 | 3 | 5.035 | 5.473 | 5.535 | 362 |
| | | 4669 | 0.056 | 0.075 | 0.071 | | 4.855 | 5.117 | 5.142 | |
| | | 4670 | 0.058 | 0.051 | 0.049 | | 4.873 | 5.259 | 5.297 | |
| | | Avg | 0.059 | 0.063 | 0.063 | | 4.921 | 5.283 | 5.325 | |
| | | SD | 0.002 | 0.012 | 0.012 | | 0.099 | 0.179 | 0.198 | |
| (b) | Bivalent FMDV vaccine serotype O with Consensus VPI sequence plus O Ozk/93 (SEQ ID Nos: 25, 28) | 4683 | 0.045 | 0.054 | 0.055 | 3 | 4.726 | 5.103 | 5.067 | 91 |
| | | 4684 | 0.045 | 0.050 | 0.052 | | 4.634 | 5.058 | 5.032 | |
| | | 4685 | 0.061 | 0.049 | 0.066 | | 4.844 | 5.263 | 5.189 | |
| | | Avg | 0.050 | 0.051 | 0.057 | | 4.735 | 5.141 | 5.096 | |
| | | SD | 0.009 | 0.002 | 0.007 | | 0.105 | 0.108 | 0.082 | |
| (c) | Trivalent FMDV vaccine serotype O with Consensus VPI sequence plus O Ozk/93 and O Myanmar (SEQ ID Nos: 25, 28, 27) | 4686 | 0.105 | 0.056 | 0.073 | 3 | 4.829 | 5.267 | 5.243 | 128 |
| | | 4687 | 0.050 | 0.055 | 0.076 | | 4.738 | 5.078 | 5.054 | |
| | | 4688 | 0.063 | 0.094 | 0.062 | | 4.756 | 5.081 | 5.053 | |
| | | Avg | 0.072 | 0.068 | 0.070 | | 4.774 | 5.142 | 5.117 | |
| | | SD | 0.029 | 0.022 | 0.007 | | 0.048 | 0.108 | 0.109 | |

TABLE 16

Immunogenicity Assessment after Two Shots for FMDV VPI Immunogen Peptides in cattle by target peptide based ELISAs and Neutralizing Antibody Titers

| | | | 0 wpi | | | | | | 6 wpi | | | | | |
|---|---|---|---|---|---|---|---|---|---|---|---|---|---|---|
| | | | FMDV VPI Peptide ELISA at 1/100 dil | | | | | | FMDV VPI Peptide ELISA at 1/100 dil | | | | | |
| Code of Form. | Description of UBITh® FMDV O vaccine | Animal No. | SEQ ID No: 2 | SEQ ID No: 8 | SEQ ID No: 7 | SEQ ID No: 15 | SEQ ID No: 18 | NA vs O Taiwan | SEQ ID No: 2 | SEQ ID No: 8 | SEQ ID No: 7 | SEQ ID No: 15 | SEQ ID No: 18 | NA vs O Taiwan |
| (d) | Bivalent cattle/Ruminant FMDV vaccine for serotypes O (Consensus, Ozk, Myanmar) (SEQ ID Nos: 25, 28, 27) and Asia 1 Jiansu (SEQ ID No: 29) | G47 | 0.050 | 0.043 | 0.055 | 0.050 | 0.048 | 3 | 4.139 | 4.171 | 4.687 | 3.284 | 3.462 | 64 |
| | | G66 | 0.046 | 0.044 | 0.052 | 0.046 | 0.045 | | 4.647 | 4.689 | 4.852 | 3.970 | 4.082 | |
| | | G68 | 0.046 | 0.041 | 0.058 | 0.047 | 0.047 | | 4.801 | 4.867 | 4.995 | 4.729 | 4.675 | |
| (e) | Trivalent FMDV vaccine serotype O with serotypes O (Consensus, Ozk, Myanmar) (SEQ ID Nos: 25, 28, 27), sequences plus Asia 1 Jiansu (SEQ ID No: 29) and A Gansu (SEQ ID No: 31) | G69 | 0.053 | 0.044 | 0.059 | 0.049 | 0.050 | 3 | 3.671 | 4.300 | 4.719 | 3.282 | 3.284 | 72 |
| | | G70 | 0.046 | 0.056 | 0.050 | 0.046 | 0.045 | | 3.510 | 4.518 | 4.621 | 4.046 | 3.857 | |
| | | G74 | 0.048 | 0.045 | 0.048 | 0.047 | 0.051 | | 4.445 | 4.653 | 4.811 | 3.991 | 3.953 | |

TABLE 17

Immunogenicity Assessment after Two shots for FMDV VPI Immunogen Peptides in Cattle by target peptide based ELISAs and Neutralizing Antibody Titers

| Code of Form. | Description of UBITh ® FMDV O vaccine | Animal No. | 0 wpi FMDV VPI Peptide ELISA at 1/100 dil SEQ ID No: 3 | SEQ ID No: 17 | SEQ ID No: 22 | SEQ ID No: 23 | NA vs O Taiwan | 6 wpi FMDV VPI Peptide ELISA $Log_{10}$ Titer SEQ ID No: 3 | SEQ ID No: 17 | SEQ ID No: 22 | SEQ ID No: 23 | NA vs O Taiwan |
|---|---|---|---|---|---|---|---|---|---|---|---|---|
| (f) | Trivalent cattle/Ruminant FMDV vaccine for serotypes O Campos, A24 and C Indaial (SEQ ID Nos: 26, 30, 32) | G69 | 0.044 | 0.040 | 0.045 | 0.044 | 3 | 4.775 | 4.990 | 4.984 | 4.884 | 75 |
| | | G70 | 0.044 | 0.047 | 0.049 | 0.044 | | 4.687 | 4.977 | 4.918 | 4.850 | |
| | | G74 | 0.044 | 0.046 | 0.048 | 0.046 | | 4.827 | 5.160 | 5.106 | 5.100 | |
| (g) | Trivalent cattle/Ruminant FMDV vaccine for serotypes O Campos, A Argentina 2001 and C Indaial (SEQ ID Nos: 26, 33, 32) | G71 | 0.043 | 0.044 | 0.045 | 0.045 | 3 | 4.789 | 5.082 | 5.008 | 4.965 | 73 |
| | | G82 | 0.045 | 0.044 | 0.046 | 0.045 | | 4.590 | 4.820 | 4.818 | 4.660 | |
| | | G96 | 0.043 | 0.044 | 0.045 | 0.045 | | 5.050 | 5.751 | 5.671 | 5.559 | |

TABLE 18

Assessment of Functional Immunogenicity upon single administration of FMDV vaccine formulations containing both FMDV VPI derived B and FMDV endogenous Th epitope cluster peptides in Swine by target peptide based ELISA (O consensus 2570a) and Neutralization Assay against FMDV O Taiwan Strain

| Group No. | FMDV VPI B epitope cluster peptides | FMDV Endogenous Th epitope cluster peptides | Type of Formulation | Animal No. | 0 wpi FMDV VPI Peptide (2570a) ELISA $A_{450}$@1:100 | NA Titer | 3 wpi FMDV VPI Peptide (2570a) ELISA $Log_{10}$ Titer | NA Titer |
|---|---|---|---|---|---|---|---|---|
| 1 | FMDV O Consensus SEQ ID No: 25 | None | FMDV B epitope peptide alone @ 25 ug/mL in ISA50V with 0.1% Tween 80 @ 1 mL per dose | S101 | 0.043 | <3 | 2.145 | <3 |
| | | | | S102 | 0.091 | | 2.022 | |
| | | | | S103 | 0.071 | | 2.355 | |
| | | | | Geomean | 0.065 | | 2.170 | |
| 2 | FMDV O Consensus SEQ ID No: 25 | SEQ ID Nos: 34-63 at equal ratio (by weight) | FMDV B epitope peptide: FMDV Ths epitope peptides at 10:1 ratio (w:w) @ (25 + 2.5)ug/mL in ISA50V with 0.1% Tween 80 @1 mL per dose | S201 | 0.053 | <3 | 2.623 | 45 |
| | | | | S202 | 0.037 | | 2.789 | 91 |
| | | | | S203 | 0.027 | | 3.042 | 56 |
| | | | | S204 | 0.064 | | 2.375 | 11 |
| | | | | S205 | 0.057 | | 2.656 | 64 |
| | | | | Geomean | 0.045 | | 2.688 | 44 |
| 3 | FMDV O Consensus SEQ ID No: 25 | SEQ ID Nos: 61-63 at equal ratio (by weight) | FMDV B epitope peptide: FMDV Ths epitope peptides at 10:1 ratio (w:w) @ (25 + 2.5)ug/mL in ISA50V with 0.1% Tween 80 @ 1 mL per dose | S301 | 0.107 | <3 | 2.623 | 16 |
| | | | | S302 | 0.062 | | 2.789 | 8 |
| | | | | S303 | 0.075 | | 3.042 | 64 |
| | | | | S304 | 0.092 | | 2.375 | 11 |
| | | | | S305 | 0.114 | | 2.656 | 45 |
| | | | | Geomean | 0.088 | | 2.688 | 21 |
| 4 | FMDV O Consensus SEQ ID No: 25 | SEQ ID No: 90 | FMDV B epitope peptide: FMDV Ths epitope peptides at 10:1 ratio (w:w) @ (25 + 2.5)ug/mL in ISA50V with 0.1% Tween 80 @1 mL per dose | S401 | 0.035 | <3 | 2.623 | 32 |
| | | | | S402 | 0.065 | | 2.789 | 32 |
| | | | | S403 | 0.071 | | 3.042 | 64 |
| | | | | S404 | 0.080 | | 2.375 | 11 |
| | | | | S405 | 0.058 | | 2.656 | 45 |
| | | | | Geomean | 0.060 | | 2.688 | 32 |
| 5 | FMDV O Consensus + O Ozk at equal ratio (by weight) SEQ ID Nos: 25, 28 | SEQ ID Nos: 34-63 at equal ratio (by weight) | FMDV B epitope peptide: FMDV Ths epitope peptides at 10:1 ratio (w:w) @ (25 + 2.5)ug/mL in ISA50V with 0.1% Tween 80 @ 1 mL per dose | S501 | 0.089 | <3 | 2.553 | 32 |
| | | | | S502 | 0.075 | | 3.015 | 11 |
| | | | | S503 | 0.088 | | 2.679 | 23 |
| | | | | S504 | 0.073 | | 2.837 | 32 |
| | | | | S505 | 0.081 | | 2.992 | 32 |
| | | | | Geomean | 0.081 | | 2.809 | 24 |

TABLE 18-continued

Assessment of Functional Immunogenicity upon single administration of FMDV vaccine formulations containing both FMDV VPI derived B and FMDV endogenous Th epitope cluster peptides in Swine by target peptide based ELISA (O consensus 2570a) and Neutralization Assay against FMDV O Taiwan Strain

| Group No. | Description of FMDV Vaccine Formulations | | | Animal No. | 0 wpi | | 3 wpi | |
|---|---|---|---|---|---|---|---|---|
| | | | | | FMDV VPI Peptide (2570a) ELISA $A_{450}$@1:100 | NA Titer | FMDV VPI Peptide (2570a) ELISA $Log_{10}$ Titer | NA Titer |
| | FMDV VPI B epitope cluster peptides | FMDV Endogenous Th epitope cluster peptides | Type of Formulation | | | | | |
| 6 | FMDV O Consensus + O Ozk at equal ratio (by weight) SEQ ID Nos: 25, 28 | SEQ ID Nos: 61-63 at equal ratio (by weight) | FMDV B epitope peptide: FMDV Ths epitope peptides at 10:1 ratio (w:w) @ (25 + 2.5)ug/mL in ISA50V with 0.1% Tween 80 @1 mL per dose | S601 S602 S603 S604 S605 Geomean | 0.085 0.068 0.053 0.083 0.058 0.068 | <3 | 2.458 2.651 2.519 2.895 2.501 2.600 | 16 11 4 23 23 13 |
| 7 | FMDV O Consensus + O Ozk at equal ratio (by weight) SEQ ID Nos: 25, 28 | SEQ ID No: 90 | FMDV B epitope peptide: FMDV Ths epitope peptides at 10:1 ratio (w:w) @ (25 + 2.5)ug/mL in ISA50V with 0.1% Tween 80 @1 mL per dose | S701 S702 S703 S704 S705 Geomean | 0.048 0.052 0.085 0.068 0.074 0.064 | <3 | 2.276 2.522 2.597 2.689 2.424 2.497 | 8 11 45 14 32 18 |
| 8 | FMDV O Consensus + O Ozk + O Myanmar at equal ratio (by weight) SEQ ID Nos: 25, 28, 27 | SEQ ID Nos: 34-63 at equal ratio (by weight) | FMDV B epitope peptide: FMDV Ths epitope peptides at 10:1 ratio (w:w) @ (25 + 2.5)ug/mL in ISA50V with 0.1% Tween 80 @1 mL per dose | S801 S802 S803 S804 S805 Geomean | 0.058 0.045 0.074 0.083 0.092 0.068 | <3 | 2.540 2.450 2.622 3.032 2.645 2.651 | 23 32 64 23 91 40 |
| 9 | FMDV O Consensus + O Ozk + O Myanmar at equal ratio (by weight) SEQ ID Nos: 25, 28, 27 | SEQ ID Nos: 61-63 at equal ratio (by weight) | FMDV B epitope peptide: FMDV Ths epitope peptides at 10:1 ratio (w:w) @ (25 + 2.5)ug/mL in ISA50V with 0.1% Tween 80 | S901 S902 S903 S904 S905 Geomean | 0.068 0.059 0.072 0.085 0.094 0.075 | <3 | 2.476 2.752 2.791 2.698 2.501 2.640 | 11 45 11 23 64 24 |
| 10 | FMDV O Consensus + O Ozk + O Myanmar at equal ratio (by weight) SEQ ID Nos: 25, 28, 27 | SEQ ID No: 90 | FMDV B epitope peptide: FMDV Ths epitope peptides at 10:1 ratio (w:w) @ (25 + 2.5)ug/mL in ISA50V with 0.1% Tween 80 | S1001 S1002 S1003 S1004 S1005 Geomean | 0.071 0.068 0.082 0.076 0.063 0.072 | <3 | 2.965 2.459 2.108 2.623 2.900 2.592 | 45 32 11 45 45 32 |
| 11 | FMDV O Consensus + O Ozk + O Myanmar 4 Asia1 Jiansu at equal ratio (by weight) SEQ ID Nos: 25, 28, 27, 29 | SEQ ID Nos: 34-63 at equal ratio (by weight) | FMDV B epitope peptide: FMDV Ths epitope peptides at 10:1 ratio (w:w) @ (25 + 2.5)ug/mL in ISA50V with 0.1% Tween 80 | S1101 S1102 S1103 S1104 S1105 Geomean | 0.065 0.080 0.072 0.053 0.058 0.065 | <3 | 2.741 2.529 3.039 2.702 2.506 2.697 | 23 23 32 11 91 28 |
| 12 | FMDV O Consensus + O Ozk + O Myanmar 4 Asia1 Jiansu at equal ratio (by weight) SEQ ID Nos: 25, 28, 27, 29 | SEQ ID Nos: 61-63 at equal ratio (by weight) | FMDV B epitope peptide: FMDV Ths epitope peptides at 10:1 ratio (w:w) @ (25 + 2.5)ug/mL in ISA50V with 0.1% Tween 80 | S1201 S1202 S1203 S1204 S1205 Geomean | 0.072 0.078 0.055 0.048 0.071 0.064 | <3 | 2.725 2.806 2.744 2.362 2.774 2.677 | 11 32 11 23 11 16 |
| 13 | FMDV O Consensus + O Ozk + O Myanmar 4 Asia1 Jiansu at equal ratio (by weight) SEQ ID Nos: 25, 28, 27, 29 | SEQ ID No: 90 | FMDV B epitope peptide: FMDV Ths epitope peptides at 10:1 ratio (w:w) @ (25 + 2.5)ug/mL in ISA50V with 0.1% Tween 80 | S1301 S1302 S1303 S1304 S1305 Geomean | 0.062 0.049 0.058 0.065 0.073 0.061 | <3 | 2.317 3.366 2.543 3.128 2.259 2.687 | 11 64 16 6 23 17 |

TABLE 19

Assessment of Functional Immunogenicity upon single administration of FMDV vaccine formulations containing both FMDV VP1 derived B and FMDV endogenous Th epitope cluster peptides in Cattle by target peptide based ELISA (O consensus 2570a) and Neutralization Assay against FMDV O Taiwan Strain

| | Description of FMDV Vaccine Formulations | | | | 0 wpi | | 3 wpi | |
|---|---|---|---|---|---|---|---|---|
| | | | | | FMDV VP1 Peptide (2570a) ELISA $A_{450}$@1:100 | NA Titer | FMDV VP1 Peptide (2570a) ELISA $Log_{10}$ Titer | NA Titer |
| Group No. | FMDV VP1 B epitope cluster peptides | FMDV Endogenous Th epitope cluster peptides | Type of Formulation (2 mL per dose) | Animal No. | | | | |
| 1 | FMDV O Consensus SEQ ID No: 25 | SEQ ID Nos: 34-63 (30 Ths) at equal ratio (by weight) | FMDV B epitope peptide: FMDV Ths epitope peptides at 10:1 ratio (w:w) @ (25 + 2.5)ug/mL in ISA50V with 0.1% Tween 80 | C101 C102 C103 Geomean | 0.059 0.069 0.069 0.065 | <3 | 2.843 2.664 3.272 2.915 | 64 16 64 40 |
| 2 | FMDV O Consensus SEQ ID No: 25 | SEQ ID Nos: 34-39, 44, 46-51, 53-63 (24 Ths) at equal ratio (by weight) | FMDV B epitope peptide: FMDV Ths epitope peptides at 10:1 ratio (w:w) @ (25 + 2.5)ug/mL in ISA50V with 0.1% Tween 80 | C201 C202 C203 Geomean | 0.227 0.075 0.065 0.103 | <3 | 2.766 2.472 3.013 2.741 | 45 11 64 32 |
| 3 | FMDV O Consensus SEQ ID No: 25 | SEQ ID Nos: 34-39, 44, 46-51, 53-60 (21 Ths) at equal ratio (by weight) | FMDV B epitope peptide: FMDV Ths epitope peptides at 10:1 ratio (w:w) @ (25 + 2.5)ug/mL in ISA50V with 0.1% Tween 80 | C301 C302 C303 Geomean | 0.068 0.060 0.055 0.061 | <3 | 3.211 3.620 2.517 3.081 | 32 11 45 25 |
| 4 | FMDV O Consensus SEQ ID No: 25 | SEQ ID Nos: 34, 36, 37, 40-43, 45, 48, 52, 53, 60-63 (15 Ths) at equal ratio (by weight) | FMDV B epitope peptide: FMDV Ths epitope peptides at 10:1 ratio (w:w) @ (25 + 2.5)ug/mL in ISA50V with 0.1% Tween 80 | C401 C402 C403 Geomean | 0.039 0.066 0.062 0.054 | <3 | 3.196 2.693 2.531 2.793 | 32 32 45 36 |
| 5 | FMDV O Consensus SEQ ID No: 25 | SEQ ID Nos: 34, 36, 37, 48, 50, 53 (6 Ths) at equal ratio (by weight) | FMDV B epitope peptide: FMDV Ths epitope peptides at 10:1 ratio (w:w) @ (25 + 2.5)ug/mL in ISA50V with 0.1% Tween 80 | C501 C502 C503 Geomean | 0.070 0.071 0.039 0.058 | <3 | 2.082 2.428 3.042 2.487 | 32 16 11 18 |
| 6 | FMDV O Consensus SEQ ID No: 25 | SEQ ID Nos: 62-78 (17 Th homologues) at equal ratio (by weight) | FMDV B epitope peptide: FMDV Ths epitope peptides at 10:1 ratio (w:w) @ (25 + 2.5)ug/mL in ISA50V with 0.1% Tween 80 | C601 C602 C603 Geomean | 0.068 0.076 0.046 0.062 | <3 | 3.305 2.590 2.985 2.945 | 32 11 45 25 |
| 7 | FMDV O Consensus SEQ ID No: 25 | SEQ ID Nos: 79-87 (9 Th short libraries) at equal ratio (by weight) | FMDV B epitope peptide: FMDV Ths epitope peptides at 10:1 ratio (w:w) @ (25 + 2.5)ug/mL in ISA50V with 0.1% Tween 80 | C701 C702 C703 Geomean | 0.060 0.067 0.068 0.065 | <3 | 2.094 3.115 2.933 2.675 | 32 11 45 25 |
| 8 | FMDV O Consensus SEQ ID No: 25 | SEQ ID Nos: 88, 89 (2 UBITh enhanced Th casettes) at equal ratio (by weight) | FMDV B epitope peptide: FMDV Ths epitope peptides at 10:1 ratio (w:w) @ (25 + 2.5)ug/mL in ISA50V with 0.1% Tween 80 | C801 C802 C803 Geomean | 0.064 0.068 0.131 0.083 | <3 | 2.980 2.347 2.415 2.566 | 8 11 32 14 |
| 9 | FMDV O Consensus + O Ozk + O Myanmar at equal ratio (by weight) SEQ ID Nos: 25, 28, 27 | SEQ ID Nos: 88, 89(2 UBITh enhanced Th casettes) at equal ratio (by weight) | FMDV B epitope peptide: FMDV Ths epitope peptides at 10:1 ratio (w:w) @ (25 + 2.5)ug/mL in ISA50V with 0.1% Tween 80 | C901 C902 C903 Geomean | 0.068 0.059 0.094 0.072 | <3 | 2.476 2.752 2.501 2.573 | 32 45 32 36 |
| 10 | FMDV O Consensus + O Ozk + O Myanmar at equal ratio (by weight) SEQ ID Nos: 25, 28, 27 | SEQ ID Nos: 91, 92 (2 UBITh enhanced Th casettes) at equal ratio (by weight) | FMDV B epitope peptide: FMDV Ths epitope peptides at 10:1 ratio (w:w) @ (25 + 2.5)ug/mL in ISA50V with 0.1% Tween 80 | C1001 C1002 C1003 Geomean | 0.071 0.068 0.063 0.067 | <3 | 2.965 2.459 2.900 2.765 | 45 91 45 57 |

TABLE 19-continued

Assessment of Functional Immunogenicity upon single administration of FMDV vaccine formulations containing both FMDV VP1 derived B and FMDV endogenous Th epitope cluster peptides in Cattle by target peptide based ELISA (O consensus 2570a) and Neutralization Assay against FMDV O Taiwan Strain

| | | Description of FMDV Vaccine Formulations | | | 0 wpi | | 3 wpi | |
|---|---|---|---|---|---|---|---|---|
| | | | | | FMDV VP1 | | FMDV VP1 | |
| Group No. | FMDV VP1 B epitope cluster peptides | FMDV Endogenous Th epitope cluster peptides | Type of Formulation (2 mL per dose) | Animal No. | Peptide (2570a) ELISA $A_{450}$@1:100 | NA Titer | Peptide (2570a) ELISA $Log_{10}$ Titer | NA Titer |
| 11 | FMDV O Consensus + O Ozk + O Myanmar at equal ratio (by weight) SEQ ID Nos: 25, 28, 27 | SEQ ID Nos: 91, 93-95 (4 UBITh enhanced Th casettes) at equal ratio (by weight) | FMDV B epitope peptide: FMDV Ths epitope peptides at 10:1 ratio (w:w) @ (25 + 2.5)ug/mL in ISA50V with 0.1% Tween 80 | C1101 C1102 C1103 Geomean | 0.065 0.080 0.058 0.067 | <3 | 2.741 2.789 3.506 2.993 | 128 64 64 81 |
| 12 | FMDV O Consensus + O Ozk + O Myanmar at equal ratio (by weight) SEQ ID Nos: 25, 28, 27 | SEQ ID Nos: 34-39, 44, 46-51, 53-60 (21 Ths) at equal ratio (by weight) | FMDV B epitope peptide: FMDV Ths epitope peptides at 1:1 ratio (w:w) @ (25 + 25)ug/mL in ISA50V with 0.1% Tween 80 | C1201 C1202 C1203 Geomean | 0.072 0.078 0.071 0.074 | <3 | 2.725 2.806 2.774 2.768 | 23 32 256 57 |
| 13 | FMDV O Consensus + O Ozk + O Myanmar at equal ratio (by weight) SEQ ID Nos: 25, 28, 27 | SEQ ID Nos: 34-39, 44, 46-51, 53-60 (21 Ths) at equal ratio (by weight) | FMDV B epitope peptide: FMDV Ths epitope peptides at 5:1 ratio (w:w) @ (25 + 5)ug/mL in ISA50V with 0.1% Tween 80 | C1301 C1302 C1303 Geomean | 0.062 0.049 0.073 0.061 | <3 | 2.317 3.366 2.259 2.602 | 32 16 181 45 |
| 14 | FMDV O Consensus + O Ozk + O Myanmar at equal ratio (by weight) SEQ ID Nos: 25, 28, 27 | SEQ ID Nos: 34-39, 44, 46-51, 53-60 (21 Ths) at equal ratio (by weight) | FMDV B epitope peptide: FMDV Ths epitope peptides at 10:1 ratio (w:w) @ (25 + 2.5)ug/mL in ISA50V with 0.1% Tween 80 | C1401 C1402 C1403 Geomean | 0.083 0.079 0.073 0.078 | <3 | 2.623 2.289 2.656 2.517 | 32 32 11 22 |
| 15 | FMDV O Consensus + O Ozk + O Myanmar at equal ratio (by weight) SEQ ID Nos: 25, 28, 27 | SEQ ID Nos: 34-39, 44, 46-51, 53-60 (21 Ths) at equal ratio (by weight) | FMDV B epitope peptide: FMDV Ths epitope peptides at 50:1 ratio (w:w) @ (25 + 0.5)ug/mL in ISA50V with 0.1% Tween 80 | C1501 C1502 C1503 Geomean | 0.083 0.079 0.073 0.078 | <3 | 2.623 2.289 2.656 2.517 | 8 8 16 10 |
| 16 | FMDV O Consensus + O Ozk + O Myanmar at equal ratio (by weight) SEQ ID Nos: 25, 28, 27 | SEQ ID Nos: 34-39, 44, 46-51, 53-60 (21 Ths) at equal ratio (by weight) | FMDV B epitope peptide: FMDV Ths epitope peptides at 100:1 ratio (w:w) @ (25 + 0.25)ug/mL in ISA50V with 0.1% Tween 80 | C1601 C1602 C1603 Geomean | 0.082 0.073 0.063 0.072 | <3 | 3.084 2.363 2.621 2.673 | 3 8 11 6 |
| 17 | FMDV O Consensus + O Ozk + O Myanmar 4 Asia1 Jiansu at equal ratio (by weight) SEQ ID Nos: 25, 28, 27, 29 | SEQ ID Nos: 34, 36, 37, 40-43, 45, 48, 52, 53, 60-63 (15 Ths) at equal ratio (by weight) | FMDV B epitope peptide: FMDV Ths epitope peptides at 10:1 ratio (w:w) @ (25 + 2.5)ug/mL in ISA50V with 0.1% Tween 80 | C1701 C1702 C1703 Geomean | 0.043 0.097 0.082 0.070 | <3 | 3.196 2.645 3.314 3.037 | 256 64 32 81 |
| 18 | FMDV O Consensus + O Ozk + O Myanmar + Asia1 Jiansu at equal ratio (by weight) SEQ ID Nos: 25, 28, 27, 29 | SEQ ID Nos: 88, 89 (2 UBITh enhanced Th casettes) at equal ratio (by weight) | FMDV B epitope peptide: FMDV Ths epitope peptides at 10:1 ratio (w:w) @ (25 + 2.5)ug/mL in ISA50V with 0.1% Tween 80 | C1801 C1802 C1803 Geomean | 0.055 0.042 0.053 0.050 | <3 | 3.597 3.167 2.654 3.115 | 16 32 64 32 |
| 19 | FMDV O Consensus + O Ozk + O Myanmar + Asia1 Jiansu at equal ratio (by weight) SEQ ID Nos: 25, 28, 27, 29 | SEQ ID Nos: 91, 92 (2 UBITh enhanced Th casettes) at equal ratio (by weight) | FMDV B epitope peptide: FMDV Ths epitope peptides at 10:1 ratio (w:w) @ (25 + 2.5)ug/mL in ISA50V with 0.1% Tween 80 | C1901 C1902 C1903 Geomean | 0.097 0.065 0.092 0.083 | <3 | 2.500 3.156 2.428 2.676 | 32 32 45 36 |
| 20 | FMDV O Consensus + O Ozk + O Myanmar + Asia1 Jiansu at equal ratio (by weight) SEQ ID Nos: 25, 28, 27, 29 | SEQ ID Nos: 91, 93, 94, 95 at equal ratio (by weight) | FMDV B epitope peptide: FMDV Ths epitope peptides at 10:1 ratio (w:w) @ (25 + 2.5)ug/mL in ISA50V with 0.1% Tween 80 | C2001 C2002 C2003 Geomean | 0.045 0.063 0.058 0.055 | <3 | 2.950 2.390 3.292 2.853 | 32 64 256 81 |

TABLE 19-continued

Assessment of Functional Immunogenicity upon single administration of FMDV vaccine formulations containing both FMDV VP1 derived B and FMDV endogenous Th epitope cluster peptides in Cattle by target peptide based ELISA (O consensus 2570a) and Neutralization Assay against FMDV O Taiwan Strain

| Group No. | FMDV VP1 B epitope cluster peptides | FMDV Endogenous Th epitope cluster peptides | Type of Formulation (2 mL per dose) | Animal No. | 0 wpi FMDV VP1 Peptide (2570a) ELISA $A_{450}$@1:100 | 0 wpi NA Titer | 3 wpi FMDV VP1 Peptide (2570a) ELISA $Log_{10}$ Titer | 3 wpi NA Titer |
|---|---|---|---|---|---|---|---|---|
| 21 | FMDV O Consensus + O Ozk + O Myanmar + Asia1 Jiansu + A Gansu at equal ratio (by weight) SEQ ID Nos: 25, 28, 27, 29, 31 | SEQ ID Nos: 34, 36, 37, 40-43, 45, 48, 52, 53, 60-63 (15 Ths) at equal ratio (by weight) | FMDV B epitope peptide: FMDV Ths epitope peptides at 10:1 ratio (w:w) @ (25 + 2.5)ug/mL in ISA50V with 0.1% Tween 80 | C2101 C2102 C2103 Geomean | 0.058 0.047 0.058 0.054 | <3 | 2.523 2.738 2.666 2.641 | 45 91 64 64 |
| 22 | FMDV O Consensus + O Ozk + O Myanmar + Asia1 Jiansu + A Gansu at equal ratio (by weight) SEQ ID Nos: 25, 28, 27, 29, 31 | SEQ ID Nos: 88, 89 (2 UBITh enhanced Th casettes) at equal ratio (by weight) | FMDV B epitope peptide: FMDV Ths epitope peptides at 10:1 ratio (w:w) @ (25 + 2.5)ug/mL in ISA50V with 0.1% Tween 80 | C2201 C2202 C2203 Geomean | 0.117 0.072 0.094 0.093 | <3 | 3.608 2.185 3.441 3.005 | 32 8 16 16 |
| 23 | FMDV O Consensus + O Ozk + O Myanmar + Asia1 Jiansu + A Gansu at equal ratio (by weight) SEQ ID Nos: 25, 28, 27, 29, 31 | SEQ ID Nos: 91, 92 (2 UBITh enhanced Th casettes) at equal ratio (by weight) | FMDV B epitope peptide: FMDV Ths epitope peptides at 10:1 ratio (w:w) @ (25 + 2.5)ug/mL in ISA50V with 0.1% Tween 80 | C2301 C2302 C2303 Geomean | 0.045 0.066 0.059 0.056 | <3 | 2.804 2.786 3.149 2.908 | 32 11 45 25 |
| 24 | FMDV O Consensus + O Ozk + O Myanmar + Asia1 Jiansu + A Gansu at equal ratio (by weight) SEQ ID Nos: 25, 28, 27, 29, 31 | SEQ ID Nos: 91, 93, 94, 95 at equal ratio (by weight) | FMDV B epitope peptide: FMDV Ths epitope peptides at 10:1 ratio (w:w) @ (25 + 2.5)ug/mL in ISA50V with 0.1% Tween 80 | C2401 C2402 C2403 Geomean | 0.079 0.065 0.071 0.071 | <3 | 3.148 3.056 2.963 3.055 | 91 32 23 41 |
| 25 | FMDV O Campos + A24 + C Indaial at equal ratio (by weight) for Brazil use SEQ ID Nos: 26, 30, 32 | SEQ ID Nos: 91, 92 at equal ratio (by weight) | FMDV B epitope peptide: FMDV Ths epitope peptides at 10:1 ratio (w:w) @ (25 + 2.5)ug/mL in ISA50V with 0.1% Tween 80 | C2501 C2502 C2503 Geomean | 0.097 0.070 0.058 0.073 | <3 | 2.793 2.894 2.145 2.588 | 32 45 11 25 |
| 26 | FMDV O Campos + A24 + C Indaial at equal ratio (by weight) for Brazil use SEQ ID Nos: 26, 30, 32 | SEQ ID Nos: 91, 93, 94, 95 at equal ratio (by weight) | FMDV B epitope peptide: FMDV Ths epitope peptides at 10:1 ratio (w:w) @ (25 + 2.5)ug/mL in ISA50V with 0.1% Tween 80 | C2601 C2602 C2603 Geomean | 0.069 0.109 0.058 0.076 | <3 | 3.148 3.056 2.963 3.055 | 45 23 45 36 |
| 27 | FMDV O Campos + A24 + C Indaial at equal ratio (by weight) for Brazil use SEQ ID Nos: 26, 30, 32 | SEQ ID Nos: 91, 92 at equal ratio (by weight) | FMDV B epitope peptide: FMDV Ths epitope peptides at 10:1 ratio (w:w) @ (25 + 2.5)ug/mL in Emulsigen D | C2701 C2702 C2703 Geomean | 0.058 0.065 0.057 0.060 | <3 | 2.804 2.786 3.149 2.908 | 91 23 32 41 |
| 28 | FMDV O Campos + A24 + C Indaial at equal ratio (by weight) for Brazil use SEQ ID Nos: 26, 30, 32 | SEQ ID Nos: 91, 93, 94, 95 at equal ratio (by weight) | FMDV B epitope peptide: FMDV Ths epitope peptides at 10:1 ratio (w:w) @ (25 + 2.5)ug/mL in Emulsigen D | C2801 C2802 C2803 Geomean | 0.076 0.049 0.056 0.059 | <3 | 2.858 3.370 3.070 3.092 | 64 32 91 57 |
| 29 | FMDV O Campos + A Argentina 2001 + C Indaial at equal ratio (by weight) for Argentina use SEQ ID Nos: 26, 33, 32 | SEQ ID Nos: 91, 92 at equal ratio (by weight) | FMDV B epitope peptide: FMDV Ths epitope peptides at 10:1 ratio (w:w) @ (25 + 2.5)ug/mL in ISA50V with 0.1% Tween 80 | C2901 C2902 C2903 Geomean | 0.054 0.062 0.048 0.054 | <3 | 3.141 3.230 2.383 2.892 | 11 32 23 20 |
| 30 | FMDV O Campos + A Argentina 2001 + C Indaial at equal ratio (by weight) for Argentina use SEQ ID Nos: 26, 33, 32 | SEQ ID Nos: 91, 93, 94, 95 at equal ratio (by weight) | FMDV B epitope peptide: FMDV Ths epitope peptides at 10:1 ratio (w:w) @ (25 + 2.5)ug/mL in ISA50V with 0.1% Tween 80 | C3001 C3002 C3003 Geomean | 0.051 0.048 0.050 0.050 | <3 | 3.141 3.230 2.383 2.892 | 32 16 16 20 |

TABLE 19-continued

Assessment of Functional Immunogenicity upon single administration of FMDV vaccine formulations containing both FMDV VP1 derived B and FMDV endogenous Th epitope cluster peptides in Cattle by target peptide based ELISA (O consensus 2570a) and Neutralization Assay against FMDV O Taiwan Strain

| | Description of FMDV Vaccine Formulations | | | | 0 wpi | | 3 wpi | |
|---|---|---|---|---|---|---|---|---|
| | | | | | FMDV VP1 | | FMDV VP1 | |
| Group No. | FMDV VP1 B epitope cluster peptides | FMDV Endogenous Th epitope cluster peptides | Type of Formulation (2 mL per dose) | Animal No. | Peptide (2570a) ELISA $A_{450}$@1:100 | NA Titer | Peptide (2570a) ELISA $Log_{10}$ Titer | NA Titer |
| 31 | FMDV O Campos + A Argentina 2001 + C Indaial at equal ratio (by weight) for Argentina use SEQ ID Nos: 26, 33, 32 | SEQ ID Nos: 91, 92 at equal ratio (by weight) | FMDV B epitope peptide: FMDV Ths epitope peptides at 10:1 ratio (w:w) @ (25 + 2.5)ug/mL in Emulsigen D | C3101 C3102 C3103 Geomean | 0.068 0.059 0.105 0.075 | <3 | 3.141 2.883 2.485 2.823 | 45 16 64 36 |
| 32 | FMDV O Campos + A Argentina 2001 + C Indaial at equal ratio (by weight) for Argentina use SEQ ID Nos: 26, 33, 32 | SEQ ID Nos: 91, 93, 94, 95 at equal ratio (by weight) | FMDV B epitope peptide: FMDV Ths epitope peptides at 10:1 ratio (w:w) @ (25 + 2.5)ug/mL in Emulsigen D | C3201 C3202 C3203 Geomean | 0.059 0.060 0.056 0.058 | <3 | 2.597 3.225 3.045 2.943 | 256 23 16 46 |

TABLE 20

Challenge Studies Conducted in Pigs

| GRP # | Formulation | # of Animal/ group | Animal ID # | Dose volume | Immunization site | Shot No |
|---|---|---|---|---|---|---|
| 1 | Groups 5, 6, 7 of Study II from Table 25 | 3 | 2222, 2223, 2224 | 2.0 mL | IM | 1 |
| 2 | | 3 | 2225, 2226, 2227 | 1.0 mL | IM | 1 |
| 3 | | 3 | 2228, 2229, 2230 | 0.5 mL | IM | 1 |
| 4 | Groups 13, 14, 15 of Study IV from Table 25 | 3 | 2231, 2232, 2233 | 2.0 mL | IM | 1 |
| 5 | | 3 | 2234, 2235, 2236 | 1.0 mL | IM | 1 |
| 6 | | 3 | 2237, 2238, 2239 | 0.5 mL | IM | 1 |
| 7 | Groups 16, 17, 18 of Study V from Table 25 | 3 | 2240, 2241, 2242 | 1.0 mL | IM | 1 |
| 8 | | 3 | 2243, 2244, 2245 | 1.0 mL | IM | 1 |
| 9 | | 3 | 2246, 2247, 2248 | 1.0 mL | IM | 1 |
| 10 | Group 19 of Study V from Table 25 | 3 | 2249, 2250, 2251 | 2.0 mL | IM | 1 |
| 11 | Group 20 of Study V from Table 25 | 2 | 2252, 2253 | No Injection | No Injection | 1 |

IM = Intramuscular

TABLE 21

The body temperature of each pig were recorded during 1~14 days after challenging.

| Grouping | | Temperature (° C.) (DPC) | | | | | | | | | | | | | | |
|---|---|---|---|---|---|---|---|---|---|---|---|---|---|---|---|---|
| GRP # | ID # | 0 | 1 | 2 | 3 | 4 | 5 | 6 | 7 | 8 | 9 | 10 | 11 | 12 | 13 | 14 |
| 1 | 2222 | 39.2 | 39.6 | 39.4 | 39.6 | 39.5 | 38.9 | 39.8 | 39.6 | 39.6 | 39.3 | 39.2 | 39.2 | 39.7 | 39.3 | 39.5 |
| | 2223 | 39.2 | 39.6 | 39.1 | 39.4 | 39.6 | 39.1 | 39.7 | 39.5 | 39.3 | 39.4 | 39.4 | 39.6 | 39.6 | 39.2 | 40.0 |
| | 2224 | 39.1 | 39.6 | 39.1 | 39.5 | 39.5 | 39.2 | 39.6 | 39.4 | 39.6 | 39.6 | 39.5 | 39.5 | 39.5 | 39.5 | 39.7 |
| 2 | 2225 | 39.0 | 39.5 | 39.3 | 39.8 | 39.3 | 39.3 | 39.7 | 39.5 | 39.8 | 39.8 | 39.5 | 39.4 | 39.0 | 39.3 | 39.7 |
| | 2226 | 39.5 | 39.4 | 39.9 | 39.8 | 39.8 | 38.7 | 39.5 | 39.8 | 39.6 | 39.7 | 39.7 | 39.3 | 39.8 | 39.7 | 39.5 |
| | 2227 | 39.0 | 38.9 | 39.7 | 39.3 | 39.7 | 39.0 | 39.7 | 39.3 | 39.1 | 39.3 | 39.3 | 39.4 | 39.7 | 39.2 | 39.7 |
| 3 | 2228 | 39.1 | 39.1 | 39.3 | 39.2 | 39.0 | 39.0 | 39.2 | 39.1 | 39.0 | 39.0 | 38.8 | 38.7 | 39.9 | 39.1 | 38.7 |
| | 2229 | 39.4 | 39.6 | 39.8 | 39.8 | 39.9 | 39.7 | 40.2 | 39.8 | 39.8 | 39.7 | 39.5 | 39.2 | 38.9 | 39.3 | 39.6 |
| | 2230 | 39.6 | 39.5 | 39.2 | 39.4 | 39.3 | 39.4 | 39.6 | 39.6 | 39.6 | 39.5 | 39.4 | 39.2 | 39.5 | 39.3 | 39.1 |
| 4 | 2231 | 40.3 | 40.2 | 40.1 | 39.5 | 38.7 | 39.0 | 40.2 | 38.9 | 38.7 | 38.7 | 38.0 | 38.2 | 38.6 | 38.8 | 39.1 |
| | 2232 | 39.1 | 39.4 | 39.5 | 39.2 | 39.5 | 39.6 | 41.1 | 39.8 | 40.0 | 39.1 | 39.0 | 39.0 | 38.9 | 38.7 | 38.7 |
| | 2233 | 39.5 | 39.5 | 39.3 | 39.2 | 39.5 | 39.6 | 39.7 | 39.9 | 39.3 | 38.9 | 39.1 | 39.1 | 39.4 | 39.2 | 39.3 |

TABLE 21-continued

The body temperature of each pig were recorded during 1~14 days after challenging.

| Grouping | | Temperature (° C.) (DPC) | | | | | | | | | | | | | | |
|---|---|---|---|---|---|---|---|---|---|---|---|---|---|---|---|---|
| GRP # | ID # | 0 | 1 | 2 | 3 | 4 | 5 | 6 | 7 | 8 | 9 | 10 | 11 | 12 | 13 | 14 |
| 5 | 2234 | 39.4 | 39.9 | 39.1 | 39.8 | 39.6 | 40.4 | 39.7 | 39.2 | 39.9 | 38.8 | 38.8 | 39.1 | 39.1 | 39.0 | 39.1 |
| | 2235 | 39.0 | 39.8 | 39.6 | 39.5 | 39.7 | 39.7 | 39.7 | 39.7 | 39.4 | 39.4 | 39.5 | 39.4 | 39.5 | 39.6 | 39.3 |
| | 2236 | 39.5 | 39.7 | 39.1 | 39.0 | 39.0 | 39.5 | 39.5 | 39.3 | 39.0 | 38.8 | 39.0 | 40.4 | 39.3 | 39.0 | 39.1 |
| 6 | 2237 | 40.0 | 39.6 | 39.5 | 39.3 | 39.5 | 39.8 | 39.6 | 39.3 | 39.4 | 39.3 | 39.1 | 39.0 | 39.2 | 39.2 | 39.1 |
| | 2238 | 39.5 | 39.9 | 39.7 | 40.0 | 40.0 | 39.6 | 39.7 | 39.5 | 39.3 | 39.2 | 39.0 | 39.1 | 39.2 | 39.0 | 39.0 |
| | 2239 | 39.1 | 39.3 | 39.0 | 38.6 | 39.1 | 39.3 | 39.1 | 39.3 | 39.2 | 39.6 | 39.1 | 39.0 | 39.5 | 39.1 | 39.0 |
| 7 | 2240 | 39.2 | 39.2 | 39.5 | 39.6 | 39.5 | 39.4 | 39.5 | 39.8 | 39.5 | 39.0 | 39.3 | 39.2 | 39.0 | 39.2 | 39.6 |
| | 2241 | 39.7 | 39.4 | 39.6 | 39.6 | 39.3 | 39.5 | 39.4 | 39.8 | 39.8 | 39.1 | 39.5 | 39.3 | 39.1 | 39.0 | 40.2 |
| | 2242 | 39.6 | 39.5 | 39.3 | 39.6 | 39.6 | 39.5 | 39.5 | 39.4 | 39.5 | 39.0 | 39.0 | 39.1 | 39.0 | 39.2 | 39.2 |
| 8 | 2243 | 39.7 | 39.7 | 39.3 | 39.5 | 39.2 | 39.2 | 39.4 | 39.5 | 39.5 | 39.2 | 39.2 | 39.3 | 39.5 | 39.4 | 39.9 |
| | 2244 | 39.5 | 39.3 | 39.0 | 39.2 | 39.1 | 39.4 | 39.3 | 39.3 | 39.1 | 39.4 | 39.3 | 39.2 | 39.4 | 39.5 | 40.1 |
| | 2245 | 39.3 | 39.5 | 39.4 | 39.8 | 39.6 | 39.6 | 39.5 | 39.9 | 39.5 | 38.9 | 39.2 | 39.1 | 39.4 | 39.1 | 40.0 |
| 9 | 2246 | 39.5 | 39.7 | 39.7 | 39.8 | 39.4 | 39.3 | 39.2 | 39.6 | 39.5 | 39.3 | 39.5 | 39.6 | 39.6 | 39.5 | 39.8 |
| | 2247 | 39.7 | 39.8 | 39.2 | 39.5 | 39.3 | 39.3 | 39.3 | 39.5 | 39.0 | 39.0 | 39.2 | 39.0 | 39.1 | 39.4 | 39.4 |
| | 2248 | 39.5 | 39.3 | 39.2 | 39.5 | 39.5 | 39.6 | 39.5 | 39.3 | 39.1 | 39.0 | 39.4 | 39.5 | 39.4 | 39.3 | 39.7 |
| 10 | 2249 | 39.9 | 39.4 | 39.4 | 39.5 | 39.6 | 39.5 | 39.6 | 39.7 | 39.2 | 39.1 | 39.1 | 39.0 | 39.2 | 39.0 | 39.8 |
| | 2250 | 39.5 | 39.5 | 39.4 | 39.6 | 39.4 | 39.4 | 39.5 | 39.8 | 39.3 | 39.2 | 39.3 | 39.0 | 39.2 | 39.1 | 39.5 |
| | 2251 | 39.9 | 39.1 | 39.5 | 39.3 | 39.5 | 39.4 | 39.2 | 39.7 | 39.3 | 39.2 | 39.1 | 39.2 | 39.3 | 39.3 | 40.3 |
| 11 | 2252 | 39.7 | 39.2 | 40.5 | 40.2 | 39.5 | 39.6 | 39.8 | 39.6 | 39.3 | 39.7 | 39.1 | 39.0 | 38.8 | 38.3 | 38.0 |
| | 2253 | 39.3 | 39.3 | 40.4 | 40.3 | 39.8 | 39.9 | 40.0 | 39.8 | 39.8 | 39.5 | 40.0 | 40.8 | 40.1 | 39.0 | 39.5 |

Note:
DPC = Day Post Challenge.

TABLE 22

Neutralization Antibody Titers for Study Animals

| Grouping | | Neutralizing antibody titer | | | |
|---|---|---|---|---|---|
| GRP # | ID# | 0 WPV | 2 WPV | 4 WPV/ 0 DPC | 6 WPV/ 14 DPC |
| 1 | 2222 | ≤3 | 8 | 128 | 256 |
| | 2223 | ≤3 | ≤3 | 4 | ≥512 |
| | 2224 | ≤3 | 4 | 16 | 16 |
| | GeoMean | ≤3 | 5 | 20 | 128 |
| 2 | 2225 | ≤3 | ≤3 | ≤3 | 64 |
| | 2226 | ≤3 | ≤3 | 16 | 256 |
| | 2227 | ≤3 | 16 | 16 | 64 |
| | GeoMean | ≤3 | 5 | 9 | 102 |
| 3 | 2228 | ≤3 | 16 | ≤3 | 64 |
| | 2229 | ≤3 | 4 | 8 | 128 |
| | 2230 | ≤3 | 16 | 32 | 256 |
| | GeoMean | ≤3 | 10 | 9 | 128 |
| 4 | 2231 | ≤3 | 128 | 32 | 64 |
| | 2232 | ≤3 | 256 | 32 | 128 |
| | 2233 | ≤3 | 64 | 32 | 32 |
| | GeoMean | ≤3 | 128 | 32 | 64 |
| 5 | 2234 | ≤3 | 256 | 16 | 128 |
| | 2235 | ≤3 | ≤3 | 4 | 32 |
| | 2236 | ≤3 | 32 | 8 | ≥512 |
| | GeoMean | ≤3 | 29 | 8 | 128 |
| 6 | 2237 | ≤3 | 32 | 3 | 8 |
| | 2238 | ≤3 | 16 | 3 | 16 |
| | 2239 | ≤3 | 16 | 4 | 256 |
| | GeoMean | ≤3 | 20 | 3 | 32 |
| 7 | 2240 | ≤3 | 16 | 16 | 64 |
| | 2241 | ≤3 | 32 | 64 | 64 |
| | 2242 | ≤3 | 4 | 16 | 32 |
| | GeoMean | ≤3 | 13 | 25 | 51 |
| 8 | 2243 | ≤3 | 4 | 32 | 128 |
| | 2244 | ≤3 | 32 | 4 | 8 |
| | 2245 | ≤3 | 4 | 8 | 16 |
| | GeoMean | ≤3 | 8 | 10 | 25 |
| 9 | 2246 | ≤3 | 8 | 128 | 256 |
| | 2247 | ≤3 | ≤3 | 4 | ≥512 |
| | 2248 | ≤3 | 4 | 16 | 16 |
| | GeoMean | ≤3 | 5 | 20 | 128 |
| 10 | 2249 | ≤3 | ≤3 | ≤3 | 64 |
| | 2250 | ≤3 | ≤3 | 16 | 256 |
| | 2251 | ≤3 | 16 | 16 | 64 |
| | GeoMean | ≤3 | 5 | 9 | 102 |
| 11 | 2252 | ≤3 | ≤3 | ≤3 | ≤3 |
| | 2253 | ≤3 | ≤3 | ≤3 | ≤3 |
| | GeoMean | ≤3 | ≤3 | ≤3 | ≤3 | a: Week(s) Post Vaccination
b: Day(s) Post Challenge
c: Geometry Mean

TABLE 23

The results of anti-FMDV NS ELISA

| Grouping | | Anti-FMDV NS Ab EIA | | |
|---|---|---|---|---|
| GRP # | ID# | 7/29 (0 WPV) | 8/26 (0 DPC) | 9/9 (14 DPC) |
| 1 | 2222 | — | — | — |
| | 2223 | — | — | — |
| | 2224 | — | — | — |
| 2 | 2225 | — | — | — |
| | 2226 | — | — | — |
| | 2227 | — | — | — |
| 3 | 2228 | — | — | — |
| | 2229 | — | — | — |
| | 2230 | — | — | — |
| 4 | 2231 | — | — | — |
| | 2232 | — | — | — |
| | 2233 | — | — | — |
| 5 | 2234 | — | — | — |
| | 2235 | — | — | — |
| | 2236 | — | — | — |
| 6 | 2237 | — | — | — |
| | 2238 | — | — | — |
| | 2239 | — | — | — |

TABLE 23-continued

The results of anti-FMDV NS ELISA

| Grouping | | Anti-FMDV NS Ab EIA | | |
|---|---|---|---|---|
| GRP # | ID# | 7/29 (0 WPV) | 8/26 (0 DPC) | 9/9 (14 DPC) |
| 7 | 2240 | — | — | — |
|   | 2241 | — | — | — |
|   | 2242 | — | — | — |
| 8 | 2243 | — | — | — |
|   | 2244 | — | — | + |
|   | 2245 | — | — | + |

Note:
WPV = Week Post Vaccination; DPC = Day Post Challenge.

TABLE 24

The results of anti-VP1 antibody ELISA titration OWPV: A450 nm at 1:100 dilution. Other time point: $Log_{10}$ Titer

| Grouping | Animal No. | 0 WPV | 2 WPV | 4 WPV | 6 WPV (2 WPC) | Challenge results (Number Protected/3) |
|---|---|---|---|---|---|---|
| G1 | 2222 | 0.065 | 0.990 | 2.808 | 2.971 | 3/3 |
|   | 2223 | 0.077 | 1.427 | 1.836 | 3.461 |   |
|   | 2224 | 0.045 | 1.482 | 2.688 | 2.769 |   |
|   | GeoMean |   | 1.300 | 2.444 | 3.067 |   |
|   | SD |   | 0.269 | 0.530 | 0.356 |   |
| G2 | 2225 | 0.046 | 1.443 | 1.830 | 2.664 | 3/3 |
|   | 2226 | 0.057 | 1.468 | 2.573 | 2.870 |   |
|   | 2227 | 0.086 | 1.551 | 2.513 | 2.701 |   |
|   | GeoMean |   | 1.487 | 2.305 | 2.745 |   |
|   | SD |   | 0.056 | 0.413 | 0.110 |   |
| G3 | 2228 | 0.068 | 1.477 | 2.665 | 2.642 | 3/3 |
|   | 2229 | 0.074 | 1.478 | 2.371 | 2.264 |   |
|   | 2230 | 0.068 | 1.508 | 2.550 | 2.536 |   |
|   | GeoMean |   | 1.488 | 2.529 | 2.481 |   |
|   | SD |   | 0.018 | 0.148 | 0.195 |   |
| G4 | 2231 | 0.048 | 2.590 | 2.835 | 2.852 | 3/3 |
|   | 2232 | 0.079 | 1.914 | 2.533 | 2.476 |   |
|   | 2233 | 0.089 | 1.737 | 2.934 | 2.862 |   |
|   | GeoMean |   | 2.080 | 2.767 | 2.730 |   |
|   | SD |   | 0.450 | 0.209 | 0.220 |   |
| G5 | 2234 | 0.096 | 2.760 | 3.042 | 3.016 | 3/3 |
|   | 2235 | 0.068 | 1.452 | 2.525 | 2.702 |   |
|   | 2236 | 0.075 | 1.673 | 2.272 | 2.872 |   |
|   | GeoMean |   | 1.962 | 2.613 | 2.863 |   |
|   | SD |   | 0.700 | 0.393 | 0.157 |   |
| G6 | 2237 | 0.068 | 1.471 | 2.157 | 2.667 | 3/3 |
|   | 2238 | 0.077 | 1.439 | 2.290 | 2.477 |   |
|   | 2239 | 0.064 | 1.497 | 2.331 | 2.403 |   |
|   | GeoMean |   | 1.469 | 2.259 | 2.516 |   |
|   | SD |   | 0.029 | 0.091 | 0.136 |   |
| G7 | 2240 | 0.075 | 1.504 | 2.071 | 2.295 | 3/3 |
|   | 2241 | 0.046 | 2.406 | 2.755 | 2.895 |   |
|   | 2242 | 0.068 | 1.841 | 2.233 | 2.362 |   |
|   | GeoMean |   | 1.917 | 2.353 | 2.517 |   |
|   | SD |   | 0.455 | 0.357 | 0.329 |   |
| G8 | 2243 | 0.068 | 1.493 | 1.885 | 2.694 | 3/3 |
|   | 2244 | 0.077 | 1.457 | 2.500 | 2.604 |   |
|   | 2245 | 0.089 | 1.441 | 1.672 | 2.404 |   |
|   | GeoMean |   | 1.464 | 2.019 | 2.567 |   |
|   | SD |   | 0.026 | 0.430 | 0.149 |   |
| G9 | 2246 | 0.075 | 1.547 | 2.430 | 2.637 | 3/3 |
|   | 2247 | 0.057 | 1.815 | 2.409 | 2.405 |   |
|   | 2248 | 0.046 | 1.903 | 2.886 | 2.815 |   |
|   | GeoMean |   | 1.755 | 2.575 | 2.619 |   |
|   | SD |   | 0.185 | 0.270 | 0.206 |   |
| G10 | 2249 | 0.057 | 1.530 | 2.178 | 2.290 | 3/3 |
|   | 2250 | 0.049 | 1.880 | 2.646 | 2.736 |   |
|   | 2251 | 0.068 | 1.691 | 1.963 | 2.661 |   |
|   | GeoMean |   | 1.700 | 2.262 | 2.562 |   |
|   | SD |   | 0.175 | 0.349 | 0.239 |   |
| G11 | 2252 | 0.046 | 1.430 | 1.335 | 1.560 | 0/2 |
|   | 2253 | 0.064 | 1.418 | 1.305 | 2.562 |   |
|   | GeoMean |   | 1.424 | 1.320 | 2.061 |   |
|   | SD |   | 0.008 | 0.021 | 0.708 |   | a: Week(s) Post Vaccination
b: Day(s) Post Challenge

TABLE 25

FMDV vaccine efficacy evaluation through challenges of pigs receiving single administration for FMDV vaccine formulations containing both FMDV VP1 derived B and FMDV endogenous Th epitope peptides with FMDV isolates of relevant serotypes

| Study No. | Grp No. | Description of FMDV Vaccine Formulations | | | FMDV isolate for challenge study | Outcome of protection | Notes regarding the challenge study |
|---|---|---|---|---|---|---|---|
| | | FMDV VP1 B epitope cluster peptides | FMDV Endogenous Th epitope peptides | Type of Formulation | | | |
| I | 1 | FMDV O Consensus SEQ ID No: 25 | SEQ ID Nos: 34-63 | FMDV B epitope peptide: FMDV Ths epitope peptides at 10:1 ratio (w:w) @ (25 + 2.5)ug/mL in ISA50V with 0.1% Tween 80 @ 1 mL per dose | FMDV O Taiwan99 | 3/3 protected | In Taiwan, viral challenge was conducted through inoculation with 1 × $10^5$ $TCID_{50}$, previously titered in tissue culture, of FMDV O1 Taiwan virus (about at least 10 times higher than the amount of viruses administered according to the OIE guidelines) into the heel bulbs of the pigs forelegs inside the P3 facility at the National Institute for Animal Health, Tamsui, Taiwan, in accordance with Council of Agriculture guidelines. Experimental animals were monitored for clinical signs of FMD over a 14-day observation period. These included daily recording of body temperature, observations of whether the animals developed lameness in their legs, and acquired vesicular lesions on the coronary bands of their legs and on their snouts. Full protection was achieved through addition of 10% of endogenous FMDV Ths to as many as 30 Ths (SEQ ID Nos: 34-63), and as few as 3 Ths (SEQ ID Nos: 61-63) or the UBITh enhanced cassette form comprising these three Ths (SEQ ID NO: 90). |
| | 2 | FMDV O Consensus SEQ ID No: 25 | SEQ ID Nos: 61-63 | FMDV B epitope peptide: FMDV Ths epitope peptides at 10:1 ratio (w:w) @ (25 + 2.5)ug/mL in ISA50V with 0.1% Tween 80 @ 1 mL per dose | FMDV O Taiwan99 | 3/3 protected | |
| | 3 | FMDV O Consensus SEQ ID No: 25 | SEQ ID No: 90 | FMDV B epitope peptide: FMDV Ths epitope peptides at 10:1 ratio (w:w) @ (25 + 2.5)ug/mL in ISA50V with 0.1% Tween 80 @ 1 mL per dose | FMDV O Taiwan99 | 3/3 protected | |
| | 4 | | | Placebo Control | FMDV O Taiwan99 | 0/2 protected | |
| II | 5 | FMDV O Consensus SEQ ID No: 25 | SEQ ID No: 90 | FMDV B epitope peptide: FMDV Ths epitope peptides at 10:1 ratio (w:w) @ (25 + 2.5)ug/mL in ISA50V with 0.1% Tween 80 @ 2 mL per dose | FMDV O Taiwan99 | 5/5 protected | In this study II which corresponds to groups 1, 2 and 3 of Table 20, FMDV VP 1 derived cyclic peptide having O consensus SEQ ID No: 25, when formulated in the presence of 10% of FMDV Ths epitope presented in a UBITh enhanced cassette form with SEQ ID NO: 90 at a 10:1 ratio by weight (i.e. 10% of FMDV Ths) allowed full (5/5) protection upon single administration when the vaccine was given at 2 mL, 1 mL or 0.5 mL. $PD_{50}$ of the vaccine formulation was calculated using Reed-Muench Method on the basis of the results of challenge tests. This vaccine formulation has a $PD_{50}$ of over 11.23. |
| | 6 | FMDV O Consensus SEQ ID No: 25 | SEQ ID No: 90 | FMDV B epitope peptide: FMDV Ths epitope peptides at 10:1 ratio (w:w) @ (25 + 2.5)ug/mL in ISA50V with 0.1% Tween 80 @ 1 mL per dose | FMDV O Taiwan99 | 5/5 protected | |
| | 7 | FMDV O Consensus SEQ ID No: 25 | SEQ ID No: 90 | FMDV B epitope peptide: FMDV Ths epitope peptides at 10:1 ratio (w:w) @ (25 + 2.5)ug/mL in ISA50V with 0.1% Tween 80 @ 0.5 mL per dose | FMDV O Taiwan99 | 5/5 protected | |
| | 8 | | | Placebo | FMDV O Taiwan99 | 0/2 protected | |
| III | 9 | FMDV O Consensus SEQ ID No: 25 | SEQ ID No: 90 | FMDV B epitope peptide: FMDV Ths epitope peptides at 1:1 ratio (w:w) @ (25 + 25)ug/mL in ISA50V with 0.1% Tween 80 @ 1 mL per dose | FMDV O Taiwan99 | 3/3 protected | In this challenge test, full protection was achieved in the presence of as little as 10% and as much as 50% of the FMDV Ths presented in an enhanced cassette form (SEQ ID No: 90) upon single administration at 1 mL per dose. |
| | 10 | FMDV O Consensus SEQ ID No: 25 | SEQ ID No: 90 | FMDV B epitope peptide: FMDV Ths epitope peptides at 5:1 ratio (w:w) @ (25 + 5)ug/mL in ISA50V with 0.1% Tween 80 @ 1 mL per dose | FMDV O Taiwan99 | 3/3 protected | |
| | 11 | FMDV O Consensus SEQ ID No: 25 | SEQ ID No: 90 | FMDV B epitope peptide: FMDV Ths epitope peptides at 10:1 ratio (w:w) @ (25 + 2.5)ug/mL in ISA50V with 0.1% Tween 80 @ 1 mL per dose | FMDV O Taiwan99 | 3/3 protected | |
| | 12 | | | Placebo Control | | 0/2 protected | |
| IV | 13 | FMDV O Consensus SEQ ID No: 25 | SEQ ID Nos: 61-63 | FMDV B epitope peptide: FMDV Ths epitope peptides at 10:1 ratio (w:w) @ (25 + 2.5)ug/mL in | FMDV O Taiwan99 | 3/3 protected | This study corresponds to groups 4, 5 and 6 in Table 20. In this challenge test, full protection was achieved in the presence of three FMDV endogenous |

TABLE 25-continued

FMDV vaccine efficacy evaluation through challenges of pigs receiving single administration for FMDV vaccine formulations containing both FMDV VP1 derived B and FMDV endogenous Th epitope peptides with FMDV isolates of relevant serotypes

| Study No. | Grp No. | FMDV VP1 B epitope cluster peptides | FMDV Endogenous Th epitope peptides | Type of Formulation | FMDV isolate for challenge study | Outcome of protection | Notes regarding the challenge study |
|---|---|---|---|---|---|---|---|
|  | 14 | FMDV O Consensus SEQ ID No: 25 | SEQ ID Nos: 61-63 | ISA50V with 0.1% Tween 80 @ 2 mL per dose FMDV B epitope peptide: FMDV Ths epitope peptides at 10:1 ratio (w:w) @ (25 + 2.5)ug/mL in ISA50V with 0.1% Tween 80 @ 1 mL per dose | FMDV O Taiwan99 | 3/3 protected | Th epitope peptides (SEQ ID Nos: 61-63) at 10% by weight upon single administration of the vaccine formulation at 2 mL, 1 mL, 0.5 mL indicating the high potency of the vaccine formulation. |
|  | 15 | FMDV O Consensus SEQ ID No: 25 | SEQ ID Nos: 61-63 | FMDV B epitope peptide: FMDV Ths epitope peptides at 10:1 ratio (w:w) @ (25 + 2.5)ug/mL in ISA50V with 0.1% Tween 80 @ 0.5 mL per dose | FMDV O Taiwan99 | 3/3 protected |  |
|  | 16 | FMDV O Consensus SEQ ID No: 25 | SEQ ID Nos: 61-63 | FMDV B epitope peptide: FMDV Ths epitope peptides at 10:1 ratio (w:w) @ (25 + 2.5)ug/mL in ISA50V with 0.1% Tween 80 @ 0.25 mL per dose | FMDV O Taiwan99 | 3/3 protected |  |
|  | 17 |  |  | Placebo | FMDV O Taiwan99 | 0/2 protected |  |
| V | 18 | FMDV O Consensus SEQ ID No: 25 | SEQ ID No: 90 | FMDV B epitope peptide: FMDV Ths epitope peptides at 10:1 ratio (w:w) @ (25 + 2.5)ug/mL in ISA50V with 0.1% Tween 80 @1 mL per dose | FMDV O Taiwan99 | 3/3 protected | This study corresponds to groups 7, 8, 9, 10 and 11 of Table 20. In this challenge test, full protection was achieved in the presence of 10% FMDV endogenous Th epitope peptides presented in a UBITh enhanced cassette form (SEQ ID NO: 90) when the B epitope peptide composition is presented either as a monovalent O serotype peptide (SEQ ID No: 25, 2570 kb), or as a O serotype combo formulation (SEQ ID Nos: 25, 28, and 27), or as a multivalent serotypes O and Asia1 combination formulation (SEQ ID Nos: 25, 28, 27 and 29) indicating the adaptability in immunogenicity of the VP1 B epitope peptides. Commercial Viral lysate based vaccine (from Russia) was used as the positive control (group 19) along with a negative control (group 20) with no injection in this study. |
|  | 19 | FMDV O Consensus SEQ ID No: 25 + O Ozk SEQ ID No: 28 + O Myanmar SEQ ID No: 27 | SEQ ID No: 90 | FMDV B epitope peptide: FMDV Ths epitope peptides at 10:1 ratio (w:w) @ (25 + 2.5)ug/mL in ISA50V with 0.1% Tween 80 @1 mL per dose | FMDV O Taiwan99 | 3/3 protected |  |
|  | 20 | FMDV O Consensus SEQ ID No: 25 + O Ozk SEQ ID No: 28 + O Myanmar SEQ ID No: 27 + Asia 1 Jiansu SEQ ID No: 29 | SEQ ID No: 90 | FMDV B epitope peptide: FMDV Ths epitope peptides at 5:1 ratio (w:w) @ (25 + 2.5)ug/mL in ISA50V with 0.1% Tween 80 @1 mL per dose | FMDV O Taiwan99 | 3/3 protected |  |
|  | 21 |  |  | Placebo Control | FMDV O Taiwan99 | 0/2 protected |  |

TABLE 26

FMDV vaccine efficacy evaluation through challenges of cattle receiving single administration of FMDV vaccine formulations containing both FMDV VP1 derived B and FMDV endogenous Th epitope peptides with FMDV isolates of relevant serotypes

| Study No. | Grp No. | FMDV VP1 B epitope peptides | FMDV Th epitope peptides | Type of Formulation | FMDV isolate for challenge study | Outcome of protection | Notes regarding the challenge study |
|---|---|---|---|---|---|---|---|
| I | 1 | FMDV O Consensus SEQ ID No: 25 | None | ISA 50V2 in w/o emulsion @ 50 ug/mL in ISA50V with 0.1% Tween 80 @ 1 mL/dose | FMDV O | 0/5 | In bovine, the viral challenge was introduced by a modified intramuscular injection on the back of the neck of the animal of 1 × 10$^4$ TCID$_{50}$ of FMDV (Bovine Infectious Unit or BIU). OS/99 strain was used for serotype O challenge and Asia 1 highly virulent strain was used for serotype Asia 1 challenge. |
|  | 2 | FMDV O Consensus SEQ ID | None | ISA 50V2 in w/o emulsion @ 50 ug/mL in ISA50V with 0.1% | FMDV O | 0/5 |  |

TABLE 26-continued

FMDV vaccine efficacy evaluation through challenges of cattle receiving single administration of FMDV vaccine formulations containing both FMDV VP1 derived B and FMDV endogenous Th epitope peptides with FMDV isolates of relevant serotypes

| Study No. | Grp No. | FMDV VP1 B epitope peptides | FMDV Th epitope peptides | Type of Formulation | FMDV isolate for challenge study | Outcome of protection | Notes regarding the challenge study |
|---|---|---|---|---|---|---|---|
| | | No: 25 | | Tween 80 @ 2 mL per dose | | | Animals were examined daily, upon viral challenge after receiving single administration of respective FMDV vaccine formulations 28 days, monitoring rectal temperatures, and a protection score based on the time of appearance and the number and severity of lesions was determined. All experiments with live animals were performed under the guidelines Ministry of Agriculture, PRC. Modifications of the dosing such as using 2X, 1X, and 0.5X dose of the test vaccine was also used for assessment of a particular formulation's potency. For quick screening of formulations with protective efficacy, 1X was used. For assessment of vaccine formulation efficacy, animals were divided into 3 to 5 animals per group depending on experimental design and availability of the animals at the time of the study. In this study, FMDV vaccine formulation containing only VP1 based B epitope peptide (SEQ ID No: 25) in the absence of endogenous FMDV Th epitope peptides, or in the presence of 10% exogenous Ths epitope peptides from DT, TT and PT toxoid proteins failed to protect the animals from FMDV serotype O strain challenge. |
| | 3 | SEQ ID No: 25 lipopeptide attached with Pam3 Cys | None | ISA 50V2 in w/o emulsion @ 50 ug/mL in ISA50V with 0.1% Tween 80 @ 2 mL/dose | FMDV O | 0/5 | |
| | 4 | FMDV O Consensus SEQ ID No: 25 | Th peptides (TT, DT and PT) | FMDV B epitope peptide: exogenous DT, TT, PT Ths epitope peptides at 10:1 ratio (w:w) @ (50 + 5)ug/mL in ISA50V with 0.1% Tween 80 @ 2 mL/dose | FMDV O | 0/5 | |
| | 5 | | | Placebo Control | FMDV O | 0/2 | |
| II | 6 | FMDV O Consensus SEQ ID No: 25 | SEQ ID Nos: 88, 89 | FMDV B epitope peptide: FMDV Ths epitope peptides at 10:1 ratio (w:w) @ (50 + 5)ug/mL in ISA50V with 0.1% Tween 80 @ 2 mL/dose | FMDV O | 4/5 | In this challenge study using FMDV serotype O OS/99 strain, when the FMDV VP1 derived B epitope peptide (SEQ ID NO: 25) was introduced with 10% of endogenous FMDV Th epitope peptides from six selected epitope sequences arranged in a cassette form which were further enhanced by UBITh as two long FMDV Th epitope peptides (SEQ ID Nos: 88, 89), 4 out of 5, 4 out of 5 and 3 out of 5 animals were protected in this study when animals in groups 6, 7 and 8 were administered with the vaccine formulation of 55 ug/mL at 2 mL, 1 mL and 0.5 mL respectively after single shot. |
| | 7 | FMDV O Consensus SEQ ID No: 25 | SEQ ID Nos: 88, 89 | FMDV B epitope peptide: FMDV Ths epitope peptides at 10:1 ratio (w:w) @ (50 + 5)ug/mL in ISA50V with 0.1% Tween 80 @ 1 mL/dose | FMDV O | 4/5 | |
| | 8 | FMDV O Consensus SEQ ID No: 25 | SEQ ID Nos: 88, 89 | FMDV B epitope peptide: FMDV Ths epitope peptides at 10:1 ratio (w:w) @ (50 + 5)ug/mL in ISA50V with 0.1% Tween 80 @ 0.5 mL/dose | FMDV O | 3/5 | |
| | 9 | | | Placebo control | FMDV O | 0/2 | |
| III | 10 | FMDV O Consensus SEQ ID No: 25 | SEQ ID Nos: 34-63 (30 Ths) at equal ratio (by wt) | FMDV B epitope peptide: FMDV Ths epitope peptides at 10:1 ratio (w:w) @ (50 + 5)ug/mL in ISA50V with 0.1% Tween 80 @ 2 mL/dose | FMDV O | 4/4 | In this challenge study using FMDV serotype O OS/99 strain, when the FMDV VP1 derived B epitope peptide (SEQ ID NO: 25) was introduced with 10% of endogenous FMDV Th epitope peptides from as many as 30 selected Th epitope peptides (SEQ ID Nos: 34-63), or 21 selected Th peptides (SEQ ID Nos: 34-39, 44, 46-51, 53-60), or 15 selected Th peptides (Groups 12, 13, and 14), full protection was achieved by all three formulations indicating the broad range of the number of endogenous FMDV Ths that can be incorporated in the vaccine formulation without negative impact in viral challenge protection. Immunization of animals with formulations containing 10%, 5% or as low as 0.5% (i.e. B: Th ratio at 10:1, 20:1 or 100:1 respectively) of a mixture of 15 endogenous FMDV Th epitope peptides, full protection would still prevail in the presence of 5% (or B: Th ratio at 20:1) of the endogenous |
| | 11 | FMDV O Consensus SEQ ID No: 25 | SEQ ID Nos: 34-39, 44, 46-51, 53-60 (21 Ths) at equal ratio (by wt) | FMDV B epitope peptide: FMDV Ths epitope peptides at 10:1 ratio (w:w) @ (50 + 5)ug/mL in ISA50V with 0.1% Tween 80 @ 2 mL/dose | FMDV O | 4/4 | |
| | 12 | FMDV O Consensus SEQ ID No: 25 | SEQ ID Nos: 34, 36, 37, 40-43, 45, 48, 52, 53, 60-63 (15 Ths) at | FMDV B epitope peptide: FMDV Ths epitope peptides at 10:1 ratio (w:w) @ (50 + 5)ug/mL in ISA50V with 0.1% Tween 80 @ 2 mL/dose | FMDV O | 4/4 | |

TABLE 26-continued

FMDV vaccine efficacy evaluation through challenges of cattle receiving single administration of FMDV vaccine formulations containing both FMDV VP1 derived B and FMDV endogenous Th epitope peptides with FMDV isolates of relevant serotypes

| Study No. | Grp No. | Description of FMDV Vaccine Formulations | | | FMDV isolate for challenge study | Outcome of protection | Notes regarding the challenge study |
|---|---|---|---|---|---|---|---|
| | | FMDV VP1 B epitope peptides | FMDV Th epitope peptides | Type of Formulation | | | |
| | 13 | FMDV O Consensus SEQ ID No: 25 | SEQ ID Nos: 34, 36, 37, 40-43, 45, 48, 52, 53, 60-63 (15 Ths) at equal ratio (by wt) | FMDV B epitope peptide: FMDV Ths epitope peptides at 20:1 ratio (w:w) @ (50 + 2.5)ug/mL in ISA50V with 0.1% Tween 80 @ 2 mL/dose | FMDV O | 4/4 | FMDV Th epitope peptides. A 50% protection of the animals upon challenge was seen in the presence of as little as 1% of the FMDV Th epitope. |
| | 14 | FMDV O Consensus SEQ ID No: 25 | SEQ ID Nos: 34, 36, 37, 40-43, 45, 48, 52, 53, 60-63 (15 Ths) at equal ratio (by wt) | FMDV B epitope peptide: FMDV Ths epitope peptides at 100:1 ratio (w:w) @ (50 + 0.5)ug/mL in ISA50V with 0.1% Tween 80 @ 2 mL/dose | FMDV O | 2/4 | |
| | 15 | | | Placebo Control | FMDV O | 0/2 | |
| IV | 16 | FMDV O Consensus + O Ozk + O Myanmar SEQ ID Nos: 25, 28, 27 at equal ratio (by weight) | SEQ ID Nos: 91, 93, 94, 95 at equal ratio (by weight) | FMDV B epitope peptide: FMDV Ths epitope peptides at 10:1 ratio (w:w) @ (50+5)ug/mL in ISA50V with 0.1% Tween 80 @ 2 mL/dose | FMDV O | 4/5 | In these two challenge tests, protection of 4 out of 5 animals for each of the studies by FMDV serotype O OS/99 strain (Study IV) or highly virulent FMDV Asia 1 strain (Study V) respectively was achieved in the presence of 10% endogenous Th epitope peptides selected from 12 FMDV Th epitopes that were presented in a cassette |
| | 17 | | | Placebo Control | FMDV O | 0/2 | |
| V | 18 | FMDV O Consensus + O Ozk + O Myanmar + Asia 1 Jiangsu + A Gansu SEQ ID Nos: 25, 28, 27, 29, 31 at equal ratio (by weight) | SEQ ID Nos: 91, 93, 94, 95 at equal ratio (by weight) | FMDV B epitope peptide: FMDV Ths epitope peptides at 10:1 ratio (w:w) @ (50+5)ug/mL in ISA50V with 0.1% Tween 80 @ 2 mL/dose | FMDV Asia 1 | 4/5 | form on four UBITh enhanced peptides (SEQ ID Nos: 91, 93, 94, 95) when the B epitope peptide composition was presented either as a Combo O serotype formulation (SEQ ID Nos: 25, 28, and 27), or as a multivalent serotypes O, Asia 1 and A Gansu formulation (SEQ ID Nos: 25, 28, 27, 29 and 31) indicating the adaptability in immunogenicity of the VP1 B epitope peptides. |
| | 19 | | | Placebo Control | FMDV Asia 1 | 0/2 | |

The invention claimed is:

1. A foot and mouth disease (FMD) vaccine composition, comprising
   a) a synthetic immunogenic peptide comprising an FMDV VP1 looped B cell epitope sequence represented by SEQ ID NOs: 1 or 2 or a homologue having at least 75% sequence identity to SEQ ID NO: 2 and a Th epitope;
   b) a separate peptide consisting of
      (i) at least one endogenous synthetic FMDV T helper epitope sequence selected from the group consisting of any of SEQ ID NOs: 34-87;
      (ii) the at least one endogenous synthetic FMDV T helper epitope sequence of (i) covalently linked an optional artificial T helper epitope sequence represented by SEQ ID NO: 24; and
      (iii) SEQ ID NOs: 94 or 95,
      wherein the T helper epitope sequences in (i) and/or (ii) are covalently linked to each other through an optional spacer; and
   c) a veterinarily acceptable delivery vehicle or adjuvant.

2. The FMD vaccine according to claim 1, wherein the composition comprises more than one of the separate peptides in (b).

3. The FMD vaccine according to claim 1, wherein the B cell epitope of the synthetic immunogenic peptide in (a) is a homologue of SEQ ID NO: 2 comprising the amino acid sequence selected from the group consisting of SEQ ID NOs: 3 to 11, and any combination thereof.

4. The FMD vaccine according to claim 1, wherein the Th epitope of the synthetic immunogenic peptide in (a) comprises the amino acid sequence of SEQ ID NO: 24.

5. The FMD vaccine according to claim 1, wherein the synthetic immunogenic peptide of (a) comprises the B cell epitope covalently linked to the carboxyl-terminus of the Th epitope.

6. The FMD vaccine according to claim 1, wherein the synthetic immunogenic peptide of (a) comprises the B cell epitope covalently linked to the Th epitope through a spacer comprising an epsilon lysine residue.

7. The FMD vaccine according to claim 1, wherein the synthetic immunogenic peptide in (a) has an amino acid sequence selected from the group consisting of SEQ ID NOs: 25 to 28, and any combination thereof.

8. The FMD vaccine according to claim 1, wherein the separate peptide in (b) is selected from the group consisting of SEQ ID NOs: 34 to 95, and any combination thereof.

9. The FMD vaccine according to claim 1, wherein the delivery vehicle or adjuvant in (c) is selected from the group consisting of Montanide ISA 50V, Polyoxyethylene (20) sorbitan monooleate, Emulsigen, Emulsigen D, and a CpG oligonucleotide.

10. The FMD vaccine according to claim 1, wherein
    the synthetic immunogenic peptide in (a) has an amino acid sequence selected from the group consisting of: any of SEQ ID NOs: 25 to 28, and any combination thereof;
    the separate peptide in (b) is selected from the group consisting of SEQ ID NOs: 34 to 95, and any combination thereof; and
    the delivery vehicle or adjuvant in (c) is selected from the group consisting of Montanide ISA 50V, Polyoxyethylene (20) sorbitan monooleate, Emulsigen, Emulsigen D, and a CpG oligonucleotide.

11. The FMD vaccine according to claim 10 further comprising a peptide selected from the group consisting of: any of SEQ ID NOs: 29 to 33, and any combination thereof.

12. The FMD vaccine of claim 1, wherein
    the synthetic immunogenic peptide in (a) is SEQ ID NO: 25;
    the separate peptide in (b) is selected from the group consisting of SEQ ID NOs: 34 to 95; and any combination thereof;
    the veterinarily acceptable delivery vehicle or adjuvant is ISA50V2 water in oil (w/o 50/50) emulsion at 27.5 µg/mL per dose; and
    wherein the synthetic immunogenic peptide in (a) is present in a ratio of about 10:1 to the separate peptide in (b).

13. The FMD vaccine of claim 1, wherein the synthetic immunogenic peptide in (a) is SEQ ID NO: 25, 27, 28, or any combination thereof;
    the separate peptide in (b) is selected from the group consisting of:
    i) a mixture of synthetic FMDV T helper peptides of SEQ ID NOs: 34-63;
    ii) a mixture of synthetic FMDV T helper peptides of SEQ ID NOs: 61-63; and
    iii) a synthetic FMDV T helper peptide of SEQ ID NO: 90.

14. The FMD vaccine of claim 13 further comprising a peptide selected from the group consisting of: any of SEQ ID NOs: 29, 31, and any combination thereof.

15. The FMD vaccine of claim 1, wherein
    the synthetic immunogenic peptide in (a) comprises a mixture of SEQ ID NOs: 25 and 28;
    the separate peptide in (b) is selected from the group consisting of:
    i) a mixture of synthetic FMDV T helper peptides of SEQ ID NOs: 34-63;
    ii) a mixture of synthetic FMDV T helper peptides of SEQ ID NOs: 34-39, 44, 46-51, 53-63;
    iii) a mixture of synthetic FMDV T helper peptides of SEQ ID NOs: 34-39, 44, 46-51, 53-60;
    iv) a mixture of synthetic FMDV T helper peptides of SEQ ID NOs: 34, 36, 37, 40-43, 45, 48, 52, 53, 60-63;
    v) a mixture of synthetic FMDV T helper peptides of SEQ ID NOs: 34, 36, 37, 48, 50, 53;
    vi) a mixture of synthetic FMDV T helper peptides of SEQ ID NOs: 62-78;
    vii) a mixture of synthetic FMDV T helper peptides of SEQ ID NOs: 79-87;
    viii) a mixture of synthetic FMDV T helper peptides of SEQ ID NOs: 88-89;

ix) a mixture of synthetic FMDV T helper peptides of SEQ ID NOs: 91-92; and x) a mixture of synthetic FMDV T helper peptides of SEQ ID NOs: 91, 93-95; and the delivery vehicle or adjuvant in (c) is selected from the group consisting of Montanide ISA 50V, Polyoxyethylene (20) sorbitan monooleate, Emulsigen, Emulsigen D, and a CpG oligonucleotide.

16. The FMD vaccine of claim 1, wherein the synthetic immunogenic peptide in (a) is SEQ ID NOs: 26;

the separate peptide in (b) is selected from the group consisting of:
  i) a mixture of synthetic FMDV T helper peptides of SEQ ID NOs: 91-92; and
  ii) a mixture of synthetic FMDV T helper peptides of SEQ ID NOs: 91, 93-95; and the delivery vehicle or adjuvant in (c) is selected from the group consisting of Montanide ISA 50V, Polyoxyethylene (20) sorbitan monooleate, Emulsigen, Emulsigen D, and a CpG oligonucleotide.

17. The FMD vaccine of claim 16 further comprising a peptide selected from the group consisting of: any of SEQ ID NOs: 30, 32, 33, and any combination thereof.

18. A method for eliciting an immune response in an animal comprising
   providing a single administration of a pharmaceutically effective amount of the vaccine according to claim 1 to the animal.

19. A method for protecting an animal from FMD infection comprising providing a single administration of a pharmaceutically effective amount of the vaccine in claim 11 to the animal.

20. The method of claim 19, wherein the animal is a pig or a cow.

21. The method of claim 19, wherein the animal is a pig.

* * * * *